(12) United States Patent
Liu et al.

(10) Patent No.: US 8,614,214 B2
(45) Date of Patent: Dec. 24, 2013

(54) PYRAZOLE AMIDE COMPOUNDS AND USES THEREOF

(75) Inventors: Changling Liu, Shenyang (CN); Lizeng Wang, Shenyang (CN); Zhinian Li, Shenyang (CN); Xufeng Sun, Shenyang (CN); Jie Lan, Shenyang (CN); Lanhui Ren, Shenyang (CN); Qiang Wu, Shenyang (CN); Huiwei Chi, Shenyang (CN)

(73) Assignee: Sinochem Corporation, Beijing (CN)

( * ) Notice: Subject to any disclaimer, the term of this patent is extended or adjusted under 35 U.S.C. 154(b) by 0 days.

(21) Appl. No.: 13/883,146

(22) PCT Filed: Nov. 2, 2011

(86) PCT No.: PCT/CN2011/081672
§ 371 (c)(1),
(2), (4) Date: May 2, 2013

(87) PCT Pub. No.: WO2012/059048
PCT Pub. Date: May 10, 2012

(65) Prior Publication Data
US 2013/0225585 A1    Aug. 29, 2013

(30) Foreign Application Priority Data
Nov. 3, 2010 (CN) .......... 2010 1 0535131

(51) Int. Cl.
| | | |
|---|---|---|
| *A61K 31/5377* | (2006.01) | |
| *C07D 413/02* | (2006.01) | |
| *C07D 231/10* | (2006.01) | |
| *A61K 31/415* | (2006.01) | |

(52) U.S. Cl.
USPC ...... 514/236.5; 514/406; 544/140; 548/374.1

(58) Field of Classification Search
USPC .............. 514/236.5, 406; 544/140; 548/374.1
See application file for complete search history.

(56) References Cited

U.S. PATENT DOCUMENTS

| | | |
|---|---|---|
| 5,705,453 A | 1/1998 | Kyomura et al. |
| 6,048,680 A | 4/2000 | Saeva et al. |
| 6,174,905 B1 | 1/2001 | Suzuki et al. |
| 7,687,525 B2 | 3/2010 | Suzuki et al. |
| 8,148,419 B2 | 4/2012 | Coqueron et al. |
| 8,357,816 B2 | 1/2013 | Ehrenfreund et al. |
| 2005/0085524 A1 | 4/2005 | Okada et al. |
| 2010/0256201 A1 | 10/2010 | Suzuki et al. |

FOREIGN PATENT DOCUMENTS

| | | |
|---|---|---|
| CN | 1091426 A | 8/1994 |
| CN | 1642963 A | 7/2005 |
| CN | 1919838 A | 2/2007 |
| CN | 1927860 A | 3/2007 |
| EP | 0 847 992 A1 | 6/1998 |
| JP | 7-112972 A | 5/1995 |
| JP | 7-173139 A | 7/1995 |
| WO | 02/083647 A1 | 10/2002 |
| WO | 2004/009533 A1 | 1/2004 |
| WO | 2007/060164 A1 | 5/2007 |

OTHER PUBLICATIONS

International Search Report for Application No. PCT/CN2011/081672 dated Feb. 116, 2012.

*Primary Examiner* — Samantha Shterengarts
(74) *Attorney, Agent, or Firm* — Smith, Gambrell & Russell, LLP

(57) ABSTRACT

Disclosed is a pyrazole amide compound having fungicidal activity, with a structure shown by the general formula (I):

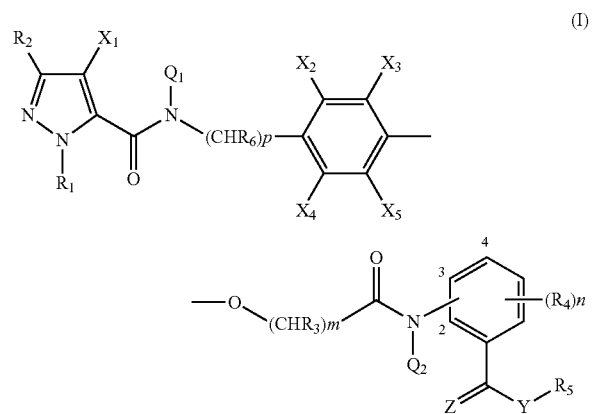

Each of the substituents of the compound being defined as in the description. The compound of the present invention has fungicidal activity, and excellent prevention and controlling effects on diseases, such as cucumber downy mildew, corn rust, wheat powdery mildew, rice blast, etc., and in particular, a better prevention and controlling effect on cucumber downy mildew and corn rust. Also disclosed is a process for preparing the compound, a fungicidal composition containing the compound of general formula (I) and the use thereof in preventing and controlling disease in crops.

21 Claims, No Drawings

PYRAZOLE AMIDE COMPOUNDS AND USES THEREOF

FIELD OF THE INVENTION

The invention relates to fungicide. Specifically to a novel pyrazole amide compounds and uses thereof.

BACKGROUND OF THE INVENTION

Plant diseases cause a lot of damage to crops, especially to food and fiber, which can meet the human demand for basic agricultural products, such as fruits, vegetables, cotton, rice, corn, wheat, soybeans and so on. To kill or inhibit the growth of bacteria and to avoid or reduce the damage to crops is an effective way to improve agricultural production. Therefore, it is necessary to constantly develop more effective novel fungicides.

As we all know, pyrazole amide compounds such as tolfenpyrad and tebufenpyrad are used as insecticides and acaricides, as well as some pyrazole amide compounds reported in the following literatures: CN1927860A, CN1919838A, CN1091426A, U.S. Pat. No. 5,705,453, WO2002083647A, etc. However, the insecticidal and fungicidal activity of some compounds of this kind were disclosed in CN1919838A, CN1091426A, U.S. Pat. No. 5,705,453 and WO2002083647A, but the uses as agricultural fungicide of the pyrazole amide compounds having general formula of the present invention had not been reported in prior art.

SUMMARY OF THE INVENTION

The object of the present invention is to provide a novel pyrazole amide compounds, which can be used to prepare fungicides against harmful fungus and bacteria in agricultural or other fields.

Detailed descriptions of the invention are as follows:
The present invention provides a kind of pyrazole amide compounds having general formula (I):

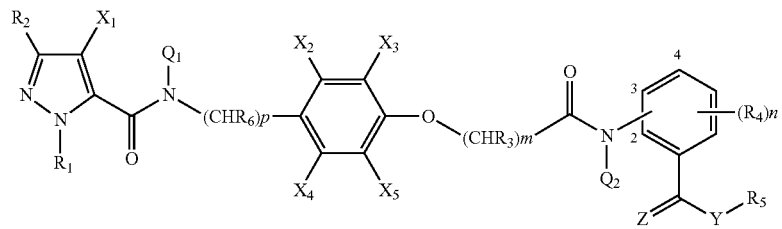

Wherein:
$R_1$ is selected from H, $C_1$-$C_{12}$alkyl, $C_1$-$C_{12}$haloalkyl, $C_1$-$C_{12}$ cyanoalkyl, $C_1$-$C_{12}$alkoxy$C_1$-$C_{12}$alkyl, $C_1$-$C_{12}$alkylcarbonyl, $C_1$-$C_{12}$haloalkylcarbonyl, $C_1$-$C_{12}$alkoxycarbonyl, $C_1$-$C_{12}$haloalkoxycarbonyl, $C_1$-$C_{12}$alkylaminocarbonyl, $C_1$-$C_{12}$haloalkylaminocarbonyl, $C_3$-$C_6$cycloalkyl or $R_8$;

$R_2$ is selected from H, halogen, CN, $C_1$-$C_{12}$cyanoalkyl, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$cyanoalkoxy, $C_1$-$C_{12}$alkylthio, $C_1$-$C_{12}$haloalkylthio, $C_1$-$C_{12}$alkoxy$C_1$-$C_{12}$alkyl, $C_1$-$C_{12}$haloalkoxy$C_1$-$C_{12}$alkyl, $C_1$-$C_{12}$alkylthio$C_1$-$C_{12}$alkyl, $C_1$-$C_{12}$haloalkylthio$C_1$-$C_{12}$alkyl, $C_1$-$C_{12}$alkylsulfinyl, $C_1$-$C_{12}$alkylsulfonyl, $C_3$-$C_6$cycloalkyl or $R_8$;

$R_3$ is selected from H or $C_1$-$C_{12}$alkyl; m is selected from 0 to 5;

$R_4$ is selected from halogen, CN, $CONH_2$, $CSNH_2$, $NO_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$haloalkylthio, $C_1$-$C_{12}$alkoxy$C_1$-$C_{12}$alkyl, $C_1$-$C_{12}$haloalkoxy$C_1$-$C_{12}$alkyl, $C_1$-$C_{12}$alkylthio$C_1$-$C_{12}$alkyl, $C_1$-$C_{12}$haloalkylthio$C_1$-$C_{12}$alkyl, $C_1$-$C_{12}$alkylamino, $C_1$-$C_{12}$haloalkylamino, $C_2$-$C_{12}$dialkylamino, piperidyl, pyrrolidyl, N-methyl piperazinyl, morpholinyl, $C_2$-$C_{12}$alkenyl, $C_2$-$C_{12}$haloalkenyl, $C_2$-$C_{12}$alkenoxy, $C_2$-$C_{12}$haloalkenoxy, $C_2$-$C_{12}$alkynyl, $C_2$-$C_{12}$haloalkynyl, $C_2$-$C_{12}$alkynoxy, $C_2$-$C_{12}$haloalkynoxy, $C_1$-$C_{12}$alkylsulfinyl, $C_1$-$C_{12}$alkylsulfonyl or $R_8$; n is selected from 0 to 4;

$R_5$ is selected from H, $C_1$-$C_{12}$alkyl, $C_1$-$C_{12}$haloalkyl, $C_1$-$C_{12}$alkoxy$C_1$-$C_{12}$alkyl, $C_3$-$C_6$cycloalkyl, $C_1$-$C_{12}$ cyanoalkyl, $C_1$-$C_{12}$alkylamino, $C_1$-$C_{12}$haloalkylamino, $C_2$-$C_{12}$dialkylamino, $C_2$-$C_{12}$alkenyl, $C_2$-$C_{12}$haloalkenyl, $C_2$-$C_{12}$alkynyl, $C_2$-$C_{12}$haloalkynyl, $C_1$-$C_{12}$alkylsulfonyl, $C_1$-$C_{12}$ haloalkylsulfonyl, $C_1$-$C_{12}$alkylcarbonyl, $C_1$-$C_{12}$haloalkylcarbonyl, $C_1$-$C_{12}$alkoxycarbonyl$C_1$-$C_{12}$alkyl, $C_1$-$C_{12}$alkylcarbonylamino

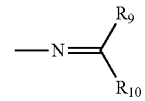

or $R_8$;

$R_6$ is selected from H, CN, SCN, H(C=O), $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$haloalkylthio, $C_1$-$C_{12}$alkylcarbonyl, $C_1$-$C_{12}$alkoxycarbonyl, $C_1$-$C_{12}$alkoxycarbonyl$C_1$-$C_{12}$alkyl, $C_1$-$C_{12}$alkylsulfinyl, $C_1$-$C_{12}$alkylsulfonyl, $C_1$-$C_{12}$cyanoalkyl, $C_1$-$C_{12}$hydroxyalkyl, $C_3$-$C_6$cycloalkyl or $R_8$; p is selected from 0 to 5;

$X_1$ is selected from H, halogen, $NO_2$, CN, SCN, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$alkylsulfinyl, $C_1$-$C_{12}$alkylsulfonyl, $C_1$-$C_{12}$haloalkylsulfinyl, $C_1$-$C_{12}$ haloalkylsulfonyl, $C_1$-$C_{12}$haloalkylthio, $C_1$-$C_{12}$alkoxy$C_1$-$C_{12}$alkyl, $C_1$-$C_{12}$haloalkoxy$C_1$-$C_{12}$alkyl, $C_1$-$C_{12}$alkylthio$C_1$-$C_{12}$alkyl or $C_1$-$C_{12}$haloalkylthio$C_1$-$C_{12}$alkyl;

$X_2$, $X_3$, $X_4$ and $X_5$ may be the same or different, mutually independently selected from H, halogen, CN, $NO_2$, OH, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio or $C_1$-$C_{12}$alkylsulfonyl;

$Q_1$ and $Q_2$ may be the same or different, mutually independently selected from H, $NH_2$, OH, CN, SCN, $C_1$-$C_{12}$cyanoalkyl, $C_1$-$C_{12}$alkyl, $C_1$-$C_{12}$haloalkyl, $C_1$-$C_{12}$alkylcarbonyl, $C_1$-$C_{12}$alkoxy, $C_1$-$C_{12}$haloalkoxy, $C_1$-$C_{12}$alkoxy$C_1$-$C_{12}$alkyl, $C_1$-$C_{12}$alkylsulfinyl, $C_1$-$C_{12}$alkylsulfonyl, $C_1$-$C_{12}$haloalkylsulfinyl, $C_1$-$C_{12}$haloalkylsulfonyl, $C_1$-$C_{12}$alkylamino, $C_2$-$C_{12}$dialkylamino, piperidyl, pyrrolidyl, N-methyl piperazinyl, morpholinyl, H(C=O), $C_1$-$C_{12}$alkylaminocarbonyl, $C_1$-$C_{12}$alkoxycarbonyl, $C_1$-$C_{12}$alkoxycarbonyl$C_1$-$C_{12}$alkyl, $C_1$-$C_{12}$alkylaminothio, $C_2$-$C_{12}$dialkylaminothio, $C_3$-$C_6$cycloalkyl or $R_8$;

Y is selected from O, S or $NR_7$;

Z is selected from O or S;

$R_7$ is selected from H, CN, $NH_2$, OH, $C_1$-$C_{12}$alkyl, $C_1$-$C_{12}$haloalkyl, $C_1$-$C_{12}$alkoxy, $C_1$-$C_{12}$haloalkoxy, $C_3$-$C_6$cycloalkyl, $C_1$-$C_{12}$cyanoalkyl, $C_1$-$C_{12}$cyanoalkoxy, $C_1$-$C_{12}$alkylamino, $C_1$-$C_{12}$haloalkylamino, $C_2$-$C_{12}$dialkylamino, piperidyl, Pyrrolidyl, N-methylpiperazinyl, morpholinyl, 2,6-dimethylmorpholinyl, $C_2$-$C_{12}$alkenyl, $C_2$-$C_{12}$haloalkenyl, $C_2$-$C_{12}$alkenoxy, $C_2$-$C_{12}$haloalkenoxy, $C_2$-$C_{12}$alkynyl, $C_2$-$C_{12}$haloalkynyl, $C_2$-$C_{12}$alkynoxy, $C_2$-$C_{12}$haloalkynoxy, $C_1$-$C_{12}$alkylthio, $C_1$-$C_{12}$haloalkylthio, $C_1$-$C_{12}$alkylsulfonyl, $C_1$-$C_{12}$haloalkylsulfonyl, $C_1$-$C_{12}$alkylcarbonyl, $C_1$-$C_{12}$haloalkylcarbonyl, $C_1$-$C_{12}$alkoxycarbonyl$C_1$-$C_{12}$alkyl, $C_1$-$C_{12}$alkylcarbonylamino,

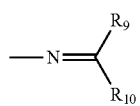

or $R_8$;

Or, when Y is selected from $NR_7$, $NR_7$ and $R_5$ form a unsubstituted or substituted five-membered or six-membered ring with 1-4 substitutents selected independently from $C_1$-$C_4$alkyl, $C_1$-$C_4$haloalkyl, $C_1$-$C_4$alkoxy, $C_1$-$C_4$haloalkoxy or $C_3$-$C_6$cycloalkyl;

$R_8$ is selected from phenyl, benzoyl, phenoxycarbonyl, phenylaminocarbonyl, phenyl$C_1$-$C_6$alkyl, naphthyl, naphthyl$C_1$-$C_6$alkyl, heteroaryl, heteroarylcarbonyl, heteroaryloxycarbonyl, heteroarylaminocarbonyl or heteroaryl$C_1$-$C_6$alkyl, which can be unsubstituted or further substituted with 1-5 substitutents, the substitutent(s) mentioned was (were) selected independently from halogen, $NO_2$, CN, SH, $C_1$-$C_{12}$alkyl, $C_1$-$C_{12}$haloalkyl, $C_3$-$C_{12}$cycloalkyl, $C_1$-$C_{12}$alkoxy, $C_1$-$C_{12}$haloalkoxy, $C_1$-$C_{12}$alkylthio, $C_1$-$C_{12}$haloalkylthio, $C_2$-$C_{12}$alkenyl, $C_2$-$C_{12}$haloalkenyl, $C_2$-$C_{12}$alkynyl, $C_2$-$C_{12}$haloalkynyl, $C_3$-$C_{12}$alkenoxy, $C_3$-$C_{12}$haloalkenoxy, $C_3$-$C_{12}$alkynoxy, $C_3$-$C_{12}$haloalkynoxy, $C_1$-$C_{12}$alkylsulfinyl, $C_1$-$C_{12}$haloalkylsulfinyl, $C_1$-$C_{12}$alkylsulfonyl, $C_1$-$C_{12}$haloalkylsulfonyl, $C_1$-$C_{12}$alkylcarbonyl, $C_1$-$C_{12}$haloalkylcarbonyl, $C_1$-$C_{12}$alkylcarbonyloxy, $C_1$-$C_{12}$alkylcarbonylamino, $C_1$-$C_{12}$alkylsulfonyloxy, $C_1$-$C_{12}$alkoxycarbonyl, $C_1$-$C_{12}$alkoxy$C_1$-$C_{12}$alkoxy, $C_1$-$C_{12}$ alkoxycarbonyl$C_1$-$C_{12}$alkyl, $C_1$-$C_{12}$alkoxycarbonylamino, $C_1$-$C_{12}$alkoxycarbonyl$C_1$-$C_{12}$alkoxy, CHO, $CO_2H$, $CO_2Na$, $CO_2NH_4$, $NR_9R_{10}$, $C(=O)NR_9R_{10}$, $OC(=O)NR_9R_{10}$, $C(=S)NR_9R_{10}$ or $SO_2NR_9R_{10}$;

$R_9$ and $R_{10}$ may be the same or different, mutually independently selected from H, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$haloalkylthio, $C_3$-$C_6$ cycloalkyl or $R_8$;

$(CHR_3)mCON(Q_2)$ links with phenyl ring at the 2, 3 or 4-position.

The preferred compounds of general formula (I) of this invention are:

$R_1$ is selected from H, $C_1$-$C_6$ alkyl, $C_1$-$C_6$haloalkyl, $C_1$-$C_6$cyanoalkyl, $C_1$-$C_6$alkoxy$C_1$-$C_6$alkyl, $C_1$-$C_6$alkylcarbonyl, $C_1$-$C_6$haloalkylcarbonyl, $C_1$-$C_6$alkoxycarbonyl, $C_1$-$C_6$haloalkoxycarbonyl, $C_1$-$C_6$alkylaminocarbonyl, $C_1$-$C_6$haloalkylaminocarbonyl, $C_3$-$C_6$cycloalkyl or $R_8$;

$R_2$ is selected from H, halogen, CN, $C_1$-$C_6$alkyl, $C_1$-$C_6$haloalkyl, $C_1$-$C_6$alkoxy, $C_1$-$C_6$haloalkoxy, $C_1$-$C_6$cyanoalkoxy, $C_1$-$C_6$alkylthio, $C_1$-$C_6$alkoxy$C_1$-$C_6$alkyl, $C_1$-$C_6$haloalkoxy$C_1$-$C_6$alkyl, $C_1$-$C_6$alkylsulfinyl, $C_1$-$C_6$alkylsulfonyl, $C_3$-$C_6$cycloalkyl or $R_8$;

$R_3$ is selected from H or $C_1$-$C_4$alkyl; m is selected from 1 to 3;

$R_4$ is selected from halogen, CN, $CONH_2$, $CSNH_2$, $NO_2$, $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$haloalkylthio, $C_1$-$C_4$alkoxy$C_1$-$C_4$alkyl, $C_1$-$C_4$haloalkoxy$C_1$-$C_4$alkyl, $C_1$-$C_4$alkylthio$C_1$-$C_4$alkyl, $C_1$-$C_4$haloalkylthio$C_1$-$C_4$alkyl, $C_1$-$C_4$alkylamino, $C_1$-$C_4$haloalkylamino, $C_2$-$C_4$dialkylamino, piperidyl, Pyrrolidyl, N-methyl piperazinyl, morpholinyl, $C_2$-$C_4$alkenyl, $C_2$-$C_4$haloalkenyl, $C_2$-$C_4$alkenoxy, $C_2$-$C_4$haloalkenoxy, $C_2$-$C_4$alkynyl, $C_2$-$C_4$haloalkynyl, $C_2$-$C_4$alkynoxy, $C_2$-$C_4$haloalkynoxy, $C_1$-$C_4$alkylsulfinyl, $C_1$-$C_4$alkylsulfonyl or $R_8$; n is selected from 0 to 3;

$R_5$ is selected from H, $C_1$-$C_4$alkyl, $C_1$-$C_4$haloalkyl, $C_1$-$C_4$alkoxy$C_1$-$C_4$alkyl, $C_3$-$C_6$cycloalkyl, $C_1$-$C_4$cyanoalkyl, $C_1$-$C_4$alkylamino, $C_1$-$C_4$haloalkylamino, $C_2$-$C_6$dialkylamino, $C_2$-$C_4$alkenyl, $C_2$-$C_4$haloalkenyl, $C_2$-$C_4$alkynyl, $C_2$-$C_4$haloalkynyl, $C_1$-$C_4$alkylsulfonyl, $C_1$-$C_4$haloalkylsulfonyl, $C_1$-$C_4$alkylcarbonyl, $C_1$-$C_4$haloalkylcarbonyl, $C_1$-$C_4$alkyloxycarbonyl$C_1$-$C_4$alkyl, $C_1$-$C_4$alkylcarbonylamino,

or $R_8$;

$R_6$ is selected from H, CN, SCN, H(C=O), $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$haloalkylthio, $C_1$-$C_4$alkylcarbonyl, $C_1$-$C_4$alkyloxycarbonyl, $C_1$-$C_4$alkylsulfinyl, $C_1$-$C_4$alkylsulfonyl, $C_1$-$C_4$cyanoalkyl, $C_1$-$C_4$hydroxyalkyl, $C_3$-$C_6$cycloalkyl or $R_8$; p is selected from 0 to 4;

$X_1$ is selected from H, halogen, $NO_2$, CN, SCN, $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylsulfinyl, $C_1$-$C_4$haloalkylsulfonyl, $C_1$-$C_4$haloalkylthio, $C_1$-$C_4$alkoxy$C_1$-$C_4$alkyl, $C_1$-$C_4$haloalkoxy$C_1$-$C_4$alkyl, $C_1$-$C_4$alkylthio$C_1$-$C_4$alkyl or $C_1$-$C_4$haloalkylthio$C_1$-$C_4$alkyl;

$X_2$, $X_3$, $X_4$ and $X_5$ may be the same or different, mutually independently selected from H, halogen, CN, $NO_2$, OH, $C_1$-$C_4$alkyl, $C_1$-$C_4$haloalkyl, $C_1$-$C_4$alkoxy, $C_1$-$C_4$haloalkoxy, $C_1$-$C_4$alkylthio or $C_1$-$C_4$alkylsulfonyl;

$Q_1$ and $Q_2$ may be the same or different, mutually independently selected from H, $NH_2$, OH, CN, SCN, $C_1$-$C_4$cyanoalkyl, $C_1$-$C_4$alkyl, $C_1$-$C_4$haloalkyl, $C_1$-$C_4$alkylcarbonyl, $C_1$-$C_4$alkoxy, $C_1$-$C_4$haloalkoxy, $C_1$-$C_4$alkoxy$C_1$-$C_4$alkyl, $C_1$-$C_4$alkylsulfinyl, $C_1$-$C_4$alkylsulfonyl, $C_1$-$C_4$haloalkylsulfonyl, $C_1$-$C_4$haloalkylsulfonyl, $C_1$-$C_4$alkylamino, $C_2$-$C_6$dialkylamino, piperidyl, Pyrrolidyl, N-methylpiperazinyl, morpholinyl, H(C=O), $C_1$-$C_4$alkylaminocarbonyl, $C_1$-$C_4$alkoxycarbonyl, $C_1$-$C_4$alkylaminothio, $C_2$-$C_4$dialkylaminothio, $C_3$-$C_6$cycloalkyl or $R_8$;

Y is selected from O, S or $NR_7$;

Z is O;

$R_7$ is selected from H, CN, $NH_2$, OH, $C_1$-$C_4$alkyl, $C_1$-$C_4$haloalkyl, $C_1$-$C_4$alkoxy, $C_1$-$C_4$haloalkoxy, $C_3$-$C_6$cycloalkyl, $C_1$-$C_4$cyanoalkyl, $C_1$-$C_4$cyanoalkoxy, $C_1$-$C_4$alkylamino, $C_1$-$C_4$haloalkylamino, $C_2$-$C_4$dialkylamino, piperidyl, pyrrolidyl, N-methylpiperazinyl, morpholinyl, 2,6-dimethylmorpholinyl, $C_2$-$C_4$alkenyl, $C_2$-$C_4$haloalkenyl, $C_2$-$C_4$alkenoxy, $C_2$-$C_4$haloalkenoxy, $C_2$-$C_4$alkynyl, $C_2$-$C_4$haloalkynyl, $C_2$-$C_4$alkynoxy, $C_2$-$C_4$haloalkynoxy, $C_1$-$C_4$alkylthio, $C_1$-$C_4$haloalkylthio, $C_1$-$C_4$alkylsulfonyl, $C_1$-$C_4$haloalkylsulfonyl, $C_1$-$C_4$alkylcarbonyl, $C_1$-$C_4$haloalkylcarbonyl, $C_1$-$C_4$alkoxycarbonyl$C_1$-$C_4$alkyl, $C_1$-$C_4$alkylcarbonylamino,

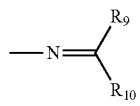

or $R_8$;

Or, when Y is selected from $NR_7$, $NR_7$ and $R_5$ form a unsubstituted or substituted five-membered or six-membered ring with 1-2 substitutents selected independently from $C_1$-$C_3$alkyl;

$R_8$ is selected from phenyl, benzoyl, phenoxycarbonyl, phenylaminocarbonyl, benzyl, phenethyl, naphthyl, pyridyl, picolyl, pyridylethyl, pyrimidyl, pyridazinyl, pyrazinyl, cyanuro, unsym-triazinyl, furanyl, thienyl, pyrrolyl, thiazolyl, pyrazolyl, imidazolyl, oxazolyl, isoxazolyl, thiadiazolyl, oxadizolyl, benzofuryl, benzothiophenyl, benzothiazolyl, benzoxazolyl, benzoxazolylmethyl, benzopyranyl, benzopyronyl, benzopyridazinyl, indolyl, quinolyl, quinoxalinyl, triazolopyrimidinyl, imidazopyridinyl, imidazothiazolyl, purinyl, pyridylformoxyl, pyrimidinylformoxyl, pyridyloxycarbonyl, pyrimidinyloxycarbonyl, pyridylaminocarbonyl, pyrimidinylaminocarbonyl or thiazolylmethyl, which can be unsubstituted or further substituted with 1-3 substitutents, the substituent(s) mentioned was (were) selected independently from halogen, $NO_2$, CN, SH, $C_1$-$C_4$alkyl, $C_1$-$C_4$haloalkyl, $C_3$-$C_6$cycloalkyl, $C_1$-$C_4$alkoxy, $C_1$-$C_4$haloalkoxy, $C_1$-$C_4$alkylthio, $C_1$-$C_4$haloalkylthio, $C_2$-$C_4$alkenyl, $C_2$-$C_4$haloalkenyl, $C_2$-$C_4$alkynyl, $C_2$-$C_4$haloalkynyl, $C_3$-$C_6$alkenoxy, $C_3$-$C_6$haloalkenoxy, $C_3$-$C_6$alkynoxy, $C_3$-$C_6$haloalkynoxy, $C_1$-$C_4$alkylsulfinyl, $C_1$-$C_4$haloalkylsulfinyl, $C_1$-$C_4$alkylsulfonyl, $C_1$-$C_4$haloalkylsulfonyl, $C_1$-$C_4$alkylcarbonyl, $C_1$-$C_4$haloalkylcarbonyl, $C_1$-$C_4$alkylcarbonyloxy, $C_1$-$C_4$alkylcarbonylamino, $C_1$-$C_4$alkylsulfonyloxy, $C_1$-$C_4$alkoxycarbonyl, $C_1$-$C_4$alkoxy$C_1$-$C_4$alkoxy, $C_1$-$C_4$alkoxycarbonyl$C_1$-$C_4$alkyl, $C_1$-$C_4$alkoxycarbonylamino, $C_1$-$C_4$alkoxycarbonyl$C_1$-$C_4$alkoxy, CHO, $CO_2H$, $CO_2Na$, $CO_2NH_4$, $NR_9R_{10}$, $C(=O)NR_9R_{10}$, $OC(=O)NR_9R_{10}$, $C(=S)NR_9R_{10}$ or $SO_2NR_9R_{10}$;

$R_9$ and $R_{10}$ may be the same or different, mutually independently selected from H, $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$haloalkylthio, $C_3$-$C_6$cycloalkyl or $R_8$;

$(CHR_3)_mCON(Q_2)$ links with phenyl ring at the 2, 3 or 4-position.

Further more, the preferred compounds of general formula (I) of this invention are:

$R_1$ is selected from H, $C_1$-$C_4$alkyl, $C_1$-$C_4$haloalkyl, $C_1$-$C_4$alkoxy$C_1$-$C_4$alkyl, $C_3$-$C_6$cycloalkyl or R;

$R_2$ is selected from H, chloride, bromine, fluorine, iodine, CN, $C_1$-$C_4$alkyl, $C_1$-$C_4$haloalkyl, $C_1$-$C_4$alkoxy, $C_1$-$C_4$haloalkoxy, $C_1$-$C_4$cyanoalkoxy, $C_1$-$C_4$alkoxy$C_1$-$C_4$alkyl, $C_1$-$C_4$haloalkoxy$C_1$-$C_4$alkyl, $C_3$-$C_6$cycloalkyl or $R_8$;

$R_3$ is selected from H, methyl or ethyl; m is selected from 1, 2 or 3;

$R_4$ is selected from fluorine, chloride, bromine, iodine, CN, $NO_2$, $C_1$-$C_3$alkyl, $C_1$-$C_3$haloalkyl, $C_1$-$C_3$alkoxy, $C_1$-$C_3$haloalkoxy, $C_1$-$C_3$alkylamino, $C_2$-$C_4$dialkylamino or $C_1$-$C_3$alkylsulfonyl; n is selected from 0, 1, 2 or 3;

$R_5$ is selected from H, $C_1$-$C_4$alkyl, $C_1$-$C_4$haloalkyl, $C_1$-$C_4$alkoxy$C_1$-$C_3$alkyl, $C_3$-$C_6$cycloalkyl, $C_1$-$C_4$cyanoalkyl, $C_1$-$C_4$alkylamino, $C_2$-$C_6$dialkylamino, $C_3$-$C_4$alkenyl, $C_3$-$C_4$alkynyl or $R_8$;

$R_6$ is selected from H, CN, SCN, $C_1$-$C_3$alkyl, $C_1$-$C_3$haloalkyl, $C_1$-$C_3$alkoxy, $C_1$-$C_3$alkylthio or $C_1$-$C_3$hydroxyalkyl; p is selected from 0, 1, 2 or 3;

$X_1$ is selected from H, fluorine, chloride, bromine, iodine, $NO_2$, CN, SCN, $C_1$-$C_3$alkyl or $C_1$-$C_3$haloalkyl;

$X_2$, $X_3$, $X_4$ and $X_5$ may be the same or different, mutually independently selected from H, fluorine, chloride, bromine, iodine, CN, $NO_2$, OH, $C_1$-$C_3$alkyl, $C_1$-$C_3$haloalkyl, $C_1$-$C_3$alkoxy or $C_1$-$C_3$haloalkoxy;

$Q_1$ and $Q_2$ may be the same or different, mutually independently selected from H, CN, SCN, $C_1$-$C_3$alkyl, $C_1$-$C_3$alkylcarbonyl, $C_1$-$C_3$alkoxy$C_1$-$C_2$alkyl or H(C=O);

Y is selected from O or $NR_7$;

Z is O;

$R_7$ is selected from H, CN, $NH_2$, OH, $C_1$-$C_4$alkyl, $C_1$-$C_4$haloalkyl, $C_1$-$C_4$alkoxy, $C_1$-$C_4$haloalkoxy, $C_3$-$C_6$cycloalkyl, $C_1$-$C_3$cyanoalkyl, $C_1$-$C_3$cyanoalkoxy, $C_1$-$C_3$alkylamino, $C_1$-$C_3$haloalkylamino, $C_2$-$C_4$dialkylamino, piperidyl, pyrrolidyl, N-methylpiperazinyl, morpholinyl, 2,6-dimethylmorpholinyl, $C_3$-$C_4$alkenyl, $C_3$-$C_4$haloalkenyl, $C_3$-$C_4$alkenoxy, $C_3$-$C_4$haloalkenoxy, $C_3$-$C_4$alkynyl, $C_3$-$C_4$haloalkynyl, $C_3$-$C_4$alkynoxy, $C_3$-$C_4$haloalkynoxy, $C_1$-$C_3$alkylsulfonyl, $C_1$-$C_3$haloalkylsulfonyl or R;

Or, when Y is selected from $NR_7$, $NR_7$ and $R_5$ form piperidine, tetrahydropyrrole, N-methylpiperazine, morpholine or 2,6-dimethylmorpholine;

R is selected from phenyl, 4-chlorophenyl, 2,4-dichlorophenyl, 4-methylphenyl, 4-trifluoromethylphenyl, 4-methoxyphenyl, 2,6-dichloro-4-trifluoromethylphenyl, benzoyl, 4-chlorobenzoyl, 2,4-dichlorobenzoyl, 4-trifluoromethylbenzoyl, phenoxycarbonyl, 4-chlorophenoxycarbonyl, 2,4-dichlorophenoxycarbonyl, 4-trifluoromethylphenoxycarbonyl, phenylaminocarbonyl, 4-chlorophenylaminocarbonyl, 2,4-dichlorophenylaminocarbonyl, 4-trifluoromethyphenylaminocarbonyl, benzyl, 4-chlorobenzyl, 4-tert-butylbenzyl, 4-trifluoromethylbenzyl, phenethyl, 2-pyridyl, 3-chloro-2-pyridyl, 3,5-dichloro-2-pyridyl, 3,5,6-trichloro-2-pyridyl, 5-trifluoromethyl-2-pyridyl, 5-methyl-2-pyridyl, 3-chloro-5-cyano-2-pyridyl, 3-chloro-5-trifluoromethyl-2-pyridyl, 2-picolyl, 2-chloro-5-picolyl, 3-chloro-5-trifluoro-2-picolyl, 2-pyridinylethyl, 3-chloro-5-trifluoromethyl-2-pyridinylethyl, 2-pyrimidinyl, 4-pyrimidinyl, 5-pyrimidinyl, thiazole-2-yl, 2-chloro-5-thiazolylmethyl, 3-pyridylformoxyl, 2-chloro-3-pyridylformoxyl, 2-chloro-5-pyridylformoxyl, 2-pyrimidinylformoxyl, 5-trifluoromethyl-2-pyrimidinylformoxyl, 2-pyridyloxycarbonyl, 3-chloro-2-pyridyloxycarbonyl, 3,5-dichloro-2-pyridyloxycarbonyl, 5-trifluoromethyl-2-pyridyloxycarbonyl, 5-methyl-2-pyridyloxycarbonyl, 3-chloro-5-cyano-2-pyridyloxycarbonyl, 3-chloro-5-trifluoromethyl-2-pyridyloxycarbonyl, 2-pyrimidinyloxycarbonyl, 5-trifluoromethyl-2-pyrimidinyloxycarbonyl, 2-pyridylaminocarbonyl, 3-chloro-2-pyridylaminocarbonyl or 2-pyrimidinylaminocarbonyl;

($CHR_3$)mCON($Q_2$) links with phenyl ring at the 2, 3 or 4-position.

Even more preferred compounds of formula (I) of this invention are:

$R_1$ is selected from H, methyl, ethyl, n-propyl, isopropyl, n-butyl, s-butyl, isobutyl, t-butyl, trifluoromethyl, trifluoroethyl, methoxymethyl, ethoxymethyl, cyclopropyl, cyclobutyl, cyclopentyl, cyclohexyl or $R_8$;

$R_2$ is selected from H, chloride, bromine, fluorine, CN, methyl, ethyl, n-propyl, i-propyl, n-butyl, s-butyl, i-butyl, t-butyl, trifluoromethyl, difluoromethyl, fluoromethyl, trifluoromethoxyl, trifluoroethoxyl, fluoromethoxyl, cyanomethoxyl, methoxymethyl, trifluoromethoxymethyl, trifluoroethoxymethyl, cyclopropyl, cyclobutyl, cyclopentyl, cyclohexyl or $R_8$;

$R_3$ is selected from H or methyl; m is 1;

$R_4$ is selected from fluorine, chloride, bromine, iodine, CN, methyl, ethyl, trifluoromethyl, methoxyl, trifluoromethoxyl or methylsulfonyl; n is selected from 0, 1, 2 or 3;

$R_5$ is selected from H, methyl, ethyl, n-propyl, i-propyl, n-butyl, i-butyl, t-butyl, trifluoromethyl, trifluoroethyl, cyclopropyl, cyclohexyl, cyanomethyl, allyl, propargyl or $R_8$;

$R_6$ is selected from H, CN, SCN, methyl or ethyl; p is selected from 0, 1, 2 or 3;

$X_1$ is selected from H, fluorine, chloride, bromine, iodine, $NO_2$, methyl or chloromethyl;

$X_2$, $X_3$, $X_4$ and $X_5$ may be the same or different, mutually independently selected from H, chloride, bromine or methoxyl;

$Q_1$ and $Q_2$ are H;

Y is selected from O or $NR_7$;

Z is O;

$R_7$ is selected from H, CN, $NH_2$, OH, methyl, ethyl, cyclopropyl, cyclopentyl, cyclohexyl, cyanomethyl, methylamino, dimethylamino, methylsulfonyl or $R_8$;

Or, when Y is selected from $NR_7$, $NR_7$ and $R_5$ form piperidine, tetrahydropyrrole, N-methylpiperazine, morpholine or 2,6-dimethylmorpholine;

$R_8$ is selected from phenyl, 4-chlorophenyl, 2,4-dichlorophenyl, 4-methylphenyl, 4-trifluoromethylphenyl, 4-methoxylphenyl, 2,6-dichloro-4-trifluoromethylphenyl, benzyl, 4-chlorobenzyl, 4-tert-butylbenzyl, 4-trifluoromethylbenzyl, phenethyl, 2-pyridyl, 3-chloro-2-pyridyl, 3,5-dichloro-2-pyridyl, 3,5,6-trichloro-2-pyridyl, 5-trifluoromethyl-2-pyridyl, 5-methyl-2-pyridyl, 3-chloro-5-cyano-2-pyridyl, 3-chloro-5-trifluoromethyl-2-pyridyl, 2-picolyl, 2-chloro-5-picolyl, 3-chloro-5-trifluoromethyl-2-picolyl, 2-pyridinylethyl, 3-chloro-5-trifluoromethyl-2-pyridinylethyl, thiazole-2-yl, 2-chloro-5-thiazolylmethyl or 2-pyrimidinyl;

($CHR_3$)mCON($Q_2$) links with phenyl ring at the 2, 3 or 4-position.

Most preferred compounds of formula (I) of this invention are:

$R_1$ is selected from H, methyl, ethyl or 3-chloro-2-pyridyl;

$R_2$ is selected from bromine, methyl, ethyl, n-propyl, i-propyl, n-butyl, i-butyl, t-butyl, trifluoromethyl, cyclopropyl or 4-chlorophenyl;

$R_3$ is selected from H or methyl; m is 1;

$R_4$ is selected from fluorine, chloride, bromine, iodine, CN or methyl; n is selected from 0, 1 or 2;

$R_6$ is selected from H or methyl; p is selected from 0, 1, 2 or 3;

$X_1$ is selected from H, chloride or methyl;

$X_2$, $X_3$, $X_4$, $X_5$, $Q_1$, $Q_2$ are H;

Z is O;

$YR_5$ is selected from amino, methylamino, ethylamino, dimethylamino, methoxyl, ethoxyl or morpholinyl;

($CHR_3$)mCON($Q_2$) links with phenyl ring at the 2, 3 or 4-position.

In the compounds having the general formula (I) of the invention, due to chiral carbon or nitrogen connecting to different groups or substituents, which results in forming the stereoisomers (R and S respectively represents different configurations). Therefore, the compounds of the invention consist of R isomers, S isomers or any proportion of the mixture.

The following is the meaning of terms in the general formula (I):

Halogen or halo is fluorine, chlorine, bromine or iodine.

The "alkyl" stands for straight-chain or branched alkyl, such as methyl, ethyl, propyl, isopropyl, n-butyl or tert-butyl.

The "cycloalkyl" is substituted or unsubstituted cyclic alkyl, such as cyclopropyl, cyclopentyl or cyclohexyl. The substitute(s) is(are) methyl, halogen etc.

The "haloalkyl" stands for straight or branched chain alkyl, in which hydrogen atoms can be all or partly substituted with halogen, such as chloromethyl, dichloromethyl, trichloromethyl, fluoromethyl, difluoromethyl, trifluoromethyl etc.

The "cyanoalkyl" stands for straight or branched chain alkyl, in which hydrogen atoms can be all or partly substituted with cyano, such as $-CH_2CN$, $-CH_2CH_2CN$, $-CH_2C(CH_3)_2CN$, $-CH_2CH(CN)_2$ etc.

The "alkoxy" refers to straight or branched chain alkyl, which is linked to the structure by oxygen atom.

The "cyanoalkoxyl" refers to straight or branched chain cyanoalkyl, which is linked to the structure by oxygen atom, such as $CNCH_2OO-$.

The "alkoxyalkyl" refers to straight or branched chain alkoxyl, which is linked to the structure by alkyl, such as $CH_3OCH_2-$, $CH_3CH_2OCH_2-$.

The "haloalkoxyalkyl" refers to the alkyl of alkoxyalkyl, in which hydrogen atoms can be all or partly substituted with halogen, such as $ClCH_2CH_2OCH_2-$.

The "alkoxycarbonyl" means alkoxyl is linked to the structure by carbonyl. such as $CH_3OCO-$, $CH_3CH_2OCO-$.

The "alkoxycarbonylalkyl" means alkoxycarbonyl is linked to the structure by alkyl.

The "haloalkoxycarbonyl" stands for alkoxy of alkoxycarbonyl, in which hydrogen atoms can be all or partly substituted with halogen, such as $ClCH_2CH_2OCO-$.

The "haloalkoxy" refers to straight or branched chain alkoxy, in which hydrogen atoms may be all or partly substituted with halogen, such as chloromethoxy, dichloromethoxy, trichloromethoxy, fluoromethoxy, difluoromethoxy, trifluoromethoxy, chlorofluoromethoxy, trifluoroethoxy etc.

The "alkylthio" refers to straight or branched chain alkyl, which is linked to the structure by sulfur atom.

The "alkylthioalkyl" refers to straight or branched chain alkylthio, which is linked to the structure by alkyl. such as $CH_3SCH_2-$.

The "haloalkylthio" refers to straight or branched chain alkylthio, in which hydrogen atoms may be all or partly substituted with halogen, such as chloromethylthio, dichloromethylthio, trichloromethylthio, fluoromethylthio, difluoromethylthio, trifluoromethylthio, chlorofluoromethylthio etc.

The "haloalkylthioalkyl" means haloalkylthio is linked to the structure by alkyl.

The "alkylamino" means straight or branched chain alkyl is linked to the structure by Nitrogen atoms.

The "alkylaminothio", such as CH₃NHS—, CH₃CH₂NHS—. The "alkylaminocarbonyl", such as CH₃NHCO—, CH₃CH₂NHCO—.

The "haloalkylaminocarbonyl" refers to alkyl of alkylaminocarbonyl, in which hydrogen atoms may be all or partly substituted with halogen, such as CF₃NHCO—.

The "haloalkylamino" refers to straight or branched chain alkylamino, in which hydrogen atoms of alkyl may be all or partly substituted with halogen.

The "alkenyl" stands for a straight-chain or branched alkenes, such as vinyl, 1-propylene, 2-propylene or different butenyl, pentenyl or hexenyl isomers. Alkenyl also includes polyene, such as 1,2-propylene alkenyl and 2,4-the adipic alkenyl.

The "haloalkenyl" refers to a straight-chain or branched alkenes, in which hydrogen atoms may be all or partly substituted with halogen.

The "alkynyl" stands for a straight-chain or branched alkynes, such as acetenyl, 1-propargyl, 2-propargyl and different butynyl, pentynyl or hexynyl isomers. Alkynyl also includes group composed of many triple bonds, such as 2,5-hexadiynyl.

The "haloalkynyl" stands for a straight-chain or branched alkynes, in which hydrogen atoms may be all or partly substituted with halogen.

The "alkenoxyl" means straight or branched chain alkynes is linked to the structure by oxygen.

The "haloalkenoxyl" stands for a straight-chain or branched alkenoxyl, in which hydrogen atoms may be all or partly substituted with halogen.

The "alkynoxyl" means straight or branched chain alkynes is linked to the structure by oxygen.

The "haloalkynoxyl" stands for a straight-chain or branched alkynoxyl, in which hydrogen atoms may be all or partly substituted with halogen.

The "alkylcarbonyl" means alkyl is linked to the structure by carbonyl. such as CH₃CO—, CH₃CH₂CO—.

The "haloalkylcarbonyl" stands for a straight-chain or branched alkylcarbonyl, in which hydrogen atoms may be all or partly substituted with halogen, such as CF₃CO—.

The "alkylsulfinyl" means a straight-chain or branched alkyl is linked to the structure by (—SO—), such as methylsulfinyl.

The "haloalkylsulfinyl" stands for a straight-chain or branched alkylsulfinyl, in which hydrogen atoms may be all or partly substituted with halogen.

The "alkylsulfonyl" means a straight-chain or branched alkyl is linked to the structure by (—SO₂—), such as methylsulfonyl.

The "haloalkylsulfonyl" stands for a straight-chain or branched alkylsulfonyl, in which hydrogen atoms may be all or partly substituted with halogen.

The "phenoxycarbonyl" means phenoxy is linked to the structure by carbonyl, such as PhOCO—.

The "phenylaminocarbonyl" means phenylamino is linked to the structure by carbonyl, such as PhNHCO—.

The "phenylalkyl" means to phenyl is linked to the structure by alkyl, such as benzyl, phenethyl etc.

The "naphthylalkyl" means naphthyl is linked to the structure by alkyl, such as naphthalenemethyl, naphthaleneethyl etc.

The "heteroaryl" of the present invention refer to five-membered ring or six-membered ring containing 1 or more N, O, S heteroatoms, such as pyridyl, pyrimidyl, pyrazinyl, pyridazinyl, triazinyl, furyl, thiazolyl, quinolyl, isothiazolyl, oxazolyl, isoxazolyl, oxadiazolyl, thiadiazolyl, pyrazolyl, pyranyl, triazolyl, tetrazyl, benzothiazolyl, benzofuryl etc.

The "heteroarylcarbonyl" means heteroaryl is linked to the structure by carbonyl, such as pyridineformoxyl, pyrimidineformoxyl, pyrazolformoxyl. The "heteroaryloxycarbonyl" means heteroaryloxy is linked to the structure by carbonyl. The "heteroarylaminocarbonyl" means heteroarylamino is linked to the structure by carbonyl. The "heteroarylalkyl" means heteroaryl is linked to the structure by alkyl, such as furfuryl, pyridylethyl etc.

Detailed descriptions of the invention also provides a novel intermediate or its salt used to prepare the compounds of the general formula (I), their structures represented by the general formula (II):

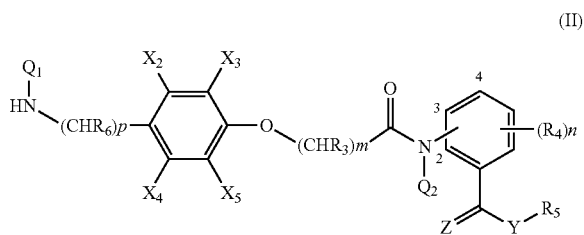

(II)

Wherein:

$R_3$ is selected from H or $C_1$-$C_{12}$alkyl; m is selected from 0 to 5;

$R_4$ is selected from halogen, CN, CONH₂, CSNH₂, NO₂, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$haloalkylthio, $C_1$-$C_{12}$alkoxy$C_1$-$C_{12}$alkyl, $C_1$-$C_{12}$haloalkoxy$C_1$-$C_{12}$alkyl, $C_1$-$C_{12}$alkylthio$C_1$-$C_{12}$alkyl, $C_1$-$C_{12}$haloalkylthio$C_1$-$C_{12}$alkyl, $C_1$-$C_{12}$alkylamino, $C_1$-$C_{12}$haloalkylamino, $C_2$-$C_{12}$dialkylamino, piperidyl, pyrrolidyl, N-methyl piperazinyl, morpholinyl, $C_2$-$C_{12}$alkenyl, $C_2$-$C_{12}$haloalkenyl, $C_2$-$C_{12}$alkenoxy, $C_2$-$C_{12}$haloalkenoxy, $C_2$-$C_{12}$alkynyl, $C_2$-$C_{12}$haloalkynyl, $C_2$-$C_{12}$alkynoxy, $C_2$-$C_{12}$haloalkynoxy, $C_1$-$C_{12}$alkylsulfinyl, $C_1$-$C_{12}$alkylsulfonyl or $R_8$; n is selected from 0 to 4;

$R_5$ is selected from H, $C_1$-$C_{12}$alkyl, $C_1$-$C_{12}$haloalkyl, $C_1$-$C_{12}$alkoxy$C_1$-$C_{12}$alkyl, $C_3$-$C_6$cycloalkyl, $C_1$-$C_{12}$cyanoalkyl, $C_1$-$C_{12}$alkylamino, $C_1$-$C_{12}$haloalkylamino, $C_2$-$C_{12}$dialkylamino, $C_2$-$C_{12}$alkenyl, $C_2$-$C_{12}$haloalkenyl, $C_2$-$C_{12}$alkynyl, $C_2$-$C_{12}$haloalkynyl, $C_1$-$C_{12}$alkylsulfonyl, $C_1$-$C_{12}$haloalkylsulfonyl, $C_1$-$C_{12}$alkylcarbonyl, $C_1$-$C_{12}$haloalkylcarbonyl, $C_1$-$C_{12}$alkoxycarbonyl$C_1$-$C_{12}$alkyl, $C_1$-$C_{12}$alkylcarbonylamino,

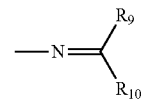

or $R_8$;

$R_6$ is selected from H, CN, SCN, H(C=O), $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$haloalkylthio, $C_1$-$C_{12}$alkylcarbonyl, $C_1$-$C_{12}$alkoxycarbonyl, $C_1$-$C_{12}$alkoxycarbonyl$C_1$-$C_{12}$alkyl, $C_1$-$C_{12}$alkylsulfinyl, $C_1$-$C_{12}$alkylsulfonyl, $C_1$-$C_{12}$cyanoalkyl, $C_1$-$C_{12}$hydroxyalkyl, $C_3$-$C_6$cycloalkyl or $R_8$; p is selected from 0 to 5;

$X_2$, $X_3$, $X_4$ and $X_5$ may be the same or different, mutually independently selected from H, halogen, CN, NO₂, OH, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio or $C_1$-$C_{12}$alkylsulfonyl;

$Q_1$ and $Q_2$ may be the same or different, mutually independently selected from H, $NH_2$, OH, CN, SCN, $C_1$-$C_{12}$cyanoalkyl, $C_1$-$C_{12}$alkyl, $C_1$-$C_{12}$haloalkyl, $C_1$-$C_{12}$alkylcarbonyl, $C_1$-$C_{12}$alkoxy, $C_1$-$C_{12}$haloalkoxy, $C_1$-$C_{12}$alkoxy$C_1$-$C_{12}$alkyl, $C_1$-$C_{12}$alkylsulfinyl, $C_1$-$C_{12}$alkylsulfonyl, $C_1$-$C_{12}$haloalkylsulfinyl, $C_1$-$C_{12}$haloalkylsulfonyl, $C_1$-$C_{12}$alkylamino, $C_2$-$C_{12}$dialkylamino, piperidyl, pyrrolidyl, N-methyl piperazinyl, morpholinyl, H(C=O), $C_1$-$C_{12}$alkylaminocarbonyl, $C_1$-$C_{12}$alkoxycarbonyl, $C_1$-$C_{12}$alkoxycarbonyl$C_1$-$C_{12}$alkyl, $C_1$-$C_2$alkylaminothio, $C_2$-$C_{12}$dialkylaminothio, $C_3$-$C_6$cycloalkyl or $R_8$;

Y is selected from O, S or $NR_7$;

Z is selected from O or S;

$R_7$ is selected from H, CN, $NH_2$, OH, $C_1$-$C_{12}$alkyl, $C_1$-$C_{12}$haloalkyl, $C_1$-$C_{12}$alkoxy, $C_1$-$C_{12}$haloalkoxy, $C_3$-$C_6$cycloalkyl, $C_1$-$C_{12}$cyanoalkyl, $C_1$-$C_{12}$cyanoalkoxy, $C_1$-$C_{12}$alkylamino, $C_1$-$C_{12}$haloalkylamino, $C_2$-$C_{12}$dialkylamino, piperidyl, Pyrrolidyl, N-methylpiperazinyl, morpholinyl, 2,6-dimethylmorpholinyl, $C_2$-$C_{12}$alkenyl, $C_2$-$C_{12}$haloalkenyl, $C_2$-$C_{12}$alkenoxy, $C_2$-$C_{12}$haloalkenoxy, $C_2$-$C_{12}$alkynyl, $C_2$-$C_{12}$haloalkynyl, $C_2$-$C_{12}$alkynoxy, $C_2$-$C_{12}$haloalkynoxy, $C_1$-$C_{12}$alkylthio, $C_1$-$C_{12}$haloalkylthio, $C_1$-$C_{12}$alkylsulfonyl, $C_1$-$C_{12}$haloalkylsulfonyl, $C_1$-$C_{12}$alkylcarbonyl, $C_1$-$C_{12}$haloalkylcarbonyl, $C_1$-$C_{12}$alkoxycarbonyl$C_1$-$C_{12}$alkyl, $C_1$-$C_{12}$alkylcarbonylamino,

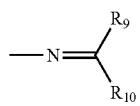

or $R_8$;

Or, when Y is selected from $NR_7$, $NR_7$ and $R_5$ form a unsubstituted or substituted five-membered or six-membered ring with 1-4 substitutents selected independently from $C_1$-$C_4$alkyl, $C_1$-$C_4$haloalkyl, $C_1$-$C_4$alkoxy, $C_1$-$C_4$haloalkoxy or $C_3$-$C_6$cycloalkyl;

$R_8$ is selected from phenyl, benzoyl, phenoxycarbonyl, phenylaminocarbonyl, phenyl$C_1$-$C_6$alkyl, naphthyl, naphthyl$C_1$-$C_6$alkyl, heteroaryl, heteroarylcarbonyl, heteroaryloxycarbonyl, heteroarylaminocarbonyl or heteroaryl$C_1$-$C_6$alkyl, which can be unsubstituted or further substituted with 1-5 substitutents, the substitutent(s) mentioned was (were) selected independently from halogen, $NO_2$, CN, SH, $C_1$-$C_{12}$alkyl, $C_1$-$C_{12}$haloalkyl, $C_3$-$C_{12}$cycloalkyl, $C_1$-$C_{12}$alkoxy, $C_1$-$C_{12}$haloalkoxy, $C_1$-$C_{12}$alkylthio, $C_1$-$C_{12}$haloalkylthio, $C_2$-$C_{12}$alkenyl, $C_2$-$C_{12}$haloalkenyl, $C_2$-$C_{12}$alkynyl, $C_2$-$C_{12}$haloalkynyl, $C_3$-$C_{12}$alkenoxy, $C_3$-$C_{12}$haloalkenoxy, $C_3$-$C_{12}$alkynoxy, $C_3$-$C_{12}$haloalkynoxy, $C_1$-$C_{12}$alkylsulfinyl, $C_1$-$C_{12}$haloalkylsulfinyl, $C_1$-$C_{12}$alkylsulfonyl, $C_1$-$C_{12}$haloalkylsulfonyl, $C_1$-$C_{12}$alkylcarbonyl, $C_1$-$C_{12}$haloalkylcarbonyl, $C_1$-$C_{12}$alkylcarbonyloxy, $C_1$-$C_{12}$alkylcarbonylamino, $C_1$-$C_2$alkylsulfonyloxy, $C_1$-$C_{12}$alkoxycarbonyl, $C_1$-$C_{12}$alkoxy$C_1$-$C_{12}$alkoxy, $C_1$-$C_{12}$ alkoxycarbonyl$C_1$-$C_{12}$alkyl, $C_1$-$C_{12}$alkoxycarbonylamino, $C_1$-$C_{12}$alkoxycarbonyl$C_1$-$C_2$alkoxy, CHO, $CO_2H$, $CO_2Na$, $CO_2NH_4$, $NR_9R_{10}$, C(=O)$NR_9R_{10}$, OC(=O)$NR_9R_{10}$, C(=S)$NR_9R_{10}$ or $SO_2NR_9R_{10}$;

$R_9$ and $R_{10}$ may be the same or different, mutually independently selected from H, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$haloalkylthio, $C_3$-$C_6$ cycloalkyl or $R_8$;

($CHR_3$)mCON($Q_2$) links with phenyl ring at the 2, 3 or 4-position.

The acid that reacts with the amines of formula (II) to give the salts includes carboxylic acid, such as acetic acid, propionic acid, butyric acid, oxalic acid, adipic acid, dodecanedioic acid, lauric acid, stearic acid, trifluoroacetic acid, fumaric acid, maleic acid, benzoic acid or phthalic acid; sulfoacid such as methanesulfonic acid, 1,3-propanedisulfonic acid, p-toluenesulfonic acid or dodecylbenzenesulfonic acid; and inorganic acid, such as hydrochloric acid, sulfuric acid, nitric acid or carbonic acid, etc.

The compounds having general formula (I) of the invention can be prepared according to the following two schemes:

Scheme 1:

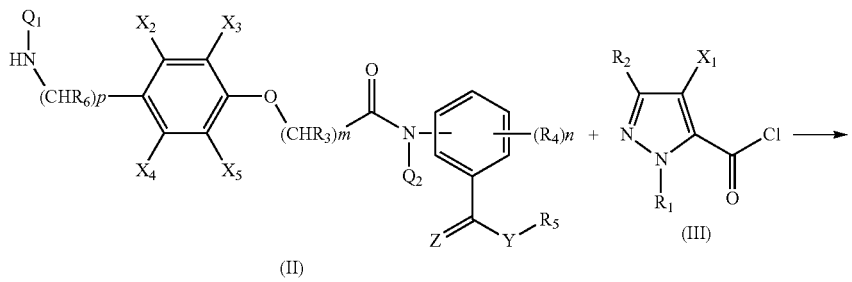

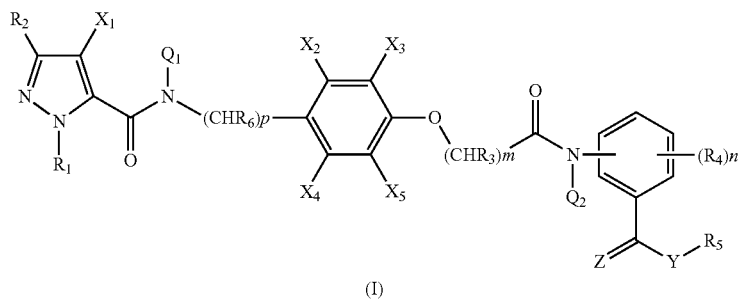

The compounds represented by general formula (I) were prepared by condensation reaction of intermediate amine compounds represented by general formula (II) with pyrazole carbonyl chloride represented by general formula (III) in proper solvents. The solvents mentioned may be selected from benzene, toluene, xylene, acetone, butanone, methyl-isobutylketone, tetrahydrofuran, acetonitrile, dioxane, N,N-Dimethylformamide, N-methyl-2-pyrrolidone, dimethylsulfoxide, pyridine, methylene chloride, chloroform, dichloroethane, methyl acetate or ethyl acetate, etc.

The reaction above can be carried out in the presence or absence of base, the reaction is promoted in the presence of base. Proper base mentioned may be selected from alkali metal hydride such as sodium hydride; alkali metal hydroxides such as sodium hydroxide or potassium hydroxide; alkali metal carbonate such as sodium carbonate or potassium carbonate; organic amine such as pyridine or triethylamine.

The proper temperature mentioned is from room temperature to boiling point of the solvent, normal temperature is from 20 to 100° C.

The reaction time is in the range of 30 minutes to 20 hours, generally being 1-10 hours.

Scheme 2:

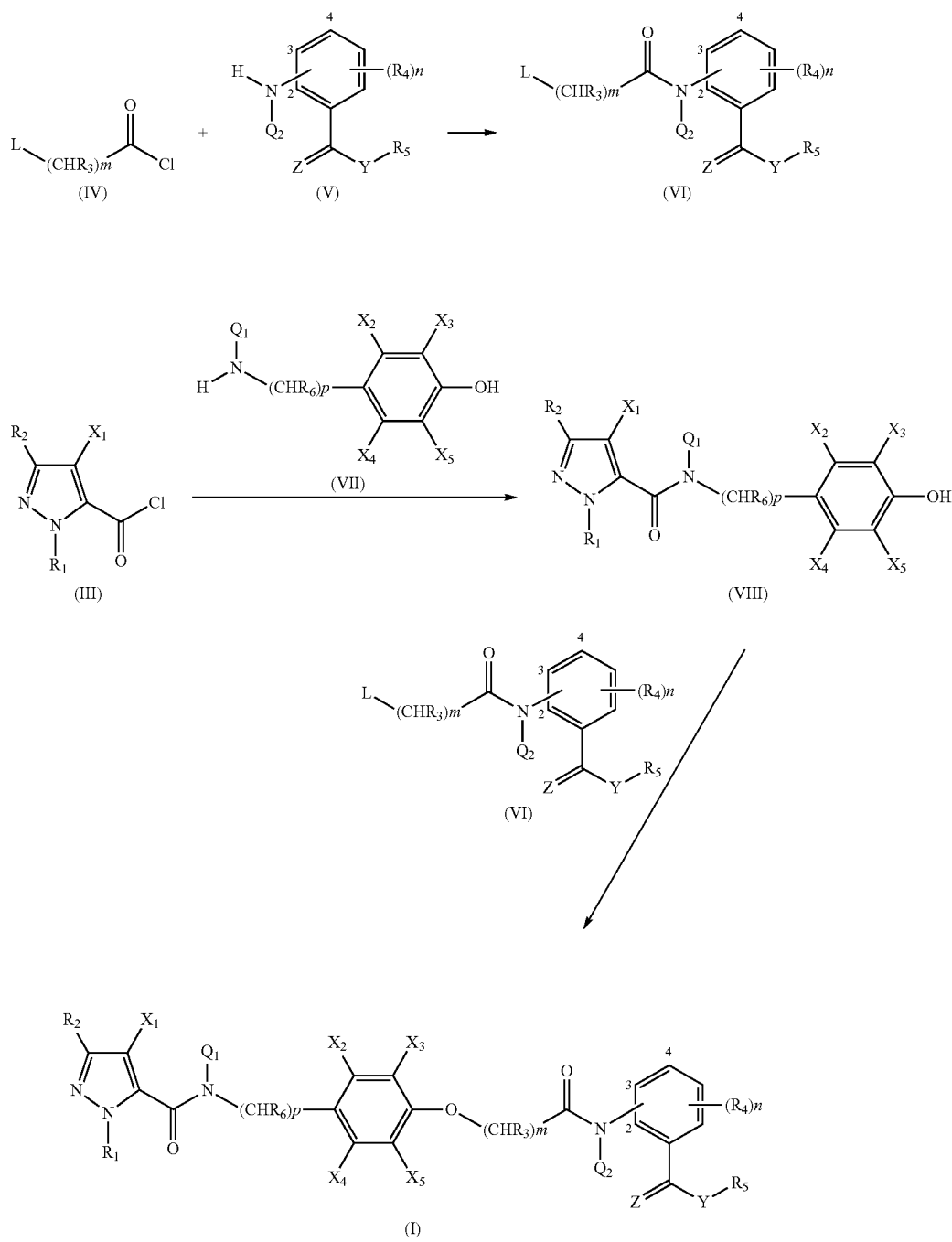

According to the scheme above:

The intermediate compounds represented by general formula (IV) and the compounds of the general formula (V) are allowed to react in the presence or absence of base in proper solvent to give the compounds of the general formula (VI); at the same time, the compounds of the general formula (VIII) are obtained by reacting the compounds of the general formula (III) and the compounds of the general formula (VII) under the same condition as the intermediate (VI); the preferred temperature is 0~100° C.; the reaction time is in the range of 30 minutes to 20 hours, generally being 0.5-10 hours. proper solvent mentioned may be selected from N,N-dimethylformamide, dimethylsulfoxide, benzene, toluene, xylene, chloroform, methylene chloride, tetrahydrofuran, acetonitrile, dioxane or N-methyl-2-pyrrolidone, etc. Proper base mentioned when needed may be selected from alkali metal hydride such as sodium hydride; alkali metal hydroxides such as sodium hydroxide or potassium hydroxide; alkali carbonate such as sodium carbonate or potassium carbonate; organic amine such as pyridine or triethylamine.

Then the compounds represented by general formula (VIII) are reacted with the compounds of the general formula (VI) in the presence of base in proper solvent to give the compounds of the general formula (I); the preferred temperature is 0~160° C.; the reaction time is in the range of 30 minutes to 20 hours, generally being 0.5-10 hours. Proper base mentioned may be selected from alkali metal hydride such as sodium hydride; alkali metal hydroxides such as sodium hydroxide or potassium hydroxide; alkali carbonate such as sodium carbonate or potassium carbonate; organic amine such as pyridine or triethylamine. proper solvent mentioned may be selected from N,N-dimethylformamide, dimethylsulfoxide, benzene, toluene, xylene, chloroform, methylene chloride, tetrahydrofuran, acetonitrile, dioxane or N-methyl-2-pyrrolidone, etc. The detailed operation refers to the methods described in WO2007087906A.

Except for the detailed description about how to prepare the protected key intermediate represented by general formula (II), other materials and intermediates described above may be purchased or may be prepared according to the known methods, as shown in the following:

Substituted parazole carbonyl chloride represented by general formula (III) can be prepared according to the methods described in Bull. Soc. Chim. France, 293 (1996), U.S. Pat. No. 4,950,668, JP2292263, JP2053776, JP4069361 or JP4069379, etc. The materials represented by general formula (IV) are commercially available, wherein, L is a leaving group, selected from halogen, methyl methanesulfonate or p-toluenesulfonates; The materials represented by general formula (V) can be prepared according to the methods described in Kundiger D. G et al. J. Am. Chem. Soc. 1960, 82:2953; CN1827610 or Applied Chemical Industry 2010, 39 (9):1436-1442. The intermediates represented by general formula (VII) can be purchased or prepared according to the methods described in J. Am. Chem. Soc, 70, 3788 (1948), 82, 681 (1960), 82, 2386 (1960); Can. J. Chem, 49, 2990 (1971); J. Org. Chem, 37, 335 (1972) or Organic Syntheses, Coll. Vol. 3, p. 229, p. 720 (1955), Vol. 23, p. 71 (1943), Vol. 27, p. 18 (1947).

The key intermediate compounds of the general formula (I) (amine compounds represented by general formula (II)) can be prepared according to the following schemes:

When $Q_1$=H, the compounds of the general formula (II) can be prepared according to the following two schemes:

Firstly, in the general formula (II), when p=0 (namely substituted aniline analogs), the preparation methods are shown as follows:

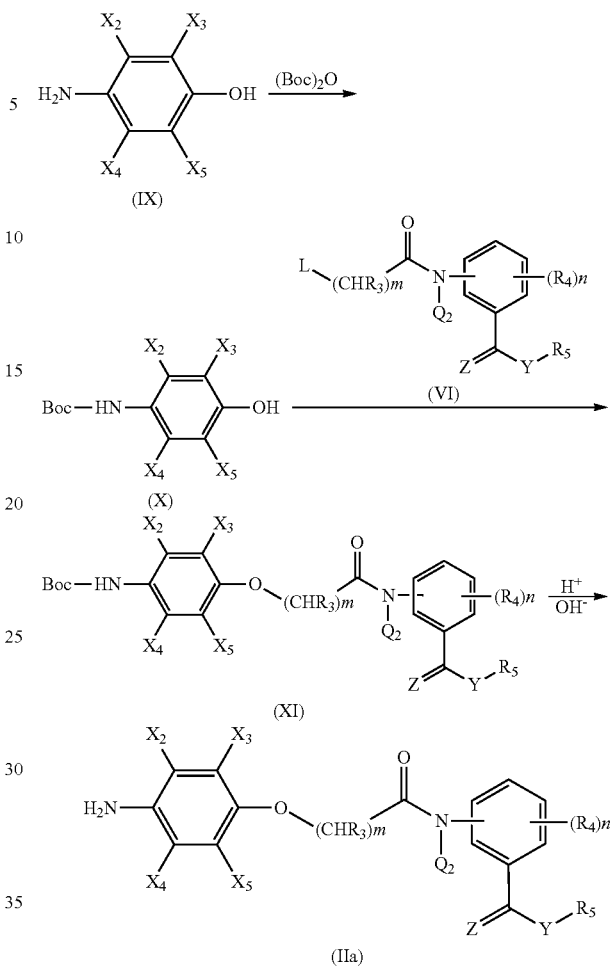

According to the scheme above, the compounds of the general formula (X) are prepared by reacting di-tert-butyl dicarbonate with the compounds of the general formula (IX) at 0~100° C. in proper solvent in the presence of proper base, the preferred temperature is 0~50° C.; the reaction time is in the range of 30 minutes to 20 hours, generally being 0.5-10 hours. Proper solvent mentioned may be selected from benzene, toluene, xylene, chloroform, methylene chloride, THF, acetonitrile, dioxane, N,N-dimethylformamide, N-methyl-2-pyrrolidone or dimethylsulfoxide, etc; proper base mentioned may be selected from alkali carbonate such as sodium carbonate, sodium bicarbonate, potassium carbonate or potassium bicarbonate.

Then the compounds represented by general formula (X) and the compounds of the general formula (VI) are allowed to react in the presence of proper base in proper solvent to give the compounds of the general formula (XI); the preferred temperature is 0~100° C.; the reaction time is in the range of 30 minutes to 20 hours, generally being 0.5-10 hours. Proper solvent mentioned may be selected from benzene, toluene, xylene, chloroform, methylene chloride, acetone, butanone, tetrahydrofuran, acetonitrile, dioxane, N,N-dimethylformamide, N-methyl-2-pyrrolidone or dimethylsulfoxide, etc; proper base mentioned may be selected from alkali metal hydride such as sodium hydride; alkali metal hydroxides such as sodium hydroxide or potassium hydroxide; alkali carbonate such as sodium carbonate or potassium carbonate; organic amine such as pyridine or triethylamine.

The compounds of the general formula (IIa) are obtained by deprotection of the compounds of the general formula (XI) in proper solvent in presence of proper acid to give corresponding salts and then alkalization. The preferred temperature is 0~50° C.; the reaction time is in the range of 30 minutes to 20 hours, generally being 0.5-10 hours. Proper solvent mentioned may be selected from ethyl acetate, methyl acetate, methyl formate, benzene, toluene, xylene, chloroform, methylene chloride, water, tetrahydrofuran, acetonitrile, dioxane, N,N-dimethylformamide, N-methyl-2-pyrrolidone or dimethylsulfoxide, etc; proper acid mentioned may be selected from hydrochloric acid, trifluoroacetic acid, sulfuric acid, acetic acid, propionic acid, butyric acid, oxalic acid, adipic acid, dodecanedioic acid, lauric acid, stearic acid, fumaric acid, maleic acid, benzoic acid or phthalic acid, etc. proper base mentioned may be selected from alkali metal hydride such as sodium hydride; alkali metal hydroxides such as sodium hydroxide or potassium hydroxide; alkali carbonate such as sodium carbonate or potassium carbonate; organic amine such as pyridine or triethylamine. The preparation method in detail refers to patent WO2004093800A.

Secondly: in the general formula (II), when p is selected from 1 to 5, the preparation methods are shown as follows.

1. Reduction of Cyano:

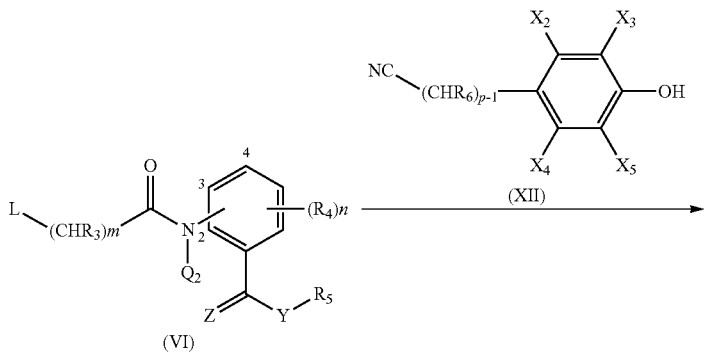

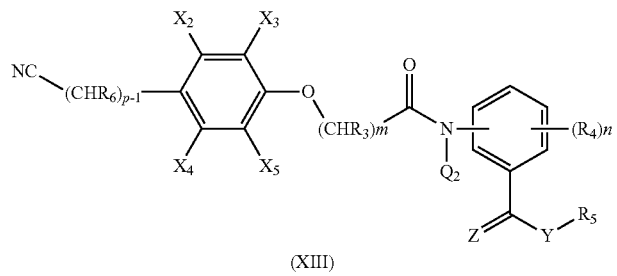

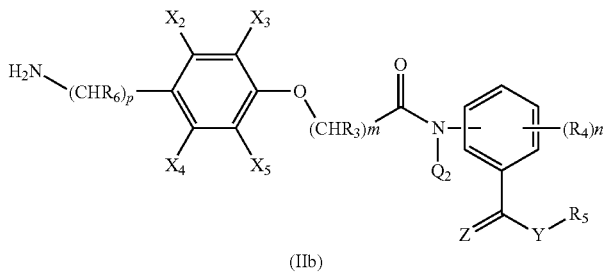

The intermediate compounds represented by general formula (VI) and the compounds of the general formula (XII) are allowed to react in the presence of proper base in proper solvent to give the compounds of the general formula (XIII); the preferred temperature is 0~100° C.; the reaction time is in the range of 30 minutes to 20 hours, generally being 0.5-10 hours. Proper solvent mentioned may be selected from benzene, toluene, xylene, chloroform, methylene chloride, acetone, butanone, tetrahydrofuran, acetonitrile, dioxane, N,N-dimethylformamide, N-methyl-2-pyrrolidone or dimethylsulfoxide, etc; proper base mentioned may be selected from alkali metal hydride such as sodium hydride; alkali metal hydroxides such as sodium hydroxide or potassium hydroxide; alkali carbonate such as sodium carbonate or potassium carbonate; organic amine such as pyridine or triethylamine.

Then the compounds represented by general formula (XIII) and hydrogen are allowed to react in the presence of a metal catalyst and aqueous ammonia in proper solvent at the temperature of 0~100° C. to give the compounds of the general formula (IIb); the preferred temperature is 20~50° C.; the reaction time is in the range of 30 minutes to 20 hours, generally being 0.5~10 hours. Proper solvent mentioned may be selected from methanol, ethanol, isopropanol, benzene, toluene, xylene, acetone, butanone, methylisobutylketone, chloroform, methylene chloride, methyl acetate, ethyl acetate, tetrahydrofuran, dioxane, N,N-dimethylformamide, N-methyl-2-pyrrolidone or dimethylsulfoxide, etc. Metal catalysts mentioned may be selected from Raney-nickel, palladium carbon or platinum oxide, etc, which are known hydrogenation catalysts to the skilled person of this field. The preparation of the compounds refer to the methods described in J. Am. Chem. Soc, 70, 3788 (1948); 82, 681 (1960); 82, 2386 (1960): Can. J. Chem, 49, 2990 (1971): J. Org. Chem., 37, 335 (1972): Organic Syntheses, Coll. Vol. 3, p. 229, p. 720 (1955), Vol. 23, p. 71 (1943) or Vol. 27, p. 18 (1947).

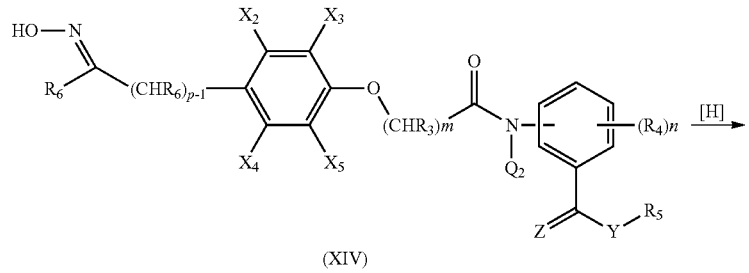

(XIV)

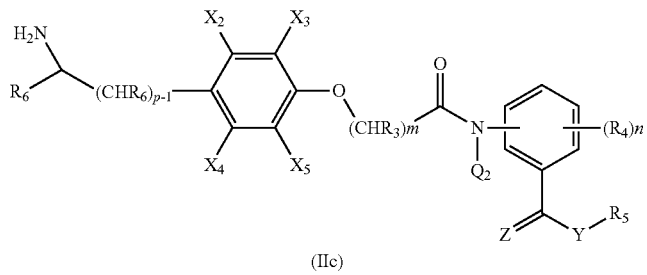

(IIc)

2. Reduction of Oxime:

The method of how to obtain the compounds of general formula (IIc) by reaction of the compounds of the general formula (XIV) and hydrogen refers to that of how to obtain the compounds of general formula (IIb) by reacting the compounds of the general formula (XIII) and hydrogen mentioned above, such as reaction conditions, solvent, base and the choice of catalyst.

phenyl alkyl aldehyde or ketone are allowed to react to give corresponding phenyl alkyl aldehyde or ketone, which is(are) then reacted with hydroxylamine in the presence of base to give the compounds of the general formula (XIV).

when $Q_1 \neq H$, the compounds of the general formula (IId), (IIe) and (IIf) can be prepared according to the following schemes:

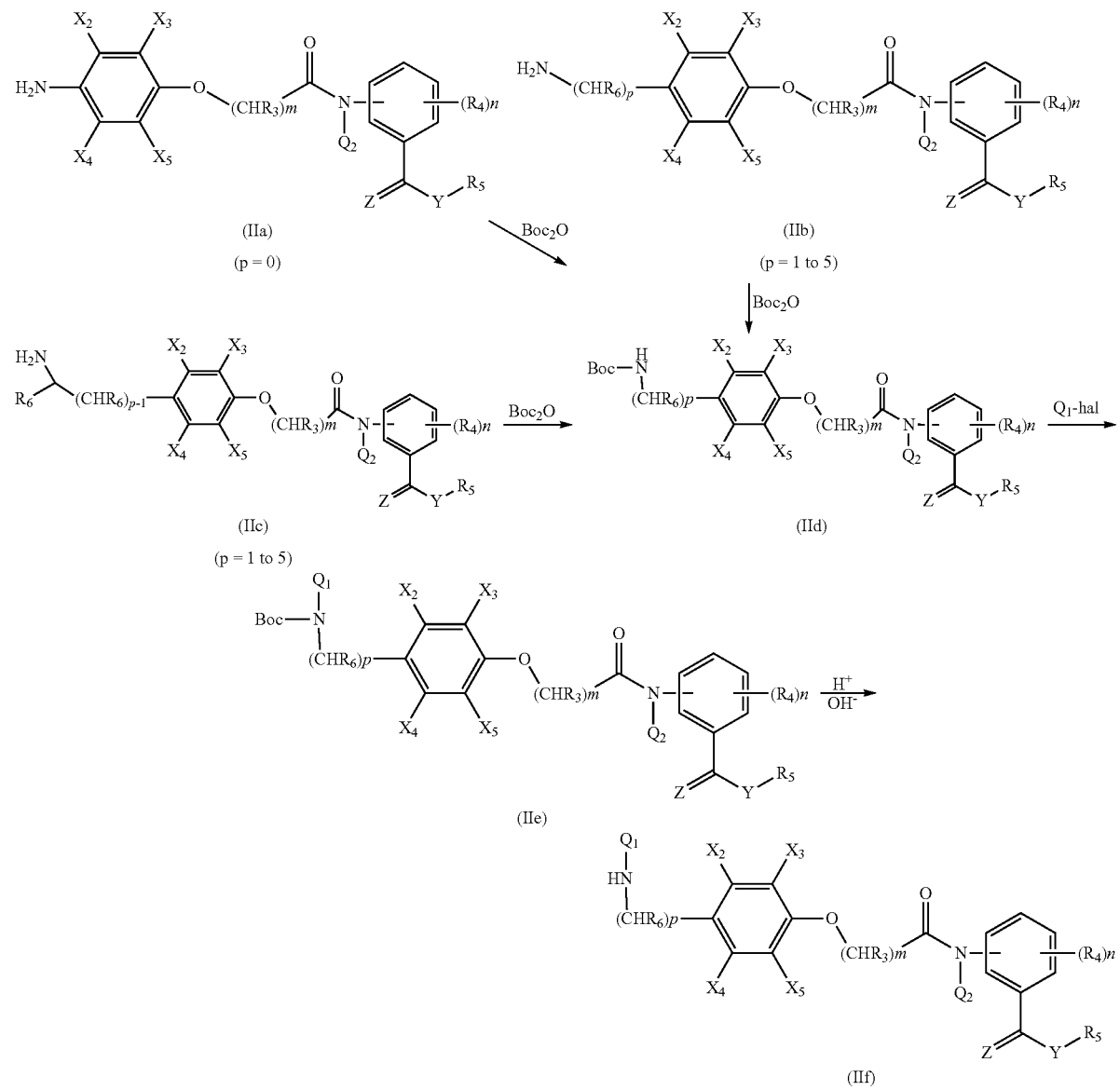

In the scheme above to prepare the intermediates of the general formula (II), $Boc_2O$ represents di-tert-butyl dicarbonate. Other substituents have the same meanings as defined above. The sources of other intermediates are as follows: intermediates represented by general formula (IX) and (XII) can be purchased, the preparation of the intermediates represented by formula (XIV) refers to the known methods described in WO2001070671A, J. Am. Chem. Soc. 1960, 82:2953, Organic Syntheses, Coll. Vol. 7, p. 149 (1990) or Organic Syntheses, Vol. 64, p. 19 (1986), substituted aminobenzoic acid, halogenated acyl chloride and 4-hydroxy Wherein, hal is a leaving group, selected from halogen, methyl methanesulfonate or p-toluenesulfonates; Other groups are as defined above.

The detailed preparation refers to the methods described in WO2004093800A.

The intermediate compounds represented by general formula (IIa), (IIb) or (IIc) and di-tert-butyl dicarbonate are allowed to react in proper solvent to give the compounds of the general formula (IId); Detailed reaction condition refers to the method of how to prepare the compounds of general formula (X) from the compounds of the general formula (IX).

The compounds (IId) is then allowed to react with $Q_1$-hal in the presence of base in proper solvent at 0~50° C. to give the compounds of the general formula (IIe). The preferred temperature is 0~25° C.; the reaction time is in the range of 30 minutes to 20 hours, generally being 0.5-10 hours. The proper solvent mentioned may be selected from N,N-dimethylformamide, tetrahydrofuran, acetonitrile, dioxane and so on. The proper base mentioned may be selected from alkali metal hydride such as sodium hydride, alkali metal hydroxides such as sodium hydroxide or potassium hydroxide, alkali carbonate such as sodium carbonate or potassium carbonate, organic amine such as pyridine or triethylamine.

The compounds (IIf) are obtained by deprotection the compounds (IIe) in proper solvent in presence of proper acid to give corresponding salts and then alkalization. Detailed reaction condition refers to the preparation method to get (XI) from (IIa).

The amine salt of compounds represented by the general formula (II) can be prepared according to the following method.

The compounds (II) and proper acid are allowed to react in proper solvent at −5~50° C. (The preferred temperature is 0~25° C.) to give the amine salt according to the known methods disclosed in CN1511142A; Organic Syntheses, Coll. Vol. 4, p. 605 (1963) or Vol. 34, p. 64 (1954), etc., the proper acid mentioned may be selected from acetic acid, propionic acid, butyric acid, oxalic acid, adipic acid, dodecanedioic acid, lauric acid, stearic acid, trifluoroacetic acid, fumaric acid, maleic acid, benzoic acid, phthalic acid, methanesulfonic acid, 1,3-propylene sulfonic acid, p-toluenesulfonic acid, dodecylbenzenesulfonic acid, hydrochloric acid, sulfuric acid, nitric acid or carbonic acid, etc. the proper solvent mentioned may be selected from benzene, toluene, xylene, acetone, butanone, methylisobutylketone, chloroform, methylene chloride, tetrahydrofuran, acetonitrile, ethyl ether, methanol, ethanol, propanol, butanol or dioxane, etc.

To sum up, the technical scheme of the present invention includes a preferred process route of compounds having the general formula (I) (wherein $Q_1$=H, p=0-5), the synthetic scheme is shown as follows:

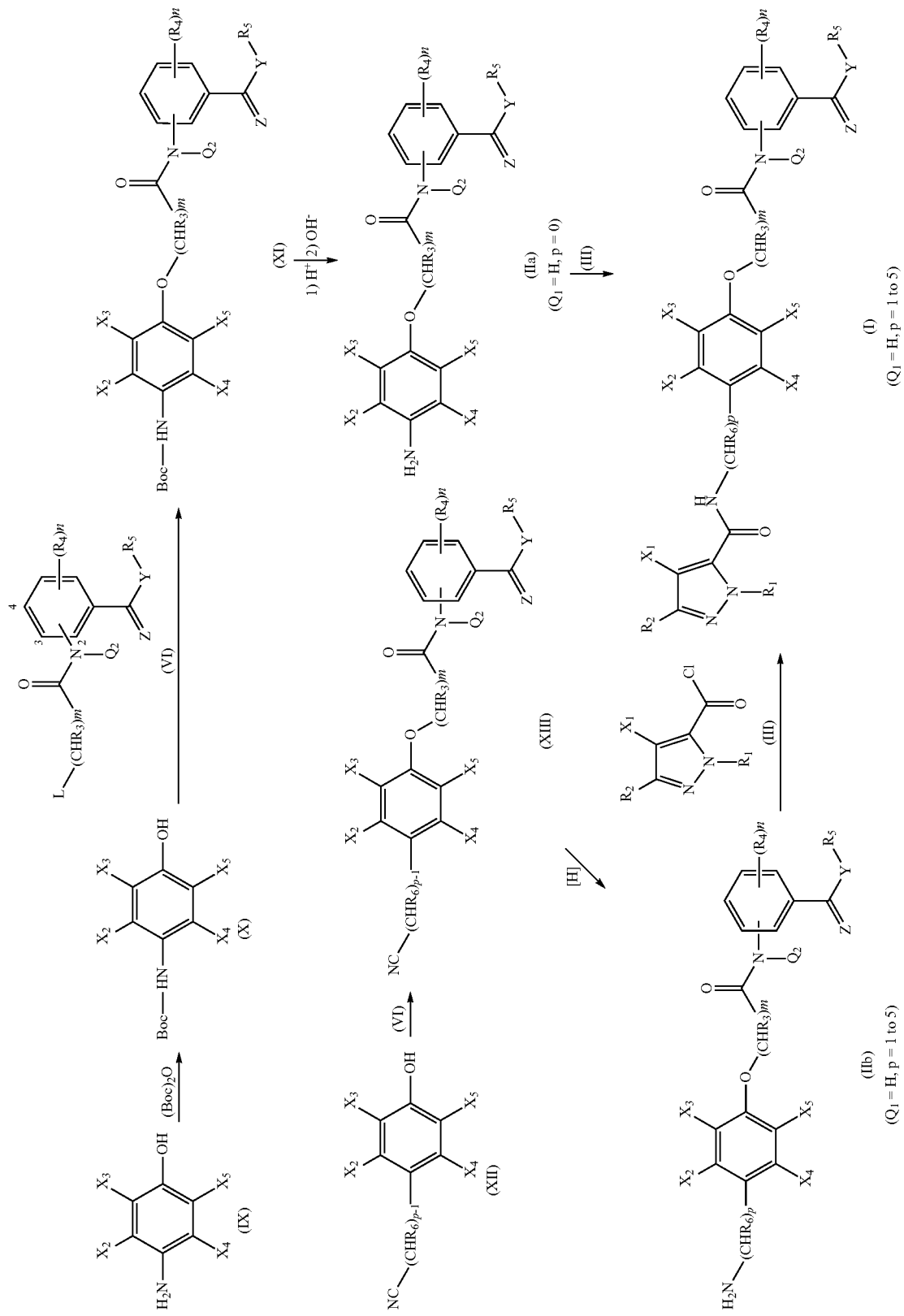

Each substituent in the reaction formula is as defined above except for special explanation.

In the general formula (I), $(CHR_3)mCON(Q_2)$ links with phenyl ring respectively at the 2, 3 or 4-position.

When $(CHR_3)mCON(Q_2)$ links with phenyl ring at the 2-position, the structure is shown by formula (I-1):

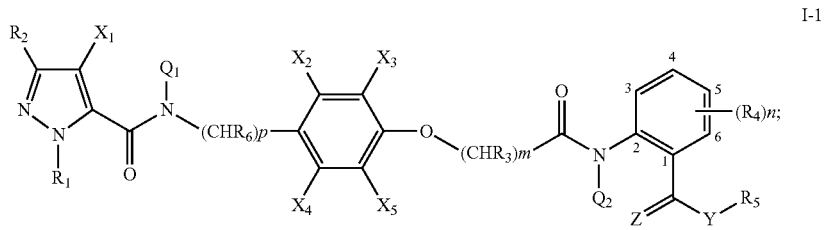

I-1

When $(CHR_3)mCON(Q_2)$ links with phenyl ring at the 3-position, the structure is shown by formula (I-2):

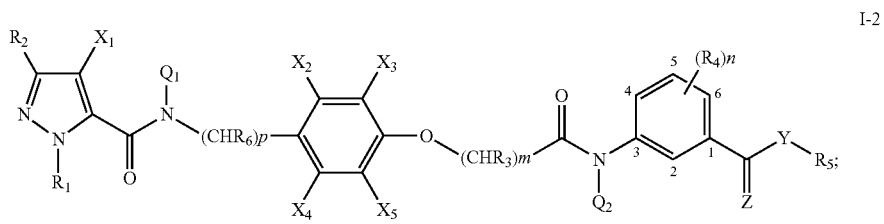

I-2

When $(CHR_3)mCON(Q_2)$ links with phenyl ring at the 4-position, the structure is shown by formula (I-3):

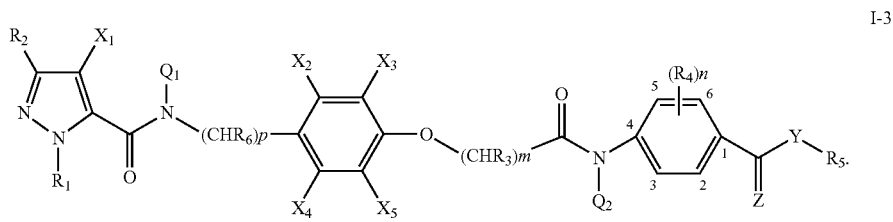

I-3

In the general formula (I), preferred substituents of $R_1$ refer to table 1; preferred substituents of $R_2$ refer to table 2; preferred substituents of $(R_4)n$ respectively refer to table 3 (when $(CHR_3)mCON(Q_2)$ links with phenyl ring at the 2-position.), table 4 (when $(CHR_3)mCON(Q_2)$ links with phenyl ring at the 3-position.) and table 5 (when $(CHR_3)mCON(Q_2)$ links with phenyl ring at the 4-position.), preferred substituents of $Y—R_5$ refer to table 6; preferred substituents of Qt and $Q_2$ refer to table 7; preferred substituents of $X_2$, $X_3$, $X_4$ and $X_5$ refer to table 8; other substituents are as defined above.

TABLE 1

| Some of $R_1$ substituents | | | | |
|---|---|---|---|---|
| —$R_1$ | —$R_1$ | —$R_1$ | —$R_1$ | —$R_1$ |
| H | $CH_3$ | Et | n-Pr | i-Pr |
| n-Bu | i-Bu | s-Bu | t-Bu | $CF_3$ |
| $CHF_2$ | $CH_2CF_3$ | $COCH_3$ | COEt | CO-n-Pr |
| CO-n-Bu | CO-t-Bu | $CO_2CH_3$ | $CO_2Et$ | $CO_2$-n-Pr |
| $CO_2$-i-Pr | $CH_2F$ | $CO_2$-t-Bu | $CONHCH_3$ | CONHEt |
| CONH-n-Pr | CONH-i-Pr | CONH-n-Bu | CONH-i-Bu | CONH-t-Bu |
| $CH_2CN$ | $CH_2OCH_3$ | $COCF_3$ | $CO_2CH_2CF_3$ | $CONHCH_2CF_3$ |

TABLE 1-continued
Some of R₁ substituents
| —R₁ | —R₁ | —R₁ | —R₁ | —R₁ |
|---|---|---|---|---|
| 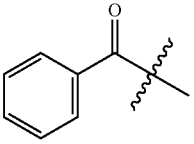 [SMILES: *C(=O)c1ccccc1] | 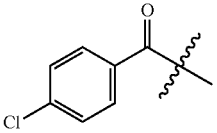 [SMILES: *C(=O)c1ccc(Cl)cc1] | 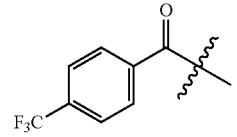 | 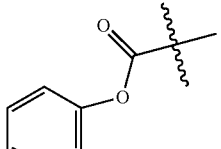 | 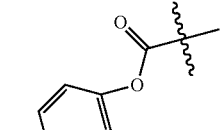 |
| 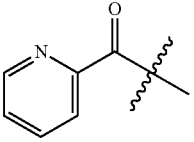 [SMILES: *C(=O)c1ccccn1] | 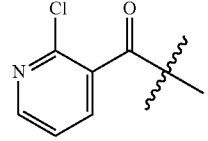 [SMILES: *C(=O)c1cccnc1Cl] | 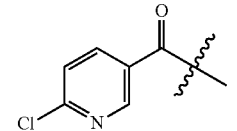 [SMILES: *C(=O)c1ccc(Cl)nc1] | 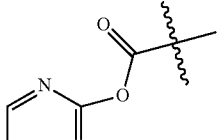 | 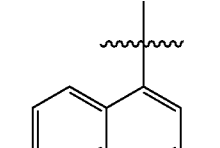 |
| 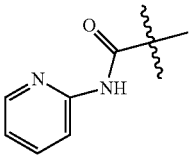 [SMILES: *C(=O)Nc1ccccn1] | 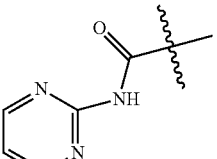 | 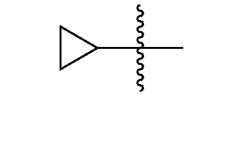 [SMILES: *C1CC1] | 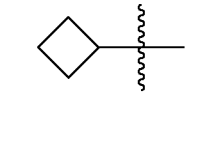 | 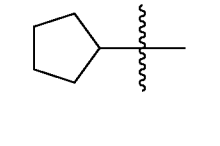 |
| 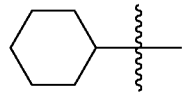 | 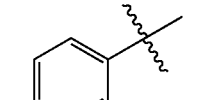 | 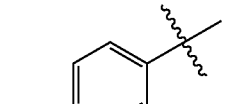 | 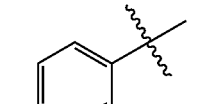 | 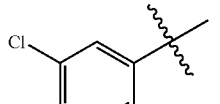 |
| 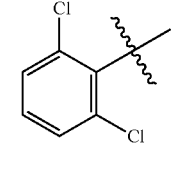 [SMILES: *c1c(Cl)cccc1Cl] | 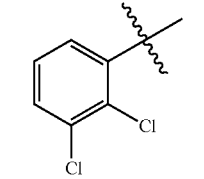 [SMILES: *c1cccc(Cl)c1Cl] | 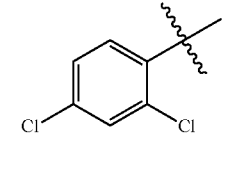 [SMILES: *c1ccc(Cl)cc1Cl] | 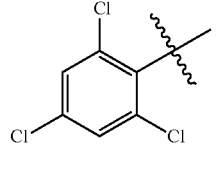 [SMILES: *c1c(Cl)cc(Cl)cc1Cl] | 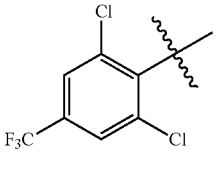 [SMILES: *c1c(Cl)cc(C(F)(F)F)cc1Cl] |
| 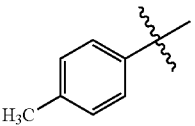 | 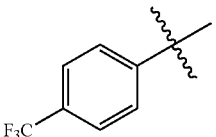 | 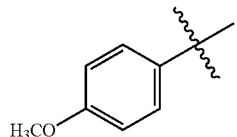 | 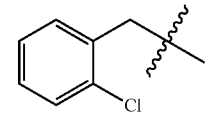 [SMILES: *Cc1ccccc1Cl] | 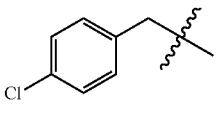 [SMILES: *Cc1ccc(Cl)cc1] |
| 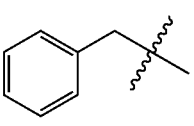 [SMILES: *Cc1ccccc1] | 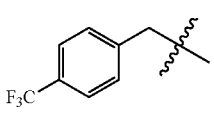 | 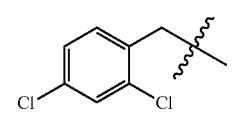 [SMILES: *Cc1ccc(Cl)cc1Cl] | 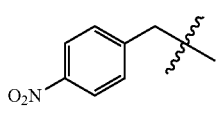 | 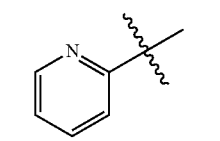 [SMILES: *c1ccccn1] |
| 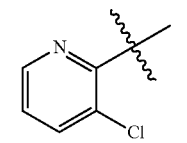 [SMILES: *c1ncccc1Cl] | 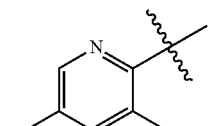 | 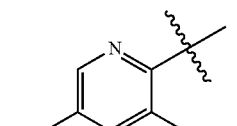 | 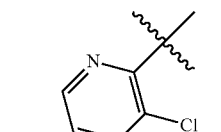 | 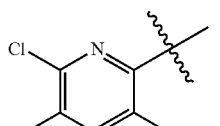 |

TABLE 1-continued

Some of R₁ substituents

| —R₁ | —R₁ | —R₁ | —R₁ | —R₁ |
|---|---|---|---|---|

TABLE 2

Some of R₂ substituents

| —R₂ | —R₂ | —R₂ | —R₂ | —R₂ |
|---|---|---|---|---|
| H | F | Cl | Br | CH₂CN |
| CN | CH₃ | Et | n-Pr | i-Pr |
| n-Bu | i-Bu | s-Bu | t-Bu | CF₃ |
| OCH₃ | OEt | OCF₃ | CHF₂ | OCH₂CF₃ |
| CH₂F | OCH₂CN | OCH₂F | OCH₂CF₃ | CH₂OCH₂CF₃ |
| CH₂OCH₃ | SCH₃ | SEt | SCH₂F | CH₂SCH₃ |
| SOCH₃ | SOCF₃ | SO₂CH₃ | SO₂Et | SO₂CH₂CF₃ |
| SO₂CF₃ | | | | |

TABLE 2-continued

Some of R₂ substituents

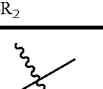 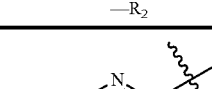 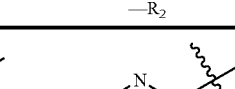 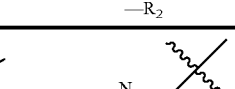 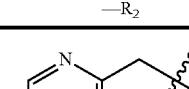

 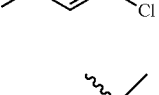  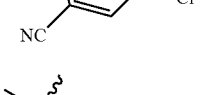 

 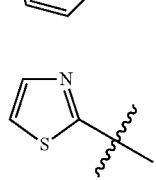 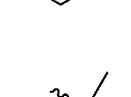  

TABLE 3

Some of (R₄)n substituents of formula I-1

I-1

| (R₄)n | (R₄)n | (R₄)n | (R₄)n | (R₄)n |
|---|---|---|---|---|
| 3-Br | 4-SCH₃ | 4-SO₂CH₃ | 4-CONH₂ | 4-CSNH₂ |
| 3-CH₃ | 4-Br | 5-OCH₃ | 3-CH₃-5-NO₂ | 6-CH₃-3,5-2Br |
| 4-CH₃ | 5-Br | 3,5-2Cl | 4-CH₃-3-NO₂ | 3-OCF₃-4,6-2Cl |
| 5-CH₃ | 6-Br | 3,5-2Br | 4-CH₃-5-NO₂ | 4-CH₃-5-NO₂-3-Br |
| 6-CH₃ | 3-I | 4-CH₃-5-Br | 5-CH₃-3-NO₂ | 3-CN-4,6-2Cl |
| 3-Cl | 4-I | 6-CH₃-5-CN | 6-CH₃-4-NO₂ | 3-CN-4-CH₃-6-Cl |
| 4-Cl | 5-I | 3,5,6-3Cl | 6-CH₃-5-NO₂ | 3-CN-4-CF₃-6-Cl |
| 5-Cl | 6-I | 3-Et | 3-NO₂-5-Cl | 4-CH₃-5-CN-6-Cl |
| 6-Cl | 3-CN | 4-Et | 3-NO₂-5-Br | 4-CF₃-5-CN-6-Cl |
| 3-CF₃ | 4-CN | 5-Et | 5-NO₂-3-Br | 3-OCF₃-6-Cl |
| 4-CF₃ | 5-CN | 6-Et | 5-CH₃-3-Br | 3-Cl-5-CN |
| 5-CF₃ | 6-CN | 5-CF₃-3-Cl | 6-CH₃-5-Br | 5-CF₃-3,6-2Cl |
| 6-CF₃ | 3-NO₂ | 5-CH₃-3-Cl | 3-CF₃-6-Cl | 3-Cl-5-CONH₂ |
| 3-F | 4-NO₂ | 3-CH₃-5-I | 3-CH₃-5-CN | 3-Cl-5-CSNH₂ |
| 4-F | 5-NO₂ | 3-CH₃-5-Cl | 3,4,5-3Cl | 3-CH₃-5-CSNH₂ |
| 5-F | 6-NO₂ | 3-CH₃-5-Br | 3,5,6-3 CH₃ | 3-CH₃-5-CSNH₂ |

TABLE 3-continued

Some of (R₄)n substituents of formula I-1

I-1

| (R₄)n | (R₄)n | (R₄)n | (R₄)n | (R₄)n |
|---|---|---|---|---|
| 6-F | 6-OCH₃ | 4,5,6-3Cl | 5-CF₃-6-Cl | 3-Cl-5-SO₂CH₃ |
| 4,5-2Cl | 4,5-2Br | 3,5-2CH₃ | 3-CN-6-Cl | 3-CH₃-5-SO₂CH₃ |

TABLE 4

Some of (R₄)n substituents of formula I-2

I-2

| (R₄)n | (R₄)n | (R₄)n | (R₄)n | (R₄)n |
|---|---|---|---|---|
| 2-CH₃ | 2-Br | 6-OCH₃ | 2-CH₃-5-NO₂ | 6-CH₃-4,5-2Br |
| 4-CH₃ | 4-Br | 5-OCH₃ | 4-CH₃-6-NO₂ | 5-OCF₃-4,6-2Cl |
| 5-CH₃ | 5-Br | 2,5-2Cl | 4-CH₃-5-NO₂ | 4-CH₃-5-NO₂-6-Br |
| 6-CH₃ | 6-Br | 2,5-2Br | 5-CH₃-6-NO₂ | 5-CN-4,6-2Cl |
| 2-Cl | 2-F | 4-CH₃-5-Br | 6-CH₃-4-NO₂ | 5-CN-4-CH₃-6-Cl |
| 4-Cl | 4-F | 6-CH₃-5-CN | 6-CH₃-5-NO₂ | 2-CN-4-CF₃-6-Cl |
| 5-Cl | 5-F | 4,5,6-3Cl | 2-NO₂-5-Cl | 2-CH₃-5-CN-6-Cl |
| 6-Cl | 6-F | 2-Et | 4-NO₂-5-Br | 4-CF₃-5-CN-6-Cl |
| 2-CF₃ | 2-CN | 4-Et | 5-NO₂-4-Br | 2-OCF₃-6-Cl |
| 4-CF₃ | 4-CN | 5-Et | 5-CH₃-5-Br | 5-CN-4-Cl |
| 5-CF₃ | 5-CN | 6-Et | 6-CH₃-4Br | 5-CF₃-4,6-2Cl |

TABLE 4-continued

Some of (R₄)n substituents of formula I-2

I-2

| (R₄)n | (R₄)n | (R₄)n | (R₄)n | (R₄)n |
|---|---|---|---|---|
| 6-CF₃ | 6-CN | 5-CF₃-6-Cl | 4-CH₃-5-Br | 5-CF₃-6-Cl |
| 2-NO₂ | 6-NO₂ | 5-CH₃-4-Cl | 4-CF₃-6-Cl | 2-CN-6-Cl |
| 4-NO₂ | 2-I | 4,5-2Cl | 5-CH₃-2-Cl | 4-CH₃-2-Cl |
| 5-NO₂ | 4-I | 5-I | 6-I | 5,6-2CH₃ |

TABLE 5

Some of (R₄)n substituents of formula I-3

I-3

| (R₄)n | (R₄)n | (R₄)n | (R₄)n | (R₄)n |
|---|---|---|---|---|
| 2-F | 2-i-Pr | 2,6-2OCH₃ | 2,3-2CH₃ | 2-Cl-5-F |
| 3-F | 3-2-i-Pr | 5,6-2OCH₃ | 2,5-2CH₃ | 2-Cl-5-Br |
| 5-F | 5-2-i-Pr | 3,5-2OCH₃ | 2,6-2CH₃ | 2-Cl-54 |
| 6-F | 6-2-i-Pr | 3,6-2NO₂ | 5,6-2CH₃ | 3-Cl-54 |
| 2-Cl | 2-CF₃ | 3,5-2NO₂ | 3,5-2CH₃ | 5-Cl-2-Br |
| 3-Cl | 3-CF₃ | 2,3-2NO₂ | 3,6-2CH₃ | 3,5,6-3F |
| 5-Cl | 5-CF₃ | 5,6-2NO₂ | 2,3-2 Et | 2,3,6-3Cl |

TABLE 5-continued

Some of (R₄)n substituents of formula I-3

I-3

| (R₄)n | (R₄)n | (R₄)n | (R₄)n | (R₄)n |
|---|---|---|---|---|
| 6-Cl | 6-CF₃ | 2,5-2NO₂ | 5,6-2 Et | 2,3,5-3Cl |
| 2-Br | 2-OCH₃ | 2,6-2NO₂ | 2,5-2 Et | 2,3,6-3I |
| 3-Br | 3-OCH₃ | 2,3-2CN | 2,6-2 Et | 3,5,6-3Cl |
| 5-Br | 5-OCH₃ | 5,6-2CN | 3,5-2 Et | 2,5,6-3Cl |
| 6-Br | 6-OCH₃ | 2,5-2CN | 3,6-2Et | 2,3,5-3Br |
| 2-I | 2-OCF₃ | 2,6-2CN | 2,3-2CF₃ | 2,3,6-3Br |
| 3-I | 3-OCF₃ | 3,5-2CN | 3,6-2CF₃ | 2,5,6-3Br |
| 5-I | 5-OCF₃ | 3,6-2CN | 3,5-2CF₃ | 3,5,6-3Br |
| 6-I | 6-OCF₃ | 2-F-5-Cl | 5-CH₃-2-Br | 5-CH₃-3-F |
| 2-CN | 2,3-2F | 2-F-5-Br | 5-CH₃-2-Cl | 6-CH₃-3-Cl |
| 3-CN | 2,5-2F | 2-F-5-I | 2,5,6-3CH₃ | 2-CH₃-3-Br |
| 5-CN | 5,6-2F | 2-F-6-Cl | 5-Et | 2-CH₃-5-Br |
| 6-CN | 2,6-2F | 3-CF₃-5-Cl | 2,6-2Br | 2-CH₃-3-F |
| 2-NO₂ | 3,6-2F | 3,5,6-3F | 6-CH₃-2-NO₂ | 2-CH₃-3-Cl |
| 3-NO₂ | 3,5-2F | 2,5-2OCF₃ | 3,6-2Br | 2-CH₃-5-F |
| 5-NO₂ | 2,3-2Cl | 2-CH₃-3-NO₂ | 2-CH₃-5-F | 2-CH₃-5-Cl |
| 6-NO₂ | 2,5-2Cl | 5-CH₃-2,6-2Br | 2,5-2F-6-Cl | 2-CH₃-6-Cl |
| 2-CH₃ | 5,6-2Cl | 5-CH₃-2-F-6-Cl | 5-CF₃-2,6-2Cl | 3-CH₃-2-Br |
| 3-CH₃ | 2,6-2Cl | 2-CN-5-Cl | 5-CH₃-2-CN | 3-CH₃-5-Cl |
| 5-CH₃ | 3,6-2Cl | 2-CN-5-Br | 3,5-2Br | 3-CH₃-5-Br |
| 6-CH₃ | 3,5-2Cl | 5-CN-2-CF₃ | 3-CH₃-2,6-2Cl | 3-CH₃-5-I |
| 2-Et₅ | 2,3-2Br | 5-CN-2-Cl | 2-CH₃-3,6-2Br | 2-CH₃-5-I |
| 3-Et | 5,6-2Br | 5-CN-2-NO₂ | 2-F-5,6-2Br | 2-CN-5,6-2Cl |
| 2,5-2Br | 5-CH₃-2-F | 5-F-2,6-2Br | 5-CN-2,6-2Cl | 6-Et |

TABLE 6

Some of substituents of YR₅

—YR₅: morpholinyl (N-linked), piperidinyl (N-linked), 4-methylpiperazinyl (N-linked), 2,6-dimethylmorpholinyl (N-linked)

pyrrolidinyl (N-linked), cyclopropyloxy (O-linked), cyclopropylamino (HN-linked), cyclohexylamino (HN-linked)

tetrahydrofuran-2-ylmethoxy, cyclohexyloxy, NH-CH(CH₃)-CH=CH₂, NHCH₂-C≡CH

| —YR₅ | —YR₅ | —YR₅ | —YR₅ |
|---|---|---|---|
| NHCH₃ | NHSO₂CH₃ | NH-s-Bu | ONHCH₃ |
| NHEt | NHCN | NHCH₂-t-Bu | ONHEt |
| N(CH₃)₂ | NHCH₂CN | OCH₃ | ON=C(CH₃)₂ |
| N(Et)₂ | NHOCH₃ | OEt | ON=C(CH₃)(Et) |
| NHCF₃ | NHOEt | O-n-Pr | ONHPh |
| NHCH₂CF₃ | NHPh | O-i-Pr | ON(CH₃)Ph |
| N(CF₃)₂ | NH-n-Pr | O-n-Bu | ON(CH₃)Ph-4-Cl |
| NHNHCH₃ | NH-n-Pr | O-i-Bu | ONH-n-Pr |
| NHN(CH₃)₂ | NH-n-Bu | O-t-Bu | ONH-i-Pr |
| NHCONHPh | NH-i-Bu | OPh | ONH-n-Bu |

TABLE 6-continued

Some of substituents of YR$_5$

| —YR$_5$ | —YR$_5$ | —YR$_5$ | —YR$_5$ |
|---|---|---|---|
| NHNHCF$_3$ | NH-t-Bu | OCH$_2$Ph | ONH-t-Bu |
| NHNHCOCH$_3$ | NHCO$_2$CH$_3$ | O(CH$_2$)$_2$Ph | OCH$_2$CO$_2$CH$_3$ |
| O(CH$_2$)$_2$OCH$_3$ | O(CH$_2$)$_2$OEt | NHCH$_2$C=CH$_2$ | NHN=C(CH$_3$)$_2$ |
| OCH$_2$CN | NHC(CH$_3$)$_2$CN | OCH$_2$C≡CH | OCH$_2$C=CH$_2$ |
| OC(CH$_3$)$_2$CN | NHCH(CH$_3$)CN | OCH$_2$CH$_2$O-n-Bu | OCH$_2$Ph-4-Cl |
| NHCH$_2$Ph | NHCH$_2$Ph-4-Cl | NH(CH$_2$)$_2$CN | NH(CH$_2$)2Ph-4-Cl |
| NHCH$_2$-2-Py | OCH$_2$CF$_3$ | NHCH$_2$-Ph-4-t-Bu | ON=C(CH$_3$)Ph-4-Cl |
| NHCH$_2$Ph-2,4-2Cl | OCH$_2$Ph-2,4-2Cl | NH(CH$_2$)$_2$Ph-4-t-Bu | NHCH$_2$Ph-2,4-2OCH$_3$ |
| OCH$_2$—Ph-4-t-Bu | OCH$_2$Ph-4-OCH$_3$ | O(CH$_2$)$_2$Ph-4-t-Bu | OCH$_2$Ph-2,4-2OCH$_3$ |

[Structures of various YR$_5$ substituents including pyrimidine, pyridine, thiazole, and chloropyridine derivatives]

TABLE 7

Some of substituents of Q$_1$ and Q$_2$

| —Q$_1$(Q$_2$) | —Q$_1$(Q$_2$) | —Q$_1$(Q$_2$) | —Q$_1$(Q$_2$) | —Q$_1$(Q$_2$) |
|---|---|---|---|---|
| H | CN | SCN | OH | NH2 |
| CH$_3$ | Et | n-Pr | i-Pr | n-Bu |
| i-Bu | s-Bu | t-Bu | CF$_3$ | CHF$_2$ |
| CH$_2$CF$_3$ | CH$_2$CN | CH$_2$CH$_2$CN | COCH$_3$ | COEt |
| CO-n-Pr | CO-n-Bu | CO-s-Bu | CO-t-B | OCH$_3$ |
| OEt | O-n-Pr | O-i-Pr | O-n-Bu | O-i-Bu |
| O-s-Bu | O-t-Bu | OCF$_3$ | CH$_2$OCH$_3$ | SOCH$_3$ |
| SO$_2$CH$_3$ | SO$_2$Et | SO$_2$CF$_3$ | SOCF$_3$ | NHCH$_3$ |
| NHEt | N(CH$_3$)$_2$ | N(Et)$_2$ | HCO | CONHCH$_3$ |
| CONHEt | COOCH$_3$ | COOEt | COO-n-Pr | COO-i-Pr |
| COO-n-Bu | COO-s-Bu | COO-t-Bu | 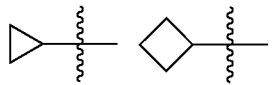 | |

TABLE 8

Some of substituents of X$_2$(X$_3$, X$_4$, X$_5$) in benzene

| —X$_2$ (X$_3$, X$_4$, X$_5$) | —X$_2$ (X$_3$, X$_4$, X$_5$) | —X$_2$ (X$_3$, X$_4$, X$_5$) | —X$_2$ (X$_3$, X$_4$, X$_5$) | —X$_2$ (X$_3$, X$_4$, X$_5$) |
|---|---|---|---|---|
| H | F | Cl | Br | I |
| CN | NO$_2$ | OH | CH$_3$ | Et |
| n-Pr | i-Pr | n-Bu | i-Bu | s-Bu |
| t-Bu | CF$_3$ | CHF$_2$ | CH$_2$CF$_3$ | OCH$_3$ |
| OEt | O—n-Pr | O—i-Pr | O—n-Bu | O—i-Bu |
| O—s-Bu | O—t-Bu | OCF$_3$ | OCH$_2$CF$_3$ | OCHF$_2$ |
| SCH$_3$ | SEt | S—n-Pr | S—i-Pr | S—n-Bu |
| S—i-Bu | S—s-Bu | S—t-Bu | SO$_2$CH$_3$ | SO$_2$Et |

The preferred intermediates of general formula (II) are listed in table 9A and table 9B:

Table 9A Some of Intermediates of General Formula (II)

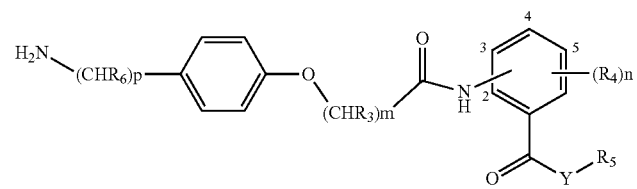

Wherein: Q$_1$ = Q$_2$ = X$_2$ = X$_3$ = X$_4$ = X$_5$ = H, Z = O, (CHR$_3$)mCON(Q$_2$) links with phenyl ring at the 2, 3 or 4-position; when (CHR$_6$)p = 0, Q$_1$—NH is connected with phenyl ring directly.

| compound | (CHR$_3$)m | (R$_4$)n | Y—R$_5$ | (CHR$_6$)p | N(Q$_2$) bonding position | melting point (° C.) |
|---|---|---|---|---|---|---|
| II-1 | CH$_2$ | H | NHCH$_3$ | CH$_2$ | 2 | 109-110 |
| II-2 | CH$_2$ | H | NHEt | CH$_2$ | 2 | |

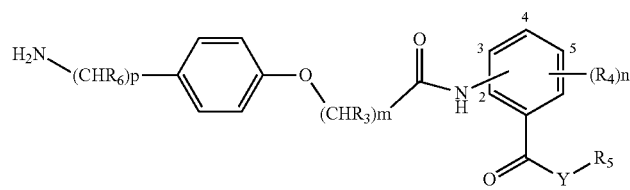

Wherein: $Q_1 = Q_2 = X_2 = X_3 = X_4 = X_5 = H$, $Z = O$, $(CHR_3)mCON(Q_2)$ links with phenyl ring at the 2, 3 or 4-position; when $(CHR_6)p = 0$, $Q_1$—NH is connected with phenyl ring directly.

| compound | $(CHR_3)m$ | $(R_4)n$ | Y—R$_5$ | $(CHR_6)p$ | $N(Q_2)$ bonding position | melting point (° C.) |
|---|---|---|---|---|---|---|
| II-3 | $CH_2$ | H | NH-i-Pr | $CH_2$ | 2 | |
| II-4 | $CH_2$ | H | NH-t-Bu | $CH_2$ | 2 | |
| II-5 | $CH_2$ | H | NHOH | $CH_2$ | 2 | |
| II-6 | $CH_2$ | H | NHOCH$_3$ | $CH_2$ | 2 | |
| II-7 | $CH_2$ | H | NHOEt | $CH_2$ | 2 | |
| II-8 | $CH_2$ | H | ONHCH$_3$ | $CH_2$ | 2 | |
| II-9 | $CH_2$ | H | NH$_2$ | $CH_2$ | 2 | 150-152 |
| II-10 | $CH_2$ | H | N(CH$_3$)$_2$ | $CH_2$ | 2 | |
| II-11 | $CH_2$ | H | N(Et)$_2$ | $CH_2$ | 2 | |
| II-12 | $CH_2$ | H | pyrrolidinyl | $CH_2$ | 2 | |
| II-13 | $CH_2$ | H | piperidinyl | $CH_2$ | 2 | |
| II-14 | $CH_2$ | H | morpholinyl | $CH_2$ | 2 | 185-186 |
| II-15 | $CH_2$ | H | NH-piperazinyl | $CH_2$ | 2 | |
| II-16 | $CH_2$ | H | NHNH$_2$ | $CH_2$ | 2 | |
| II-17 | $CH_2$ | H | NHCH$_2$CN | $CH_2$ | 2 | |
| II-18 | $CH_2$ | H | NHC(CH$_3$)$_2$CN | $CH_2$ | 2 | |
| II-19 | $CH_2$ | H | NHN(CH$_3$)$_2$ | $CH_2$ | 2 | |
| II-20 | $CH_2$ | H | N(CH$_3$)NH$_2$ | $CH_2$ | 2 | |
| II-21 | $CH_2$ | H | OCH$_3$ | $CH_2$ | 2 | 160-161 |
| II-22 | $CH_2$ | H | OEt | $CH_2$ | 2 | |
| II-23 | $CH_2$ | 3-CH$_3$ | OCH$_3$ | $CH_2$ | 2 | 155-156 |
| II-24 | $CH_2$ | H | O(CH$_2$)$_2$OCH$_3$ | $CH_2$ | 2 | |
| II-25 | $CH_2$ | H | OCH$_2$Ph | $CH_2$ | 2 | |
| II-26 | $CH_2$ | H | OCH$_2$-5-Py-2-Cl | $CH_2$ | 2 | |
| II-27 | $CH_2$ | H | N(CH$_3$)Ph | $CH_2$ | 2 | |
| II-28 | $CH_2$ | H | NHCH$_2$Ph | $CH_2$ | 2 | |
| II-29 | $CH_2$ | H | NHCH$_2$Ph-4-Cl | $CH_2$ | 2 | |
| II-30 | $CH_2$ | H | NHCH$_2$Ph-4-OH-3-OCH$_3$ | $CH_2$ | 2 | |
| II-31 | $CH_2$ | H | NHCH$_2$Ph-3,4-2OCH$_3$ | $CH_2$ | 2 | |
| II-32 | $CH_2$ | H | NHCH$_2$-5-Py-2-Cl | $CH_2$ | 2 | |
| II-33 | $CH_2$ | H | NH(CH$_2$)2Ph-4-Cl | $CH_2$ | 2 | |
| II-34 | $CH_2$ | H | NH(CH$_2$)2Ph-3,4-2OCH$_3$ | $CH_2$ | 2 | |
| II-35 | $CH_2$ | H | NN=C(CH$_3$)$_2$ | $CH_2$ | 2 | |
| II-36 | $CH_2$ | 3-CH$_3$ | NHCH$_3$ | $CH_2$ | 2 | 120-121 |
| II-37 | $CH_2$ | 3-CH$_3$-5-Cl | NHCH$_3$ | $CH_2$ | 2 | |
| II-38 | $CH_2$ | 3-CH$_3$-5-Br | NHCH$_3$ | $CH_2$ | 2 | 97-99 |
| II-39 | $CH_2$ | 3-CH$_3$-5-I | NHCH$_3$ | $CH_2$ | 2 | |
| II-40 | $CH_2$ | 3-CH$_3$-5-CN | NHCH$_3$ | $CH_2$ | 2 | 210-212 |
| II-41 | $CH_2$ | 3-CH$_3$-5-CONH$_2$ | NHCH$_3$ | $CH_2$ | 2 | |
| II-42 | $CH_2$ | 3-Cl | NHCH$_3$ | $CH_2$ | 2 | |
| II-43 | $CH_2$ | 3,5-2Cl | NHCH$_3$ | $CH_2$ | 2 | |
| II-44 | $CH_2$ | 3-Cl-5-Br | NHCH$_3$ | $CH_2$ | 2 | |
| II-45 | $CH_2$ | 3-Cl-5-CN | NHCH$_3$ | $CH_2$ | 2 | |
| II-46 | $CH_2$ | 3-Cl-5-CONH$_2$ | NHCH$_3$ | $CH_2$ | 2 | |
| II-47 | $CH_2$ | 3-F | NHCH$_3$ | $CH_2$ | 2 | |
| II-48 | $CH_2$ | 3-F-5-Cl | NHCH$_3$ | $CH_2$ | 2 | |

-continued

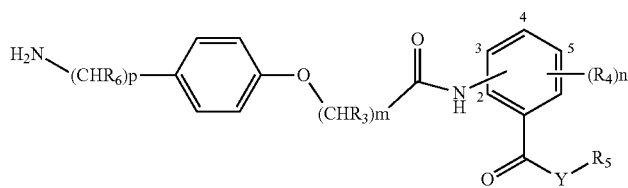

Wherein: $Q_1 = Q_2 = X_2 = X_3 = X_4 = X_5 = H$, $Z = O$, $(CHR_3)mCON(Q_2)$ links with phenyl ring at the 2, 3 or 4-position; when $(CHR_6)p = 0$, $Q_1$—NH is connected with phenyl ring directly.

| compound | $(CHR_3)m$ | $(R_4)n$ | Y—$R_5$ | $(CHR_6)p$ | $N(Q_2)$ bonding position | melting point (° C.) |
|---|---|---|---|---|---|---|
| II-49 | $CH_2$ | 3-F-5-Br | $NHCH_3$ | $CH_2$ | 2 | |
| II-50 | $CH_2$ | 3-F-5-CN | $NHCH_3$ | $CH_2$ | 2 | |
| II-51 | $CH_2$ | 5-F | $NHCH_3$ | $CH_2$ | 2 | 97-98 |
| II-52 | $CH(CH_3)$ | H | $NHCH_3$ | $CH_2$ | 2 | sticky liquid |
| II-53 | $CH(CH_3)$ | H | NHEt | $CH_2$ | 2 | |
| II-54 | $CH(CH_3)$ | H | NH-i-Pr | $CH_2$ | 2 | |
| II-55 | $CH(CH_3)$ | 3-$CH_3$ | $NHCH_3$ | $CH_2$ | 2 | |
| II-56 | $CH(CH_3)$ | 3-$CH_3$-5-Cl | $NHCH_3$ | $CH_2$ | 2 | |
| II-57 | $CH(CH_3)$ | 3-$CH_3$-5-Br | $NHCH_3$ | $CH_2$ | 2 | |
| II-58 | $CH(CH_3)$ | 3-$CH_3$-5-I | $NHCH_3$ | $CH_2$ | 2 | |
| II-59 | $CH(CH_3)$ | 3-$CH_3$-5-CN | $NHCH_3$ | $CH_2$ | 2 | |
| II-60 | $CH(CH_3)$ | 3-$CH_3$-5-$CONH_2$ | $NHCH_3$ | $CH_2$ | 2 | |
| II-61 | $CH(CH_3)$ | 3-Cl | $NHCH_3$ | $CH_2$ | 2 | |
| II-62 | $CH(CH_3)$ | 3,5-2Cl | $NHCH_3$ | $CH_2$ | 2 | |
| II-63 | $CH(CH_3)$ | 3-Cl-5-Br | $NHCH_3$ | $CH_2$ | 2 | |
| II-64 | $CH(CH_3)$ | 3-Cl-5-CN | $NHCH_3$ | $CH_2$ | 2 | |
| II-65 | $CH(CH_3)$ | 3-Cl-5-$CONH_2$ | $NHCH_3$ | $CH_2$ | 2 | |
| II-66 | $CH(CH_3)$ | 3-F | $NHCH_3$ | $CH_2$ | 2 | |
| II-67 | $CH(CH_3)$ | 3-F-5-Cl | $NHCH_3$ | $CH_2$ | 2 | |
| II-68 | $CH(CH_3)$ | 3-F-5-Br | $NHCH_3$ | $CH_2$ | 2 | |
| II-69 | $CH(CH_3)$ | 3-F-5-CN | $NHCH_3$ | $CH_2$ | 2 | |
| II-70 | $CH(CH_3)$ | 5-F | $NHCH_3$ | $CH_2$ | 2 | |
| II-71 | $(CH_2)_2$ | H | $NHCH_3$ | $CH_2$ | 2 | 89-90 |
| II-72 | $(CH_2)_2$ | H | NHEt | $CH_2$ | 2 | |
| II-73 | $(CH_2)_2$ | H | NH-i-Pr | $CH_2$ | 2 | |
| II-74 | $(CH_2)_2$ | 3-$CH_3$ | $NHCH_3$ | $CH_2$ | 2 | |
| II-75 | $(CH_2)_2$ | 3-$CH_3$-5-Cl | $NHCH_3$ | $CH_2$ | 2 | |
| II-76 | $(CH_2)_2$ | 3-$CH_3$-5-Br | $NHCH_3$ | $CH_2$ | 2 | |
| II-77 | $(CH_2)_2$ | 3-$CH_3$-5-I | $NHCH_3$ | $CH_2$ | 2 | |
| II-78 | $(CH_2)_2$ | 3-$CH_3$-5-CN | $NHCH_3$ | $CH_2$ | 2 | |
| II-79 | $(CH_2)_2$ | 3-$CH_3$-5-$CONH_2$ | $NHCH_3$ | $CH_2$ | 2 | |
| II-80 | $(CH_2)_2$ | 3-Cl | $NHCH_3$ | $CH_2$ | 2 | |
| II-81 | $(CH_2)_2$ | 3,5-2Cl | $NHCH_3$ | $CH_2$ | 2 | |
| II-82 | $(CH_2)_2$ | 3-Cl-5-Br | $NHCH_3$ | $CH_2$ | 2 | |
| II-83 | $(CH_2)_2$ | 3-Cl-5-CN | $NHCH_3$ | $CH_2$ | 2 | |
| II-84 | $(CH_2)_2$ | 3-Cl-5-$CONH_2$ | $NHCH_3$ | $CH_2$ | 2 | |
| II-85 | $(CH_2)_2$ | 3-F | $NHCH_3$ | $CH_2$ | 2 | |
| II-86 | $(CH_2)_2$ | 3-F-5-Cl | $NHCH_3$ | $CH_2$ | 2 | |
| II-87 | $(CH_2)_2$ | 3-F-5-Br | $NHCH_3$ | $CH_2$ | 2 | |
| II-88 | $(CH_2)_2$ | 3-F-5-CN | $NHCH_3$ | $CH_2$ | 2 | |
| II-89 | $(CH_2)_2$ | 5-F | $NHCH_3$ | $CH_2$ | 2 | |
| II-90 | $CH_2$ | H | $NHCH_3$ | $CH(CH_3)$ | 2 | |
| II-91 | $CH_2$ | H | NHEt | $CH(CH_3)$ | 2 | |
| II-92 | $CH_2$ | H | NH-i-Pr | $CH(CH_3)$ | 2 | |
| II-93 | $CH_2$ | 3-$CH_3$ | $NHCH_3$ | $CH(CH_3)$ | 2 | |
| II-94 | $CH_2$ | 3-$CH_3$-5-Cl | $NHCH_3$ | $CH(CH_3)$ | 2 | |
| II-95 | $CH_2$ | 3-$CH_3$-5-Br | $NHCH_3$ | $CH(CH_3)$ | 2 | |
| II-96 | $CH_2$ | 3-$CH_3$-5-I | $NHCH_3$ | $CH(CH_3)$ | 2 | |
| II-97 | $CH_2$ | 3-$CH_3$-5-CN | $NHCH_3$ | $CH(CH_3)$ | 2 | |
| II-98 | $CH_2$ | 3-Cl | $NHCH_3$ | $CH(CH_3)$ | 2 | |
| II-99 | $CH_2$ | 3,5-2Cl | $NHCH_3$ | $CH(CH_3)$ | 2 | |
| II-100 | $CH_2$ | 3-Cl-5-Br | $NHCH_3$ | $CH(CH_3)$ | 2 | |
| II-101 | $CH_2$ | 3-Cl-5-CN | $NHCH_3$ | $CH(CH_3)$ | 2 | |
| II-102 | $CH_2$ | 3-F | $NHCH_3$ | $CH(CH_3)$ | 2 | |
| II-103 | $CH_2$ | 3-F-5-Cl | $NHCH_3$ | $CH(CH_3)$ | 2 | |
| II-104 | $CH_2$ | 3-F-5-Br | $NHCH_3$ | $CH(CH_3)$ | 2 | |
| II-105 | $CH_2$ | 3-F-5-CN | $NHCH_3$ | $CH(CH_3)$ | 2 | |
| II-106 | $CH_2$ | 5-F | $NHCH_3$ | $CH(CH_3)$ | 2 | |
| II-107 | $CH(CH_3)$ | H | $NHCH_3$ | $CH(CH_3)$ | 2 | |
| II-108 | $CH(CH_3)$ | H | NHEt | $CH(CH_3)$ | 2 | |
| II-109 | $CH(CH_3)$ | H | NH-i-Pr | $CH(CH_3)$ | 2 | |
| II-110 | $CH(CH_3)$ | 3-$CH_3$ | $NHCH_3$ | $CH(CH_3)$ | 2 | |
| II-111 | $CH(CH_3)$ | 3-$CH_3$-5-Cl | $NHCH_3$ | $CH(CH_3)$ | 2 | |

-continued

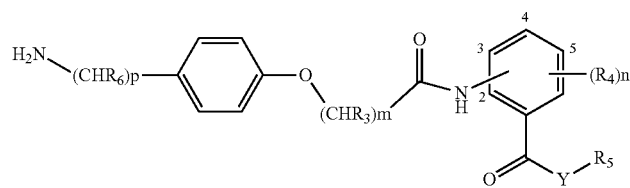

Wherein: $Q_1 = Q_2 = X_2 = X_3 = X_4 = X_5 = H$, $Z = O$, $(CHR_3)mCON(Q_2)$ links with phenyl ring at the 2, 3 or 4-position; when $(CHR_6)p = 0$, $Q_1$—NH is connected with phenyl ring directly.

| compound | $(CHR_3)m$ | $(R_4)n$ | Y—$R_5$ | $(CHR_6)p$ | $N(Q_2)$ bonding position | melting point (° C.) |
|---|---|---|---|---|---|---|
| II-112 | $CH(CH_3)$ | 3-$CH_3$-5-Br | $NHCH_3$ | $CH(CH_3)$ | 2 | |
| II-113 | $CH(CH_3)$ | 3-$CH_3$-5-I | $NHCH_3$ | $CH(CH_3)$ | 2 | |
| II-114 | $CH(CH_3)$ | 3-$CH_3$-5-CN | $NHCH_3$ | $CH(CH_3)$ | 2 | |
| II-115 | $CH(CH_3)$ | 3-Cl | $NHCH_3$ | $CH(CH_3)$ | 2 | |
| II-116 | $CH(CH_3)$ | 3,5-2Cl | $NHCH_3$ | $CH(CH_3)$ | 2 | |
| II-117 | $CH(CH_3)$ | 3-Cl-5-Br | $NHCH_3$ | $CH(CH_3)$ | 2 | |
| II-118 | $CH(CH_3)$ | 3-Cl-5-CN | $NHCH_3$ | $CH(CH_3)$ | 2 | |
| II-119 | $CH(CH_3)$ | 3-F | $NHCH_3$ | $CH(CH_3)$ | 2 | |
| II-120 | $CH(CH_3)$ | 3-F-5-Cl | $NHCH_3$ | $CH(CH_3)$ | 2 | |
| II-121 | $CH(CH_3)$ | 3-F-5-Br | $NHCH_3$ | $CH(CH_3)$ | 2 | |
| II-122 | $CH(CH_3)$ | 3-F-5-CN | $NHCH_3$ | $CH(CH_3)$ | 2 | |
| II-123 | $CH(CH_3)$ | 5-F | $NHCH_3$ | $CH(CH_3)$ | 2 | |
| II-124 | $(CH_2)_2$ | H | $NHCH_3$ | $CH(CH_3)$ | 2 | |
| II-125 | $(CH_2)_2$ | H | NHEt | $CH(CH_3)$ | 2 | |
| II-126 | $(CH_2)_2$ | H | NH-i-Pr | $CH(CH_3)$ | 2 | |
| II-127 | $(CH_2)_2$ | 3-$CH_3$ | $NHCH_3$ | $CH(CH_3)$ | 2 | |
| II-128 | $(CH_2)_2$ | 3-$CH_3$-5-Cl | $NHCH_3$ | $CH(CH_3)$ | 2 | |
| II-129 | $(CH_2)_2$ | 3-$CH_3$-5-Br | $NHCH_3$ | $CH(CH_3)$ | 2 | |
| II-130 | $(CH_2)_2$ | 3-$CH_3$-5-I | $NHCH_3$ | $CH(CH3)$ | 2 | |
| II-131 | $(CH_2)_2$ | 3-$CH_3$-5-CN | $NHCH_3$ | $CH(CH_3)$ | 2 | |
| II-132 | $(CH_2)_2$ | 3-$CH_3$-5-$CONH_2$ | $NHCH_3$ | $CH(CH_3)$ | 2 | |
| II-133 | $(CH_2)_2$ | 3-Cl | $NHCH_3$ | $CH(CH_3)$ | 2 | |
| II-134 | $(CH_2)_2$ | 3,5-2Cl | $NHCH_3$ | $CH(CH_3)$ | 2 | |
| II-135 | $(CH_2)_2$ | 3-Cl-5-Br | $NHCH_3$ | $CH(CH_3)$ | 2 | |
| II-136 | $(CH_2)_2$ | 3-Cl-5-CN | $NHCH_3$ | $CH(CH_3)$ | 2 | |
| II-137 | $(CH_2)_2$ | 3-Cl-5-$CONH_2$ | $NHCH_3$ | $CH(CH_3)$ | 2 | |
| II-138 | $(CH_2)_2$ | 3-F | $NHCH_3$ | $CH(CH_3)$ | 2 | |
| II-139 | $(CH_2)_2$ | 3-F-5-Cl | $NHCH_3$ | $CH(CH_3)$ | 2 | |
| II-140 | $(CH_2)_2$ | 3-F-5-Br | $NHCH_3$ | $CH(CH_3)$ | 2 | |
| II-141 | $(CH_2)_2$ | 3-F-5-CN | $NHCH_3$ | $CH(CH_3)$ | 2 | |
| II-142 | $(CH_2)_2$ | 5-F | $NHCH_3$ | $CH(CH_3)$ | 2 | |
| II-143 | $CH_2$ | H | $NHCH_3$ | CH(CN) | 2 | |
| II-144 | $(CH_2)_2$ | H | $NHCH_3$ | CH(CN) | 2 | |
| II-145 | $CH(CH_3)$ | H | $NHCH_3$ | CH(CN) | 2 | |
| II-146 | $CH_2$ | H | $NHCH_3$ | $(CH_2)$ | 2 | |
| II-147 | $CH(CH_3)$ | H | $NHCH_3$ | $(CH_2)$ | 2 | |
| II-148 | $(CH_2)_2$ | H | $NHCH_3$ | $(CH_2)$ | 2 | |
| II-149 | $CH_2$ | 3-$CH_3$ | $NHCH_3$ | $(CH_2)$ | 2 | |
| II-150 | $CH_2$ | 3-$CH_3$-5-Cl | $NHCH_3$ | $(CH_2)$ | 2 | |
| II-151 | $CH_2$ | 3-$CH_3$-5-Br | $NHCH_3$ | $(CH_2)$ | 2 | |
| II-152 | $CH_2$ | 3-$CH_3$-5-I | $NHCH_3$ | $(CH_2)$ | 2 | |
| II-153 | $CH_2$ | 3-$CH_3$-5-CN | $NHCH_3$ | $(CH_2)$ | 2 | |
| II-154 | $CH_2$ | 3-$CH_3$-5-$CONH_2$ | $NHCH_3$ | $(CH_2)$ | 2 | |
| II-155 | $CH_2$ | 3-Cl | $NHCH_3$ | $(CH_2)$ | 2 | |
| II-156 | $CH_2$ | 3,5-2Cl | $NHCH_3$ | $(CH_2)$ | 2 | |
| II-157 | $CH_2$ | 3-Cl-5-Br | $NHCH_3$ | $(CH_2)$ | 2 | |
| II-158 | $CH_2$ | 3-Cl-5-CN | $NHCH_3$ | $(CH_2)$ | 2 | |
| II-159 | $CH_2$ | 3-Cl-5-$CONH_2$ | $NHCH_3$ | $(CH_2)$ | 2 | |
| II-160 | $CH_2$ | 3-F | $NHCH_3$ | $(CH_2)$ | 2 | |
| II-161 | $CH_2$ | 3-F-5-Cl | $NHCH_3$ | $(CH_2)$ | 2 | |
| II-162 | $CH_2$ | 3-F-5-Br | $NHCH_3$ | $(CH_2)$ | 2 | |
| II-163 | $CH_2$ | 3-F-5-CN | $NHCH_3$ | $(CH_2)$ | 2 | |
| II-164 | $CH_2$ | 5-F | $NHCH_3$ | $(CH_2)$ | 2 | |
| II-165 | $CH_2$ | H | $NHCH_3$ | $CH_2$ | 3 | |
| II-166 | $CH_2$ | H | $NHCH_3$ | $CH_2$ | 3 | |
| II-167 | $CH_2$ | H | NHEt | $CH_2$ | 3 | |
| II-168 | $CH_2$ | H | NH-i-Pr | $CH_2$ | 3 | |
| II-169 | $CH_2$ | H | $OCH_3$ | $CH_2$ | 4 | |
| II-170 | $CH_2$ | H | $NHCH_3$ | $CH_2$ | 4 | |
| II-171 | $CH_2$ | H | NHEt | $CH_2$ | 4 | |

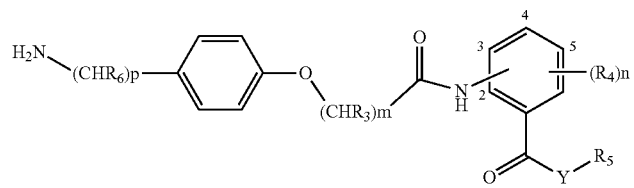

Wherein: $Q_1 = Q_2 = X_2 = X_3 = X_4 = X_5 = H$, $Z = O$, $(CHR_3)mCON(Q_2)$ links with phenyl ring at the 2, 3 or 4-position; when $(CHR_6)p = 0$, $Q_1$—NH is connected with phenyl ring directly.

| compound | $(CHR_3)m$ | $(R_4)n$ | Y—$R_5$ | $(CHR_6)p$ | $N(Q_2)$ bonding position | melting point (° C.) |
|---|---|---|---|---|---|---|
| II-172 | $CH_2$ | H | NH-i-Pr | $CH_2$ | 4 | |
| II-173 | $CH_2$ | H | $NHCH_3$ | — | 2 | 239-240 (hydrochloride) |
| II-174 | $CH(CH_3)$ | H | $NHCH_3$ | — | 2 | |
| II-175 | $(CH_2)_2$ | H | $NHCH_3$ | — | 2 | |
| II-176 | $CH_2$ | H | OCH3 | — | 2 | |
| II-177 | $CH_2$ | H | OEt | — | 2 | |
| II-178 | $CH_2$ | H | o-i-Pr | — | 2 | |
| II-179 | $CH_2$ | H | NHEt | — | 2 | |
| II-180 | $CH_2$ | $3\text{-}CH_3$ | $NHCH_3$ | — | 2 | |
| II-181 | $CH_2$ | $3\text{-}CH_3\text{-}5\text{-}Cl$ | $NHCH_3$ | — | 2 | |
| II-182 | $CH_2$ | $3\text{-}CH_3\text{-}5\text{-}Br$ | $NHCH_3$ | — | 2 | |
| II-183 | $CH_2$ | $3\text{-}CH_3\text{-}5\text{-}I$ | $NHCH_3$ | — | 2 | |
| II-184 | $CH_2$ | $3\text{-}CH_3\text{-}5\text{-}CN$ | $NHCH_3$ | — | 2 | |
| II-185 | $CH_2$ | $3\text{-}CH_3\text{-}5\text{-}CONH_2$ | $NHCH_3$ | — | 2 | |
| II-186 | $CH_2$ | 3-Cl | $NHCH_3$ | — | 2 | |
| II-187 | $CH_2$ | H | OEt | $CH_2$ | 4 | 138-139 |

"—" represents p = 0, namely chemical bond, means two groups were connected directly.

$^1$HNMR spectrum ($^1$HNMR, 300 MHz, internal standard: TMS, solvent CDCl$_3$) of some intermediates(II) in table 9A are shown as follows:

II-1: δppm 3.73(3H, d), 3.81(2H, t), 5.18(2H, s), 7.02(2H, d), 7.24-7.27(3H, m), 7.51-7.52(1H, m), 7.72-7.77(2H, m), 8.28-8.31(1H, s).

II-14: δppm 3.47(8H, s), 3.96(2H, s), 4.68(2H, d), 7.02(2H, d), 7.20(1H, t), 7.29-7.32(1H, m), 7.90(1H, d), 8.39(1H, m), 9.96(1H, s).

II-38: δppm 3.25(3H, s), 3.60(3H, s), 3.66(2H, s), 5.22(2H, s), 6.99(2H, d), 7.23(2H, d), 7.77(1H, s), 8.03(1H, s).

II-40: δppm 2.62(3H, s), 3.74(3H, s), 3.82(2H, s), 5.21(2H, s), 7.03(2H, d), 7.76(1H, s), 8.45(1H, s).

II-52: δppm 1.57(3H, d), 1.80-1.84(1H, m), 3.73(3H, d), 5.18-5.23(2H, m), 7.00(1H, d), 7.06-7.09(2H, m), 7.24-7.31(2H, m), 7.50-7.54 (1H, m), 7.71-7.75(2H, m), 8.26-8.30(1H, m).

II-173: δppm 3.82(3H, s), 5.31(2H, s), 7.18(2H, d), 7.38(2H, d), 7.53(1H, t), 7.70-7.79 (2H, m), 8.13-8.16(1H, m), 10.43(3H, s).

II-187: δppm 1.39(3H, t), 1.95-1.99(2H, m), 4.37(2H, t), 4.59(2H, s), 6.84(2H, d), 7.21(2H, d), 7.69(2H, d), 8.02(1H, s), 8.58(1H, s).

TABLE 9B

Some of intermediates of general formula (II)

Wherein: $X_2 = X_4 = R_3 = H$, $Z = O$, $m = 1$, $n = 0$ namely $(R_4)n = H$, $(CHR_3)mCON(Q_2)$ links with phenyl ring at the 2-position;

| compound | $Q_1$ | $Q_2$ | $X_3$ | $X_5$ | Y—$R_5$ | $(CHR_6)p$ |
|---|---|---|---|---|---|---|
| II-188 | H | H | H | Cl | $NHCH_3$ | $CH_2$ |
| II-189 | H | H | H | Cl | NHEt | $CH_2$ |
| II-190 | H | H | H | Cl | NH-i-Pr | $CH_2$ |
| II-191 | H | H | H | Cl | NH-t-Bu | $CH_2$ |
| II-192 | H | H | H | Cl | NHOH | $CH_2$ |
| II-193 | H | H | H | Cl | $NHOCH_3$ | $CH_2$ |
| II-194 | H | H | H | Cl | NHOEt | $CH_2$ |
| II-195 | H | H | H | Cl | $ONHCH_3$ | $CH_2$ |
| II-196 | H | H | H | Cl | $NH_2$ | $CH_2$ |
| II-197 | H | H | H | Cl | $N(CH_3)_2$ | $CH_2$ |
| II-198 | H | H | H | Cl | $N(Et)_2$ | $CH_2$ |
| II-199 | H | H | H | Cl | pyrrolidinyl | $CH_2$ |
| II-200 | H | H | H | Cl | piperidinyl | $CH_2$ |
| II-201 | H | H | H | Cl | morpholinyl | $CH_2$ |

Wherein: $X_2 = X_4 = R_3 = H$, $Z = O$, $m = 1$, $n = 0$ namely $(R_4)n = H$, $(CHR_3)mCON(Q_2)$ links with phenyl ring at the 2-position;

TABLE 9B-continued

Some of intermediates of general formula (II)

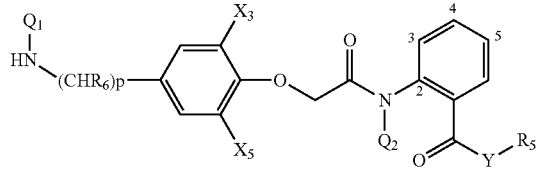

Wherein: $X_2 = X_4 = R_3 = H$, $Z = O$, $m = 1$, $n = 0$ namely $(R_4)n = H$, $(CHR_3)mCON(Q_2)$ links with phenyl ring at the 2-position;

| compound | $Q_1$ | $Q_2$ | $X_3$ | $X_5$ | Y—$R_5$ | $(CHR_6)p$ |
|---|---|---|---|---|---|---|
| II-202 | H | H | H | Cl | 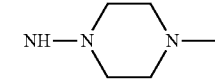 | $CH_2$ |
| II-203 | H | H | H | Cl | $NHNH_2$ | $CH_2$ |
| II-204 | H | H | H | Cl | $NHCH_2CN$ | $CH_2$ |
| II-205 | H | H | H | Cl | $NHC(CH_3)_2CN$ | $CH_2$ |
| II-206 | H | H | H | Cl | $NHN(CH_3)_2$ | $CH_2$ |
| II-207 | H | H | H | Cl | $N(CH_3)NH_2$ | $CH_2$ |
| II-208 | H | H | H | Cl | $OCH_3$ | $CH_2$ |
| II-209 | H | H | H | Cl | OEt | $CH_2$ |
| II-210 | H | H | H | Cl | O-i-Pr | $CH_2$ |
| II-211 | H | H | H | Cl | $O(CH_2)_2OCH_3$ | $CH_2$ |
| II-212 | H | H | H | Cl | $OCH_2Ph$ | $CH_2$ |
| II-213 | H | H | H | Cl | $OCH_2$-5-Py-2-Cl | $CH_2$ |
| II-214 | H | H | H | Cl | $N(CH_3)Ph$ | $CH_2$ |
| II-215 | H | H | H | Cl | $NHCH_2Ph$ | $CH_2$ |
| II-216 | H | H | H | Cl | $NHCH_2Ph$-4-Cl | $CH_2$ |
| II-217 | H | H | H | Cl | $NHCH_2Ph$-4-OH-3-$OCH_3$ | $CH_2$ |
| II-218 | H | H | H | Cl | $NHCH_2Ph$-3,4-$2OCH_3$ | $CH_2$ |
| II-219 | H | H | H | Cl | $NHCH_2$-5-Py-2-Cl | $CH_2$ |
| II-220 | H | H | H | Cl | $NH(CH_2)2Ph$-4-Cl | $CH_2$ |
| II-221 | H | H | H | Cl | $NH(CH_2)2Ph$-3,4-$2OCH_3$ | $CH_2$ |
| II-222 | H | H | H | Cl | $NN=C(CH_3)_2$ | $CH_2$ |
| II-223 | H | H | H | Br | $NHCH_3$ | $CH_2$ |
| II-224 | H | H | H | Br | NHEt | $CH_2$ |
| II-225 | H | H | H | Br | NH-i-Pr | $CH_2$ |
| II-226 | H | H | H | OEt | $NHCH_3$ | $CH_2$ |
| II-227 | H | H | H | OEt | NHEt | $CH_2$ |
| II-228 | H | H | H | OEt | NH-i-Pr | $CH_2$ |
| II-229 | H | H | H | OEt | $NHCH_3$ | $CH_2$ |
| II-230 | H | H | H | OEt | NHEt | $CH_2$ |
| II-231 | H | H | H | OEt | NH-i-Pr | $CH_2$ |
| II-232 | H | H | Cl | Cl | $NHCH_3$ | $CH_2$ |
| II-233 | H | H | Cl | Cl | NHEt | $CH_2$ |
| II-234 | H | H | Cl | Cl | NH-i-Pr | $CH_2$ |

TABLE 9B-continued

Some of intermediates of general formula (II)

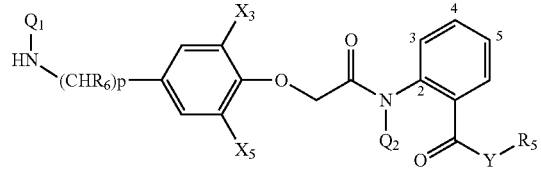

Wherein: $X_2 = X_4 = R_3 = H$, $Z = O$, $m = 1$, $n = 0$ namely $(R_4)n = H$, $(CHR_3)mCON(Q_2)$ links with phenyl ring at the 2-position;

| compound | $Q_1$ | $Q_2$ | $X_3$ | $X_5$ | Y—$R_5$ | $(CHR_6)p$ |
|---|---|---|---|---|---|---|
| II-235 | H | H | Cl | Br | $NHCH_3$ | $CH_2$ |
| II-236 | H | H | Cl | Br | NHEt | $CH_2$ |
| II-237 | H | H | Cl | Br | NH-i-Pr | $CH_2$ |
| II-238 | H | H | Cl | $OCH_3$ | NHCH3 | $CH_2$ |
| II-239 | H | H | Cl | $OCH_3$ | NHEt | $CH_2$ |
| II-240 | H | H | Cl | $OCH_3$ | NH-i-Pr | $CH_2$ |
| II-241 | H | H | H | Cl | $NHCH_3$ | $CH(CH_3)$ |
| II-242 | H | H | H | Br | $NHCH_3$ | $CH(CH_3)$ |
| II-243 | H | H | H | $OCH_3$ | $NHCH_3$ | $CH(CH_3)$ |
| II-244 | H | H | Cl | Cl | $NHCH_3$ | $CH(CH_3)$ |
| II-245 | H | H | Cl | Br | $NHCH_3$ | $CH(CH_3)$ |
| II-246 | H | H | Cl | $OCH_3$ | $NHCH_3$ | $CH(CH_3)$ |
| II-247 | H | H | H | Cl | $NHCH_3$ | CH(CN) |
| II-248 | H | H | H | Br | $NHCH_3$ | CH(CN) |
| II-249 | H | H | H | $OCH_3$ | $NHCH_3$ | CH(CN) |
| II-250 | H | H | Cl | Cl | $NHCH_3$ | CH(CN) |
| II-251 | H | H | Cl | Br | $NHCH_3$ | CH(CN) |
| II-252 | H | H | Cl | $OCH_3$ | $NHCH_3$ | CH(CN) |
| II-253 | H | H | H | Cl | $NHCH_3$ | $CH_2CH_2$ |
| II-254 | H | H | H | Br | $NHCH_3$ | $CH_2CH_2$ |
| II-255 | H | H | H | $OCH_3$ | $NHCH_3$ | $CH_2CH_2$ |
| II-256 | H | H | Cl | Cl | $NHCH_3$ | $CH_2CH_2$ |
| II-257 | H | H | Cl | Br | $NHCH_3$ | $CH_2CH_2$ |
| II-258 | H | H | Cl | $OCH_3$ | $NHCH_3$ | $CH_2CH_2$ |
| II-259 | CN | H | H | Cl | $NHCH_3$ | $CH_2$ |
| II-260 | CN | H | H | Br | $NHCH_3$ | $CH_2$ |
| II-261 | CN | H | H | $OCH_3$ | $NHCH_3$ | $CH_2$ |
| II-262 | CN | H | Cl | Cl | $NHCH_3$ | $CH_2$ |
| II-263 | CN | H | Cl | Br | $NHCH_3$ | $CH_2$ |
| II-264 | CN | H | Cl | $OCH_3$ | $NHCH_3$ | $CH_2$ |
| II-265 | H | $CH_3$ | H | Cl | $NHCH_3$ | $CH_2$ |
| II-266 | H | $CH_3$ | H | Br | $NHCH_3$ | $CH_2$ |
| II-267 | H | $CH_3$ | H | $OCH_3$ | $NHCH_3$ | $CH_2$ |
| II-268 | H | $CH_3$ | Cl | Cl | $NHCH_3$ | $CH_2$ |
| II-269 | H | $CH_3$ | Cl | Br | $NHCH_3$ | $CH_2$ |
| II-270 | H | $CH_3$ | Cl | $OCH_3$ | $NHCH_3$ | $CH_2$ |

Some of intermediates (VI) are presented in table 10.

TABLE 10

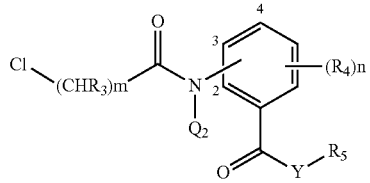

In formula (VI), L = Cl, Z = O, $(CHR_3)mCON(Q_2)$ links with phenyl ring at the 2, 3 or 4-position;

| compound | $(CHR_3)m$ | $Q_2$ | $(R_4)n$ | Y—$R_5$ | $N(Q_2)$ Bonding position | melting point (° C.) |
|---|---|---|---|---|---|---|
| VI-1 | $CH_2$ | H | H | $NHCH_3$ | 2 | 155-157 |
| VI-2 | $CH_2$ | H | H | NHEt | 2 | |
| VI-3 | $CH_2$ | H | H | NH-i-Pr | 2 | |
| VI-4 | $CH_2$ | H | H | NH-t-Bu | 2 | |

TABLE 10-continued

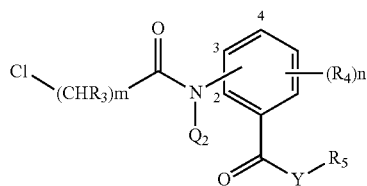

In formula (VI), L = Cl, Z = O, (CHR₃)mCON(Q₂) links with phenyl ring at the 2, 3 or 4-position;

| compound | (CHR₃)m | Q₂ | (R₄)n | Y—R₅ | N(Q₂) Bonding position | melting point (° C.) |
|---|---|---|---|---|---|---|
| VI-5 | CH₂ | H | H | NHOH | 2 | |
| VI-6 | CH₂ | H | H | NHOCH₃ | 2 | |
| VI-7 | CH₂ | H | H | NHOEt | 2 | |
| VI-8 | CH₂ | H | H | ONHCH₃ | 2 | |
| VI-9 | CH₂ | H | H | NH₂ | 2 | 175-176 |
| VI-10 | CH₂ | H | H | N(CH₃)₂ | 2 | 115-116 |
| VI-11 | CH₂ | H | H | N(Et)₂ | 2 | |
| VI-12 | CH₂ | H | H | pyrrolidinyl | 2 | |
| VI-13 | CH₂ | H | H | piperidinyl | 2 | |
| VI-14 | CH₂ | H | H | morpholinyl | 2 | |
| VI-15 | CH₂ | H | H | NH—piperazinyl | 2 | |
| VI-16 | CH₂ | H | H | NHNH₂ | 2 | |
| VI-17 | CH₂ | H | H | NHNHCH₃ | 2 | |
| VI-18 | CH₂ | H | H | NHN(CH₃)₂ | 2 | |
| VI-19 | CH₂ | H | H | N(CH₃)NH₂ | 2 | |
| VI-20 | CH₂ | H | H | OCH₃ | 2 | 92-94 |
| VI-21 | CH₂ | H | H | OEt | 2 | |
| VI-22 | CH₂ | H | H | O-i-Pr | 2 | |
| VI-23 | CH₂ | H | H | O(CH₂)₂OCH₃ | 2 | |
| VI-24 | CH₂ | H | H | OCH₂Ph | 2 | |
| VI-25 | CH₂ | H | H | OCH₂-5-Py-2-Cl | 2 | |
| VI-26 | CH₂ | H | H | N(CH₃)Ph | 2 | |
| VI-27 | CH₂ | H | H | NHCH₂Ph | 2 | |
| VI-28 | CH₂ | H | H | NHCH₂Ph-4-Cl | 2 | |
| VI-29 | CH₂ | H | H | NHCH₂Ph-4-OH-3-OCH₃ | 2 | |
| VI-30 | CH₂ | H | H | NHCH₂Ph-3,4-2OCH₃ | 2 | |
| VI-31 | CH₂ | H | H | NHCH₂-5-Py-2-Cl | 2 | |
| VI-32 | CH₂ | H | H | NH(CH₂)2Ph-4-Cl | 2 | |
| VI-33 | CH₂ | H | H | NH(CH₂)2Ph-3,4-2OCH₃ | 2 | |
| VI-34 | CH₂ | H | H | NN=C(CH₃)2 | 2 | |
| VI-33 | CH₂ | H | H | NHCH₂CN | 2 | |
| VI-34 | CH₂ | H | H | NHC(CH₃)₂CN | 2 | |
| VI-35 | CH₂ | H | 3-CH₃ | NHCH₃ | 2 | 195-196 |
| VI-36 | CH₂ | H | 3-CH₃-5-Cl | NHCH₃ | 2 | >250 |
| VI-37 | CH₂ | H | 3-CH₃-5-Br | NHCH₃ | 2 | 201-202 |
| VI-38 | CH₂ | H | 3-CH₃-5-I | NHCH₃ | 2 | |
| VI-39 | CH₂ | H | 3-CH₃-5-CN | NHCH₃ | 2 | 221-222 |
| VI-40 | CH₂ | H | 3-CH₃-5-CONH₂ | NHCH₃ | 2 | |
| VI-41 | CH₂ | H | 3-Cl | NHCH₃ | 2 | |
| VI-42 | CH₂ | H | 3,5-2Cl | NHCH₃ | 2 | |
| VI-43 | CH₂ | H | 3-Cl-5-Br | NHCH₃ | 2 | |
| VI-44 | CH₂ | H | 3-Cl-5-CN | NHCH₃ | 2 | |
| VI-45 | CH₂ | H | 3-Cl-5-CONH₂ | NHCH₃ | 2 | |
| VI-46 | CH₂ | H | 3-F | NHCH₃ | 2 | |
| VI-47 | CH₂ | H | 3-F-5-Cl | NHCH₃ | 2 | |
| VI-48 | CH₂ | H | 3-F-5-Br | NHCH₃ | 2 | |

TABLE 10-continued

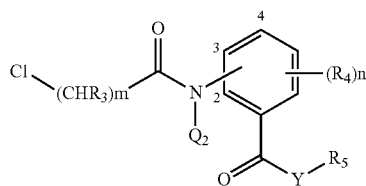

In formula (VI), L = Cl, Z = O, (CHR₃)mCON(Q₂) links with phenyl ring at the 2, 3 or 4-position;

| compound | (CHR₃)m | Q₂ | (R₄)n | Y—R₅ | N(Q₂) Bonding position | melting point (° C.) |
|---|---|---|---|---|---|---|
| VI-49 | CH₂ | H | 3-F-5-CN | NHCH₃ | 2 | |
| VI-50 | CH₂ | H | 5-F | NHCH₃ | 2 | |
| VI-51 | CH₂ | CH₃ | H | NHCH₃ | 2 | |
| VI-52 | CH₂ | CH₃ | H | OCH₃ | 2 | |
| VI-53 | CH₂ | CH₃ | H | OEt | 2 | |
| VI-54 | CH(CH₃) | H | H | NHCH₃ | 2 | 121-122 |
| VI-56 | CH(CH₃) | H | H | OCH₃ | 2 | 63-65° C. |
| VI-57 | CH(CH₃) | H | H | OEt | 2 | |
| VI-58 | CH(CH₃) | CH₃ | H | NHCH₃ | 2 | |
| VI-59 | CH(CH₃) | CH₃ | H | OCH₃ | 2 | |
| VI-60 | (CH₂)₂ | H | H | NHCH₃ | 2 | |
| VI-61 | (CH₂)₂ | H | H | OCH₃ | 2 | |
| VI-62 | CH₂ | H | H | NHCH₃ | 3 | 190-191 |
| VI-63 | CH₂ | H | H | OCH₃ | 3 | |
| VI-64 | CH(CH₃) | H | H | NHCH₃ | 3 | |
| VI-65 | CH(CH₃) | H | H | OCH₃ | 3 | |
| VI-66 | (CH₂)₂ | H | H | NHCH₃ | 3 | |
| VI-67 | (CH₂)₂ | H | H | OCH₃ | 3 | |
| VI-68 | CH₂ | H | H | NHCH₃ | 4 | |
| VI-69 | CH₂ | H | H | OCH₃ | 4 | |
| VI-70 | CH(CH₃) | H | H | NHCH₃ | 4 | |
| VI-71 | CH(CH₃) | H | H | OCH₃ | 4 | |
| VI-72 | (CH2)₂ | H | H | NHCH₃ | 4 | |
| VI-73 | (CH₂)₂ | H | H | OCH₃ | 4 | |
| VI-74 | (CH₂)₃ | H | H | NHCH₃ | 2 | 98-99 |
| VI-75 | CH₂ | H | H | OEt | 4 | 106-107 |
| VI-76 | CH₂ | H | 5-Cl | OCH₃ | 2 | 217-218 |
| VI-77 | CH₂ | H | 3-CH₃ | NHEt | 2 | 119-120 |
| VI-78 | CH₂ | H | 3-CH₃ | N(CH₃)₂ | 2 | 209-210 |
| VI-79 | CH₃ | H | H | OEt | 2 | 150-152 |

¹HNMR spectrum (¹HNMR, 300 MHz, internal standard: TMS, solvent CDCl₃) of some intermediates(VI) in table 10 are shown as follows:
VI-1: δppm 3.02(3H, s), 4.18(2H, s), 6.36(1H, s), 7.11-7.16(1H, m), 7.47-7.52(2H, m), 8.57(1H, d), 11.91(1H, s).
VI-35: δppm 2.36(3H, s), 2.94(3H, d), 4.17(2H, s), 6.21(1H, s), 7.16-7.21(1H, m), 7.27-7.35(1H, m), 9.69(1H, s).
VI-37: δppm 2.16(3H, s), 2.70(3H, d), 4.23(2H, s), 7.45(1H, d), 7.56-7.57(1H, d), 8.25(1H, d), 9.86(1H, s).
VI-39: δppm 2.26(3H, s), 2.74(3H, d), 4.26(2H, s), 7.31(1H, s), 7.82(1H, s), 8.37(1H, d), 10.16(1H, s).
VI-56: δppm 1.83(3H, d), 3.96(3H, s), 4.50-4.61(1H, m), 7.14(1H, t), 7.53-7.60(1H, m), 8.03-8.09(1H, m), 8.70(1H, d), 11.81(1H, s).
VI-62: δppm 3.02(3H, d), 4.21(2H, s), 6.19(1H, s), 7.42(1H, t), 7.55(1H, d), 7.74(1H, d), 7.96(1H, s), 8.36(1H, s).
VI-75: δppm 1.39(3H, t), 4.22(2H, s), 4.36-4.38(2H,m), 7.65(2H, d), 8.04(2H, d), 8.40(1H, s).
VI-79: δppm 1.40(3H, t), 4.22(2H, s), 4.36-4.43(2H,m), 7.45(1H, t), 7.86(1H, d), 7.95(1H, d), 8.04-8.05(1H, m), 8.39(1H, s).

Some of intermediates (VIII) are presented in table 11.

TABLE 11

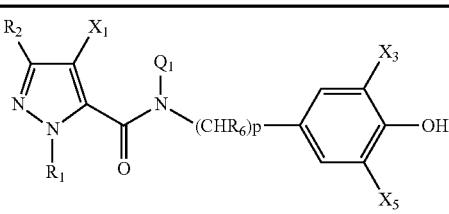

| compound | R₁ | R₂ | X₁ | Q₁ | X₃ | X₅ | (CHR₆)p | physical property/° C. |
|---|---|---|---|---|---|---|---|---|
| VIII-1 | CH₃ | CH₃ | Cl | H | H | H | CH₂ | 131-133 |
| VIII-2 | CH₃ | Et | Cl | H | H | H | CH₂ | 167-168 |

TABLE 11-continued

| compound | R₁ | R₂ | X₁ | Q₁ | X₃ | X₅ | (CHR₆)p | physical property/° C. |
|---|---|---|---|---|---|---|---|---|
| VIII-3 | CH₃ | n-Pr | Cl | H | H | H | CH₂ | |
| VIII-4 | CH₃ | i-Pr | Cl | H | H | H | CH₂ | |
| VIII-5 | CH₃ | t-Bu | Cl | H | H | H | CH₂ | |
| VIII-6 | CH₃ | ▷ | Cl | H | H | H | CH₂ | |
| VIII-7 | CH₃ | CF₃ | C | H | H | H | CH₂ | |
| VIII-8 | CH₃ | CH₂OCH₃ | Cl | H | H | H | CH₂ | |
| VIII-9 | CH₃ | CH₂OCH₂CF₃ | Cl | H | H | H | CH₂ | |
| VIII-10 | CH₃ | CH₂Cl | Cl | H | H | H | CH₂ | |
| VIII-11 | CH₃ | CH₂CN | Cl | H | H | H | CH₂ | |
| VIII-12 | CH₃ | Cl | Cl | H | H | H | CH₂ | |
| VIII-13 | CH₃ | Br | Cl | H | H | H | CH₂ | |
| VIII-14 | CH₃ | OCF₃ | Cl | H | H | H | CH₂ | |
| VIII-15 | CH₃ | OCH₂CF₃ | Cl | H | H | H | CH₂ | |
| VIII-16 | CH₃ | OCH₂CN | Cl | H | H | H | CH₂ | |
| VIII-17 | CH₃ | Ph | Cl | H | H | H | CH₂ | |
| VIII-18 | CH₃ | Ph-4-Cl | Cl | H | H | H | CH₂ | |
| VIII-19 | CH₃ | Ph-2,4-2Cl | Cl | H | H | H | CH₂ | |
| VIII-20 | CH₃ | Ph-4-CH₃ | Cl | H | H | H | CH₂ | |
| VIII-21 | CH₃ | Ph-2,4-2CH₃ | Cl | H | H | H | CH₂ | |
| VIII-22 | CH₃ | Ph-4-CF₃ | Cl | H | H | H | CH₂ | |
| VIII-23 | CH₃ | Ph-4-OCF₃ | Cl | H | H | H | CH₂ | CH₂ |
| VIII-24 | CH₃ | 3-Py-2-Cl | Cl | H | H | H | CH₂ | |
| VIII-25 | CH₃ | 2-Py-5-Cl | Cl | H | H | H | CH₂ | |
| VIII-26 | CH₃ | 3-Py | Cl | H | H | H | CH₂ | |
| VIII-27 | CH₃ | CH₃ | H | H | H | H | CH₂ | |
| VIII-28 | CH₃ | Et | H | H | H | H | CH₂ | |
| VIII-29 | CH₃ | n-Pr | H | H | H | H | CH₂ | |
| VIII-30 | CH₃ | i-Pr | H | H | H | H | CH₂ | |
| VIII-31 | CH₃ | t-Bu | H | H | H | H | CH₂ | |
| VIII-32 | CH₃ | ▷ | H | H | H | H | CH₂ | |
| VIII-33 | CH₃ | CF₃ | H | H | H | H | CH₂ | |
| VIII-34 | CH₃ | CH₃ | Br | H | H | H | CH₂ | |
| VIII-35 | CH₃ | Et | Br | H | H | H | CH₂ | |
| VIII-36 | CH₃ | n-Pr | Br | H | H | H | CH₂ | |
| VIII-37 | CH₃ | i-Pr | Br | H | H | H | CH₂ | |
| VIII-38 | CH₃ | t-Bu | Br | H | H | H | CH₂ | |
| VIII-39 | CH₃ | ▷ | Br | H | H | H | CH₂ | |
| VIII-40 | CH₃ | CF₃ | Br | H | H | H | CH₂ | |
| VIII-41 | Et | CH₃ | H | H | H | H | CH₂ | |
| VIII-42 | Et | Et | H | H | H | H | CH₂ | |
| VIII-43 | Et | n-Pr | H | H | H | H | CH₂ | |
| VIII-44 | Et | i-Pr | H | H | H | H | CH₂ | |
| VIII-45 | Et | t-Bu | H | H | H | H | CH₂ | |
| VIII-46 | Et | ▷ | H | H | H | H | CH₂ | |
| VIII-47 | Et | CF₃ | H | H | H | H | CH₂ | |
| VIII-48 | Et | CH₃ | Cl | H | H | H | CH₂ | |
| VIII-49 | Et | Et | Cl | H | H | H | CH₂ | |
| VIII-50 | Et | Pr | Cl | H | H | H | CH₂ | |
| VIII-51 | Et | i-Pr | Cl | H | H | H | CH₂ | |
| VIII-52 | Et | t-Bu | Cl | H | H | H | CH₂ | |

TABLE 11-continued

| compound | R₁ | R₂ | X₁ | Q₁ | X₃ | X₅ | (CHR₆)p | physical property/° C. |
|---|---|---|---|---|---|---|---|---|
| VIII-53 | Et |  | Cl | H | H | H | CH₂ | |
| VIII-54 | Et | CF₃ | Cl | H | H | H | CH₂ | |
| VIII-55 | i-Pr | CH₃ | Cl | H | H | H | CH₂ | |
| VIII-56 | i-Pr | CH₃ | H | H | H | H | CH₂ | |
| VIII-57 |  | CH₃ | Cl | H | H | H | CH₂ | |
| VIII-58 |  | CH₃ | H | H | H | H | CH₂ | |
| VIII-59 | CH₂CF₃ | CH₃ | Cl | H | H | H | CH₂ | |
| VIII-60 | CH₂CF₃ | CH₃ | H | H | H | H | CH₂ | |
| VIII-61 | Ph | CH₃ | Cl | H | H | H | CH₂ | |
| VIII-62 | Ph | CH₃ | H | H | H | H | CH₂ | |
| VIII-63 | Ph | Cl | H | H | H | H | CH₂ | |
| VIII-64 | Ph | Br | H | H | H | H | CH₂ | |
| VIII-65 | Ph-2-Cl | CH₃ | Cl | H | H | H | CH₂ | |
| VIII-66 | Ph-2-Cl | CH₃ | H | H | H | H | CH₂ | |
| VIII-67 | Ph-2-Cl | Cl | H | H | H | H | CH₂ | |
| VIII-68 | Ph-2-Cl | Br | H | H | H | H | CH₂ | |
| VIII-69 | Ph-4-Cl | CH₃ | Cl | H | H | H | CH₂ | |
| VIII-70 | Ph-4-Cl | CH₃ | H | H | H | H | CH₂ | |
| VIII-71 | Ph-4-Cl | Cl | H | H | H | H | CH₂ | |
| VIII-72 | Ph-4-Cl | Br | H | H | H | H | CH₂ | |
| VIII-73 | 2-Py-3-Cl | CH₃ | Cl | H | H | H | CH₂ | |
| VIII-74 | 2-Py-3-Cl | CH₃ | H | H | H | H | CH₂ | |
| VIII-75 | 2-Py-3-Cl | Cl | H | H | H | H | CH₂ | |
| VIII-76 | 2-Py-3-Cl | Br | H | H | H | H | CH₂ | |
| VIII-77 | 2-Py-3-Cl | CF₃ | H | H | H | H | CH₂ | |
| VIII-78 | 2-Py-3-Cl | CHF₂ | H | H | H | H | CH₂ | |
| VIII-79 | 2-Py-3-Cl | OCF₃ | H | H | H | H | CH₂ | |
| VIII-80 | 2-Py-3-Cl | OCH₂CF₃ | H | H | H | H | CH₂ | |
| VIII-81 | 2-Py-3-Cl | OCH₂CN | H | H | H | H | CH₂ | |
| VIII-82 | 2-Py-3-Cl | OCH₂F | H | H | H | H | CH₂ | |
| VIII-83 | 2-Py-3,5-2Cl | Cl | H | H | H | H | CH₂ | |
| VIII-84 | 2-Py-3,5-2Cl | Br | H | H | H | H | CH₂ | |
| VIII-85 | 2-Py-3,5,6-3Cl | Cl | H | H | H | H | CH₂ | |
| VIII-86 | 2-Py-3,5,6-3Cl | Br | H | H | H | H | CH₂ | |
| VIII-87 | 2-Py-3-Cl-5-CF₃Cl | H | H | H | H | CH₂ | CH₂ | |
| VIII-88 | 2-Py-3-Cl-5-CF₃Br | H | H | H | H | CH₂ | CH₂ | |
| VIII-89 | 2-Py-5-CF₃ | Cl | H | H | H | H | CH₂ | |
| VIII-90 | 2-Py-5-CF₃ | Br | H | H | H | H | CH₂ | |
| VIII-91 | 2-Py-3-Cl-5-CH₃ | Cl | H | H | H | H | CH₂ | |
| VIII-92 | 2-Py-3-Cl-5-CH₃ | Br | H | H | H | H | CH₂ | |
| VIII-93 | CH₃ | CH₃ | Cl | CH₃ | H | H | CH₂ | |
| VIII-94 | CH₃ | Et | Cl | CH₃ | H | H | CH₂ | |
| VIII-95 | CH₃ | CF₃ | Cl | CH₃ | H | H | CH₂ | |
| VIII-96 | CH₃ | CH₃ | Cl | CN | H | H | CH₂ | |
| VIII-97 | CH₃ | Et | Cl | CN | H | H | CH₂ | |
| VIII-98 | CH₃ | CF₃ | Cl | CN | H | H | CH₂ | |
| VIII-99 | CH₃ | CH₃ | Cl | H | H | Cl | CH₂ | |
| VIII-100 | CH₃ | Et | Cl | H | H | Cl | CH₂ | |
| VIII-101 | CH₃ | CF₃ | Cl | H | H | Cl | CH₂ | |
| VIII-102 | CH₃ | CH₃ | Cl | H | H | Br | CH₂ | |
| VIII-103 | CH₃ | Et | Cl | H | H | Br | CH₂ | |
| VIII-104 | CH₃ | CF₃ | Cl | H | H | Br | CH₂ | |
| VIII-105 | CH₃ | CH₃ | Cl | H | H | OCH₃ | CH₂ | |
| VIII-106 | CH₃ | Et | Cl | H | H | OCH₃ | CH₂ | |
| VIII-107 | CH₃ | CF₃ | Cl | H | H | OCH₃ | CH₂ | |
| VIII-108 | CH₃ | CH₃ | Cl | H | Cl | Cl | CH₂ | |
| VIII-109 | CH₃ | Et | Cl | H | Cl | Cl | CH₂ | |

TABLE 11-continued

| compound | R₁ | R₂ | X₁ | Q₁ | X₃ | X₅ | (CHR₆)p | physical property/° C. |
|---|---|---|---|---|---|---|---|---|
| VIII-110 | CH₃ | CF₃ | C | H | Cl | Cl | CH₂ | |
| VIII-111 | CH₃ | CH₃ | Cl | H | Cl | OCH₃ | CH₂ | |
| VIII-112 | CH₃ | Et | Cl | H | Cl | OCH₃ | CH₂ | |
| VIII-113 | CH₃ | CF₃ | Cl | H | Cl | OCH₃ | CH₂ | |
| VIII-114 | Et | CH₃ | Cl | H | H | Cl | CH₂ | |
| VIII-115 | Et | CH₃ | Cl | H | H | Br | CH₂ | |
| VIII-116 | Et | CH₃ | Cl | H | H | OCH₃ | CH₂ | |
| VIII-117 | Ph | CH₃ | Cl | H | H | OCH₃ | CH₂ | |
| VIII-118 | Ph-2-Cl | CH₃ | Cl | H | H | OCH₃ | CH₂ | |
| VIII-119 | Ph-4-Cl | CH₃ | Cl | H | H | OCH₃ | CH₂ | |
| VIII-120 | 2-Py-3-Cl | Cl | H | H | H | OCH₃ | CH₂ | |
| VIII-121 | 2-Py-3,5-2Cl | Cl | H | H | H | OCH₃ | CH₂ | |
| VIII-122 | 2-Py-3,5,6-3Cl | Cl | H | H | H | OCH₃ | CH₂ | |
| VIII-123 | 2-Py-3-Cl-5-CF₃ | Cl | H | H | H | OCH₃ | CH₂ | |
| VIII-124 | 2-Py-5-CF₃ | Cl | H | H | H | OCH₃ | CH₂ | |
| VIII-125 | 2-Py-3-Cl-5-CH₃ | Cl | H | H | H | OCH₃ | CH₂ | |
| VIII-126 | CH₃ | CH₃ | Cl | H | H | H | CH₂(CH₃) | |
| VIII-127 | CH₃ | Et | Cl | H | H | H | CH₂(CH₃) | |
| VIII-128 | CH₃ | CF₃ | Cl | H | H | H | CH₂(CH₃) | |
| VIII-129 | CH₃ | CH₃ | H | H | H | H | CH₂(CH₃) | |
| VIII-130 | CH₃ | Et | H | H | H | H | CH₂(CH₃) | |
| VIII-131 | CH₃ | CF₃ | H | H | H | H | CH₂(CH₃) | |
| VIII-132 | CH₃ | CH₃ | Cl | H | H | H | CH₂(CN) | |
| VIII-133 | CH₃ | Et | Cl | H | H | H | CH₂(CN) | |
| VIII-134 | CH₃ | CF₃ | Cl | H | H | H | CH₂(CN) | |
| VIII-135 | CH₃ | CH₃ | H | H | H | H | CH₂(CN) | |
| VIII-136 | CH₃ | Et | H | H | H | H | CH₂(CN) | |
| VIII-137 | CH₃ | CF₃ | H | H | H | H | CH₂(CN) | |
| VIII-138 | CH₃ | CH₃ | Cl | H | H | H | (CH₂)₂ | 157-159 |
| VIII-139 | CH₃ | Et | Cl | H | H | H | (CH₂)₂ | 170-171 |
| VIII-140 | CH₃ | CF₃ | Cl | H | H | H | (CH₂)₂ | |
| VIII-141 | Et | CH₃ | Cl | H | H | H | (CH₂)₂ | |
| VIII-142 | Et | Et | Cl | H | H | H | (CH₂)₂ | |
| VIII-143 | Et | CF₃ | Cl | H | H | H | (CH₂)₂ | |
| VIII-144 | CH₃ | CH₃ | H | H | H | OCH₃ | CH₂ | |
| VIII-145 | CH₃ | Et | H | H | H | OCH₃ | CH₂ | |
| VIII-146 | CH₃ | CF₃ | H | H | H | OCH₃ | CH₂ | |
| VIII-147 | Et | CH₃ | H | H | H | OCH₃ | CH₂ | |
| VIII-148 | Ph | CH₃ | H | H | H | OCH₃ | CH₂ | |
| VIII-149 | CH₃ | CH₃ | H | H | H | OCH₃ | (CH₂)₂ | |
| VIII-150 | Et | CH₃ | H | H | H | OCH₃ | (CH₂)₂ | |

¹HNMR spectrum (¹HNMR, 300 MHz, internal standard: TMS, solvent CDCl₃) of some intermediates in table 11 are shown as follows:

VIII-1: δppm 2.23(3H, s), 4.14(3H, s), 4.56(2H, d), 5.25(1H, s), 6.82(2H, d), 7.24(2H, d).

VIII-2: δppm 1.23(3H, t), 2.62-2.64(2H, m), 4.14(3H, s), 4.56(2H, d), 5.21(1H, s), 6.82(2H, d), 7.23(2H, d).

VIII-138: δppm 1.62(3H, s), 2.85(2H, t), 3.60-3.75 (2H, m), 4.10(3H, s), 5.33(1H, s), 6.72(1H, s), 6.80(2H, d), 7.10(2H, d).

VIII-139: δppm 7.22(3H, t), 2.55-2.67(2H, m), 2.86(2H, t), 3.60-3.76(2H, m), 4.11(3H, s), 6.74(1H, s), 6.79(2H, d), 7.10(2H, d).

The present invention are also explained by the following compounds listed in tables 12-17, but without being restricted thereby.

TABLE 12

Some of compounds of formula I-1

$(Q_1, Q_2, X_2, X_3, X_4, X_5 = H, Z = O)$

| No. | $R_1$ | $R_2$ | $(CHR_3)m$ | $(R_4)n$ | $X_1$ | $Y-R_5$ | $(CHR_6)p$ |
|---|---|---|---|---|---|---|---|
| 1 | $CH_3$ | Cl | $CH_2$ | H | H | $NHCH_3$ | $CH_2$ |
| 2 | $CH_3$ | $CH_3$ | $CH_2$ | H | H | $NHCH_3$ | $CH_2$ |
| 3 | $CH_3$ | Et | $CH_2$ | H | H | $NHCH_3$ | $CH_2$ |
| 4 | $CH_3$ | n-Pr | $CH_2$ | H | H | $NHCH_3$ | $CH_2$ |
| 5 | $CH_3$ | i-Pr | $CH_2$ | H | H | $NHCH_3$ | $CH_2$ |
| 6 | $CH_3$ | n-Bu | $CH_2$ | H | H | $NHCH_3$ | $CH_2$ |
| 7 | $CH_3$ | i-Bu | $CH_2$ | H | H | $NHCH_3$ | $CH_2$ |
| 8 | $CH_3$ | cyclopropyl | $CH_2$ | H | Cl | $NHCH_3$ | $CH_2$ |
| 9 | $CH_3$ | t-Bu | $CH_2$ | H | H | $NHCH_3$ | $CH_2$ |
| 10 | $CH_3$ | $CF_3$ | $CH_2$ | H | H | $NHCH_3$ | $CH_2$ |
| 11 | $CH_3$ | $OCH_3$ | $CH_2$ | H | H | $NHCH_3$ | $CH_2$ |
| 12 | $CH_3$ | OEt | $CH_2$ | H | H | $NHCH_3$ | $CH_2$ |
| 13 | $CH_3$ | Ph | $CH_2$ | H | H | $NHCH_3$ | $CH_2$ |
| 14 | $CH_3$ | Ph-4-Cl | $CH_2$ | H | H | $NHCH_3$ | $CH_2$ |
| 15 | $CH_3$ | $CH_3$ | $CH_2$ | H | Cl | $NHCH_3$ | $CH_2$ |
| 16 | $CH_3$ | Et | $CH_2$ | H | Cl | $NHCH_3$ | $CH_2$ |
| 17 | $CH_3$ | n-Pr | $CH_2$ | H | Cl | $NHCH_3$ | $CH_2$ |
| 18 | $CH_3$ | i-Pr | $CH_2$ | H | Cl | $NHCH_3$ | $CH_2$ |
| 19 | $CH_3$ | n-Bu | $CH_2$ | H | Cl | $NHCH_3$ | $CH_2$ |
| 20 | $CH_3$ | i-Bu | $CH_2$ | H | Cl | $NHCH_3$ | $CH_2$ |
| 21 | $CH_3$ | s-Bu | $CH_2$ | H | Cl | $NHCH_3$ | $CH_2$ |
| 22 | $CH_3$ | t-Bu | $CH_2$ | H | Cl | $NHCH_3$ | $CH_2$ |
| 23 | $CH_3$ | $CF_3$ | $CH_2$ | H | Cl | $NHCH_3$ | $CH_2$ |
| 24 | $CH_3$ | $OCH_3$ | $CH_2$ | H | Cl | $NHCH_3$ | $CH_2$ |
| 25 | $CH_3$ | Ph-4-Cl | $CH_2$ | H | Cl | $NHCH_3$ | $CH_2$ |
| 26 | $CH_3$ | $CH_3$ | $CH_2$ | H | Br | $NHCH_3$ | $CH_2$ |
| 27 | $CH_3$ | Et | $CH_2$ | H | Br | $NHOCH_3$ | $CH_2$ |
| 28 | $CH_3$ | n-Pr | $CH_2$ | H | Br | $NHNHCH_3$ | $CH_2$ |
| 29 | $CH_3$ | $OCH_2F$ | $CH_2$ | H | Br | $NHCH_3$ | $CH_2$ |
| 30 | $CH_3$ | $OCH_2CF_3$ | $CH_2$ | H | Cl | $NHCH_3$ | $CH_2$ |
| 31 | $CH_3$ | Ph-4-Cl | $CH_2$ | H | Br | $NHCH_3$ | $CH_2$ |
| 32 | $CH_3$ | $CH_3$ | $CH_2$ | H | $NO_2$ | $NHCH_3$ | $CH_2$ |
| 33 | $CH_3$ | Et | $CH_2$ | H | $NO_2$ | $NHCH_3$ | $CH_2$ |
| 34 | $CH_3$ | n-Pr | $CH_2$ | H | $NO_2$ | $NHCH_3$ | $CH_2$ |
| 35 | $CH_3$ | i-Pr | $CH_2$ | H | $NO_2$ | $NHCH_3$ | $CH_2$ |
| 36 | $CH_3$ | Et | $CH_2$ | H | $NO_2$ | $NHCH_3$ | $CH_2$ |
| 37 | $CH_3$ | $CF_3$ | $CH_2$ | H | $NO_2$ | $NHCH_3$ | $CH_2$ |
| 38 | $CH_3$ | $OCF_3$ | $CH_2$ | H | $NO_2$ | $NHCH_3$ | $CH_2$ |
| 39 | $CH_3$ | Ph-4-Cl | $CH_2$ | H | $NO_2$ | $NHCH_3$ | $CH_2$ |
| 40 | $CH_3$ | $CH_3$ | $CH(CH_3)$ | H | $CH_3$ | $NHCH_3$ | $CH_2$ |
| 41 | $CH_3$ | Et | $CH_2$ | H | Cl | $NHCH_3$ | R-*CH($CH_3$) |
| 42 | $CH_3$ | $CF_3$ | $CH_2$ | H | $CH_3$ | $NHCH_3$ | $CH_2$ |
| 43 | $CH_3$ | Ph | $CH_2$ | H | $CH_3$ | $NHCH_3$ | $CH_2$ |
| 44 | $CH_3$ | Ph-4-Cl | $CH_2$ | H | $CH_3$ | $NHCH_3$ | $CH_2$ |
| 45 | $CH_3$ | $CH_3$ | $CH_2$ | H | CN | $NHCH_3$ | $CH_2$ |
| 46 | $CH_3$ | Et | $CH_2$ | H | Cl | $NHCH_3$ | S-*CH($CH_3$) |
| 47 | $CH_3$ | $CF_3$ | $CH_2$ | H | CN | $NHCH_3$ | $CH_2$ |
| 48 | $CH_3$ | $OCH_3$ | $CH_2$ | H | CN | $NHCH_3$ | $CH_2$ |
| 49 | $CH_3$ | Ph-4-Cl | $CH_2$ | H | CN | $NHCH_3$ | $CH_2$ |
| 50 | $CH_3$ | $CH_3$ | $CH_2$ | H | $SO_2CF_3$ | $NHCH_3$ | $CH_2$ |
| 51 | $CH_3$ | Et | $CH_2$ | H | $SO_2CF_3$ | $NHCH_3$ | $CH_2$ |
| 52 | $CH_3$ | $CF_3$ | $CH_2$ | H | $SO_2CF_3$ | $NHCH_3$ | $CH_2$ |
| 53 | $CH_3$ | Ph-4-Cl | $CH_2$ | H | $SO_2CF_3$ | $NHCH_3$ | $CH_2$ |
| 54 | $CH_3$ | $CH_3$ | $CH_2$ | H | $SOCF_3$ | $NHCH_3$ | $CH_2$ |

TABLE 12-continued

Some of compounds of formula I-1

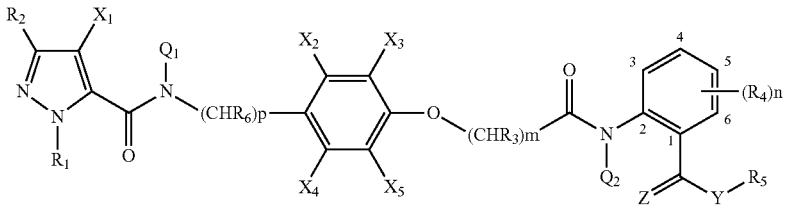

(Q$_1$, Q$_2$, X$_2$, X$_3$, X$_4$, X$_5$ = H, Z = O)

| No. | R$_1$ | R$_2$ | (CHR$_3$)m | (R$_4$)n | X$_1$ | Y—R$_5$ | (CHR$_6$)p |
|---|---|---|---|---|---|---|---|
| 55 | CH$_3$ | Et | CH$_2$ | H | SOCF$_3$ | NHCH$_3$ | CH$_2$ |
| 56 | CH$_3$ | CF$_3$ | CH$_2$ | H | SOCF$_3$ | NHCH$_3$ | CH$_2$ |
| 57 | CH$_3$ | Ph-4-Cl | CH$_2$ | H | SOCF$_3$ | NHCH$_3$ | CH$_2$ |
| 58 | CH$_3$ | CH$_3$ | CH$_2$ | H | OCH$_3$ | NHCH$_3$ | CH$_2$ |
| 59 | CH$_3$ | CF$_3$ | CH$_2$ | H | OCH$_3$ | NHCH$_3$ | CH$_2$ |
| 60 | CH$_3$ | Ph-4-Cl | CH$_2$ | H | OCH$_3$ | NHCH$_3$ | CH$_2$ |
| 61 | CH$_3$ | CH$_3$ | CH(CH$_3$) | H | H | NHCH$_3$ | CH$_2$ |
| 62 | CH$_3$ | Et | CH(CH$_3$) | H | Cl | NHCH$_3$ | (CH$_2$)$_2$ |
| 63 | CH$_3$ | OCH$_3$ | CH(CH$_3$) | H | H | NHCH$_3$ | CH$_2$ |
| 64 | CH$_3$ | Ph-4-Cl | CH(CH$_3$) | H | H | NHCH$_3$ | CH$_2$ |
| 65 | CH$_3$ | CH$_3$ | CH(CH$_3$) | H | Cl | NHCH$_3$ | CH$_2$ |
| 66 | CH$_3$ | Et | R-*CH(CH$_3$) | H | Cl | NHCH$_3$ | CH$_2$ |
| 67 | CH$_3$ | n-Pr | CH(CH$_3$) | H | Cl | NHCH$_3$ | CH$_2$ |
| 68 | CH$_3$ | i-Pr | CH(CH$_3$) | H | Cl | NHCH$_3$ | CH$_2$ |
| 69 | CH$_3$ | Et | S-*CH(CH$_3$) | H | Cl | NHCH$_3$ | CH$_2$ |
| 70 | CH$_3$ | CF$_3$ | CH(CH$_3$) | H | Cl | NHCH$_3$ | CH$_2$ |
| 71 | CH$_3$ | Ph-4-Cl | CH(CH$_3$) | H | Cl | NHCH$_3$ | CH$_2$ |
| 72 | CH$_3$ | CH$_3$ | CH(CH$_3$) | H | Br | NHCH$_3$ | CH$_2$ |
| 73 | CH$_3$ | Et | CH(CH$_3$) | H | Br | NHCH$_3$ | CH$_2$ |
| 74 | CH$_3$ | CH$_3$ | CH(CH$_3$) | H | NO$_2$ | NHCH$_3$ | CH$_2$ |
| 75 | CH$_3$ | Et | CH(CH$_3$) | H | NO$_2$ | NHCH$_3$ | CH$_2$ |
| 76 | CH$_3$ | CF$_3$ | CH(CH$_3$) | H | NO$_2$ | NHCH$_3$ | CH$_2$ |
| 77 | CH$_3$ | CH$_3$ | CH$_2$ | H | CH$_3$ | NHCH$_3$ | CH$_2$ |
| 78 | CH$_3$ | CH$_3$ | CH(CH$_3$) | H | Cl | NHCH$_3$ | (CH$_2$)$_2$ |
| 79 | CH$_3$ | CF$_3$ | CH(CH$_3$) | H | CH$_3$ | NHCH$_3$ | CH$_2$ |
| 80 | CH$_3$ | CH$_3$ | (CH$_2$)$_2$ | H | H | NHCH$_3$ | CH$_2$ |
| 81 | CH$_3$ | CH$_3$ | (CH$_2$)$_2$ | H | Cl | NHCH$_3$ | CH$_2$ |
| 82 | CH$_3$ | Et | (CH$_2$)$_2$ | H | H | NHCH$_3$ | CH$_2$ |
| 83 | CH$_3$ | Et | (CH$_2$)$_2$ | H | Cl | NHCH$_3$ | CH$_2$ |
| 84 | CH$_3$ | CH$_3$ | (CH$_2$)$_3$ | H | H | NHCH$_3$ | CH$_2$ |
| 85 | CH$_3$ | CH$_3$ | (CH$_2$)$_3$ | H | Cl | NHCH$_3$ | CH$_2$ |
| 86 | CH$_3$ | Et | (CH$_2$)$_3$ | H | H | NHCH$_3$ | CH$_2$ |
| 87 | CH$_3$ | Et | (CH$_2$)$_3$ | H | Cl | NHCH$_3$ | CH$_2$ |
| 88 | CH$_3$ | CH$_3$ | CH$_2$ | H | H | OCH$_3$ | CH$_2$ |
| 89 | CH$_3$ | Et | CH$_2$ | H | H | OCH$_3$ | CH$_2$ |
| 90 | CH$_3$ | n-Pr | CH$_2$ | H | H | OCH$_3$ | CH$_2$ |
| 91 | CH$_3$ | i-Pr | CH$_2$ | H | H | OCH$_3$ | CH$_2$ |
| 92 | CH$_3$ | i-Bu | CH$_2$ | H | H | OCH$_3$ | CH$_2$ |
| 93 | H | CF$_3$ | CH$_2$ | H | H | OCH$_3$ | CH$_2$ |
| 94 | CH$_3$ | CH$_3$ | CH$_2$ | 3-CH$_3$ | Cl | OEt | CH$_2$ |
| 95 | CH$_3$ | CH$_3$ | CH$_2$ | H | Cl | OEt | CH$_2$ |
| 96 | CH$_3$ | n-Pr | CH$_2$ | H | Cl | OCH$_3$ | CH$_2$ |
| 97 | CH$_3$ | i-Pr | CH$_2$ | H | Cl | OCH$_3$ | CH$_2$ |
| 98 | CH$_3$ | i-Bu | CH$_2$ | H | Cl | OCH$_3$ | CH$_2$ |
| 99 | CH$_3$ | Et | CH$_2$ | H | Cl | OEt | CH$_2$ |
| 100 | CH$_3$ | t-Bu | CH$_2$ | H | Cl | OCH$_3$ | CH$_2$ |
| 101 | CH$_3$ | CF$_3$ | CH$_2$ | H | Cl | OCH$_3$ | CH$_2$ |
| 102 | CH$_3$ | OCH$_3$ | CH$_2$ | H | Cl | OCH$_3$ | CH$_2$ |
| 103 | CH$_3$ | Ph | CH$_2$ | H | Cl | OCH$_3$ | CH$_2$ |
| 104 | Et | CH$_3$ | CH$_2$ | H | H | NHCH$_3$ | CH$_2$ |
| 105 | Et | Et | CH$_2$ | H | H | NHCH$_3$ | CH$_2$ |
| 106 | Et | CF$_3$ | CH$_2$ | H | H | OCH$_3$ | CH$_2$ |
| 107 | Et | CH$_3$ | CH$_2$ | H | Cl | NHCH$_3$ | CH$_2$ |
| 108 | Et | Et | CH$_2$ | H | Cl | NHCH$_3$ | CH$_2$ |
| 109 | Et | n-Pr | CH$_2$ | H | Cl | OCH$_3$ | CH$_2$ |
| 110 | Et | i-Pr | CH$_2$ | H | Cl | OCH$_3$ | CH$_2$ |
| 111 | Et | CF$_3$ | CH$_2$ | H | Cl | NHOCH$_3$ | CH$_2$ |
| 112 | 2-Py-3-Cl | CH$_3$ | CH$_2$ | H | H | NHCH$_3$ | CH$_2$ |
| 113 | 2-Py-3-Cl | CF$_3$ | CH$_2$ | H | H | NHCH$_3$ | CH$_2$ |
| 114 | 2-Py-3-Cl | Cl | CH$_2$ | H | H | NHCH$_3$ | CH$_2$ |
| 115 | 2-Py-3-Cl | OCH$_2$CF$_3$ | CH$_2$ | H | H | NHCH$_3$ | CH$_2$ |
| 116 | 2-Py-3-Cl | OCH$_2$CN | CH$_2$ | H | H | NHCH$_3$ | CH$_2$ |

TABLE 12-continued

Some of compounds of formula I-1

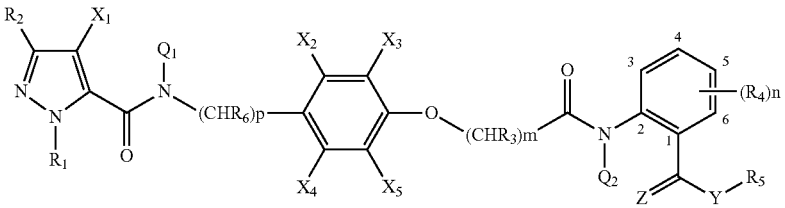

I-1

($Q_1$, $Q_2$, $X_2$, $X_3$, $X_4$, $X_5$ = H, Z = O)

| No. | $R_1$ | $R_2$ | $(CHR_3)m$ | $(R_4)n$ | $X_1$ | $Y-R_5$ | $(CHR_6)p$ |
|---|---|---|---|---|---|---|---|
| 117 | 2-Py-3-Cl | Br | $CH_2$ | H | H | $NHCH_3$ | $CH_2$ |
| 118 | 2-Py-3-Cl | Br | $CH_2$ | 3-$CH_3$-5-CN | H | $NHCH_3$ | $CH_2$ |
| 119 | 2-Py-3-Cl | $OCH_2F$ | $CH_2$ | H | H | $NHCH_3$ | $CH_2$ |
| 120 | 2-Py-3,5-2Cl | $CF_3$ | $CH_2$ | H | H | $NHCH_3$ | $CH_2$ |
| 121 | 2-Py-3-Cl | Br | $CH_2$ | 3-$CH_3$-5-Br | H | $NHCH_3$ | $CH_2$ |
| 122 | 2-Py-3,5-2Cl | $CH_3$ | $CH_2$ | H | H | $NHCH_3$ | $CH_2$ |
| 123 | 2-Py-3,5-2Cl | Br | $CH_2$ | H | H | $NHCH_3$ | $CH_2$ |
| 124 | 2-Py-3-Cl-5-$CF_3$ | Br | $CH_2$ | H | H | $NHCH_3$ | $CH_2$ |
| 125 | 2-Py-3-Cl-5-$CH_3$ | $CH_3$ | $CH_2$ | H | H | $NHCH_3$ | $CH_2$ |
| 126 | 2-Py-3-Cl-5-$CF_3$ | $CH_3$ | $CH_2$ | H | H | $NHCH_3$ | $CH_2$ |
| 127 | 2-Py-5-$CF_3$ | $CH_3$ | $CH_2$ | H | H | $NHCH_3$ | $CH_2$ |
| 128 | 2-Py-5-$CF_3$ | Cl | $CH_2$ | H | H | $NHCH_3$ | $CH_2$ |
| 129 | H | $CF_3$ | $CH_2$ | H | H | $NHCH_3$ | $CH_2$ |
| 130 | H | $CH_3$ | $CH_2$ | H | Cl | $NHCH_3$ | $CH_2$ |
| 131 | H | Et | $CH_2$ | H | Cl | $NHCH_3$ | $CH_2$ |
| 132 | H | $CF_3$ | $CH_2$ | H | Cl | $NHCH_3$ | $CH_2$ |
| 133 | $CH_3$ | $CH_3$ | $CH_2$ | H | H | NHEt | $CH_2$ |
| 134 | $CH_3$ | Et | $CH_2$ | H | H | NHEt | $CH_2$ |
| 135 | $CH_3$ | $OCH_2CF_3$ | $CH_2$ | H | H | $NHCH_3$ | $CH_2$ |
| 136 | $CH_3$ | $CH_2OCH_3$ | $CH_2$ | H | H | $NHCH_3$ | $CH_2$ |
| 137 | $CH_3$ | $CF_3$ | $CH_2$ | H | H | NHEt | $CH_2$ |
| 138 | $CH_3$ | $CH_3$ | $CH_2$ | H | Cl | NHEt | $CH_2$ |
| 139 | $CH_3$ | Et | $CH_2$ | H | Cl | NHEt | $CH_2$ |
| 140 | $CH_3$ | $OCH_2CN$ | $CH_2$ | H | Cl | $NHCH_3$ | $CH_2$ |
| 141 | $CH_3$ | Et | $CH_2$ | 5-F | Cl | NHEt | $CH_2$ |
| 142 | $CH_3$ | $CF_3$ | $CH_2$ | H | Cl | NHEt | $CH_2$ |
| 143 | $CH_3$ | $CH_3$ | $CH_2$ | H | H | $N(CH_3)_2$ | $CH_2$ |
| 144 | $CH_3$ | Et | $CH_2$ | H | H | $N(CH_3)_2$ | $CH_2$ |
| 145 | $CH_3$ | n-Pr | $CH_2$ | H | H | $N(CH_3)_2$ | $CH_2$ |
| 146 | $CH_3$ | $CF_3$ | $CH_2$ | H | H | $N(CH_3)_2$ | $CH_2$ |
| 147 | $CH_3$ | $CH_3$ | $CH_2$ | H | Cl | $N(CH_3)_2$ | $CH_2$ |
| 148 | $CH_3$ | Et | $CH_2$ | H | Cl | $N(CH_3)_2$ | $CH_2$ |
| 149 | $CH_3$ | i-Pr | $CH_2$ | H | Cl | $N(CH_3)_2$ | $CH_2$ |
| 150 | $CH_3$ | $CF_3$ | $CH_2$ | H | Cl | $N(CH_3)_2$ | $CH_2$ |
| 151 | $CH_3$ | $CH_3$ | $CH_2$ | H | H | $NH_2$ | $CH_2$ |
| 152 | $CH_3$ | Et | $CH_2$ | H | H | $NH_2$ | $CH_2$ |
| 153 | $CH_3$ | n-Pr | $CH_2$ | 3-$CH_3$-4-CN | H | $NH_2$ | $CH_2$ |
| 154 | $CH_3$ | 3-Py | $CH_2$ | H | H | $NH_2$ | $CH_2$ |
| 155 | $CH_3$ | $CF_3$ | $CH_2$ | H | H | $NH_2$ | $CH_2$ |
| 156 | $CH_3$ | $CH_3$ | $CH_2$ | H | Cl | $NH_2$ | $CH_2$ |
| 157 | $CH_3$ | Et | $CH_2$ | H | Cl | $NH_2$ | $CH_2$ |
| 158 | $CH_3$ | n-Pr | $CH_2$ | 2-$CH_3$-5-I | Cl | $NH_2$ | $CH_2$ |
| 159 | $CH_3$ | i-Pr | $CH_2$ | H | Cl | $NH_2$ | $CH_2$ |
| 160 | $CH_3$ | $CF_3$ | $CH_2$ | H | Cl | $NH_2$ | $CH_2$ |
| 161 | $CH_3$ | $CH_3$ | $CH_2$ | 5-Cl | H | $NHCH_3$ | $CH_2$ |
| 162 | $CH_3$ | $CH_3$ | $CH_2$ | 3-$CH_3$-5-I | Cl | $NHCH_3$ | $CH_2$ |
| 163 | $CH_3$ | $CH_3$ | $CH_2$ | 3-$CH_3$-5-Cl | H | $NHCH_3$ | $CH_2$ |
| 164 | $CH_3$ | $CH_3$ | $CH_2$ | 3-$CH_3$ | H | $NHCH_3$ | $CH_2$ |
| 165 | $CH_3$ | $CH_3$ | $CH_2$ | 5-Br | H | $NHCH_3$ | $CH_2$ |
| 166 | $CH_3$ | $CH_3$ | $CH_2$ | 3-$CH_3$-5-Br | Cl | $NHCH_3$ | $CH_2$ |
| 167 | $CH_3$ | $CH_3$ | $CH_2$ | 3-$CH_3$-5-CN | Cl | $NHCH_3$ | $CH_2$ |
| 168 | $CH_3$ | $CH_3$ | $CH_2$ | 3,5-2Cl | H | $NHCH_3$ | $CH_2$ |
| 169 | $CH_3$ | $CH_3$ | $CH_2$ | 5-F | H | $NHCH_3$ | $CH_2$ |
| 170 | $CH_3$ | Et | $CH_2$ | 3-$CH_3$ | Cl | $NHCH_3$ | $CH_2$ |
| 171 | $CH_3$ | $CH_3$ | $CH_2$ | 3-$CH_3$ | Cl | $NHCH_3$ | $CH_2$ |
| 172 | $CH_3$ | Et | $CH_2$ | 3-$CH_3$-5-Cl | Cl | $NHCH_3$ | $CH_2$ |
| 173 | Ph | $CH_3$ | $CH_2$ | H | Cl | $NHCH_3$ | $CH_2$ |
| 174 | Ph-4-Cl | $CH_3$ | $CH_2$ | H | Cl | $NHCH_3$ | $CH_2$ |
| 175 | Ph | $CH_3$ | $CH_2$ | H | H | $NHCH_3$ | $(CH_2)_3$ |
| 176 | Ph-4-Cl | $CH_3$ | $CH_2$ | H | H | $NHCH_3$ | $(CH_2)_3$ |
| 177 | $CH_3$ | $CH_3$ | $CH_2$ | 3-$CH_3$ | H | NHEt | $CH_2$ |
| 178 | $CH_3$ | Et | $CH_2$ | 3-$CH_3$ | Cl | OEt | $CH_2$ |

TABLE 12-continued

Some of compounds of formula I-1

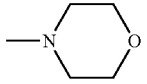

I-1

($Q_1$, $Q_2$, $X_2$, $X_3$, $X_4$, $X_5$ = H, Z = O)

| No. | $R_1$ | $R_2$ | $(CHR_3)m$ | $(R_4)n$ | $X_1$ | $Y—R_5$ | $(CHR_6)p$ |
|---|---|---|---|---|---|---|---|
| 179 | $CH_3$ | $CH_3$ | $CH_2$ | 5-F | H | NHEt | $CH_2$ |
| 180 | $CH_3$ | $CH_3$ | $CH_2$ | 3-$CH_3$-5-CN | H | $NHCH_3$ | $CH_2$ |
| 181 | $CH_3$ | Et | $CH_2$ | 3-$CH_3$-5-Br | Cl | $NHCH_3$ | $CH_2$ |
| 182 | $CH_3$ | $CH_3$ | $CH_2$ | 3-$CH_3$-5-Cl | Cl | $NHCH_3$ | $CH_2$ |
| 183 | $CH_3$ | Et | $CH_2$ | 3,5-2Cl | Cl | $NHCH_3$ | $CH_2$ |
| 184 | $CH_3$ | $CH_3$ | $CH_2$ | 5-$CH_3$-3-Cl | H | NHEt | $CH_2$ |
| 185 | $CH_3$ | Et | $CH_2$ | 3-CN-5-$CH_3$ | Cl | OEt | $CH_2$ |
| 186 | $CH_3$ | $CH_3$ | $CH_2$ | H | Cl | $NHCH_3$ | $(CH_2)_2$ |
| 187 | $CH_3$ | Et | $CH_2$ | H | Cl | $NHCH_3$ | $(CH_2)_2$ |
| 188 | $CH_3$ | $CH_3$ | $CH_2$ | 5-F | H | $NHCH_3$ | $(CH_2)_2$ |
| 189 | 2-Py-3-Cl | Br | $CH_2$ | 3-$CH_3$-5-Cl | H | $NHCH_3$ | $CH_2$ |
| 190 | $CH_3$ | Et | $CH_2$ | 3-$CH_3$-5-CN | H | $NHCH_3$ | $CH_2$ |
| 191 | 2-Py-3-Cl | Br | $CH_2$ | 3,5-2Cl | H | $NHCH_3$ | $CH_2$ |
| 192 | 2-Py-3-Cl | $CH_3$ | $CH_2$ | 3-$CH_3$ | H | $NHCH_3$ | $CH_2$ |
| 193 | $CH_3$ | Et | $CH_2$ | 3-$CH_3$-5-CN | Cl | $NHCH_3$ | $CH_2$ |
| 194 | $CH_3$ | $CH_3$ | $CH_2$ | H | Cl | $NHCH_3$ | $(CH_2)_3$ |
| 195 | $CH_3$ | $CH_3$ | $CH_2$ | H | Cl | 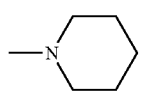 | $CH_2$ |
| 196 | $CH_3$ | $CH_3$ | $CH_2$ | H | H | 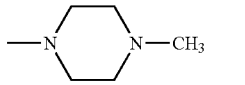 | $CH_2$ |
| 197 | $CH_3$ | Et | $CH_2$ | H | H | 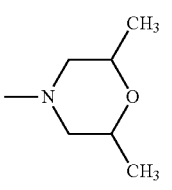 | $CH_2$ |
| 198 | $CH_3$ | $CH_3$ | $CH_2$ | H | Cl |  | $CH_2$ |
| 199 | $CH_3$ | $CH_3$ | $CH_2$ | H | $CH_3$ | $NHCH_3$ | $(CH_2)_3$ |
| 200 | $CH_3$ | $CH_3$ | $CH_2$ | H | Cl | $N(CH_3)_2$ | — |
| 201 | $CH_3$ | Et | $CH_2$ | H | Cl | $N(CH_3)_2$ | — |
| 202 | $CH_3$ | $CH_3$ | $CH_2$ | H | Cl | $NHCH_3$ | — |
| 203 | $CH_3$ | Et | $CH_2$ | H | Cl | $N(CH_3)_2$ | — |
| 204 | $CH_3$ | $CH_3$ | $CH_2$ | 3-$CH_3$-5-Cl | Cl | $N(CH_3)_2$ | $CH_2$ |
| 205 | $CH_3$ | Et | $CH_2$ | 3-$CH_3$-5-CN | Cl | $N(CH_3)_2$ | $CH_2$ |

TABLE 13

Some of compounds of formula I-2

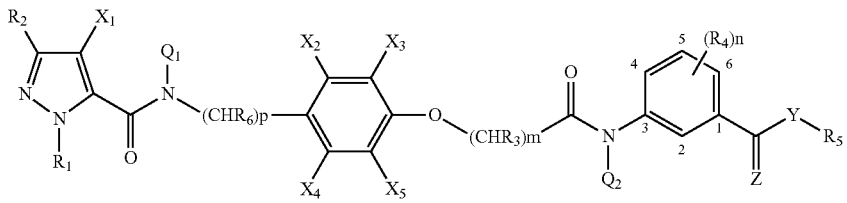

I-2

($Q_1$, $Q_2$, $X_2$, $X_3$, $X_4$, $X_5$ = H, Z = O)

| No. | $R_1$ | $R_2$ | $(CHR_3)m$ | $(R_4)n$ | $X_1$ | $Y-R_5$ | $(CHR_6)p$ |
|---|---|---|---|---|---|---|---|
| 206 | $CH_3$ | Cl | $CH_2$ | H | H | $NHCH_3$ | $CH_2$ |
| 207 | $CH_3$ | $CH_3$ | $CH_2$ | H | H | $NHCH_3$ | $CH_2$ |
| 208 | $CH_3$ | Et | $CH_2$ | H | H | $NHCH_3$ | $CH_2$ |
| 209 | $CH_3$ | n-Pr | $CH_2$ | H | H | $NHCH_3$ | $CH_2$ |
| 210 | $CH_3$ | i-Pr | $CH_2$ | H | H | $NHCH_3$ | $CH_2$ |
| 211 | $CH_3$ | n-Bu | $CH_2$ | H | H | $NHCH_3$ | $CH_2$ |
| 212 | $CH_3$ | i-Bu | $CH_2$ | H | H | $NHCH_3$ | $CH_2$ |
| 213 | $CH_3$ | cyclopropyl | $CH_2$ | H | Cl | $NHCH_3$ | $CH_2$ |
| 214 | $CH_3$ | t-Bu | $CH_2$ | H | H | $NHCH_3$ | $CH_2$ |
| 215 | $CH_3$ | $CF_3$ | $CH_2$ | H | H | $NHCH_3$ | $CH_2$ |
| 216 | $CH_3$ | $OCH_3$ | $CH_2$ | H | H | $NHCH_3$ | $CH_2$ |
| 217 | $CH_3$ | OEt | $CH_2$ | H | H | $NHCH_3$ | $CH_2$ |
| 218 | $CH_3$ | Ph | $CH_2$ | H | H | $NHCH_3$ | $CH_2$ |
| 219 | $CH_3$ | Ph-4-Cl | $CH_2$ | H | H | $NHCH_3$ | $CH_2$ |
| 220 | $CH_3$ | $CH_3$ | $CH_2$ | H | Cl | $NHCH_3$ | $CH_2$ |
| 221 | $CH_3$ | Et | $CH_2$ | H | Cl | $NHCH_3$ | $CH_2$ |
| 222 | $CH_3$ | n-Pr | $CH_2$ | H | Cl | $NHCH_3$ | $CH_2$ |
| 223 | $CH_3$ | i-Pr | $CH_2$ | H | Cl | $NHCH_3$ | $CH_2$ |
| 224 | $CH_3$ | n-Bu | $CH_2$ | H | Cl | $NHCH_3$ | $CH_2$ |
| 225 | $CH_3$ | i-Bu | $CH_2$ | H | Cl | $NHCH_3$ | $CH_2$ |
| 226 | $CH_3$ | s-Bu | $CH_2$ | H | Cl | $NHCH_3$ | $CH_2$ |
| 227 | $CH_3$ | t-Bu | $CH_2$ | H | Cl | $NHCH_3$ | $CH_2$ |
| 228 | $CH_3$ | $CF_3$ | $CH_2$ | H | Cl | $NHCH_3$ | $CH_2$ |
| 229 | $CH_3$ | $OCH_3$ | $CH_2$ | H | Cl | $NHCH_3$ | $CH_2$ |
| 230 | $CH_3$ | Ph-4-Cl | $CH_2$ | H | Cl | $NHCH_3$ | $CH_2$ |
| 231 | $CH_3$ | $CH_3$ | $CH_2$ | H | Br | $NHCH_3$ | $CH_2$ |
| 232 | $CH_3$ | Et | $CH_2$ | H | Br | $NHOCH_3$ | $CH_2$ |
| 233 | $CH_3$ | n-Pr | $CH_2$ | H | Br | $NHNHCH_3$ | $CH_2$ |
| 234 | $CH_3$ | $OCH_2F$ | $CH_2$ | H | Br | $NHCH_3$ | $CH_2$ |
| 235 | $CH_3$ | $OCH_2CF_3$ | $CH_2$ | H | Cl | $NHCH_3$ | $CH_2$ |
| 236 | $CH_3$ | Ph-4-Cl | $CH_2$ | H | Br | $NHCH_3$ | $CH_2$ |
| 237 | $CH_3$ | $CF_3$ | $CH_2$ | H | $NO_2$ | $NHCH_3$ | $CH_2$ |
| 238 | $CH_3$ | Et | $CH_2$ | H | $NO_2$ | $NHCH_3$ | $CH_2$ |
| 239 | $CH_3$ | n-Pr | $CH_2$ | H | $NO_2$ | $NHCH_3$ | $CH_2$ |
| 240 | $CH_3$ | i-Pr | $CH_2$ | H | $NO_2$ | $NHCH_3$ | $CH_2$ |
| 241 | $CH_3$ | n-Bu | $CH_2$ | H | $NO_2$ | $NHCH_3$ | $CH_2$ |
| 242 | $CH_3$ | $CF_3$ | $CH_2$ | H | $NO_2$ | $NHCH_3$ | $CH_2$ |
| 243 | $CH_3$ | $OCF_3$ | $CH_2$ | H | $NO_2$ | $NHCH_3$ | $CH_2$ |
| 244 | $CH_3$ | Ph-4-Cl | $CH_2$ | H | $NO_2$ | $NHCH_3$ | $CH_2$ |
| 245 | $CH_3$ | $CH_3$ | $CH(CH_3)$ | H | $CH_3$ | $NHCH_3$ | $CH_2$ |
| 246 | $CH_3$ | Et | $CH_2$ | H | Cl | $NHCH_3$ | R-*$CH(CH_3)$ |
| 247 | $CH_3$ | $CF_3$ | $CH_2$ | H | $CH_3$ | $NHCH_3$ | $CH_2$ |
| 248 | $CH_3$ | Ph | $CH_2$ | H | $CH_3$ | $NHCH_3$ | $CH_2$ |
| 249 | $CH_3$ | Ph-4-Cl | $CH_2$ | H | $CH_3$ | $NHCH_3$ | $CH_2$ |
| 250 | $CH_3$ | $CH_3$ | $CH_2$ | H | CN | $NHCH_3$ | $CH_2$ |
| 251 | $CH_3$ | Et | $CH_2$ | H | Cl | $NHCH_3$ | S-*$CH(CH_3)$ |
| 252 | $CH_3$ | $CF_3$ | $CH_2$ | H | CN | $NHCH_3$ | $CH_2$ |
| 253 | $CH_3$ | $OCH_3$ | $CH_2$ | H | CN | $NHCH_3$ | $CH_2$ |
| 254 | $CH_3$ | Ph-4-Cl | $CH_2$ | H | CN | $NHCH_3$ | $CH_2$ |
| 255 | $CH_3$ | $CH_3$ | $CH_2$ | H | $SO_2CF_3$ | $NHCH_3$ | $CH_2$ |
| 256 | $CH_3$ | Et | $CH_2$ | H | $SO_2CF_3$ | $NHCH_3$ | $CH_2$ |
| 257 | $CH_3$ | $CF_3$ | $CH_2$ | H | $SO_2CF_3$ | $NHCH_3$ | $CH_2$ |
| 258 | $CH_3$ | Ph-4-Cl | $CH_2$ | H | $SO_2CF_3$ | $NHCH_3$ | $CH_2$ |
| 259 | $CH_3$ | $CH_3$ | $CH_2$ | H | $SOCF_3$ | $NHCH_3$ | $CH_2$ |
| 260 | $CH_3$ | Et | $CH_2$ | H | $SOCF_3$ | $NHCH_3$ | $CH_2$ |
| 261 | $CH_3$ | $CF_3$ | $CH_2$ | H | $SOCF_3$ | $NHCH_3$ | $CH_2$ |
| 262 | $CH_3$ | Ph-4-Cl | $CH_2$ | H | $SOCF_3$ | $NHCH_3$ | $CH_2$ |
| 263 | $CH_3$ | $CH_3$ | $CH_2$ | H | $OCH_3$ | $NHCH_3$ | $CH_2$ |
| 264 | $CH_3$ | $CF_3$ | $CH_2$ | H | $OCH_3$ | $NHCH_3$ | $CH_2$ |

TABLE 13-continued

Some of compounds of formula I-2

$(Q_1, Q_2, X_2, X_3, X_4, X_5 = H, Z = O)$

| No. | $R_1$ | $R_2$ | $(CHR_3)m$ | $(R_4)n$ | $X_1$ | $Y-R_5$ | $(CHR_6)p$ |
|---|---|---|---|---|---|---|---|
| 265 | $CH_3$ | 4-Cl—Ph | $CH_2$ | H | $OCH_3$ | $NHCH_3$ | $CH_2$ |
| 266 | $CH_3$ | $CH_3$ | $CH(CH_3)$ | H | H | $NHCH_3$ | $CH_2$ |
| 267 | $CH_3$ | Et | $CH(CH_3)$ | H | Cl | $NHCH_3$ | $(CH_2)_2$ |
| 268 | $CH_3$ | $OCH_3$ | $CH(CH_3)$ | H | H | $NHCH_3$ | $CH_2$ |
| 269 | $CH_3$ | Ph-4-Cl | $CH(CH_3)$ | H | H | $NHCH_3$ | $CH_2$ |
| 270 | $CH_3$ | $CH_3$ | $CH(CH_3)$ | H | Cl | $NHCH_3$ | $CH_2$ |
| 271 | $CH_3$ | Et | R-*$CH(CH_3)$ | H | Cl | $NHCH_3$ | $CH_2$ |
| 272 | $CH_3$ | n-Pr | $CH(CH_3)$ | H | Cl | $NHCH_3$ | $CH_2$ |
| 273 | $CH_3$ | i-Pr | $CH(CH_3)$ | H | Cl | $NHCH_3$ | $CH_2$ |
| 274 | $CH_3$ | Et | S-*$CH(CH_3)$ | H | Cl | $NHCH_3$ | $CH_2$ |
| 275 | $CH_3$ | $CF_3$ | $CH(CH_3)$ | H | Cl | $NHCH_3$ | $CH_2$ |
| 276 | $CH_3$ | Ph-4-Cl | $CH(CH_3)$ | H | Cl | $NHCH_3$ | $CH_2$ |
| 277 | $CH_3$ | $CH_3$ | $CH(CH_3)$ | H | Br | $NHCH_3$ | $CH_2$ |
| 278 | $CH_3$ | Et | $CH(CH_3)$ | H | Br | $NHCH_3$ | $CH_2$ |
| 279 | $CH_3$ | $CH_3$ | $CH(CH_3)$ | H | $NO_2$ | $NHCH_3$ | $CH_2$ |
| 280 | $CH_3$ | Et | $CH(CH_3)$ | H | $NO_2$ | $NHCH_3$ | $CH_2$ |
| 281 | $CH_3$ | $CF_3$ | $CH(CH_3)$ | H | $NO_2$ | $NHCH_3$ | $CH_2$ |
| 282 | $CH_3$ | $CH_3$ | $CH_2$ | H | $CH_3$ | $NHCH_3$ | $CH_2$ |
| 283 | $CH_3$ | $CH_3$ | $CH(CH_3)$ | H | Cl | $NHCH_3$ | $(CH_2)_2$ |
| 284 | $CH_3$ | $CF_3$ | $CH(CH_3)$ | H | $CH_3$ | $NHCH_3$ | $CH_2$ |
| 285 | $CH_3$ | $CH_3$ | $(CH_2)_2$ | H | H | $NHCH_3$ | $CH_2$ |
| 286 | $CH_3$ | $CH_3$ | $(CH_2)_2$ | H | Cl | $NHCH_3$ | $CH_2$ |
| 287 | $CH_3$ | Et | $(CH_2)_2$ | H | H | $NHCH_3$ | $CH_2$ |
| 288 | $CH_3$ | Et | $(CH_2)_2$ | H | Cl | $NHCH_3$ | $CH_2$ |
| 289 | $CH_3$ | $CH_3$ | $(CH_2)_3$ | H | H | $NHCH_3$ | $CH_2$ |
| 290 | $CH_3$ | $CH_3$ | $(CH_2)_3$ | H | Cl | $NHCH_3$ | $CH_2$ |
| 291 | $CH_3$ | Et | $(CH_2)_3$ | H | H | $NHCH_3$ | $CH_2$ |
| 292 | $CH_3$ | Et | $(CH_2)_3$ | H | Cl | $NHCH_3$ | $CH_2$ |
| 293 | $CH_3$ | $CH_3$ | $CH_2$ | H | H | $OCH_3$ | $CH_2$ |
| 294 | $CH_3$ | Et | $CH_2$ | H | H | $OCH_3$ | $CH_2$ |
| 295 | $CH_3$ | n-Pr | $CH_2$ | H | H | $OCH_3$ | $CH_2$ |
| 296 | $CH_3$ | i-Pr | $CH_2$ | H | H | $OCH_3$ | $CH_2$ |
| 297 | $CH_3$ | i-Bu | $CH_2$ | H | H | $OCH_3$ | $CH_2$ |
| 298 | H | $CF_3$ | $CH_2$ | H | H | $OCH_3$ | $CH_2$ |
| 299 | $CH_3$ | $CH_3$ | $CH_2$ | 3-$CH_3$ | Cl | OEt | $CH_2$ |
| 300 | $CH_3$ | $CH_3$ | $CH_2$ | H | Cl | OEt | $CH_2$ |
| 301 | $CH_3$ | n-Pr | $CH_2$ | H | Cl | $OCH_3$ | $CH_2$ |
| 302 | $CH_3$ | i-Pr | $CH_2$ | H | Cl | $OCH_3$ | $CH_2$ |
| 303 | $CH_3$ | i-Bu | $CH_2$ | H | Cl | $OCH_3$ | $CH_2$ |
| 304 | $CH_3$ | Et | $CH_2$ | H | Cl | OEt | $CH_2$ |
| 305 | $CH_3$ | t-Bu | $CH_2$ | H | Cl | $OCH_3$ | $CH_2$ |
| 306 | $CH_3$ | $CF_3$ | $CH_2$ | H | Cl | $OCH_3$ | $CH_2$ |
| 307 | $CH_3$ | $OCH_3$ | $CH_2$ | H | Cl | $OCH_3$ | $CH_2$ |
| 308 | $CH_3$ | Ph | $CH_2$ | H | Cl | $OCH_3$ | $CH_2$ |
| 309 | Et | $CH_3$ | $CH_2$ | H | H | $NHCH_3$ | $CH_2$ |
| 310 | Et | Et | $CH_2$ | H | H | $NHCH_3$ | $CH_2$ |
| 311 | Et | $CF_3$ | $CH_2$ | H | H | $OCH_3$ | $CH_2$ |
| 312 | Et | $CH_3$ | $CH_2$ | H | Cl | $NHCH_3$ | $CH_2$ |
| 313 | Et | Et | $CH_2$ | H | Cl | $NHCH_3$ | $CH_2$ |
| 314 | Et | n-Pr | $CH_2$ | H | Cl | $OCH_3$ | $CH_2$ |
| 315 | Et | i-Pr | $CH_2$ | H | Cl | $OCH_3$ | $CH_2$ |
| 316 | Et | $CF_3$ | $CH_2$ | H | Cl | $NHOCH_3$ | $CH_2$ |
| 317 | 2-Py-3-Cl | $CH_3$ | $CH_2$ | H | H | $NHCH_3$ | $CH_2$ |
| 318 | 2-Py-3-Cl | $CF_3$ | $CH_2$ | H | H | $NHCH_3$ | $CH_2$ |
| 319 | 2-Py-3-Cl | Cl | $CH_2$ | H | H | $NHCH_3$ | $CH_2$ |
| 320 | 2-Py-3-Cl | $OCH_2CF_3$ | $CH_2$ | H | H | $NHCH_3$ | $CH_2$ |
| 321 | 2-Py-3-Cl | $OCH_2CN$ | $CH_2$ | H | H | $NHCH_3$ | $CH_2$ |
| 322 | 2-Py-3-Cl | Br | $CH_2$ | H | H | $NHCH_3$ | $CH_2$ |
| 323 | 2-Py-3-Cl | Br | $CH_2$ | 3-$CH_3$-5-CN | H | $NHCH_3$ | $CH_2$ |
| 324 | 2-Py-3-Cl | $OCH_2F$ | $CH_2$ | H | H | $NHCH_3$ | $CH_2$ |
| 325 | 2-Py-3,5-2Cl | $CF_3$ | $CH_2$ | H | H | $NHCH_3$ | $CH_2$ |
| 326 | 2-Py-3-Cl | Br | $CH_2$ | 3-$CH_3$-5-Br | H | $NHCH_3$ | $CH_2$ |

TABLE 13-continued

Some of compounds of formula I-2

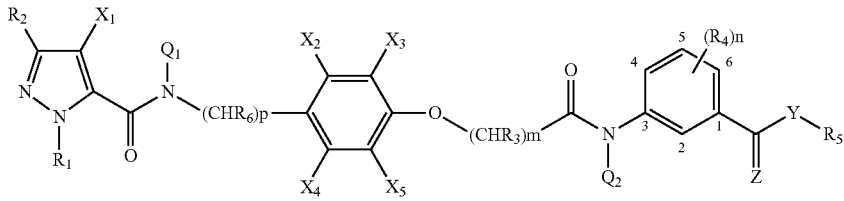

I-2

$(Q_1, Q_2, X_2, X_3, X_4, X_5 = H, Z = O)$

| No. | $R_1$ | $R_2$ | $(CHR_3)m$ | $(R_4)n$ | $X_1$ | $Y-R_5$ | $(CHR_6)p$ |
|---|---|---|---|---|---|---|---|
| 327 | 2-Py-3,5-2Cl | $CH_3$ | $CH_2$ | H | H | $NHCH_3$ | $CH_2$ |
| 328 | 2-Py-3,5-2Cl | Br | $CH_2$ | H | H | $NHCH_3$ | $CH_2$ |
| 329 | 2-Py-3-Cl-5-$CF_3$ | Br | $CH_2$ | H | H | $NHCH_3$ | $CH_2$ |
| 330 | 2-Py-3-Cl-5-$CF_3$ | $CH_3$ | $CH_2$ | H | H | $NHCH_3$ | $CH_2$ |
| 331 | 2-Py-3-Cl-5-$CF_3$ | $CH_3$ | $CH_2$ | H | H | $NHCH_3$ | $CH_2$ |
| 332 | 2-Py-5-$CF_3$ | $CH_3$ | $CH_2$ | H | H | $NHCH_3$ | $CH_2$ |
| 333 | 2-Py-5-$CF_3$ | Cl | $CH_2$ | H | H | $NHCH_3$ | $CH_2$ |
| 334 | H | $CF_3$ | $CH_2$ | H | H | $NHCH_3$ | $CH_2$ |
| 335 | H | $CH_3$ | $CH_2$ | H | Cl | $NHCH_3$ | $CH_2$ |
| 336 | H | Et | $CH_2$ | H | Cl | $NHCH_3$ | $CH_2$ |
| 337 | H | $CF_3$ | $CH_2$ | H | Cl | $NHCH_3$ | $CH_2$ |
| 338 | $CH_3$ | $CH_3$ | $CH_2$ | H | H | NHEt | $CH_2$ |
| 339 | $CH_3$ | Et | $CH_2$ | H | H | NHEt | $CH_2$ |
| 340 | $CH_3$ | $OCH_2CF_3$ | $CH_2$ | H | H | $NHCH_3$ | $CH_2$ |
| 341 | $CH_3$ | $CH_2OCH_3$ | $CH_2$ | H | H | $NHCH_3$ | $CH_2$ |
| 342 | $CH_3$ | $CF_3$ | $CH_2$ | H | H | NHEt | $CH_2$ |
| 343 | $CH_3$ | $CH_3$ | $CH_2$ | H | Cl | NHEt | $CH_2$ |
| 344 | $CH_3$ | Et | $CH_2$ | H | Cl | NHEt | $CH_2$ |
| 345 | $CH_3$ | $OCH_2CN$ | $CH_2$ | H | Cl | $NHCH_3$ | $CH_2$ |
| 346 | $CH_3$ | Et | $CH_2$ | 5-F | Cl | NHEt | $CH_2$ |
| 347 | $CH_3$ | $CF_3$ | $CH_2$ | H | Cl | NHEt | $CH_2$ |
| 348 | $CH_3$ | $CH_3$ | $CH_2$ | H | H | $N(CH_3)_2$ | $CH_2$ |
| 349 | $CH_3$ | Et | $CH_2$ | H | H | $N(CH_3)_2$ | $CH_2$ |
| 350 | $CH_3$ | n-Pr | $CH_2$ | H | H | $N(CH_3)_2$ | $CH_2$ |
| 351 | $CH_3$ | $CF_3$ | $CH_2$ | H | H | $N(CH_3)_2$ | $CH_2$ |
| 352 | $CH_3$ | $CH_3$ | $CH_2$ | H | Cl | $N(CH_3)_2$ | $CH_2$ |
| 353 | $CH_3$ | Et | $CH_2$ | H | Cl | $N(CH_3)_2$ | $CH_2$ |
| 354 | $CH_3$ | i-Pr | $CH_2$ | H | Cl | $N(CH_3)_2$ | $CH_2$ |
| 355 | $CH_3$ | $CF_3$ | $CH_2$ | H | Cl | $N(CH_3)_2$ | $CH_2$ |
| 356 | $CH_3$ | $CH_3$ | $CH_2$ | H | H | $NH_2$ | $CH_2$ |
| 357 | $CH_3$ | Et | $CH_2$ | H | H | $NH_2$ | $CH_2$ |
| 358 | $CH_3$ | n-Pr | $CH_2$ | 3-$CH_3$-4-CN | H | $NH_2$ | $CH_2$ |
| 359 | $CH_3$ | 3-Py | $CH_2$ | H | H | $NH_2$ | $CH_2$ |
| 360 | $CH_3$ | $CF_3$ | $CH_2$ | H | H | $NH_2$ | $CH_2$ |
| 361 | $CH_3$ | $CH_3$ | $CH_2$ | H | Cl | $NH_2$ | $CH_2$ |
| 362 | $CH_3$ | Et | $CH_2$ | H | Cl | $NH_2$ | $CH_2$ |
| 363 | $CH_3$ | n-Pr | $CH_2$ | 2-$CH_3$-5-I | Cl | $NH_2$ | $CH_2$ |
| 364 | $CH_3$ | i-Pr | $CH_2$ | H | Cl | $NH_2$ | $CH_2$ |
| 365 | $CH_3$ | $CF_3$ | $CH_2$ | H | Cl | $NH_2$ | $CH_2$ |
| 366 | $CH_3$ | $CH_3$ | $CH_2$ | 5-Cl | H | $NHCH_3$ | $CH_2$ |
| 367 | $CH_3$ | $CH_3$ | $CH_2$ | 3-$CH_3$-5-I | Cl | $NHCH_3$ | $CH_2$ |
| 368 | $CH_3$ | $CH_3$ | $CH_2$ | 3-$CH_3$-5-Cl | H | $NHCH_3$ | $CH_2$ |
| 369 | $CH_3$ | $CH_3$ | $CH_2$ | 3-$CH_3$ | H | $NHCH_3$ | $CH_2$ |
| 370 | $CH_3$ | $CH_3$ | $CH_2$ | 5-Br | H | $NHCH_3$ | $CH_2$ |
| 371 | $CH_3$ | $CH_3$ | $CH_2$ | 3-$CH_3$-5-Br | Cl | $NHCH_3$ | $CH_2$ |
| 372 | $CH_3$ | $CH_3$ | $CH_2$ | 3-$CH_3$-5-CN | Cl | $NHCH_3$ | $CH_2$ |
| 373 | $CH_3$ | $CH_3$ | $CH_2$ | 3,5-2Cl | H | $NHCH_3$ | $CH_2$ |
| 374 | $CH_3$ | $CH_3$ | $CH_2$ | 5-F | H | $NHCH_3$ | $CH_2$ |
| 375 | $CH_3$ | Et | $CH_2$ | 3-$CH_3$ | Cl | $NHCH_3$ | $CH_2$ |
| 376 | $CH_3$ | $CH_3$ | $CH_2$ | 3-$CH_3$ | Cl | $NHCH_3$ | $CH_2$ |
| 377 | $CH_3$ | Et | $CH_2$ | 3-$CH_3$-5-Cl | Cl | $NHCH_3$ | $CH_2$ |
| 378 | Ph | $CH_3$ | $CH_2$ | H | Cl | $NHCH_3$ | $CH_2$ |
| 379 | Ph-4-Cl | $CH_3$ | $CH_2$ | H | Cl | $NHCH_3$ | $CH_2$ |
| 380 | Ph | $CH_3$ | $CH_2$ | H | H | $NHCH_3$ | $(CH_2)_3$ |
| 381 | Ph-4-Cl | $CH_3$ | $CH_2$ | H | H | $NHCH_3$ | $(CH_2)_3$ |
| 382 | $CH_3$ | $CH_3$ | $CH_2$ | 3-$CH_3$ | H | NHEt | $CH_2$ |
| 383 | $CH_3$ | Et | $CH_2$ | 3-$CH_3$ | Cl | OEt | $CH_2$ |
| 384 | $CH_3$ | $CH_3$ | $CH_2$ | 5-F | H | $NHCH_3$ | $CH_2$ |
| 385 | $CH_3$ | $CH_3$ | $CH_2$ | 3-$CH_3$-5-CN | Cl | $NHCH_3$ | $CH_2$ |
| 386 | $CH_3$ | Et | $CH_2$ | 3-$CH_3$-5-Br | Cl | $NHCH_3$ | $CH_2$ |
| 387 | $CH_3$ | $CH_3$ | $CH_2$ | 3-$CH_3$-5-Cl | Cl | $NHCH_3$ | $CH_2$ |
| 388 | $CH_3$ | Et | $CH_2$ | 3,5-2Cl | Cl | $NHCH_3$ | $CH_2$ |

TABLE 13-continued

Some of compounds of formula I-2

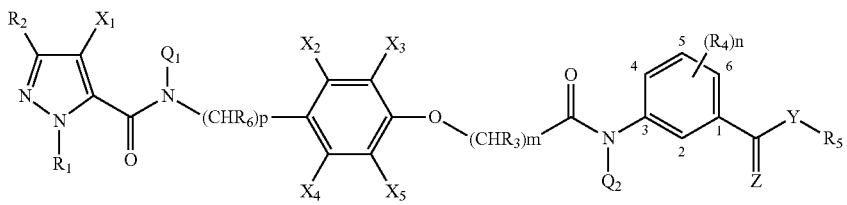

I-2

($Q_1$, $Q_2$, $X_2$, $X_3$, $X_4$, $X_5$ = H, Z = O)

| No. | $R_1$ | $R_2$ | $(CHR_3)m$ | $(R_4)n$ | $X_1$ | Y—$R_5$ | $(CHR_6)p$ |
|---|---|---|---|---|---|---|---|
| 389 | $CH_3$ | $CH_3$ | $CH_2$ | 5-$CH_3$-3-Cl | H | NHEt | $CH_2$ |
| 390 | $CH_3$ | Et | $CH_2$ | 3-CN-5-$CH_3$ | Cl | OEt | $CH_2$ |
| 391 | $CH_3$ | $CH_3$ | $CH_2$ | H | Cl | $NHCH_3$ | $(CH_2)_2$ |
| 392 | $CH_3$ | Et | $CH_2$ | H | Cl | $NHCH_3$ | $(CH_2)_2$ |
| 393 | $CH_3$ | $CH_3$ | $CH_2$ | 5-F | H | $NHCH_3$ | $CH_2$ |
| 394 | 2-Py-3-Cl | Br | $CH_2$ | 3-$CH_3$-5-Cl | H | $NHCH_3$ | $CH_2$ |
| 395 | $CH_3$ | $CH_3$ | $CH_2$ | 3-$CH_3$-5-CN | H | $NHCH_3$ | $CH_2$ |
| 396 | 2-Py-3-Cl | Br | $CH_2$ | 3,5-2Cl | H | $NHCH_3$ | $CH_2$ |
| 397 | 2-Py-3-Cl | $CH_3$ | $CH_2$ | 3-$CH_3$ | H | $NHCH_3$ | $CH_2$ |
| 398 | $CH_3$ | Et | $CH_2$ | 3-$CH_3$-5-CN | Cl | $NHCH_3$ | $CH_2$ |
| 399 | $CH_3$ | $CH_3$ | $CH_2$ | H | Cl | $NHCH_3$ | $(CH_2)_3$ |
| 400 | $CH_3$ | Et | $CH_2$ | H | Cl | morpholin-4-yl | $CH_2$ |
| 401 | $CH_3$ | $CH_3$ | $CH_2$ | H | H | piperidin-1-yl | $CH_2$ |
| 402 | $CH_3$ | Et | $CH_2$ | H | H | 4-methylpiperazin-1-yl | $CH_2$ |
| 403 | $CH_3$ | $CH_3$ | $CH_2$ | H | Cl | 2,6-dimethylmorpholin-4-yl | $CH_2$ |
| 404 | $CH_3$ | $CH_3$ | $CH_2$ | H | $CH_3$ | $NHCH_3$ | $(CH_2)_3$ |
| 405 | $CH_3$ | $CH_3$ | $CH_2$ | H | Cl | $N(CH_3)_2$ | — |
| 406 | $CH_3$ | Et | $CH_2$ | H | Cl | $N(CH_3)_2$ | — |
| 407 | $CH_3$ | $CH_3$ | $CH_2$ | H | Cl | $NHCH_3$ | — |
| 408 | $CH_3$ | Et | $CH_2$ | H | Cl | $N(CH_3)_2$ | — |
| 409 | $CH_3$ | $CH_3$ | $CH_2$ | 3-$CH_3$-5-Cl | Cl | $N(CH_3)_2$ | $CH_2$ |
| 410 | $CH_3$ | Et | $CH_2$ | 3-$CH_3$-5-CN | Cl | $N(CH_3)_2$ | $CH_2$ |

TABLE 14

Some of compounds of formula I-3

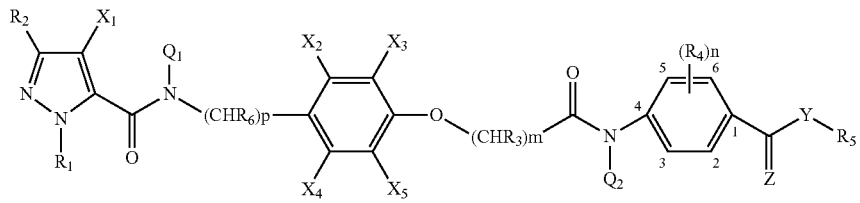

I-3

($Q_1$, $Q_2$, $X_2$, $X_3$, $X_4$, $X_5$ = H, Z = O)

| No. | $R_1$ | $R_2$ | $(CHR_3)m$ | $(R_4)n$ | $X_1$ | Y—$R_5$ | $(CHR_6)p$ |
|---|---|---|---|---|---|---|---|
| 411 | $CH_3$ | Cl | $CH_2$ | H | H | $NHCH_3$ | $CH_2$ |
| 412 | $CH_3$ | $CH_3$ | $CH_2$ | H | H | $NHCH_3$ | $CH_2$ |
| 413 | $CH_3$ | Et | $CH_2$ | H | H | $NHCH_3$ | $CH_2$ |
| 414 | $CH_3$ | n-Pr | $CH_2$ | H | H | $NHCH_3$ | $CH_2$ |
| 415 | $CH_3$ | i-Pr | $CH_2$ | H | H | $NHCH_3$ | $CH_2$ |
| 416 | $CH_3$ | n-Bu | $CH_2$ | H | H | $NHCH_3$ | $CH_2$ |
| 417 | $CH_3$ | i-Bu | $CH_2$ | H | H | $NHCH_3$ | $CH_2$ |
| 418 | $CH_3$ | ▷ | $CH_2$ | H | Cl | $NHCH_3$ | $CH_2$ |
| 419 | $CH_3$ | t-Bu | $CH_2$ | H | H | $NHCH_3$ | $CH_2$ |
| 420 | $CH_3$ | $CF_3$ | $CH_2$ | H | H | $NHCH_3$ | $CH_2$ |
| 421 | $CH_3$ | $OCH_3$ | $CH_2$ | H | H | $NHCH_3$ | $CH_2$ |
| 422 | $CH_3$ | OEt | $CH_2$ | H | H | $NHCH_3$ | $CH_2$ |
| 423 | $CH_3$ | Ph | $CH_2$ | H | H | $NHCH_3$ | $CH_2$ |
| 424 | $CH_3$ | Ph-4-Cl | $CH_2$ | H | H | $NHCH_3$ | $CH_2$ |
| 425 | $CH_3$ | $CH_3$ | $CH_2$ | H | Cl | $NHCH_3$ | $CH_2$ |
| 426 | $CH_3$ | Et | $CH_2$ | H | Cl | $NHCH_3$ | $CH_2$ |
| 427 | $CH_3$ | n-Pr | $CH_2$ | H | Cl | $NHCH_3$ | $CH_2$ |
| 428 | $CH_3$ | i-Pr | $CH_2$ | H | Cl | $NHCH_3$ | $CH_2$ |
| 429 | $CH_3$ | n-Bu | $CH_2$ | H | Cl | $NHCH_3$ | $CH_2$ |
| 430 | $CH_3$ | i-Bu | $CH_2$ | H | Cl | $NHCH_3$ | $CH_2$ |
| 431 | $CH_3$ | s-Bu | $CH_2$ | H | Cl | $NHCH_3$ | $CH_2$ |
| 432 | $CH_3$ | t-Bu | $CH_2$ | H | Cl | $NHCH_3$ | $CH_2$ |
| 433 | $CH_3$ | $CF_3$ | $CH_2$ | H | Cl | $NHCH_3$ | $CH_2$ |
| 434 | $CH_3$ | $OCH_3$ | $CH_2$ | H | Cl | $NHCH_3$ | $CH_2$ |
| 435 | $CH_3$ | Ph-4-Cl | $CH_2$ | H | Cl | $NHCH_3$ | $CH_2$ |
| 436 | $CH_3$ | $CH_3$ | $CH_2$ | H | Br | $NHCH_3$ | $CH_2$ |
| 437 | $CH_3$ | Et | $CH_2$ | H | Br | $NHOCH_3$ | $CH_2$ |
| 438 | $CH_3$ | n-Pr | $CH_2$ | H | Br | $NHNHCH_3$ | $CH_2$ |
| 439 | $CH_3$ | $OCH_2F$ | $CH_2$ | H | Br | $NHCH_3$ | $CH_2$ |
| 440 | $CH_3$ | $OCH_2CF_3$ | $CH_2$ | H | Cl | $NHCH_3$ | $CH_2$ |
| 441 | $CH_3$ | Ph-4-Cl | $CH_2$ | H | Br | $NHCH_3$ | $CH_2$ |
| 442 | $CH_3$ | $CF_3$ | $CH_2$ | H | $NO_2$ | $NHCH_3$ | $CH_2$ |
| 443 | $CH_3$ | Et | $CH_2$ | H | $NO_2$ | $NHCH_3$ | $CH_2$ |
| 444 | $CH_3$ | n-Pr | $CH_2$ | H | $NO_2$ | $NHCH_3$ | $CH_2$ |
| 445 | $CH_3$ | i-Pr | $CH_2$ | H | $NO_2$ | $NHCH_3$ | $CH_2$ |
| 446 | $CH_3$ | n-Bu | $CH_2$ | H | $NO_2$ | $NHCH_3$ | $CH_2$ |
| 447 | $CH_3$ | $CF_3$ | $CH_2$ | H | $NO_2$ | $NHCH_3$ | $CH_2$ |
| 448 | $CH_3$ | $OCF_3$ | $CH_2$ | H | $NO_2$ | $NHCH_3$ | $CH_2$ |
| 449 | $CH_3$ | Ph-4-Cl | $CH_2$ | H | $NO_2$ | $NHCH_3$ | $CH_2$ |
| 450 | $CH_3$ | $CH_3$ | $CH(CH_3)$ | H | $CH_3$ | $NHCH_3$ | $CH_2$ |
| 451 | $CH_3$ | Et | $CH_2$ | H | Cl | $NHCH_3$ | R-*$CH(CH_3)$ |
| 452 | $CH_3$ | $CF_3$ | $CH_2$ | H | $CH_3$ | $NHCH_3$ | $CH_2$ |
| 453 | $CH_3$ | Ph | $CH_2$ | H | $CH_3$ | $NHCH_3$ | $CH_2$ |
| 454 | $CH_3$ | Ph-4-Cl | $CH_2$ | H | $CH_3$ | $NHCH_3$ | $CH_2$ |
| 455 | $CH_3$ | $CH_3$ | $CH_2$ | H | CN | $NHCH_3$ | $CH_2$ |
| 456 | $CH_3$ | Et | $CH_2$ | H | Cl | $NHCH_3$ | S-*$CH(CH_3)$ |
| 457 | $CH_3$ | $CF_3$ | $CH_2$ | H | CN | $NHCH_3$ | $CH_2$ |
| 458 | $CH_3$ | $OCH_3$ | $CH_2$ | H | CN | $NHCH_3$ | $CH_2$ |
| 459 | $CH_3$ | Ph-4-Cl | $CH_2$ | H | CN | $NHCH_3$ | $CH_2$ |
| 460 | $CH_3$ | $CH_3$ | $CH_2$ | H | $SO_2CF_3$ | $NHCH_3$ | $CH_2$ |
| 461 | $CH_3$ | Et | $CH_2$ | H | $SO_2CF_3$ | $NHCH_3$ | $CH_2$ |
| 462 | $CH_3$ | $CF_3$ | $CH_2$ | H | $SO_2CF_3$ | $NHCH_3$ | $CH_2$ |
| 463 | $CH_3$ | Ph-4-Cl | $CH_2$ | H | $SO_2CF_3$ | $NHCH_3$ | $CH_2$ |
| 464 | $CH_3$ | $CH_3$ | $CH_2$ | H | $SOCF_3$ | $NHCH_3$ | $CH_2$ |
| 465 | $CH_3$ | Et | $CH_2$ | H | $SOCF_3$ | $NHCH_3$ | $CH_2$ |
| 466 | $CH_3$ | $CF_3$ | $CH_2$ | H | $SOCF_3$ | $NHCH_3$ | $CH_2$ |
| 467 | $CH_3$ | Ph-4-Cl | $CH_2$ | H | $SOCF_3$ | $NHCH_3$ | $CH_2$ |
| 469 | $CH_3$ | $CH_3$ | $CH_2$ | H | $OCH_3$ | $NHCH_3$ | $CH_2$ |
| 469 | $CH_3$ | $CF_3$ | $CH_2$ | H | $OCH_3$ | $NHCH_3$ | $CH_2$ |

TABLE 14-continued

Some of compounds of formula I-3

I-3

($Q_1$, $Q_2$, $X_2$, $X_3$, $X_4$, $X_5$ = H, Z = O)

| No. | $R_1$ | $R_2$ | $(CHR_3)m$ | $(R_4)n$ | $X_1$ | Y—$R_5$ | $(CHR_6)p$ |
|---|---|---|---|---|---|---|---|
| 470 | $CH_3$ | Ph-4-Cl | $CH_2$ | H | $OCH_3$ | $NHCH_3$ | $CH_2$ |
| 471 | $CH_3$ | $CH_3$ | $CH(CH_3)$ | H | H | $NHCH_3$ | $CH_2$ |
| 472 | $CH_3$ | Et | $CH(CH_3)$ | H | Cl | $NHCH_3$ | $(CH_2)_2$ |
| 473 | $CH_3$ | $OCH_3$ | $CH(CH_3)$ | H | H | $NHCH_3$ | $CH_2$ |
| 474 | $CH_3$ | Ph-4-Cl | $CH(CH_3)$ | H | H | $NHCH_3$ | $CH_2$ |
| 475 | $CH_3$ | $CH_3$ | $CH(CH_3)$ | H | Cl | $NHCH_3$ | $CH_2$ |
| 476 | $CH_3$ | Et | R-*$CH(CH_3)$ | H | Cl | $NHCH_3$ | $CH_2$ |
| 477 | $CH_3$ | n-Pr | $CH(CH_3)$ | H | Cl | $NHCH_3$ | $CH_2$ |
| 478 | $CH_3$ | i-Pr | $CH(CH_3)$ | H | Cl | $NHCH_3$ | $CH_2$ |
| 479 | $CH_3$ | Et | S-*$CH(CH_3)$ | H | Cl | $NHCH_3$ | $CH_2$ |
| 480 | $CH_3$ | $CF_3$ | $CH(CH_3)$ | H | Cl | $NHCH_3$ | $CH_2$ |
| 481 | $CH_3$ | Ph-4-Cl | $CH(CH_3)$ | H | Cl | $NHCH_3$ | $CH_2$ |
| 482 | $CH_3$ | $CH_3$ | $CH(CH_3)$ | H | Br | $NHCH_3$ | $CH_2$ |
| 483 | $CH_3$ | Et | $CH(CH_3)$ | H | Br | $NHCH_3$ | $CH_2$ |
| 484 | $CH_3$ | $CH_3$ | $CH(CH_3)$ | H | $NO_2$ | $NHCH_3$ | $CH_2$ |
| 485 | $CH_3$ | Et | $CH(CH_3)$ | H | $NO_2$ | $NHCH_3$ | $CH_2$ |
| 486 | $CH_3$ | $CF_3$ | $CH(CH_3)$ | H | $NO_2$ | $NHCH_3$ | $CH_2$ |
| 487 | $CH_3$ | $CH_3$ | $CH_2$ | H | $CH_3$ | $NHCH_3$ | $CH_2$ |
| 488 | $CH_3$ | $CH_3$ | $CH(CH_3)$ | H | Cl | $NHCH_3$ | $(CH_2)_2$ |
| 489 | $CH_3$ | $CF_3$ | $CH(CH_3)$ | H | $CH_3$ | $NHCH_3$ | $CH_2$ |
| 490 | $CH_3$ | $CH_3$ | $(CH_2)_2$ | H | H | $NHCH_3$ | $CH_2$ |
| 491 | $CH_3$ | $CH_3$ | $(CH_2)_2$ | H | Cl | $NHCH_3$ | $CH_2$ |
| 492 | $CH_3$ | Et | $(CH_2)_2$ | H | H | $NHCH_3$ | $CH_2$ |
| 493 | $CH_3$ | Et | $(CH_2)_2$ | H | Cl | $NHCH_3$ | $CH_2$ |
| 494 | $CH_3$ | $CH_3$ | $(CH_2)_3$ | H | H | $NHCH_3$ | $CH_2$ |
| 495 | $CH_3$ | $CH_3$ | $(CH_2)_3$ | H | Cl | $NHCH_3$ | $CH_2$ |
| 496 | $CH_3$ | Et | $(CH_2)_3$ | H | H | $NHCH_3$ | $CH_2$ |
| 497 | $CH_3$ | Et | $(CH_2)_3$ | H | Cl | $NHCH_3$ | $CH_2$ |
| 498 | $CH_3$ | $CH_3$ | $CH_2$ | H | H | $OCH_3$ | $CH_2$ |
| 499 | $CH_3$ | Et | $CH_2$ | H | H | $OCH_3$ | $CH_2$ |
| 500 | $CH_3$ | n-Pr | $CH_2$ | H | H | $OCH_3$ | $CH_2$ |
| 501 | $CH_3$ | i-Pr | $CH_2$ | H | H | $OCH_3$ | $CH_2$ |
| 502 | $CH_3$ | i-Bu | $CH_2$ | H | H | $OCH_3$ | $CH_2$ |
| 503 | H | $CF_3$ | $CH_2$ | H | H | $OCH_3$ | $CH_2$ |
| 504 | $CH_3$ | $CH_3$ | $CH_2$ | 3-$CH_3$ | Cl | OEt | $CH_2$ |
| 505 | $CH_3$ | $CH_3$ | $CH_2$ | H | Cl | OEt | $CH_2$ |
| 506 | $CH_3$ | n-Pr | $CH_2$ | H | Cl | $OCH_3$ | $CH_2$ |
| 507 | $CH_3$ | i-Pr | $CH_2$ | H | Cl | $OCH_3$ | $CH_2$ |
| 508 | $CH_3$ | i-Bu | $CH_2$ | H | Cl | $OCH_3$ | $CH_2$ |
| 509 | $CH_3$ | Et | $CH_2$ | H | Cl | OEt | $CH_2$ |
| 510 | $CH_3$ | t-Bu | $CH_2$ | H | Cl | $OCH_3$ | $CH_2$ |
| 511 | $CH_3$ | $CF_3$ | $CH_2$ | H | Cl | $OCH_3$ | $CH_2$ |
| 512 | $CH_3$ | $OCH_3$ | $CH_2$ | H | Cl | $OCH_3$ | $CH_2$ |
| 513 | $CH_3$ | Ph | $CH_2$ | H | Cl | $OCH_3$ | $CH_2$ |
| 514 | Et | $CH_3$ | $CH_2$ | H | H | $NHCH_3$ | $CH_2$ |
| 515 | Et | Et | $CH_2$ | H | H | $NHCH_3$ | $CH_2$ |
| 516 | Et | $CF_3$ | $CH_2$ | H | H | $OCH_3$ | $CH_2$ |
| 517 | Et | $CH_3$ | $CH_2$ | H | Cl | $NHCH_3$ | $CH_2$ |
| 518 | Et | Et | $CH_2$ | H | Cl | $NHCH_3$ | $CH_2$ |
| 519 | Et | n-Pr | $CH_2$ | H | Cl | $OCH_3$ | $CH_2$ |
| 520 | Et | i-Pr | $CH_2$ | H | Cl | $OCH_3$ | $CH_2$ |
| 521 | Et | $CF_3$ | $CH_2$ | H | Cl | $NHOCH_3$ | $CH_2$ |
| 522 | 2-Py-3-Cl | $CH_3$ | $CH_2$ | H | H | $NHCH_3$ | $CH_2$ |
| 523 | 2-Py-3-Cl | $CF_3$ | $CH_2$ | H | H | $NHCH_3$ | $CH_2$ |
| 524 | 2-Py-3-Cl | Cl | $CH_2$ | H | H | $NHCH_3$ | $CH_2$ |
| 525 | 2-Py-3-Cl | $OCH_2CF_3$ | $CH_2$ | H | H | $NHCH_3$ | $CH_2$ |
| 526 | 2-Py-3-Cl | $OCH_2CN$ | $CH_2$ | H | H | $NHCH_3$ | $CH_2$ |
| 527 | 2-Py-3-Cl | Br | $CH_2$ | H | H | $NHCH_3$ | $CH_2$ |
| 528 | 2-Py-3-Cl | Br | $CH_2$ | 3-$CH_3$-5-CN | H | $NHCH_3$ | $CH_2$ |
| 529 | 2-Py-3-Cl | $OCH_2F$ | $CH_2$ | H | H | $NHCH_3$ | $CH_2$ |
| 530 | 2-Py-3,5-2Cl | $CF_3$ | $CH_2$ | H | H | $NHCH_3$ | $CH_2$ |
| 531 | 2-Py-3-Cl | Br | $CH_2$ | 3-$CH_3$-5-Br | H | $NHCH_3$ | $CH_2$ |

TABLE 14-continued

Some of compounds of formula I-3

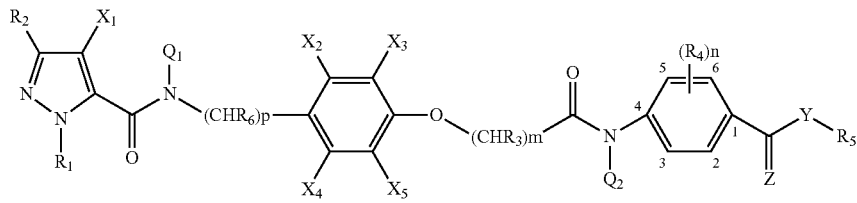

I-3

($Q_1, Q_2, X_2, X_3, X_4, X_5$ = H, Z = O)

| No. | $R_1$ | $R_2$ | $(CHR_3)m$ | $(R_4)n$ | $X_1$ | $Y-R_5$ | $(CHR_6)p$ |
|---|---|---|---|---|---|---|---|
| 532 | 2-Py-3,5-2Cl | $CH_3$ | $CH_2$ | H | H | $NHCH_3$ | $CH_2$ |
| 533 | 2-Py-3,5-2Cl | Br | $CH_2$ | H | H | $NHCH_3$ | $CH_2$ |
| 534 | 2-Py-3-Cl-5-$CF_3$ | Br | $CH_2$ | H | H | $NHCH_3$ | $CH_2$ |
| 535 | 2-Py-3-Cl-5-$CF_3$ | $CH_3$ | $CH_2$ | H | H | $NHCH_3$ | $CH_2$ |
| 536 | 2-Py-3-Cl-5-$CF_3$ | $CH_3$ | $CH_2$ | H | H | $NHCH_3$ | $CH_2$ |
| 537 | 2-Py-5-$CF_3$ | $CH_3$ | $CH_2$ | H | H | $NHCH_3$ | $CH_2$ |
| 538 | 2-Py-5-$CF_3$ | Cl | $CH_2$ | H | H | $NHCH_3$ | $CH_2$ |
| 539 | H | $CF_3$ | $CH_2$ | H | H | $NHCH_3$ | $CH_2$ |
| 540 | H | $CH_3$ | $CH_2$ | H | Cl | $NHCH_3$ | $CH_2$ |
| 541 | H | Et | $CH_2$ | H | Cl | $NHCH_3$ | $CH_2$ |
| 542 | H | $CF_3$ | $CH_2$ | H | Cl | $NHCH_3$ | $CH_2$ |
| 543 | $CH_3$ | $CH_3$ | $CH_2$ | H | H | NHEt | $CH_2$ |
| 544 | $CH_3$ | Et | $CH_2$ | H | H | NHEt | $CH_2$ |
| 545 | $CH_3$ | $OCH_2CF_3$ | $CH_2$ | H | H | $NHCH_3$ | $CH_2$ |
| 546 | $CH_3$ | $CH_2OCH_3$ | $CH_2$ | H | H | $NHCH_3$ | $CH_2$ |
| 547 | $CH_3$ | $CF_3$ | $CH_2$ | H | H | NHEt | $CH_2$ |
| 548 | $CH_3$ | $CH_3$ | $CH_2$ | H | Cl | NHEt | $CH_2$ |
| 549 | $CH_3$ | Et | $CH_2$ | H | Cl | NHEt | $CH_2$ |
| 550 | $CH_3$ | $OCH_2CN$ | $CH_2$ | H | Cl | $NHCH_3$ | $CH_2$ |
| 551 | $CH_3$ | Et | $CH_2$ | 5-F | Cl | NHEt | $CH_2$ |
| 552 | $CH_3$ | $CF_3$ | $CH_2$ | H | Cl | NHEt | $CH_2$ |
| 553 | $CH_3$ | $CH_3$ | $CH_2$ | H | H | $N(CH_3)_2$ | $CH_2$ |
| 554 | $CH_3$ | Et | $CH_2$ | H | H | $N(CH_3)_2$ | $CH_2$ |
| 555 | $CH_3$ | n-Pr | $CH_2$ | H | H | $N(CH_3)_2$ | $CH_2$ |
| 556 | $CH_3$ | $CF_3$ | $CH_2$ | H | H | $N(CH_3)_2$ | $CH_2$ |
| 557 | $CH_3$ | $CH_3$ | $CH_2$ | H | Cl | $N(CH_3)_2$ | $CH_2$ |
| 558 | $CH_3$ | Et | $CH_2$ | H | Cl | $N(CH_3)_2$ | $CH_2$ |
| 559 | $CH_3$ | i-Pr | $CH_2$ | H | Cl | $N(CH_3)_2$ | $CH_2$ |
| 560 | $CH_3$ | $CF_3$ | $CH_2$ | H | Cl | $N(CH_3)_2$ | $CH_2$ |
| 561 | $CH_3$ | $CH_3$ | $CH_2$ | H | H | $NH_2$ | $CH_2$ |
| 562 | $CH_3$ | Et | $CH_2$ | H | H | $NH_2$ | $CH_2$ |
| 563 | $CH_3$ | n-Pr | $CH_2$ | 3-$CH_3$-4-CN | H | $NH_2$ | $CH_2$ |
| 564 | $CH_3$ | 3-Py | $CH_2$ | H | H | $NH_2$ | $CH_2$ |
| 565 | $CH_3$ | $CF_3$ | $CH_2$ | H | H | $NH_2$ | $CH_2$ |
| 566 | $CH_3$ | $CH_3$ | $CH_2$ | H | Cl | $NH_2$ | $CH_2$ |
| 567 | $CH_3$ | Et | $CH_2$ | H | Cl | $NH_2$ | $CH_2$ |
| 568 | $CH_3$ | n-Pr | $CH_2$ | 2-$CH_3$-5-I | Cl | $NH_2$ | $CH_2$ |
| 569 | $CH_3$ | i-Pr | $CH_2$ | H | Cl | $NH_2$ | $CH_2$ |
| 570 | $CH_3$ | $CF_3$ | $CH_2$ | H | Cl | $NH_2$ | $CH_2$ |
| 571 | $CH_3$ | $CH_3$ | $CH_2$ | 5-Cl | H | $NHCH_3$ | $CH_2$ |
| 572 | $CH_3$ | $CH_3$ | $CH_2$ | 3-$CH_3$-5-I | Cl | $NHCH_3$ | $CH_2$ |
| 573 | $CH_3$ | $CH_3$ | $CH_2$ | 3-$CH_3$-5-Cl | H | $NHCH_3$ | $CH_2$ |
| 574 | $CH_3$ | $CH_3$ | $CH_2$ | 3-$CH_3$ | H | $NHCH_3$ | $CH_2$ |
| 575 | $CH_3$ | $CH_3$ | $CH_2$ | 5-Br | H | $NHCH_3$ | $CH_2$ |
| 576 | $CH_3$ | $CH_3$ | $CH_2$ | 3-$CH_3$-5-Br | Cl | $NHCH_3$ | $CH_2$ |
| 577 | $CH_3$ | $CH_3$ | $CH_2$ | 3-$CH_3$-5-CN | Cl | $NHCH_3$ | $CH_2$ |
| 578 | $CH_3$ | $CH_3$ | $CH_2$ | 3,5-2Cl | H | $NHCH_3$ | $CH_2$ |
| 579 | $CH_3$ | $CH_3$ | $CH_2$ | 5-F | H | $NHCH_3$ | $CH_2$ |
| 580 | $CH_3$ | Et | $CH_2$ | 3-$CH_3$ | Cl | $NHCH_3$ | $CH_2$ |
| 581 | $CH_3$ | $CH_3$ | $CH_2$ | 3-$CH_3$ | Cl | $NHCH_3$ | $CH_2$ |
| 582 | $CH_3$ | Et | $CH_2$ | 3-$CH_3$-5-Cl | Cl | $NHCH_3$ | $CH_2$ |
| 583 | Ph | $CH_3$ | $CH_2$ | H | Cl | $NHCH_3$ | $CH_2$ |
| 584 | Ph-4-Cl | $CH_3$ | $CH_2$ | H | Cl | $NHCH_3$ | $CH_2$ |
| 585 | Ph | $CH_3$ | $CH_2$ | H | H | $NHCH_3$ | $(CH_2)_3$ |
| 586 | Ph-4-Cl | $CH_3$ | $CH_2$ | H | H | $NHCH_3$ | $(CH_2)_3$ |
| 587 | $CH_3$ | $CH_3$ | $CH_2$ | 3-$CH_3$ | H | NHEt | $CH_2$ |
| 588 | $CH_3$ | Et | $CH_2$ | 3-$CH_3$ | Cl | OEt | $CH_2$ |
| 589 | $CH_3$ | $CH_3$ | $CH_2$ | 5-F | H | $NHCH_3$ | $CH_2$ |
| 590 | $CH_3$ | $CH_3$ | $CH_2$ | 3-$CH_3$-5-CN | Cl | $NHCH_3$ | $CH_2$ |
| 591 | $CH_3$ | Et | $CH_2$ | 3-$CH_3$-5-Br | Cl | $NHCH_3$ | $CH_2$ |
| 592 | $CH_3$ | $CH_3$ | $CH_2$ | 3-$CH_3$-5-Cl | Cl | $NHCH_3$ | $CH_2$ |
| 593 | $CH_3$ | Et | $CH_2$ | 3,5-2Cl | Cl | $NHCH_3$ | $CH_2$ |

TABLE 14-continued

Some of compounds of formula I-3

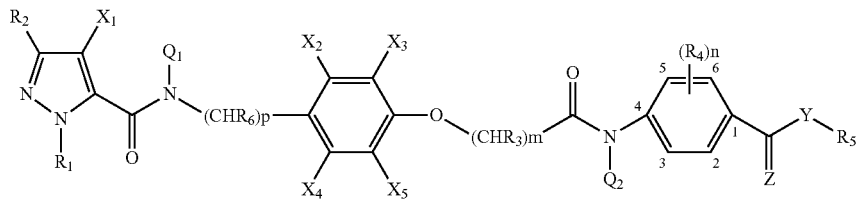

I-3

($Q_1$, $Q_2$, $X_2$, $X_3$, $X_4$, $X_5$ = H, Z = O)

| No. | $R_1$ | $R_2$ | $(CHR_3)m$ | $(R_4)n$ | $X_1$ | Y—$R_5$ | $(CHR_6)p$ |
|-----|-------|-------|------------|----------|-------|---------|------------|
| 594 | $CH_3$ | $CH_3$ | $CH_2$ | 5-$CH_3$-3-Cl | H | NHEt | $CH_2$ |
| 595 | $CH_3$ | Et | $CH_2$ | 3-CN-5-$CH_3$ | Cl | OEt | $CH_2$ |
| 596 | $CH_3$ | $CH_3$ | $CH_2$ | H | Cl | $NHCH_3$ | $(CH_2)_2$ |
| 597 | $CH_3$ | Et | $CH_2$ | H | Cl | $NHCH_3$ | $(CH_2)_2$ |
| 598 | $CH_3$ | $CH_3$ | $CH_2$ | 5-F | H | $NHCH_3$ | $CH_2$ |
| 599 | 2-Py-3-Cl | Br | $CH_2$ | 3-$CH_3$-5-Cl | H | $NHCH_3$ | $CH_2$ |
| 600 | $CH_3$ | $CH_3$ | $CH_2$ | 3-$CH_3$-5-CN | H | $NHCH_3$ | $CH_2$ |
| 601 | 2-Py-3-C | Br | $CH_2$ | 3,5-2Cl | H | $NHCH_3$ | $CH_2$ |
| 602 | 2-Py-3-C | $CH_3$ | $CH_2$ | 3-$CH_3$ | H | $NHCH_3$ | $CH_2$ |
| 603 | $CH_3$ | Et | $CH_2$ | 3-$CH_3$-5-CN | Cl | $NHCH_3$ | $CH_2$ |
| 604 | $CH_3$ | $CH_3$ | $CH_2$ | H | Cl | $NHCH_3$ | $(CH_2)_3$ |
| 605 | $CH_3$ | Et | $CH_2$ | H | Cl | morpholin-4-yl | $CH_2$ |
| 606 | $CH_3$ | $CH_3$ | $CH_2$ | H | H | piperidin-1-yl | $CH_2$ |
| 607 | $CH_3$ | Et | $CH_2$ | H | H | 4-methylpiperazin-1-yl | $CH_2$ |
| 608 | $CH_3$ | $CH_3$ | $CH_2$ | H | Cl | 2,6-dimethylmorpholin-4-yl | $CH_2$ |
| 609 | $CH_3$ | $CH_3$ | $CH_2$ | H | $CH_3$ | $NHCH_3$ | $(CH_2)_3$ |
| 610 | $CH_3$ | $CH_3$ | $CH_2$ | H | Cl | $N(CH_3)_2$ | — |
| 611 | $CH_3$ | Et | $CH_2$ | H | Cl | $N(CH_3)_2$ | — |
| 612 | $CH_3$ | $CH_3$ | $CH_2$ | H | Cl | $NHCH_3$ | — |
| 613 | $CH_3$ | Et | $CH_2$ | H | Cl | $N(CH_3)_2$ | — |
| 614 | $CH_3$ | $CH_3$ | $CH_2$ | 3-$CH_3$-5-Cl | Cl | $N(CH_3)_2$ | $CH_2$ |
| 615 | $CH_3$ | Et | $CH_2$ | 3-$CH_3$-5-CN | Cl | $N(CH_3)_2$ | $CH_2$ |

The abbreviations in the tables above of Et, n-Pr, i-Pr, n-Bu, i-Bu, s-Bu, t-Bu, Bn, Py and Ph respectively represents ethyl, n-propyl, isopropyl, n-butyl, isobutyl, sec-butyl, tert-butyl, benzyl, pyridyl and phenyl. In tables 12, 13 and 14, "-" represents p0, namely chemical bond, namely means the two chemical groups are connected directly.

The other compounds of the present invention are listed in table 15, wherein: $R_3=R_6=Q_1=Q_2=X_2=X_4=H$, $p=1$, $m=1$, $n=0$, $Z=O$, $YR_5=NHCH_3$, $N-Q_2$ links with phenyl ring at the 2-position.

TABLE 15

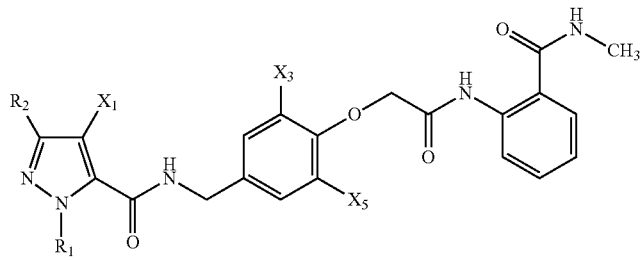

| compound | $R_1$ | $R_2$ | $X_1$ | $X_3$ | $X_5$ |
| --- | --- | --- | --- | --- | --- |
| 616 | $CH_3$ | $CH_3$ | Cl | H | Cl |
| 617 | $CH_3$ | Et | Cl | H | Cl |
| 618 | $CH_3$ | n-Pr | Cl | H | Cl |
| 619 | $CH_3$ | i-Pr | Cl | H | Cl |
| 620 | $CH_3$ | t-Bu | Cl | H | Cl |
| 621 | $CH_3$ | cyclopropyl | Cl | H | Cl |
| 622 | $CH_3$ | $CF_3$ | Cl | H | Cl |
| 623 | $CH_3$ | $CH_2OCH_3$ | Cl | H | Cl |
| 624 | $CH_3$ | $CH_2OCH_2CF_3$ | Cl | H | Cl |
| 625 | $CH_3$ | $CH_2Cl$ | Cl | H | Cl |
| 626 | $CH_3$ | $CH_2CN$ | Cl | H | Cl |
| 627 | $CH_3$ | Cl | Cl | H | Cl |
| 628 | $CH_3$ | Br | Cl | H | Cl |
| 629 | $CH_3$ | $OCF_3$ | Cl | H | Cl |
| 630 | $CH_3$ | $OCH_2CF_3$ | Cl | H | Cl |
| 631 | $CH_3$ | $OCH_2CN$ | Cl | H | Cl |
| 632 | $CH_3$ | Ph | Cl | H | Cl |
| 633 | $CH_3$ | Ph-4-Cl | Cl | H | Cl |
| 634 | $CH_3$ | Ph-2,4-2Cl | Cl | H | Cl |
| 635 | $CH_3$ | Ph-4-$CH_3$ | Cl | H | Cl |
| 636 | $CH_3$ | Ph-2,4-2$CH_3$ | Cl | H | Cl |
| 637 | $CH_3$ | Ph-4-$CF_3$ | Cl | H | Cl |
| 638 | $CH_3$ | Ph-4-$OCF_3$ | Cl | H | Cl |
| 639 | $CH_3$ | 3-Py-2-Cl | Cl | H | Cl |
| 640 | $CH_3$ | 2-Py-5-Cl | Cl | H | Cl |
| 641 | $CH_3$ | 3-Py | Cl | H | Cl |
| 642 | $CH_3$ | $CH_3$ | H | H | Cl |
| 643 | $CH_3$ | Et | H | H | Cl |
| 644 | $CH_3$ | n-Pr | H | H | Cl |
| 645 | $CH_3$ | i-Pr | H | H | Cl |
| 646 | $CH_3$ | t-Bu | H | H | Cl |
| 647 | $CH_3$ | cyclopropyl | H | H | Cl |
| 648 | $CH_3$ | $CF_3$ | H | H | Cl |
| 649 | $CH_3$ | $CH_3$ | Br | H | Cl |
| 650 | $CH_3$ | Et | Br | H | Cl |
| 651 | $CH_3$ | n-Pr | Br | H | Cl |
| 652 | $CH_3$ | i-Pr | Br | H | Cl |
| 653 | $CH_3$ | t-Bu | Br | H | Cl |
| 654 | $CH_3$ | cyclopropyl | Br | H | Cl |
| 655 | $CH_3$ | $CF_3$ | Br | H | Cl |
| 656 | Et | $CH_3$ | H | H | Cl |
| 657 | Et | Et | H | H | Cl |
| 658 | Et | n-Pr | H | H | Cl |
| 659 | Et | i-Pr | H | H | Cl |
| 660 | Et | t-Bu | H | H | Cl |

TABLE 15-continued

| compound | R₁ | R₂ | X₁ | X₃ | X₅ |
|---|---|---|---|---|---|
| 661 | Et |  | H | H | Cl |
| 662 | Et | CF₃ | H | H | Cl |
| 663 | Et | CH₃ | Cl | H | Cl |
| 664 | Et | Et | Cl | H | Cl |
| 665 | Et | n-Pr | Cl | H | Cl |
| 666 | Et | i-Pr | Cl | H | Cl |
| 667 | Et | t-Bu | Cl | H | Cl |
| 668 | Et |  | Cl | H | Cl |
| 669 | Et | CF₃ | Cl | H | Cl |
| 670 | i-Pr | CH₃ | Cl | H | Cl |
| 671 | i-Pr | CH₃ | H | H | Cl |
| 672 |  | CH₃ | Cl | H | Cl |
| 673 |  | CH₃ | H | H | Cl |
| 674 | CH₂CF₃ | CH₃ | Cl | H | Cl |
| 675 | CH₂CF₃ | CH₃ | H | H | Cl |
| 676 | Ph | CH₃ | Cl | H | Cl |
| 677 | Ph | CH₃ | H | H | Cl |
| 678 | Ph | Cl | H | H | Cl |
| 679 | Ph | Br | H | H | Cl |
| 680 | Ph-2-Cl | CH₃ | Cl | H | Cl |
| 681 | Ph-2-Cl | CH₃ | H | H | Cl |
| 682 | Ph-2-Cl | Cl | H | H | Cl |
| 683 | Ph-2-Cl | Br | H | H | Cl |
| 684 | Ph-4-Cl | CH₃ | Cl | H | Cl |
| 685 | Ph-4-Cl | CH₃ | H | H | Cl |
| 686 | Ph-4-Cl | Cl | H | H | Cl |
| 687 | Ph-4-Cl | Br | H | H | Cl |
| 688 | 2-Py-3-Cl | CH₃ | Cl | H | Cl |
| 689 | 2-Py-3-Cl | CH₃ | H | H | Cl |
| 690 | 2-Py-3-Cl | Cl | H | H | Cl |
| 691 | 2-Py-3-Cl | Br | H | H | Cl |
| 692 | 2-Py-3-Cl | CF₃ | H | H | Cl |
| 693 | 2-Py-3-Cl | CHF₂ | H | H | Cl |
| 694 | 2-Py-3-Cl | OCF3 | H | H | Cl |
| 695 | 2-Py-3-Cl | OCH₂CF3 | H | H | Cl |
| 696 | 2-Py-3-Cl | OCH₂CN | H | H | Cl |
| 697 | 2-Py-3-Cl | OCH₂F | H | H | Cl |
| 698 | 2-Py-3,5-2Cl | Cl | H | H | Cl |
| 699 | 2-Py-3,5-2Cl | Br | H | H | Cl |
| 670 | 2-Py-3,5,6-3Cl | Cl | H | H | Cl |
| 671 | 2-Py-3,5,6-3Cl | Br | H | H | Cl |
| 672 | 2-Py-3-Cl-5-CF₃ | Cl | H | H | Cl |
| 673 | 2-Py-3-Cl-5-CF₃ | Br | H | H | Cl |
| 674 | 2-Py-5-CF₃ | Cl | H | H | Cl |
| 675 | 2-Py-5-CF₃ | Br | H | H | Cl |
| 676 | 2-Py-3-Cl-5-CH₃ | Cl | H | H | Cl |
| 677 | 2-Py-3-Cl-5-CH₃ | Br | H | H | Cl |
| 678 | CH₃ | CH₃ | Cl | H | OCH₃ |
| 679 | CH₃ | Et | Cl | H | OCH₃ |
| 680 | CH₃ | n-Pr | Cl | H | OCH₃ |
| 681 | CH₃ | i-Pr | Cl | H | OCH₃ |
| 682 | CH₃ | t-Bu | Cl | H | OCH₃ |

TABLE 15-continued

| compound | R₁ | R₂ | X₁ | X₃ | X₅ |
|---|---|---|---|---|---|
| 683 | CH₃ |  | Cl | H | OCH₃ |
| 684 | CH₃ | CF₃ | Cl | H | OCH₃ |
| 685 | CH₃ | CH₂OCH₃ | Cl | H | OCH₃ |
| 686 | CH₃ | CH₂OCH₂CF₃ | Cl | H | OCH₃ |
| 687 | CH₃ | CH₂Cl | Cl | H | OCH₃ |
| 688 | CH₃ | CH₂CN | Cl | H | OCH₃ |
| 689 | CH₃ | Cl | Cl | H | OCH₃ |
| 690 | CH₃ | Br | Cl | H | OCH₃ |
| 691 | CH₃ | OCF3 | Cl | H | OCH₃ |
| 692 | CH₃ | OCH₂CF3 | Cl | H | OCH₃ |
| 693 | CH₃ | OCH₂CN | Cl | H | OCH₃ |
| 694 | CH₃ | Ph | Cl | H | OCH₃ |
| 695 | CH₃ | Ph-4-Cl | Cl | H | OCH₃ |
| 696 | CH₃ | Ph-2,4-2Cl | Cl | H | OCH₃ |
| 697 | CH₃ | Ph-4-CH₃ | Cl | H | OCH₃ |
| 698 | CH₃ | Ph-2,4-2CH₃ | Cl | H | OCH₃ |
| 699 | CH₃ | Ph-4-CF₃ | Cl | H | OCH₃ |
| 700 | CH₃ | Ph-4-OCF₃ | Cl | H | OCH₃ |
| 701 | CH₃ | 3-Py-2-Cl | Cl | H | OCH₃ |
| 702 | CH₃ | 2-Py-5-Cl | Cl | H | OCH₃ |
| 703 | CH₃ | 3-Py | Cl | H | OCH₃ |
| 704 | CH₃ | CH₃ | H | H | OCH₃ |
| 705 | CH₃ | Et | H | H | OCH₃ |
| 706 | CH₃ | n-Pr | H | H | OCH₃ |
| 707 | CH₃ | I-Pr | H | H | OCH₃ |
| 708 | CH₃ | t-Bu | H | H | OCH₃ |
| 709 | CH₃ |  | H | H | OCH₃ |
| 710 | CH₃ | CF₃ | H | H | OCH₃ |
| 711 | CH₃ | CH₃ | Br | H | OCH₃ |
| 712 | CH₃ | Et | Br | H | OCH₃ |
| 713 | CH₃ | n-Pr | Br | H | OCH₃ |
| 714 | CH₃ | i-Pr | Br | H | OCH₃ |
| 715 | CH₃ | t-Bu | Br | H | OCH₃ |
| 716 | CH₃ |  | Br | H | OCH₃ |
| 717 | CH₃ | CF₃ | Br | H | OCH₃ |
| 718 | Et | CH₃ | H | H | OCH₃ |
| 719 | Et | Et | H | H | OCH₃ |
| 720 | Et | n-Pr | H | H | OCH₃ |
| 721 | Et | i-Pr | H | H | OCH₃ |
| 722 | Et | t-Bu | H | H | OCH₃ |
| 723 | Et |  | H | H | OCH₃ |
| 724 | Et | CF₃ | H | H | OCH₃ |
| 725 | Et | CH₃ | Cl | H | OCH₃ |
| 726 | Et | Et | Cl | H | OCH₃ |
| 727 | Et | n-Pr | Cl | H | OCH₃ |
| 728 | Et | i-Pr | Cl | H | OCH₃ |
| 729 | Et | t-Bu | Cl | H | OCH₃ |
| 730 | Et |  | Cl | H | OCH₃ |

TABLE 15-continued

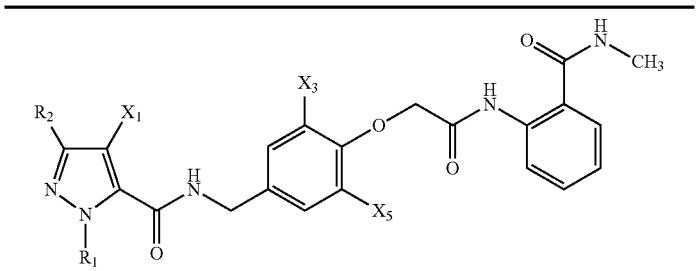

| compound | R₁ | R₂ | X₁ | X₃ | X₅ |
|---|---|---|---|---|---|
| 731 | Et | CF₃ | Cl | H | OCH₃ |
| 732 | i-Pr | CH₃ | Cl | H | OCH₃ |
| 733 | i-Pr | CH₃ | H | H | OCH₃ |
| 734 | cyclopropyl | CH₃ | Cl | H | OCH₃ |
| 735 | cyclopropyl | CH₃ | H | H | OCH₃ |
| 736 | CH₂CF₃ | CH₃ | Cl | H | OCH₃ |
| 737 | CH₂CF₃ | CH₃ | H | H | OCH₃ |
| 738 | Ph | CH₃ | Cl | H | OCH₃ |
| 739 | Ph | CH₃ | H | H | OCH₃ |
| 740 | Ph | Cl | H | H | OCH₃ |
| 741 | Ph | Br | H | H | OCH₃ |
| 742 | Ph-2-Cl | CH₃ | Cl | H | OCH₃ |
| 743 | Ph-2-Cl | CH₃ | H | H | OCH₃ |
| 744 | Ph-2-Cl | Cl | H | H | OCH₃ |
| 745 | Ph-2-Cl | Br | H | H | OCH₃ |
| 746 | Ph-4-Cl | CH₃ | Cl | H | OCH₃ |
| 747 | Ph-4-Cl | CH₃ | H | H | OCH₃ |
| 748 | Ph-4-Cl | Cl | H | H | OCH₃ |
| 749 | Ph-4-Cl | Br | H | H | OCH₃ |
| 750 | 2-Py-3-Cl | CH₃ | Cl | H | OCH₃ |
| 751 | 2-Py-3-Cl | CH₃ | H | H | OCH₃ |
| 752 | 2-Py-3-Cl | Cl | H | H | OCH₃ |
| 753 | 2-Py-3-Cl | Br | H | H | OCH₃ |
| 754 | 2-Py-3-Cl | CF₃ | H | H | OCH₃ |
| 755 | 2-Py-3-Cl | CHF₂ | H | H | OCH₃ |
| 756 | 2-Py-3-Cl | OCF3 | H | H | OCH₃ |
| 757 | 2-Py-3-Cl | OCH₂CF3 | H | H | OCH₃ |
| 758 | 2-Py-3-Cl | OCH₂CN | H | H | OCH₃ |
| 759 | 2-Py-3-Cl | OCH₂F | H | H | OCH₃ |
| 760 | 2-Py-3,5-2Cl | Cl | H | H | OCH₃ |
| 761 | 2-Py-3,5-2Cl | Br | H | H | OCH₃ |
| 762 | 2-Py-3,5,6-3Cl | Cl | H | H | OCH₃ |
| 763 | 2-Py-3,5,6-3Cl | Br | H | H | OCH₃ |
| 764 | 2-Py-3-Cl-5-CF₃ | Cl | H | H | OCH₃ |
| 765 | 2-Py-3-Cl-5-CF₃ | Br | H | H | OCH₃ |
| 766 | 2-Py-5-CF₃ | Cl | H | H | OCH₃ |
| 767 | 2-Py-5-CF₃ | Br | H | H | OCH₃ |
| 768 | 2-Py-3-Cl-5-CH₃ | Cl | H | H | OCH₃ |
| 769 | 2-Py-3-Cl-5-CH₃ | Br | H | H | OCH₃ |
| 770 | CH₃ | CH₃ | Cl | Cl | Cl |
| 771 | CH₃ | Et | Cl | Cl | Cl |
| 772 | CH₃ | CF₃ | Cl | Cl | Cl |
| 773 | CH₃ | CH₃ | Cl | Cl | Cl |
| 774 | CH₃ | Et | Cl | Cl | Cl |
| 775 | CH₃ | CF₃ | Cl | Cl | Cl |
| 776 | CH₃ | CH₃ | H | Cl | Cl |
| 777 | CH₃ | Et | H | Cl | Cl |
| 778 | CH₃ | CF₃ | H | Cl | Cl |
| 779 | CH₃ | CH₃ | H | Cl | Cl |
| 780 | CH₃ | Et | H | Cl | Cl |
| 781 | CH₃ | CF₃ | H | Cl | Cl |
| 782 | CH₃ | CH₃ | Cl | Cl | OCH₃ |
| 783 | CH₃ | Et | Cl | Cl | OCH₃ |
| 784 | CH₃ | CF₃ | Cl | Cl | OCH₃ |
| 785 | CH₃ | CH₃ | Cl | Cl | OCH₃ |
| 786 | CH₃ | Et | Cl | Cl | OCH₃ |
| 787 | CH₃ | CF₃ | Cl | Cl | OCH₃ |

Another part of compounds of the present invention are listed in table 16, wherein: $R_3=R_6=Q_1=Q_2=X_2=X_4=H$, p=2, m=1, n=0, Z=O, $YR_5=NHCH_3$, $N-Q_2$ links with phenyl ring at the 2-position.

TABLE 16

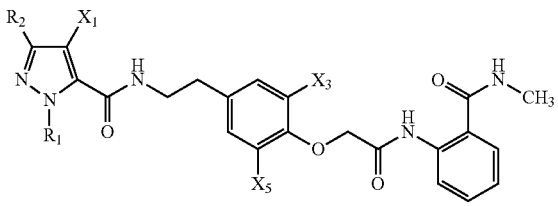

The substituents of compounds 788-959 in table 16 in turns correspond to the substituents of compounds 616-787 in table 15.

Another part of compounds of the present invention are listed in table 17, wherein: $R_3=CH_3$, $R_6=Q_1=Q_2=X_2=X_4=H$, p=2, m=1, n=0, Z=O, $YR_5=NHCH_3$, $N-Q_2$ links with phenyl ring at the 2-position.

TABLE 17

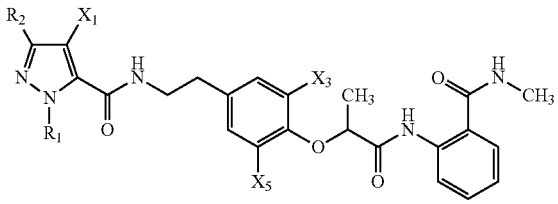

The substituents of compounds 960-1131 in table 17 in turns correspond to the substituents of compounds 616-787 in table 15.

The compounds having general formula (I) exhibit preferably fungicidal activities on plant pathogen such as rice blast, powdery mildew, rust, downy mildew, etc., and in particular, a better prevention and controlling effect on cucumber downy mildew, rice blast and corn rust. The compounds mentioned can be used as active ingredient in agricultural field such as farming and gardening. Therefore, a further object of the present invention relates to the use of the compounds having general formula (I) as fungicides, both in agriculture and other fields. For example, the use of the compounds having general formula (I) used to prepare fungicidal drugs. The plant pathogen prevented by the compounds of the present invention is not limited to the harmful fungus mentioned above.

Due to their positive performance, the compounds mentioned above can be advantageously used in protecting crops of farming and gardening, domestic and breeding animals, as well as environments frequented by human beings, from pathogens.

In order to obtain desired effect, the dosage of the compound to be applied can vary with various factors, for example, the used compound, the protected crop, the type of harmful organism, the degree of infestation, the climatic conditions, the application method and the adopted formulation.

The dosage of compounds in the range of 10 g to 1000 g per hectare can provide a sufficient control.

An another object of the present invention also relates to a method for controlling phytopathogenic fungi in crops of farming and gardening and/or on domestic and breeding animals and/or environments frequented by human beings, by application of the compounds having general formula I. In particular, the dosage of compounds to be applied varies from 10 g to 1000 g per hectare.

For practical application in agriculture, it is usually beneficial to use compositions containing one or more compounds of general formula I.

Therefore, a further object of the present invention relates to fungicidal compositions containing one or more compounds having general formula I as active ingredient, the weight percentage of the active ingredient in the compositions is 0.1-99%.

Compositions can be used in the form of dry powders, wettable powders, emulsifiable concentrates, microemulsions, pastes, granulates, solutions, suspensions, etc,. The selection of the type of compositions depends on the specific application.

The compositions are prepared in the known method, for example by diluting or dissolving the active substance with a solvent medium and/or a solid diluent, optionally in the presence of surface-active agents.

Solid diluents or carriers which can be used are, for example: silica, kaolin, bentonite, talc, diatomite, dolomite, calcium carbonate, magnesia, chalk, clays, synthetic silicates, attapulgite, sepiolite.

Liquid diluents which can be used are, for example, besides water, aromatic organic solvents (xylols or mixtures of alkylbenzols, chlorobenzene, etc.), paraffins (petroleum fractions), alcohols (methanol, propanol, butanol, octanol, glycerin, etc.), esters (ethyl acetate, isobutyl acetate, etc.), ketones (cyclohexanone, acetone, acetophenone, isophorone, ethylamylketone, etc.), amides (N, N-dimethylformamide, N-methylpyrrolidone, etc.).

Surface-active agents which can be used are salts of sodium, calcium, triethylamine or triethanolamine of alkylsulfonates, alkylarylsulfonates, polyethoxylated alkylphenols, polyethoxylated esters of sorbitol, ligninsulfonates, etc.

The compositions can also contain special additives for particular purposes, for example adhesion agents such as Arabic gum, polyvinyl alcohol, polyvinyl-pyrrolidone, etc.

The concentration of active ingredient in the above compositions can vary within a wide range depending on the active compound, the applications for which they are destined, the environmental conditions and the type of adopted formulation. In general the concentration of active ingredient ranges from 0.1 to 99%, preferably from 5% to 60%.

If required, other active ingredients being compatible with the compounds having general formula I can be added to the compositions, such as, other acaricides/insecticides, fungicides, plant growth regulators, antibiotics, herbicides, fertilizers.

But for the form of compositions without being restricted thereby, also one or two or more composition can be mixed as active ingredient.

The preparation methods of several common formulation examples in the present invention are as follows:

The preparation of suspension concentrate: the common active component in formula is 5%-35%. With water as the medium, the compound in the invention, dispersing agent, suspending agent and antifreeze are added to sanding machine for grinding to make suspension concentrate.

The preparation of water emulsion: the compound in the invention, solvent and emulsifier are mixed together, to make a homogeneous oil phase. The water is mixed with antifreeze to make a homogeneous aqueous phase. In the high-speed stirring, the aqueous phase is added to the oil phase or oil phase is added to the aqueous phase, forming the water emulsion with good dispersity. The active component of water emulsions is generally 5%-15% in this invention. For the production of concentrated emulsions, the compounds of this invention are dissolved in one or more of the mixed solvent, and then emulsifier was added to enhance dispersion effects in the water.

The preparation of wettable powder: according to formulation requirements, the compound in the invention, surfactants and solid diluents are mixed well, after smashing through ultrafine pulverizer, that is the wettable powder products (for example, 10-60%). To prepare the spraying wettable powder, the compounds of this invention can form a mixture with solid powder, such as clay, inorganic silicates, carbonates, as well as wetting agents, adhesives and/or dispersant agent.

The preparation of water dispersible granules: the compound in the invention and powdered solid diluents, wetting agents and adhesives are mixed to smash, kneading together with water, added to the granulation certain mesh machine for granulation, then by drying and sieving (at the scope screen). Also, the compound, in the invention dispersants, disintegrants, wetting agents and solid diluent are added to sanding machine, grinding in water to produce suspension and then spray-drying granulation, usually the content of the prepared granular products is 20%-30%.

DESCRIPTION OF THE INVENTION IN DETAIL

The following examples are illustrative of the present invention, but without being restricted thereby. (except special explanation that all the materials can be purchased).

PREPARATION EXAMPLE

Example 1

The Preparation of Intermediate (II-1)

1) The Preparation of Benzoxazine Ketone

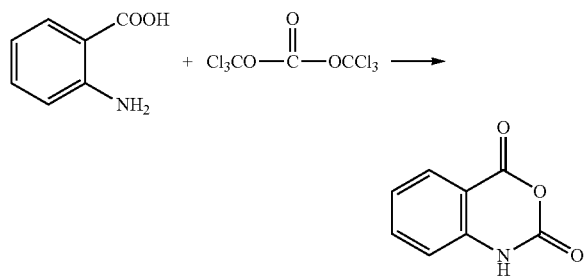

To a solution of anthranilic acid 13.70 g (0.1 mol) in 150 mL tetrahydrofuran was added 19.80 g (0.067 mol) solid phosgene in batches at room temperature for 1.5 hours. Then the reaction mixture was continued stirring at room temperature for another 2-3 hours and monitored by TLC. After the reaction was over, the mixture was concentrated under reduced pressure, the residual was poured into 80 ml water and stirred until excessive phosgene was completely decomposed, the solid was then filtered, washed with 50 ml of water and 50 ml of petroleum ether successively, dried to give 14.00 g benzoxazine ketone as white solid with yield of 86.0%, m.p. 239-240° C.

2) The Preparation of 2-amino-N-methylbenzamide

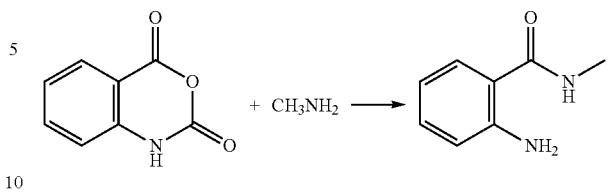

To a solution of benzoxazine ketone 16.30 g (0.1 mol) in 150 mL acetonitrile was slowly dropwise added 40% methylamine aqueous solution at room temperature until the solid disappeared, about 80 ml methylamine aqueous solution was added. Then the reaction mixture was continued stirring at room temperature for another 0.5 hours and monitored by TLC. After the reaction was over, the mixture was concentrated under reduced pressure, the residual was filtered and washed with 50 ml of water and 50 ml of petroleum ether successively, then dried to give 13.73 g 2-amino-N-methylbenzamide as white solid with yield of 91.5%, m.p. 78-79° C.

3) The Preparation of 2-(2-chloroacetamido)-N-methylbenzamide

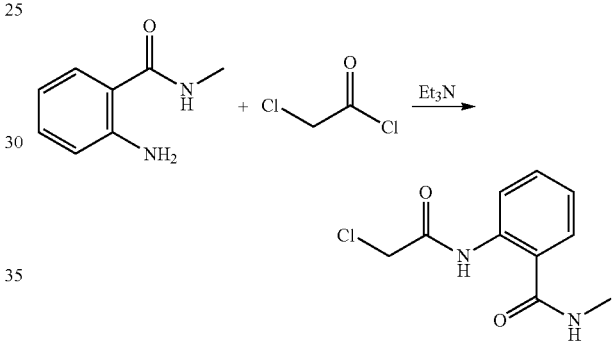

To a solution of 2-amino-N-methylbenzamide 15.00 g (0.1 mol) and triethylamine 12.10 g (0.12 mol) in 150 mL dichloromethane was added 12.40 g (0.11 mol) chloroacetyl chloride in 30 mL dichloromethane at room temperature for 0.5 hours. Then the reaction mixture was continued stirring at room temperature for another 2-3 hours and monitored by TLC. After the reaction was over, the mixture was concentrated under reduced pressure, the residual was filtered and washed with 50 ml of 10% diluted hydrochloric acid, 50 ml of saturated sodium bicarbonate solution, 50 ml of water and 50 ml of petroleum ether successively, then dried to give 18.90 g intermediate 2-(2-chloroacetamido)-N-methylbenzamide as white solid with yield of 83.4%, m.p. 155-157° C.

4) The Preparation of 2-(2-(4-cyanophenoxy)acetamido)-N-methylbenzamide (XII-1)

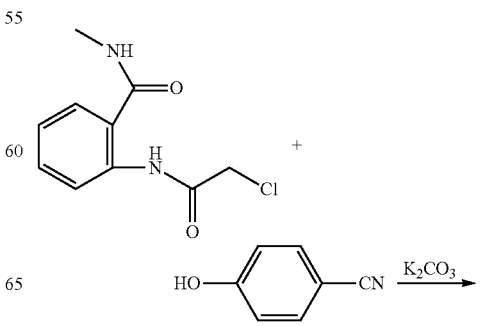

-continued

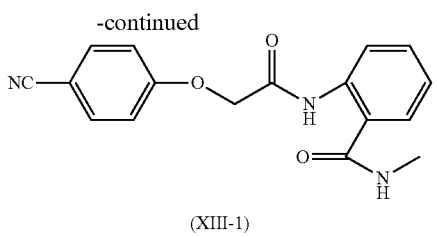

(XIII-1)

To a solution of 2-(2-chloroacetamido)-N-methylbenzamide 22.65 g (0.1 mol) and 4-hydroxybenzonitrile 14.29 g (0.12 mol) in 200 mL butanone was added 27.60 g (0.2 mol) potassium carbonate, then the reaction mixture was stirred and heated to reflux for 4-5 hours, and monitored by TLC until the reaction was over, the mixture was concentrated under reduced pressure and extracted with 300 mL of ethyl acetate to separate the organic phase, the organic phase was washed with 50 ml of 5% sodium hydroxide aqueous solution and 50 ml of brine successively, dried via anhydrous magnesium sulfate and evaporated, the residual was purified via silica gel column chromatography to obtain 25.00 g intermediate (XIII-1) as white solid with yield of 81.0%, m.p. 130-131° C.

5) The Preparation of 2-(2-(4-(aminomethyl)phenoxy)acetamido)-N-methylbenzamide (II-1)

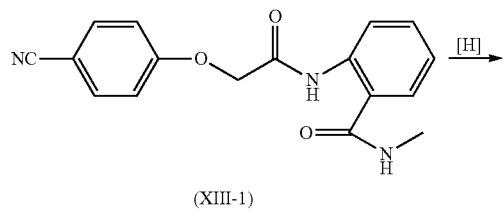

(XIII-1)

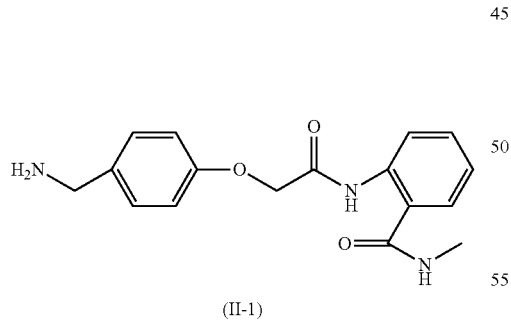

(II-1)

To a solution of intermediate (XIII-1) 3.09 g (0.01 mol), Raney nickel (1.0 g) and 10 mL of 25% aqueous ammonia in 50 mL ethanol was filled with hydrogen, then the reaction mixture was continued stirring at room temperature for another 3-4 hours and monitored by TLC until the reaction was over, Raney nickel was filtered, the filtrate was concentrated under reduced pressure to give sticky liquid (II-1), which was cooled to give 2.16 g intermediate (II-1) as white solid with yield of 69.0%, m.p. 109-110° C.

Example 2

The Preparation of Intermediate (II-52)

1) The Preparation of 22-(4-acetylphenoxy)acetamido)-N-methylbenzamide

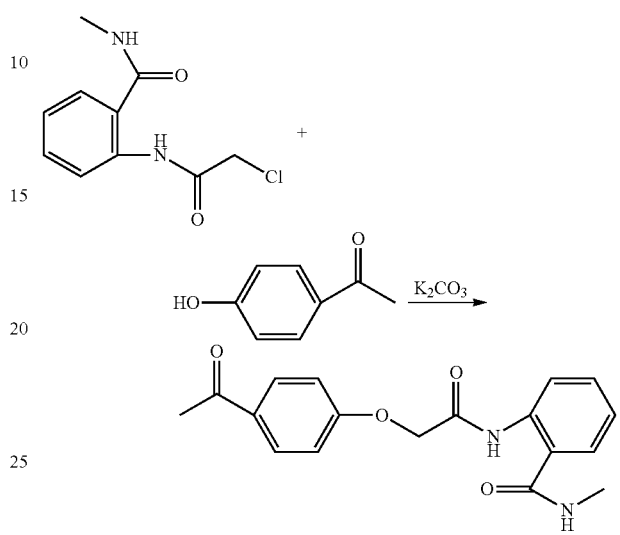

To a solution of 2-(2-chloroacetamido)-N-methylbenzamide 22.65 g (0.1 mol) and p-hydroxyacetophenone 16.32 g (0.12 mol) in 200 mL of butanone was added 27.60 g (0.2 mol) potassium carbonate. The mixture was stirred and heated to reflux for 4-5 hours, and monitored by TLC until the reaction was over, the reaction mixture was concentrated under reduced pressure and extracted with 300 mL of ethyl acetate to separate the organic phase, the organic phase was washed with 50 ml of 5% sodium hydroxide aqueous solution and 50 ml of brine successively, dried via anhydrous magnesium sulfate and evaporated, and the residual was purified via silica gel column chromatography to obtain 27.50 g 2-(2-(4-acetylphenoxy)acetamido)-N-methylbenzamide as white solid with yield of 84.4%, m.p. 252-253° C.

2) The Preparation of Oxime (XIV-1)

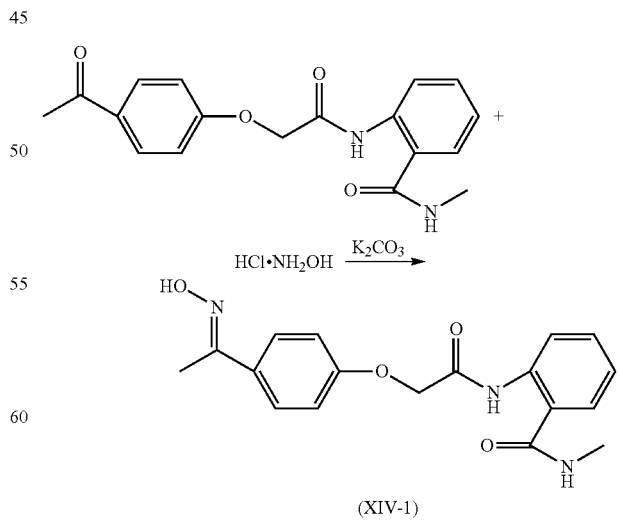

(XIV-1)

To a solution of 2-(2-(4-acetylphenoxy)acetamido)-N-methylbenzamide 1.60 g (0.005 mol) and hydroxylamine hydrochloride 0.63 g (0.0075 mol) in 30 mL of ethanol was dropwise added 1.38 g (0.01 mol) potassium carbonate in 3 mL of water at room temperature. The reaction mixture was stirred and heated to reflux for 4-5 hours, and monitored by TLC until the reaction was over, the mixture was concentrated under reduced pressure and extracted with ethyl acetate (30 mL) to separate the organic phase, the organic phase was washed with 20 ml of water and 20 ml of brine successively, dried via anhydrous magnesium sulfate and evaporated, and the residual was purified via silica gel column chromatography to obtain 27.50 g intermediate Oxime (XIV-1) as white solid with yield of 84.8%, m.p. 188-190° C.

3) The Preparation of Intermediate (II-52)

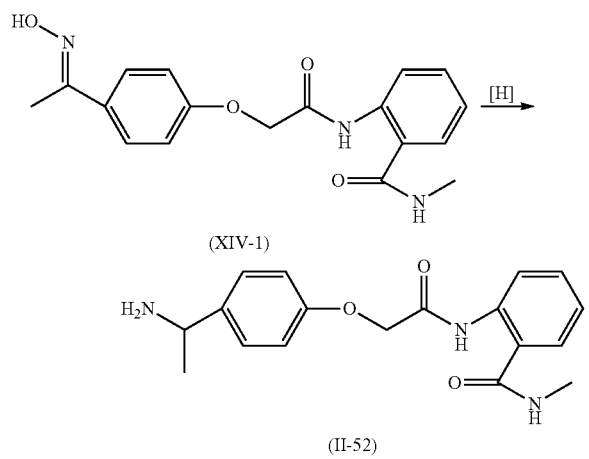

To a solution of intermediate (XIV-1) 3.41 g (0.01 mol), Raney nickel (2.0 g) and 12 mL of 25% aqueous ammonia in 50 mL ethanol was filled with hydrogen, then the reaction mixture was continued stirring at room temperature for 6-7 hours and monitored by TLC until the reaction was over, Raney nickel was filtered, the solution was concentrated under reduced pressure to give 2.56 g intermediate (II-52) as sticky liquid with yield of 78.3%.

Example 3

The Preparation of Intermediate (II-173)

1) The Preparation of tert-butyl-4-hydroxyphenylcarbamate

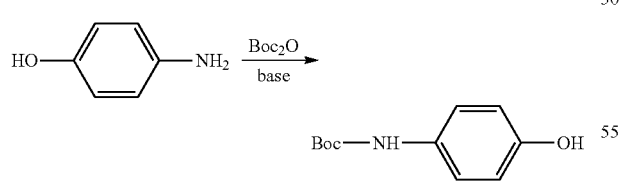

To a solution of p-aminophenol 10.9 g (0.1 mol), sodium bicarbonate 10.08 g (0.12 mol) and 150 mL water in 250 mL tetrahydrofuran was added di-tert-butyl dicarbonate 25.0 g (0.115 mol). The reaction mixture was continued stirring at room temperature for 24 hours, and monitored by TLC until the reaction was over, the mixture was concentrated under reduced pressure and extracted with ethyl acetate (500 mL) to separate the organic phase, the organic phase was washed with 50 ml of water and 50 ml of brine successively, dried via anhydrous magnesium sulfate and evaporated and the residual was purified via silica gel column chromatography to obtain 19.02 g tert-butyl-4-hydroxyphenylcarbamate as white solid with yield of 91.0%, m.p. 144-145° C.

$^1$HNMR: δ ppm 1.49 (9H, s), 5.08 (1H, s), 6.37 (1H, s), 6.74 (2H, d), 7.18 (2H, d).

2) The Preparation of Intermediate (XI-1)

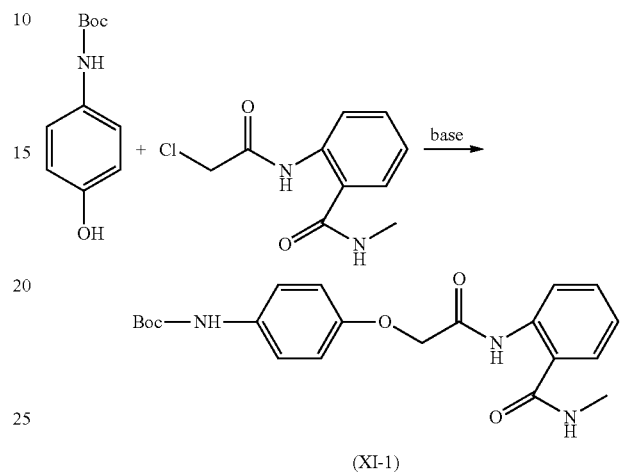

To a solution of tert-butyl-4-hydroxyphenylcarbamate 6.27 g (0.03 mol) and 2-(2-chloroacetamido)-N-methylbenzamide 6.80 g (0.03 mol) in 100 mL butanone was added 8.30 g (0.06 mol) potassium carbonate. The reaction mixture was stirred and heated to reflux for 7-8 hours, and monitored by TLC until the reaction was over, the mixture was concentrated under reduced pressure and extracted with ethyl acetate (100 mL) to separate the organic phase, the organic phase was washed with 50 ml of water and 50 ml of brine successively, dried via anhydrous magnesium sulfate and evaporated and the residual was purified via silica gel column chromatography to obtain 10.05 g intermediate (XI-1) as white solid with yield of 84.0%, m.p. 142-143° C.

$^1$HNMR: δ ppm 1.61 (9H, s), 3.74 (3H, d), 5.14 (2H, s), 6.40 (1H, s), 6.98-7.01 (2H, d), 7.29 (2H, d), 7.47-7.50 (1H, m), 7.75-7.77 (2H, m), 8.30 (1H, d).

3) The Preparation of Intermediate (II-173)

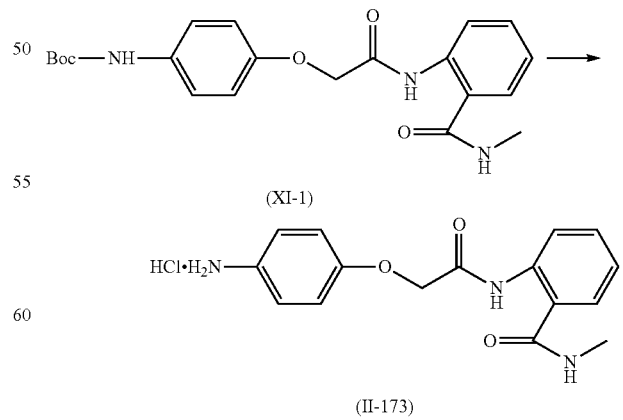

To a solution of intermediate (XI-1) 3.99 g (0.01 mol) in 20 mL ethyl acetate was dropwise added 10 mL 1N or 3N HCl.

The reaction mixture was continued stirring at room temperature for 5-15 hours, and monitored by TLC until the reaction was over, filtered and the filter cake was washed with ethyl acetate to give 3.35 g intermediate (II-173) as white solid with yield of 99.8%, m.p. 239-240° C.

Example 4

The Preparation of Compound 15

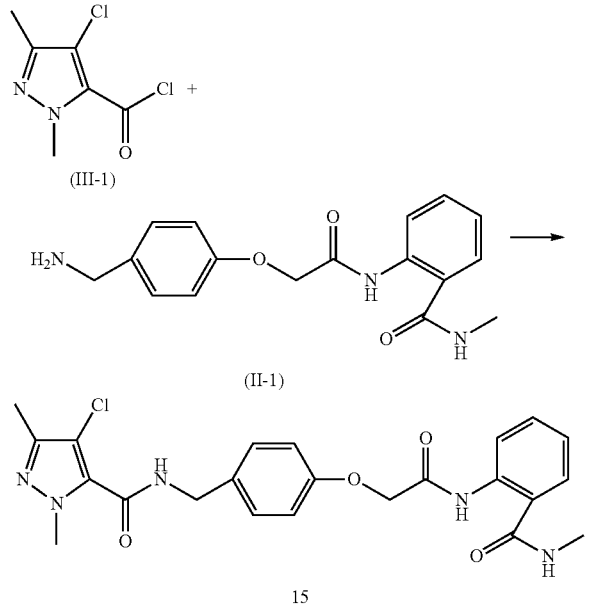

To a solution of intermediate (II-1) 0.31 g (0.001 mol) and triethylamine 0.12 g (0.0012 mol) in 20 mL dichloromethane was dropwise added 4-chloro-1,3-dimethyl-1H-pyrazole-5-carbonyl formyl chloride (III-1) 0.21 g (0.0011 mol) in 10 mL dichloromethane. The reaction mixture was was continued stirring at room temperature for 1 hour, and monitored by TLC until the reaction was over, then the mixture was poured into 20 mL of water to separate the organic layer, the organic phase was washed with 10 ml of 5% diluted hydrochloric acid, 10 ml of saturated sodium bicarbonate solution and 10 ml of brine successively, dried via anhydrous magnesium sulfate and evaporated, the residual was purified via silica gel column chromatography to obtain 0.40 g compound 15 with yield of 81.5%, m.p. 157-158° C.

Example 5

The Preparation of Compound 16

Method 1:

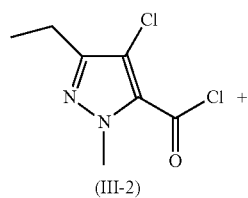

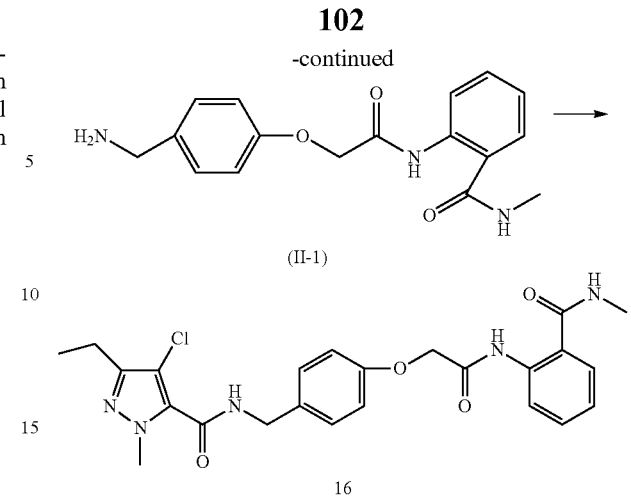

To a solution of intermediate (II-1) 0.31 g (0.001 mol) and triethylamine 0.12 g (0.0012 mol) in mL dichloromethane was dropwise added 4-chloro-3-ethyl-1-methyl-1H-pyrazole-5-carbonyl formyl chloride (III-2) 0.23 g (0.0011 mol) in 10 mL dichloromethane. The reaction mixture was continued stirring at room temperature for 1 hour, and monitored by TLC until the reaction was over, then the mixture was poured into 20 mL of water to separate the organic layer, the organic phase was washed with 10 ml of 5% diluted hydrochloric acid, 10 ml of saturated sodium bicarbonate solution and 10 ml of brine successively, dried via anhydrous magnesium sulfate and evaporated, the residual was purified via silica gel column chromatography to obtain 0.41 g compound 16 with yield of 85.0%, m.p. 160-161° C.

Method 2:

1) The Preparation of Intermediate (VIII-2)

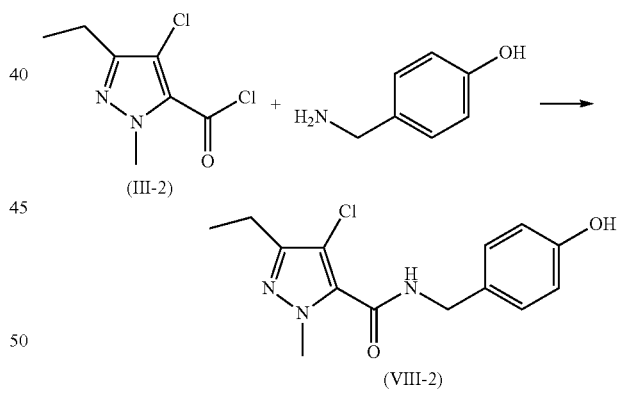

To a solution of 4-(aminomethyl)phenol 1.23 g (0.01 mol) and triethylamine 1.2 g (0.012 mol) in 50 mL dichloromethane was dropwise added 4-chloro-3-ethyl-1-methyl-1H-pyrazole-5-carbonyl formyl chloride (III-2) 2.3 g (0.011 mol) in 30 mL dichloromethane. The reaction mixture was continued stirring at room temperature for 4-5 hour, and monitored by TLC until the reaction was over, then the mixture was poured into 50 mL of water to separate the organic layer, the organic phase was washed with 10 ml of 5% diluted hydrochloric acid, 10 ml of saturated sodium bicarbonate solution and 10 ml of brine successively, dried via anhydrous magnesium sulfate and evaporated, the residual was purified via silica gel column chromatography to obtain 2.50 g intermediate (VIII-2) with yield of 85.2%, m.p. 167-168° C.

2) The Preparation of Compound 16

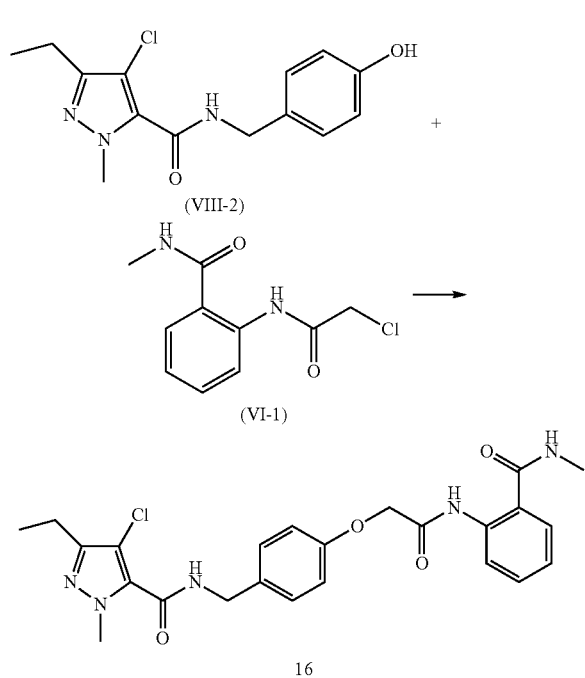

To a solution of intermediate (VIII-2) 0.30 g (0.001 mol) and potassium carbonate 0.17 g (0.0012 mol) in 30 mL N,N-dimethylformamide was added intermediate (VI-1) 0.27 g (0.0011 mol) to react at room temperature for 1 hour, then continually stirred and heated to reflux for 7-8 hours, and monitored by TLC until the reaction was over, the mixture was concentrated under reduced pressure and poured into 20 mL of water, then extracted with ethyl acetate (100 mL) to separate the organic layer, the organic phase was washed with 10 ml of brine, dried via anhydrous magnesium sulfate and evaporated, the residual was purified via silica gel column chromatography to obtain 0.32 g compound 16 with yield of 66.0%, m.p. 160-161° C.

Example 6

The Preparation of Compound 41

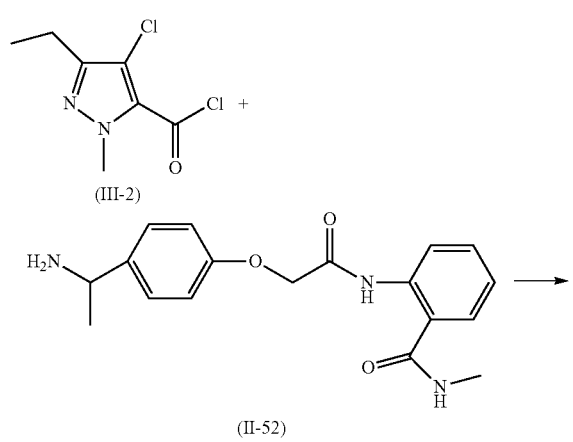

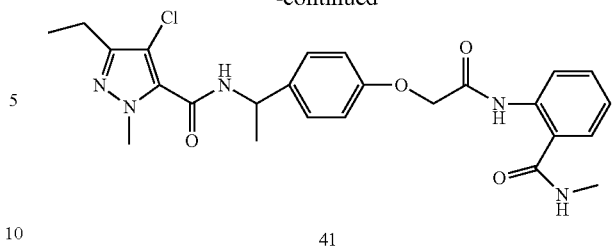

To a solution of intermediate (II-52) 0.33 g (0.001 mol) and triethylamine 0.12 g (0.0012 mol) in 20 mL dichloromethane was dropwise added 4-chloro-3-ethyl-1-methyl-1H-pyrazole-5-carbonyl formyl chloride (III-2) 0.23 g (0.0011 mol) in 10 mL dichloromethane. The reaction mixture was continued stirring at room temperature for 1 hour, and monitored by TLC until the reaction was over, then the mixture was poured into 20 mL of water to separate the organic layer, the organic phase was washed with 10 ml of 10% diluted hydrochloric acid, 10 ml of saturated sodium bicarbonate solution and 10 ml of brine successively, dried via anhydrous magnesium sulfate and evaporated, the residual was purified via silica gel column chromatography to obtain 0.43 g compound 41 with yield of 89.7%, m.p. 138-139° C.

Example 7

The Preparation of Compound 202

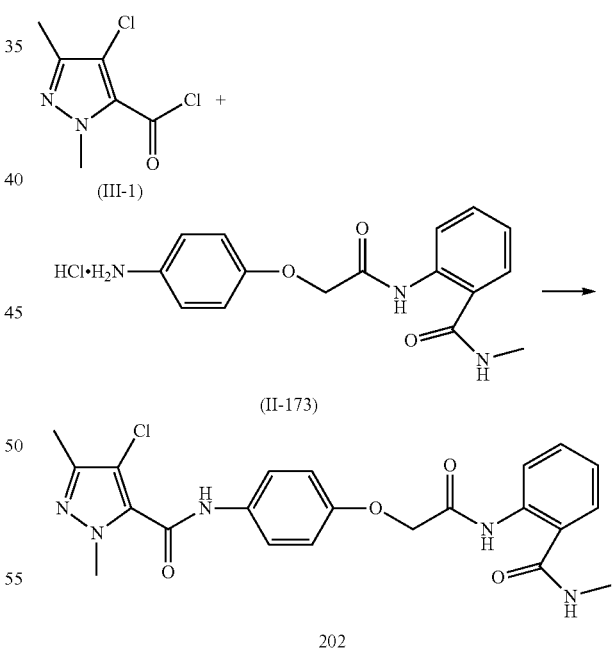

To a solution of intermediate (II-173) 0.34 g (0.001 mol) and triethylamine 0.22 g (0.0022 mol) in 20 mL dichloromethane was dropwise added 4-chloro-1,3-dimethyl-1H-pyrazole-5-carbonyl formyl chloride (III-1) 0.21 g (0.0011 mol) in 10 mL dichloromethane. The reaction mixture was continued stirring at room temperature for 1 hour, and monitored by TLC until the reaction was over, then the mixture was poured into 20 mL of water to separate the organic layer, the organic phase was washed with 10 ml of 10% diluted hydrochloric acid, 10 ml of saturated sodium bicarbonate solution and 10 ml of brine successively, dried via anhydrous magnesium sulfate and evaporated, the residual was purified via silica gel column chromatography to obtain 0.42 g compound 202, yield (92.2%), m.p. 182-183° C.

Other compounds of the general formula (I) were prepared according to the above examples.

Melting point (Melting point meter not corrected) and $^1$HNMR spectrum ($^1$HNMR, 300 MHz, internal standard: TMS, solvent CDCl$_3$) of some compounds of this invention are as follows:

Compound 2: m.p. 173-174° C. δ ppm 2.23 (3H, s), 3.73 (3H, s), 4.12 (3H, s), 4.49-4.51 (2H, m), 5.19 (2H, s), 6.26 (1H, s), 7.02-7.05 (2H, m), 7.25-7.28 (2H, m), 7.50-7.55 (1H, m), 7.70-7.74 (2H, m), 8.28-8.33 (1H, m).

Compound 3: m.p. 147-148° C. δ ppm 1.23 (3H, t), 2.56-2.61 (2H, m), 3.73 (3H, s), 4.12 (3H, s), 4.50 (2H, d), 5.18 (2H, s), 6.28 (1H, s), 7.02-7.07 (2H, m), 7.26-7.29 (2H, m), 7.51-7.54 (1H, m), 7.69-7.76 (2H, m), 8.27-8.30 (1H, m).

Compound 4: m.p. 172-174° C. δ ppm 0.99 (3H, t), 1.66-1.69 (2H, m), 2.55 (2H, t), 3.73-3.78 (6H, m), 4.54 (2H, d), 5.17 (2H, s), 6.59 (1H, s), 7.00-7.03 (3H, m), 7.27-7.32 (2H, m), 7.48-7.52 (1H, m), 7.70-7.74 (2H, m), 8.28-8.32 (1H, m).

Compound 7: m.p. 126-128° C. δ ppm 0.95 (6H, d), 1.83-1.87 (1H, m), 2.46 (2H, d), 3.72-3.74 (6H, m), 4.54 (2H, d), 5.16 (2H, s), 6.57 (1H, s), 7.00-7.03 (2H, m), 7.10 (1H, s), 7.28-7.31 (2H, m), 7.48-7.52 (1H, m), 7.71-7.76 (2H, m), 8.27-8.30 (1H, m).

Compound 8: m.p. 124-125° C. δ ppm 0.87-0.89 (2H, m), 1.03-1.06 (2H, m), 1.61 (1H, m), 3.73 (3H, s), 3.85 (3H, s), 4.53 (2H, d), 5.17 (2H, s), 7.00-7.03 (3H, m), 7.28-7.31 (2H, m), 7.49-7.52 (1H, m), 7.71-7.76 (2H, m), 8.28-8.32 (1H, m).

Compound 14: m.p. 159-161° C. δ ppm 3.74 (3H, s), 4.22 (3H, s), 4.53-4.55 (2H, m), 5.19 (2H, s), 6.30 (1H, s), 6.72 (1H, s), 7.04-7.07 (2H, m), 7.26-7.36 (6H, m), 7.49-7.52 (1H, m), 7.65-7.77 (4H, m), 8.26-8.30 (1H, m).

Compound 15: m.p. 157-158° C. δ ppm 2.22 (3H, s), 3.74 (3H, s), 4.13 (3H, s), 4.57 (2H, d), 5.20 (2H, s), 7.04-7.07 (3H, m), 7.27-7.32 (2H, m), 7.50-7.54 (1H, m), 7.73-7.77 (2H, m), 8.28-8.31 (1H, m).

Compound 16: m.p. 160-161° C. δ ppm 1.23 (3H, t), 2.59-2.66 (2H, m), 3.76 (3H, s), 4.13 (3H, s), 4.57 (2H, d), 5.26 (2H, s), 7.06-7.08 (4H, m), 7.27-7.33 (2H, m), 7.52-7.56 (1H, m), 7.78-7.79 (2H, m), 8.29-8.32 (1H, m).

Compound 17: m.p. 122-123° C. δ ppm 0.96 (3H, t), 1.60-1.62 (2H, m), 2.64 (2H, t), 3.73 (3H, s), 3.78 (3H, s), 4.54 (2H, d), 5.17 (2H, s), 7.01-7.04 (3H, m), 7.27-7.33 (2H, m), 7.49-7.53 (1H, m), 7.72-7.77 (2H, m), 8.28-8.31 (1H, m).

Compound 20: m.p. 119-120° C. δ ppm 0.95 (6H, d), 1.90-2.00 (1H, m), 2.51 (2H, d), 3.73 (3H, s), 3.77 (3H, s), 4.54 (2H, d), 5.17 (2H, s), 7.00-7.03 (3H, m), 7.28-7.33 (2H, m), 7.48-7.52 (1H, m), 7.71-7.72 (2H, m), 8.28-8.32 (1H, m).

Compound 26: m.p. 158-159° C. δ ppm 2.23 (3H, s), 3.74 (3H, s), 4.13 (3H, s), 4.57 (2H, d), 5.19 (2H, s), 7.04-7.07 (3H, m), 7.27-7.33 (2H, m), 7.51-7.55 (1H, m), 7.71-7.72 (2H, m), 8.28-8.32 (1H, m).

Compound 36: m.p. 100-102° C. δ ppm 1.25 (3H, t), 3.00-3.02 (2H, m), 3.64 (3H, s), 3.84 (3H, s), 4.38 (2H, d), 5.22 (2H, s), 7.03-7.05 (2H, m), 7.28-7.31 (2H, m), 7.43-7.47 (1H, m), 7.61-7.65 (1H, m), 7.66-7.70 (1H, m), 8.16-8.20 (1H, m), 8.82 (1H, s).

Compound 41: m.p. 138-139° C. δ ppm 1.25 (3H, t), 1.57 (3H, d), 1.80-1.84 (1H, m), 2.58-2.66 (2H, m), 3.73 (3H, s), 4.09 (3H, s), 5.18-5.23 (2H, m), 6.96 (1H, d), 7.04-7.07 (2H, m), 7.27-7.34 (2H, m), 7.48-7.53 (1H, m), 7.69-7.76 (2H, m), 8.28-8.30 (1H, m).

Compound 46: m.p. 139-141° C. δ ppm 1.22 (3H, t), 1.55 (3H, d), 2.58-2.66 (2H, m), 3.20 (3H, s), 4.12 (3H, d), 4.93-4.97 (2H, m), 5.16-5.20 (1H, m), 6.63 (1H, d), 6.80-6.87 (3H, m), 6.92-6.95 (1H, m), 7.23-7.29 (4H, m), 7.88-7.91 (1H, m).

Compound 62: m.p. 120-122° C. δ ppm 1.21 (3H, t), 1.84 (3H, d), 2.52-2.60 (2H, m), 2.84 (2H, t), 3.60-3.66 (2H, m), 3.72 (3H, s), 4.09 (3H, s), 5.49-5.61 (1H, m), 6.65 (1H, s), 6.96 (2H, d), 7.14 (2H, d), 7.42-7.55 (1H, m), 7.69-7.81 (2H, m), 8.22-8.31 (1H, m).

Compound 66: m.p. 135-137° C. δ ppm 1.22 (3H, t), 1.85 (3H, d), 2.57-2.65 (2H, m), 3.75 (3H, s), 4.11 (3H, s), 4.54 (2H, d), 5.53-5.55 (1H, m), 6.97-7.00 (2H, m), 7.24-7.27 (2H, m), 7.49-7.51 (1H, m), 7.72-7.76 (2H, m), 8.25-8.28 (1H, m).

Compound 69: m.p. 138-139° C. δ ppm 1.22 (3H, t), 1.68 (3H, d), 2.57-2.66 (2H, m), 2.91 (3H, d), 4.09 (3H, s), 4.54 (2H, d), 4.75-4.77 (1H, m), 6.50 (1H, s), 6.99-7.07 (4H, m), 7.26-7.29 (2H, m), 7.39-7.44 (2H, m), 8.55-8.59 (1H, m), 11.85 (1H, s).

Compound 77: m.p. 186-187° C. δ ppm 2.08 (3H, s), 2.16 (3H, s), 3.74 (3H, d), 4.01 (3H, s), 4.57 (2H, d), 6.00 (2H, s), 7.04-7.07 (3H, m), 7.50-7.54 (2H, m), 7.72-7.74 (2H, m), 8.23-8.27 (1H, m).

Compound 78: m.p. 114-116° C. δ ppm 1.84 (3H, d), 2.16 (3H, s), 2.84 (2H, t), 3.65 (2H, t), 3.68 (3H, s), 4.07 (3H, s), 5.51-5.55 (2H, m), 6.63 (1H, s), 6.96 (2H, d), 7.14 (2H, d), 7.43-7.50 (1H, t), 7.62-7.80 (2H, m), 8.26 (1H, d).

Compound 94: m.p. 166-168° C. δ ppm 1.37 (3H, t), 2.24 (3H, s), 2.29 (3H, s), 4.13 (3H, s), 4.31-4.33 (2H, m), 4.60 (2H, d), 4.67 (2H, s), 7.03-7.05 (3H, m), 7.23-7.27 (2H, m), 7.33-7.36 (2H, m), 7.42-7.45 (1H, m), 7.80-7.83 (1H, m), 9.83 (1H, s).

Compound 95: m.p. 170-171° C. δ ppm 1.41 (3H, t), 2.23 (3H, s), 4.14 (3H, s), 4.40-4.42 (2H, m), 4.59 (2H, d), 4.65 (2H, s), 7.07-7.14 (5H, m), 7.33-7.35 (2H, m), 7.57-7.60 (1H, m), 8.08 (1H, m), 8.80 (1H, m).

Compound 99: m.p. 211-212° C. δ ppm 1.24 (3H, t), 1.39 (3H, t), 2.62-2.64 (2H, m), 4.15 (3H, s), 4.40-4.43 (2H, m), 4.59 (2H, d), 4.65 (2H, s), 7.07-7.14 (5H, m), 7.33-7.35 (2H, m), 7.57 (1H, m), 8.08 (1H, m), 8.78-8.82 (1H, m).

Compound 104: m.p. 178-180° C. δ ppm 1.42 (3H, t), 2.24 (3H, s), 3.74 (3H, s), 4.50-4.54 (4H, m), 5.19 (2H, s), 6.23 (2H, d), 7.03-7.06 (2H, m), 7.26-7.29 (3H, m), 7.52 (1H, t), 7.70-7.74 (2H, m), 8.23-8.27 (1H, m).

Compound 105: m.p. 138-139° C. δ ppm 1.24 (3H, t), 1.41 (3H, t), 2.59-2.67 (2H, m), 3.74 (3H, s), 4.52-4.59 (4H, m), 5.19 (2H, s), 6.97 (1H, s), 7.04-7.07 (2H, m), 7.19-7.32 (3H, m), 7.49-7.54 (1H, m), 7.69-7.87 (2H, m), 8.28-8.31 (1H, m).

Compound 107: m.p. 137-138° C. δ ppm 1.38 (3H, t), 2.26-2.27 (3H, s), 3.73 (3H, s), 4.02-4.09 (2H, m), 4.54 (2H, d), 5.17 (2H, s), 7.01-7.05 (3H, m), 7.27-7.33 (2H, m), 7.50-7.53 (1H, m), 7.69-7.76 (2H, m), 8.27-8.31 (1H, m).

Compound 108: m.p. 144-145° C. δ ppm 1.23 (3H, t), 1.41 (3H, t), 2.59-2.64 (2H, m), 3.74 (3H, s), 4.52-4.58 (4H, m), 5.19 (2H, s), 6.90 (1H, s), 7.04-7.07 (2H, m), 7.26-7.32 (3H, m), 7.49-7.53 (1H, m), 7.69-7.76 (2H, m), 8.28-8.31 (1H, m).

Compound 117: m.p. 172-174° C. δ ppm 3.61 (3H, s), 4.27 (2H, d), 5.21 (2H, s), 7.00-7.03 (2H, m), 7.16-7.21 (3H, m), 7.52-7.65 (3H, m), 7.76-7.79 (1H, m), 8.07-8.15 (2H, m), 8.45-8.47 (1H, m), 9.11-9.15 (1H, m).

Compound 118: m.p. 118-120° C. δ ppm 2.62 (3H, s), 3.73 (3H, s), 4.42 (2H, d), 5.21 (2H, s), 6.46 (1H, s), 6.70 (1H, s), 7.02 (2H, d), 7.21 (2H, d), 7.37-7.42 (1H, m), 7.76 (1H, s), 7.86-7.92 (1H, d), 8.43 (1H, s).

Compound 121: m.p. 141-143° C. δ ppm 2.59 (3H, s), 3.72 (3H, s), 4.43 (2H, d), 5.19 (2H, s), 6.36 (1H, s), 6.71 (1H, s), 7.03 (2H, d), 7.19 (2H, d), 7.38-7.43 (1H, m), 7.72 (1H, s), 7.90 (1H, d), 8.25 (1H, s), 8.44 (1H, d).

Compound 129: m.p. 225-226° C. δ ppm 3.72 (3H, s), 4.49 (2H, d), 5.22 (2H, s), 7.03-7.06 (2H, m), 7.14-7.18 (1H, m), 7.28-7.31 (2H, m), 7.50-7.55 (1H, m), 7.67-7.78 (3H, m), 8.22-8.24 (1H, m), 8.70 (1H, s), 14.00 (1H, s).

Compound 141: m.p. 118-119° C. δ ppm 1.24 (3H, t), 1.42 (3H, t), 2.59-2.66 (2H, m), 4.14 (3H, s), 4.25-4.29 (2H, m), 4.58 (2H, d), 5.19 (2H, s), 7.05-7.08 (3H, m), 7.26-7.34 (2H, m), 7.48-7.49 (1H, m), 7.73-7.76 (1H, m), 7.91-7.94 (1H, m).

Compound 147: m.p. 138-140° C. δ ppm 2.23 (3H, s), 3.02 (6H, d), 4.14 (3H, s), 4.58-4.60 (4H, m), 7.01-7.04 (3H, m), 7.12-7.17 (1H, m), 7.25-7.34 (4H, m), 7.40-7.46 (1H, m), 10.00 (1H, s).

Compound 148: m.p. 117-119° C. δ ppm 1.23 (3H, t), 2.62-2.64 (2H, m), 2.97-3.04 (6H, m), 4.14 (3H, s), 4.58-4.60 (4H, m), 7.01-7.13 (4H, m), 7.25-7.34 (4H, m), 7.40-7.44 (1H, m), 8.34 (1H, d), 9.98 (1H, s).

Compound 156: m.p. 234-236° C. δ ppm 2.23 (3H, s), 4.14 (3H, s), 4.58-4.60 (2H, m), 5.09 (2H, s), 7.00-7.09 (3H, m), 7.26-7.35 (1H, m), 7.49-7.54 (2H, m), 7.68-7.83 (2H, m), 8.27-8.29 (1H, m), 9.70 (1H, s).

Compound 157: m.p. 237-238° C. δ ppm 1.23 (3H, t), 2.59-2.64 (2H, m), 4.13 (3H, s), 4.54-4.60 (2H, m), 5.47 (2H, d), 7.00-7.08 (3H, m), 7.26-7.35 (1H, m), 7.46-7.61 (2H, m), 7.71-7.83 (2H, m), 8.17-8.34 (2H, m).

Compound 162: m.p. 140-142° C. δ ppm 1.66 (3H, s), 2.22 (3H, s), 3.72 (3H, s), 4.12 (3H, s), 4.57 (2H, d), 5.21 (1H, s), 7.06 (1H, s), 7.09 (2H, d), 7.30 (2H, d), 7.38 (1H, t), 7.59 (1H, d), 8.12 (1H, d).

Compound 166: m.p. 177-178° C. δ ppm 2.22 (3H, s), 2.58 (3H, s), 3.72 (3H, s), 4.13 (3H, s), 4.57 (2H, d), 5.18 (2H, s), 6.97 (1H, s), 7.06 (2H, d), 7.30 (2H, d), 7.69 (1H, s), 8.26 (1H, d).

Compound 167: m.p. 184-186° C. δ ppm 2.23 (3H, s), 2.62 (3H, s), 3.74 (3H, s), 4.13 (3H, s), 4.57 (2H, d), 5.22 (1H, s), 7.01 (1H, s), 7.06 (2H, d), 7.29 (2H, d), 7.78 (1H, s), 8.46 (1H, s).

Compound 169: m.p. 157-159° C. δ ppm 2.15 (3H, s), 3.62 (3H, s), 3.97 (3H, s), 4.33 (2H, d), 5.20 (2H, s), 6.58 (1H, s), 7.00-7.03 (2H, m), 7.22-7.25 (2H, m), 7.69-7.71 (1H, m), 7.76-7.78 (2H, m), 8.73-8.77 (1H, m).

Compound 170: m.p. 152-153° C. δ ppm 1.22 (3H, t), 2.58-2.66 (5H, m), 3.73 (3H, s), 4.14 (3H, s), 4.57 (2H, d), 5.23 (2H, s), 6.98 (1H, s), 7.07-7.09 (2H, m), 7.26-7.32 (3H, m), 7.39-7.41 (1H, m), 8.18 (1H, d).

Compound 171: m.p. 143-144° C. δ ppm 2.22 (3H, s), 2.62 (3H, s), 3.73 (3H, s), 4.13 (3H, s), 4.57 (2H, d), 5.22 (2H, s), 7.01 (1H, s), 7.06-7.09 (2H, m), 7.26-7.32 (2H, m), 7.36-7.41 (1H, m), 7.59 (1H, d), 8.12 (1H, d).

Compound 172: m.p. 154-155° C. δ ppm 1.23 (3H, t), 2.58 (3H, s), 2.61-2.66 (2H, m), 3.73 (3H, s), 4.13 (3H, s), 4.57 (2H, d), 5.21 (2H, s), 6.99 (1H, s), 7.04-7.07 (2H, m), 7.27-7.32 (2H, m), 7.53-7.54 (1H, m), 8.08-8.09 (1H, m).

Compound 177: m.p. 107-108° C. δ ppm 1.26 (3H, t), 2.25 (3H, s), 2.63 (3H, s), 4.14 (3H, s), 4.26-4.28 (2H, m), 4.48-4.52 (2H, m), 5.23 (2H, s), 6.31 (1H, s), 7.06-7.09 (2H, m), 7.27 (2H, m), 7.37-7.42 (1H, m), 7.59-7.61 (1H, m), 8.12-8.14 (1H, m).

Compound 178: m.p. 139-140° C. δ ppm 1.23 (3H, t), 1.36 (3H, t), 2.29 (3H, s), 2.59-2.67 (2H, m), 4.13 (3H, s), 4.28-4.35 (2H, m), 4.59 (2H, d), 4.67 (2H, s), 7.02-7.05 (3H, m), 7.19-7.26 (1H, m), 7.33-7.36 (1H, m), 7.42-7.45 (1H, m), 7.80-7.82 (1H, m), 9.85 (1H, s).

Compound 186: m.p. 144-146° C. δ ppm 2.19 (3H, s), 2.87 (2H, t), 3.64-3.71 (2H, m), 3.75 (3H, s), 4.10 (3H, s), 5.18 (2H, s), 6.67 (1H, s), 7.02 (2H, d), 7.19 (2H, d), 7.49-7.54 (1H, m, 7.70-7.77 (2H, m), 8.29-8.31 (1H, s).

Compound 187: m.p. 145-146° C. δ ppm 1.22 (3H, t), 2.55-2.62 (2H, m), 2.87 (2H, t), 3.65-3.71 (2H, m), 3.75 (3H, s), 4.10 (3H, s), 5.18 (2H, s), 6.68 (1H, s), 7.02 (2H, d), 7.19 (2H, d), 7.49-7.54 (1H, m), 7.70-7.79 (2H, m), 8.29-8.31 (1H, s).

Compound 194: m.p. 136-138° C. δ ppm 1.87-1.97 (2H, m), 2.22 (3H, d), 2.67 (2H, t), 3.42-3.49 (2H, m), 3.60 (3H, s), 4.11 (3H, s), 5.16 (2H, s), 6.70 (1H, s), 6.98 (2H, d), 7.13 (2H, d), 7.48-7.53 (1H, m, 7.70-7.76 (2H, m), 8.28-8.31 (1H, s).

Compound 195: oil. δ ppm 2.23 (3H, s), 3.26-3.79 (8H, s), 4.13 (3H, s), 4.58 (2H, d), 4.61 (2H, s), 7.01 (3H, t), 7.168 (1H, t), 7.22 (1H, t), 7.33 (1H, d), 7.43 (1H, t), 8.35 (1H, d), 9.85 (1H, s).

Compound 199: m.p. 170-171° C. δ ppm 1.89-1.94 (2H, m), 2.04 (3H, s), 2.13 (3H, d), 2.66 (2H, t), 3.42-3.49 (2H, m), 3.74 (3H, s), 3.98 (3H, s), 5.16 (2H, s), 5.72 (1H, s), 6.99 (2H, d), 7.13 (2H, d), 7.51-7.53 (1H, m), 7.69-7.76 (2H, m), 8.28-8.31 (1H, m).

Compound 202: m.p. 182-183° C. δ ppm 2.27 (3H, s), 3.75 (3H, d), 4.16 (3H, s), 5.20 (2H, s), 7.08-7.12 (2H, m), 7.54-7.72 (6H, m), 8.32-8.36 (2H, m).

Compound 220: m.p. 175-177° C. δ ppm 2.18 (3H, s), 2.78 (3H, d), 3.84 (3H, s), 4.40 (2H, d), 4.65 (2H, s), 6.96 (2H, d), 7.28 (2H, d), 7.34 (1H, t), 7.49 (1H, d), 7.80 (1H, d), 8.04 (1H, s), 8.31 (1H, d), 8.63 (1H, t), 8.36 (1H, s), 10.14 (1H, s).

Compound 300: m.p. 188-190° C. δ ppm 1.39 (3H, t), 2.23 (3H, s), 4.14 (3H, s), 4.34-4.38 (2H, m), 4.59-4.63 (2H, m), 6.98-7.01 (2H, m), 7.34-7.37 (2H, m), 7.67-7.70 (2H, m), 8.04-8.06 (2H, m), 8.40 (1H, s).

Compound 304: m.p. 168-170° C. δ ppm 1.23 (3H, t), 1.40 (3H, t), 2.62-2.64 (2H, m), 4.15 (3H, s), 4.36-4.40 (2H, m), 4.60-4.63 (4H, m), 6.99-7.02 (2H, m), 7.34-7.37 (2H, m), 7.40-7.42 (1H, m), 7.80-7.81 (1H, m), 8.04-8.05 (2H, m), 8.38 (1H, s).

Compound 504: m.p. 185-186° C. δ ppm 1.40 (3H, t), 2.24 (3H, s), 4.14 (3H, s), 4.36-4.43 (2H, m), 4.60-4.63 (4H, m), 6.99-7.02 (3H, m), 7.34-7.37 (2H, m), 7.42-7.48 (1H, m), 7.83-7.86 (1H, m), 8.02-8.04 (2H, m), 8.37 (1H, s).

Compound 509: m.p. 172-173° C. δ ppm 1.23 (3H, t), 1.39 (3H, t), 2.59-2.64 (2H, m), 4.14 (3H, s), 4.34-4.41 (2H, m), 4.59-4.63 (4H, m), 6.98-7.01 (3H, m), 7.34-7.37 (2H, m), 7.67-7.70 (2H, m), 8.03-8.06 (2H, m), 8.41 (1H, s).

FORMULATION EXAMPLE

Base on 100% Active Ingredient (Weight/Weight %)

Example 8

30% Wettable Powders

| | |
|---|---|
| Compound 15 | 30% |
| Sodium dodecyl sulfate | 2% |
| Lignin sulfonate | 3% |
| Naphthalene sulfonic acid formaldehyde condensate | 5% |
| Precipitated calcium carbonate | Make up to 100% |

Compound 15 and other components are fully mixed, after smashing through ultrafine pulverizer, 30% compound 15 wettable powders products were obtained.

Example 9

20% Suspension Concentrate

| | |
|---|---|
| Compound 15 | 20% |
| Glycol | 5% |
| Nonylphenols polyethylene glycol ether | 3% |
| Lignin sulfonate | 5% |
| Carboxymethyl cellulose | 1% |
| 75% of silicone oil water emulsion | 0.4% |
| Water | Make up to 100% |

Fully mixing compound 15 and other components, suspension concentrate can be obtained, and then any required concentration dilution can be obtained by diluting the above obtained concentrated suspension with water.

Example 10

60% Water Dispersible Granules

| | |
|---|---|
| Compound 16 | 60% |
| Naphthalene sulfonate formaldehyde condensate | 12% |
| N-methyl-N-oil acyl - bovine sodium | 8% |
| Polyvinylpyrrolidone | 2% |
| Carboxymethyl cellulose | 2% |
| Kaolin | Make up to 100% |

To mix compound 16 and other components, after smashing, kneading together with water, added to the granulation 10-100 mesh machine for granulation, then by drying and sieving (at the scope screen).

Test of Biological Activity

Example 11

Determination of Greenhouse Biological Activity
(Cucumber Downy Mildew)

The tests were carried out with the method of pot seedling assay. The compounds of the present invention were diluted to given concentrations and sprayed on the leaves of cucumber seedling at the same stage, on which growing point were cut off and two euphyllas were kept, meanwhile, water were set as the blank control, 3 replicates were set for each treatment. Cucumber downy mildew spore suspension were inoculated on the second day after treatment, then, the plants were placed in a chamber (temperature: day 25° C., and night 20° C., relative humidity 95 to 100%), and then placed in greenhouse (25±2° C.) 24 hours later and routine management was conducted. The test results were investigated 5 days later, disease classification refers to the national standard of the People's Republic of China—"Pesticide-Guidelines for The Field Efficacy Trials", the control effect was calculated by disease index.

Some of the test results are as follows:

At 400 ppm, compounds 2, 3, 15, 16, 66, 69 and 177 showed 100% control of cucumber downy mildew.

At 50 ppm, compounds 2, 3, 15, 16 and 177 showed 100% control of cucumber downy mildew.

At 25 ppm, compounds 15, 16 and 177 showed 100% control of cucumber downy mildew. compound 3 showed 95% control of cucumber downy mildew, compound 2 showed 75% control of cucumber downy mildew.

The comparative test was carried out against cucumber downy mildew between compound 15 of the present invention and three contrasts Dimethomorph, famoxadone and metalaxyl(tech. commercially available), the test results were listed in table 18.

TABLE 18

| | Control (%) | | | | |
|---|---|---|---|---|---|
| Compd. | 100 ppm | 50 ppm | 25 ppm | 12.5 ppm | 6.25 ppm |
| Compd. 15 | 100 | 96 | 88 | 66 | 44 |
| dimethomorph | 100 | 88 | 85 | 74 | 29 |
| famoxadone | 81 | 74 | 51 | 22 | 14 |
| metalaxyl | 59 | 29 | 22 | 7 | 0 |
| untreated control | (disease index) 100 | | | | |

The persistence comparative test was carried out against cucumber downy mildew between compound 15 of the present invention and Dimethomorph, the test results were listed in table 19.

TABLE 19

| | | Control (%) | | | | |
|---|---|---|---|---|---|---|
| the days after treatment | Compd. | 400 ppm | 200 ppm | 100 ppm | 50 ppm | 25 ppm |
| 3 | Compd. 15 | 100 | 100 | 96 | 74 | 52 |
| | dimethomorph | 100 | 74 | 44 | 30 | 0 |
| 7 | Compd. 15 | 81 | 74 | 70 | 62 | 44 |
| | dimethomorph | 74 | 44 | 0 | 0 | 0 |
| untreated control | | inoculation on the 3th, 7th days after treatment: (disease index) 100 | | | | |

Example 12

Determination of Greenhouse Biological Activity
(Wheat Powdery Mildew)

The tests were carried out with the method of pot seedling assay. The compounds of the present invention were diluted to given concentrations and sprayed on the leaves of wheat seedling at the same two-leaf stage, meanwhile, water were set as the blank control, 3 replicates were set for each treatment. Wheat powdery mildew spore suspension were inoculated on the second day after treatment, and then placed in greenhouse (25±2° C.) and routine management was conducted. The test results were investigated on 8th day, Disease grading refers to the National Standard of the People's Republic of China—"Pesticide-Guidelines for The Field Efficacy Trials", the control effect was calculated by disease index.

Some of the test results are as follows:

At 400 ppm, compounds 2, 3, 15, 16 and 177 showed 100% control of wheat powdery mildew.

Example 13

Determination of Greenhouse Biological Activity
(Corn Rust)

The tests were carried out with the method of pot seedling assay. The compounds of the present invention were diluted to given concentrations and sprayed on the leaves of corn seedling at the same two-leaf stage, meanwhile, water were set as the blank control, 3 replicates were set for each treatment. Corn rust spore suspension were inoculated on the second day after treatment, then, the plants were placed in an environmental chamber (temperature: day 25° C., and night 20° C., relative humidity 95 to 100%), and then placed in greenhouse (25±2° C.) 24 hours later, routine management was conducted. The test results were investigated on 8th day, disease grading refers to the National Standard of the People's Republic of China—"Pesticide-Guidelines for The Field Efficacy Trials", the control effect was calculated by disease index.

Some of the test results are as follows:

At 400 ppm, compounds 2, 3, 15, 16, 17, 66, 69, 94, 95, 99, 156, 177 showed 100% control of corn rust.

At 25 ppm, compound 15 showed 100% control of corn rust.

The comparative test was carried out against corn rust between compound 15 of the present invention and Epoxiconazole (tech. commercially available), the test results were listed in table 20.

TABLE 20

| Compd. | Control (%) | | | | | |
|---|---|---|---|---|---|---|
| | 100 ppm | 50 ppm | 25 ppm | 12.5 ppm | 6.25 ppm | 3.13 ppm |
| Compd. 15 | 100 | 100 | 95 | 80 | 60 | 20 |
| epoxiconazole | 100 | 100 | 95 | 90 | 75 | 40 |
| untreated control | (disease index) 100 | | | | | |

Example 14

Determination of Greenhouse Biological Activity In Vitro (Rice Blast Etc.)

The tests were carried out with the method of spore germination. According to the design concentration, the compounds of the present invention were added into the cells of 96 cells culture plates, then rice blast spore suspension was dropped into the cells, meanwhile, water were set as the blank control, 3 replicates were set for each treatment. the treated culture plates were placed in an incubator (temperature: 24° C. to 26° C.), The test results were investigated on the second day after treatment, and the spore germinations rate were calculated.

Some of the test results are as follows:

At 25 ppm, compounds 2, 3, 15, 16, 95 and 177 showed 100% inhibition ratio on spore germination of rice blast.

At 0.3 ppm, compound 15 showed 100% inhibition ratio on spore germination of rice blast.

Example 15

Determination of Greenhouse Biological Activity In Vitro (Rice Sheath Blight Etc.)

Referring to the determination method of activity in vitro above, lots of inhibition activity tests of compound 15 against many fungus were carried out, and the test results are as follows: Compound 15 has good activity against rice sheath blight, mango anthracnose, sigatoka, corn southern leaf blight, banana anthracnose and so on, with $EC_{50}$ values of 0.799, 1.518, 2.389, 0.035, 2.867 ppm respectively.

Example 16

Biological activities in greenhouse of compound 15 and some intermediates of this invention against cucumber downy mildew, wheat powdery mildew and corn rust at 400 ppm were listed in table 21. The method was mentioned before.

TABLE 21

| compound or Intermediate | cucumber downy mildew | wheat powdery mildew | corn rust |
|---|---|---|---|
| Compd. 15 | 100 | 100 | 100 |
| VI-1 | 0 | 0 | 0 |
| VI-54 | 30 | 0 | 0 |
| VI-20 | 0 | 0 | 0 |
| VI-56 | 75 | 0 | 30 |
| VIII-1 | 95 | 0 | 50 |
| VIII-138 | 0 | 0 | 0 |
| VIII-139 | 0 | 0 | 0 |
| II-1 | 0 | 100 | 0 |

The structure of each intermediate is as follows:

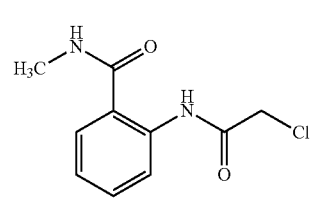

VI-1

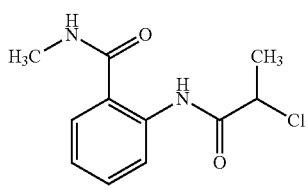

VI-54

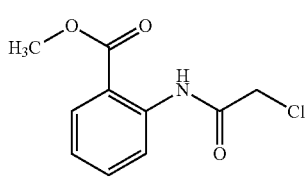

VI-20

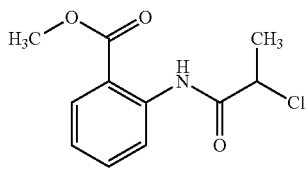

VI-56

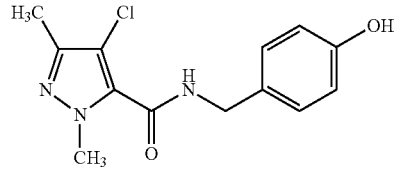

VIII-1

-continued

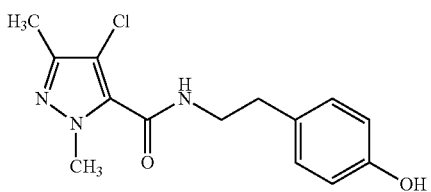

VIII-138

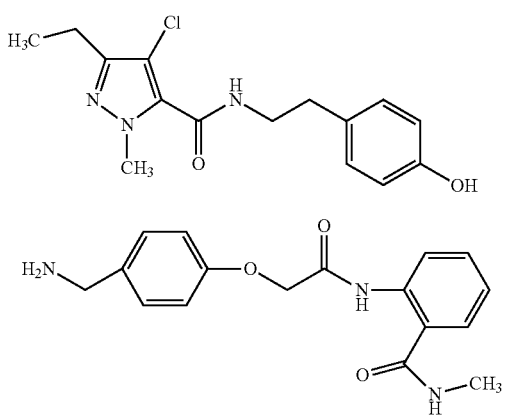

VIII-139

II-1

Example 17

Field Trials Against Cucumber Downy Mildew

The trial was carried out in a greenhouse in July 2011 in Yangling district, Shanxi Province. Before the treatment, the cucumber plants were at the beginning of infection. The trial method was based on the National Standard of the People's Republic of China—"Pesticide-Guidelines for The Field Efficacy Trials". The concentrations of Compound 15 (20% SC of Example 9, the same below) of this invention were 400 ppm, 200 ppm and 100 ppm. Chlorothalonil 75% WP and dimethomorph 50% WP (standards, both commercially available) were respectively 800 ppm and 200 ppm. The Area of plot was 15 m$^2$, random arrangement and 3 times replication. The volume was about 600 L/hm$^2$, and water was as the control. The results of Compound 15 on cucumber downy mildew in field were listed in table 22.

TABLE 22

| Compd. | concentration(ppm) | Control (%) | | | |
|---|---|---|---|---|---|
| | | I | II | III | average |
| Compd. 15 | 400 | 80 | 81 | 86 | 82 |
| | 200 | 60 | 65 | 72 | 66 |
| | 100 | 33 | 53 | 69 | 52 |
| dimethomorph | 200 | 44 | 52 | 63 | 53 |
| chlorothalonil | 800 | 68 | 73 | 81 | 74 |
| untreated control | (disease index) | (58) | (52) | (42) | (51) |

Example 18

Field Trials Against Rice Blast

The trial was carried out in a rice field on Shuguang farm of Heilongjiang Province in July 2011. Before the first treatment the rice was at the end of pregnancy, and on the second treatment, the rice was at heading stage. The trial method was based on the National Standard of the People's Republic of China—"Pesticide-Guidelines for The Field Efficacy Trials". The concentrations of Compound 15 of this invention were 800 ppm, 600 ppm and 400 ppm. Fluazinam 50% SC (standard, commercially available) was 600 ppm. The Area of plot was 30 m$^2$, random arrangement and 3 times replication. The volume was about 600 L/hm$^2$, and water was as the control. The results of Compound 15 on cucumber downy mildew in field were listed in table 23.

TABLE 23

| Compd. | Treatment concentration(ppm) | Control (%) | | | |
|---|---|---|---|---|---|
| | | I | II | III | average |
| Compd. 15 | 800 | 84 | 89 | 88 | 87 |
| | 600 | 77 | 81 | 77 | 78 |
| | 400 | 69 | 71 | 67 | 69 |
| fluazinam | 600 | 70 | 75 | 80 | 75 |
| untreated control | (disease index) | (11) | (10) | (12) | (11) |

Efficacy calculation method is as follows:

$$\text{Disease index (\%)} = \frac{\sum (\text{number of infected leaves} \times \text{corresponding grading})}{\text{total investigated leaves} \times \text{highest grading}} \times 100$$

$$\text{Efficacy (\%)} = \frac{\text{control disease index} - \text{treatment disease index}}{\text{control disease index}} \times 100$$

What is claimed is:

1. A pyrazole amide compound represented by the following formula (I):

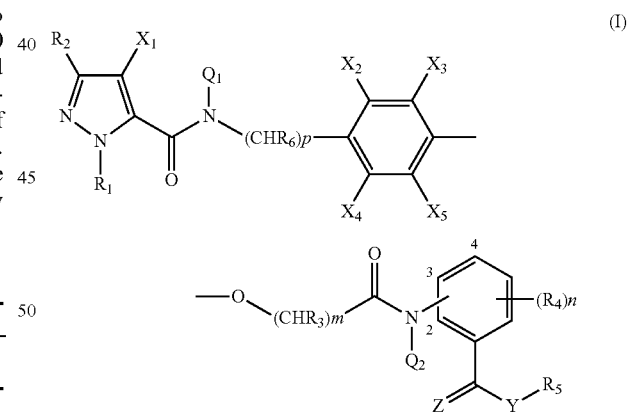

(I)

wherein:
R$_1$ is selected from H, C$_1$-C$_{12}$alkyl, C$_1$-C$_{12}$haloalkyl, C$_1$-C$_{12}$cyanoalkyl, C$_1$-C$_{12}$alkoxyC$_1$-C$_{12}$alkyl, C$_1$-C$_{12}$alkylcarbonyl, C$_1$-C$_{12}$haloalkylcarbonyl, C$_1$-C$_{12}$alkoxycarbonyl, C$_1$-C$_{12}$haloalkoxycarbonyl, C$_1$-C$_{12}$alkylaminocarbonyl, C$_1$-C$_{12}$haloalkylaminocarbonyl, C$_3$-C$_6$cycloalkyl or R$_8$;
R$_2$ is selected from H, halogen, CN, C$_1$-C$_{12}$cyanoalkyl, C$_1$-C$_{12}$alkyl, C$_1$-C$_{12}$haloalkyl, C$_1$-C$_{12}$alkoxy, C$_1$-C$_{12}$haloalkoxy, C$_1$-C$_{12}$cyanoalkoxy, C$_1$-C$_{12}$alkylthio, C$_1$-C$_{12}$haloalkylthio, C$_1$-C$_{12}$alkoxyC$_1$-C$_{12}$alkyl, C$_1$-C$_{12}$haloalkoxyC$_1$-

$C_{12}$alkyl, $C_1$-$C_{12}$alkylthio$C_1$-$C_{12}$alkyl, $C_1$-$C_{12}$haloalkylthio$C_1$-$C_{12}$alkyl, $C_1$-$C_{12}$alkylsulfinyl, $C_1$-$C_{12}$alkylsulfonyl, $C_3$-$C_6$cycloalkyl or $R_8$;

$R_3$ is selected from H or $C_1$-$C_{12}$alkyl; m is selected from 0 to 5;

$R_4$ is selected from halogen, CN, $CONH_2$, $CSNH_2$, $NO_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$haloalkylthio, $C_1$-$C_{12}$alkoxy$C_1$-$C_{12}$alkyl, $C_1$-$C_{12}$haloalkoxy$C_1$-$C_{12}$alkyl, $C_1$-$C_{12}$alkylthio$C_1$-$C_{12}$alkyl, $C_1$-$C_{12}$haloalkylthio$C_1$-$C_{12}$alkyl, $C_1$-$C_{12}$alkylamino, $C_1$-$C_{12}$haloalkylamino, $C_2C_{12}$dialkylamino, piperidyl, pyrrolidyl, N-methyl piperazinyl, morpholinyl, $C_2$-$C_{12}$alkenyl, $C_2$-$C_{12}$haloalkenyl, $C_2$-$C_{12}$alkenoxy, $C_2$-$C_{12}$haloalkenoxy, $C_2$-$C_{12}$alkynyl, $C_2$-$C_{12}$haloalkynyl, $C_2$-$C_{12}$alkynoxy, $C_2$-$C_{12}$haloalkynoxy, $C_1$-$C_{12}$alkylsulfinyl, $C_1$-$C_{12}$alkylsulfonyl or $R_8$; n is selected from 0 to 4;

$R_5$ is selected from H, $C_1$-$C_{12}$alkyl, $C_1$-$C_{12}$alkoxy$C_1$-$C_{12}$alkyl, $C_3$-$C_6$cycloalkyl, $C_1$-$C_{12}$cyanoalkyl, $C_1$-$C_{12}$alkylamino, $C_1$-$C_{12}$haloalkylamino, $C_2$-$C_{12}$dialkylamino, $C_2$-$C_{12}$alkenyl, $C_2$-$C_{12}$haloalkenyl, $C_2$-$C_{12}$alkynyl, $C_2$-$C_{12}$haloalkynyl, $C_1$-$C_{12}$alkylsulfonyl, $C_1$-$C_{12}$haloalkylsulfonyl, $C_1$-$C_{12}$alkylcarbonyl, $C_1$-$C_{12}$haloalkylcarbonyl, $C_1$-$C_{12}$alkoxycarbonyl$C_1$-$C_{12}$alkyl, $C_1$-$C_{12}$alkylcarbonylamino,

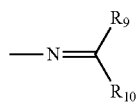

or $R_8$;

$R_6$ is selected from H, CN, SCN, H(C=O), $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$haloalkylthio, $C_1$-$C_{12}$alkylcarbonyl, $C_1$-$C_{12}$alkoxycarbonyl, $C_1$-$C_{12}$alkoxycarbonyl$C_1$-$C_{12}$alkyl, $C_1$-$C_{12}$alkylsulfinyl, $C_1$-$C_{12}$alkylsulfonyl, $C_1$-$C_{12}$cyanoalkyl, $C_1$-$C_{12}$hydroxyalkyl, $C_3$-$C_6$cycloalkyl or $R_8$; p is selected from 0 to 5;

$X_1$ is selected from H, halogen, $NO_2$, CN, SCN, $C_1$-$C_{12}$alkyl, $C_1$-$C_{12}$haloalkyl, $C_r$-$C_{12}$alkoxy, $C_1$-$C_{12}$haloalkoxy, $C_1$-$C_{12}$alkylthio, $C_1$-$C_{12}$alkylsulfinyl, $C_1$-$C_{12}$alkylsulfonyl, $C_1$-$C_{12}$haloalkylsulfinyl, $C_1$-$C_{12}$haloalkylsulfonyl, $C_1$-$C_{12}$haloalkylthio, $C_1$-$C_{12}$alkoxy$C_1$-$C_{12}$alkyl, $C_1$-$C_{12}$haloalkoxy$C_1$-$C_{12}$alkyl, $C_1$-$C_{12}$alkylthio$C_1$-$C_{12}$alkyl or $C_1$-$C_{12}$haloalkylthio$C_1$-$C_{12}$alkyl;

$X_2$, $X_3$, $X_4$ and $X_5$ may be the same or different, mutually independently selected from H, halogen, CN, $NO_2$, OH, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio or $C_1$-$C_{12}$alkylsulfonyl;

$Q_1$ and $Q_2$ may be the same or different, mutually independently selected from H, $NH_2$, OH, CN, SCN, $C_1$-$C_{12}$cyanoalkyl, $C_1$-$C_{12}$alkyl, $C_1$-$C_{12}$haloalkyl, $C_1$-$C_{12}$alkylcarbonyl, $C_1$-$C_{12}$alkoxy, $C_1$-$C_{12}$haloalkoxy, $C_1$-$C_{12}$alkoxy$C_1$-$C_{12}$alkyl, $C_1$-$C_{12}$alkylsulfinyl, $C_1$-$C_{12}$alkylsulfonyl, $C_1$-$C_{12}$haloalkylsulfinyl, $C_1$-$C_{12}$haloalkylsulfonyl, $C_1$-$C_{12}$alkylamino, $C_2$-$C_{12}$dialkylamino, piperidyl, pyrrolidyl, N-methyl piperazinyl, morpholinyl, H(C=O), $C_1$-$C_{12}$alkylaminocarbonyl, $C_1$-$C_{12}$alkoxycarbonyl, $C_{12}$alkoxycarbonyl$C_1$-$C_{12}$alkyl, $C_1$-$C_{12}$alkylaminothio, $C_2$-$C_{12}$dialkylaminothio, $C_3$-$C_6$cycloalkyl or $R_8$;

Y is selected from O, S or $NR_7$;

Z is selected from O or S;

$R_7$ is selected from H, CN, $NH_2$, OH, $C_1$-$C_{12}$alkyl, $C_1$-$C_{12}$haloalkyl, $C_{12}$alkoxy, $C_1$-$C_{12}$haloalkoxy, $C_3$-$C_6$cycloalkyl, $C_1$-$C_{12}$cyanoalkyl, $C_1$-$C_{12}$cyanoalkoxy, $C_1$-$C_{12}$alkylamino, $C_1$-$C_{12}$haloalkylamino, $C_2$-$C_{12}$dialkylamino, piperidyl, Pyrrolidyl, N-methylpiperazinyl, morpholinyl, 2,6-dimethylmorpholinyl, $C_2$-$C_{12}$alkenyl, $C_2$-$C_{12}$haloalkenyl, $C_2$-$C_{12}$alkenoxy, $C_2$-$C_{12}$haloalkenoxy, $C_2$-$C_{12}$alkynyl, $C_2$-$C_{12}$haloalkynyl, $C_2$-$C_{12}$alkynoxy, $C_2$-$C_{12}$haloalkynoxy, $C_1$-$C_{12}$alkylthio, $C_1$-$C_{12}$haloalkylthio, $C_1$-$C_{12}$alkylsulfonyl, $C_1$-$C_{12}$haloalkylsulfonyl, $C_1$-$C_{12}$alkylcarbonyl, $C_1$-$C_{12}$haloalkylcarbonyl, $C_1$-$C_{12}$alkoxycarbonyl$C_1$-$C_{12}$alkyl, $C_1$-$C_{12}$alkylcarbonylamino,

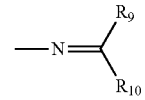

or $R_8$;

Or, when Y is selected from $NR_7$, $NR_7$ and $R_5$ form a unsubstituted or substituted five-membered or six-membered ring with 1-4 substitutents selected independently from $C_1$-$C_4$alkyl, $C_1$-$C_4$haloalkyl, $C_1$-$C_4$alkoxy, $C_1$-$C_4$haloalkoxy or $C_3$-$C_6$cycloalkyl;

$R_8$ is selected from phenyl, benzoyl, phenoxycarbonyl, phenylaminocarbonyl, phenyl$C_1$-$C_6$alkyl, naphthyl, naphthyl$C_1$-$C_6$alkyl, heteroaryl, heteroarylcarbonyl, heteroaryloxycarbonyl, heteroarylaminocarbonyl or heteroaryl$C_1$-$C_6$alkyl, which can be unsubstituted or further substituted with 1-5 substitutents, the substitutent(s) mentioned was (were) selected independently from halogen, $NO_2$, CN, SH, $C_1$-$C_{12}$alkyl, $C_1$-$C_{12}$haloalkyl, $C_3$-$C_{12}$cycloalkyl, $C_1$-$C_{12}$alkoxy, $C_1$-$C_{12}$haloalkoxy, $C_1$-$C_{12}$alkylthio, $C_1$-$C_{12}$haloalkylthio, $C_2$-$C_{12}$alkenyl, $C_2$-$C_{12}$haloalkenyl, $C_2$-$C_{12}$alkynyl, $C_2$-$C_{12}$haloalkynyl, $C_3$-$C_{12}$alkenoxy, $C_3$-$C_{12}$haloalkenoxy, $C_3$-$C_{12}$alkynoxy, $C_3$-$C_{12}$haloalkynoxy, $C_1$-$C_{12}$alkylsulfinyl, $C_1$-$C_{12}$haloalkylsulfinyl, $C_1$-$C_{12}$alkylsulfonyl, $C_1$-$C_{12}$haloalkylsulfonyl, $C_1$-$C_{12}$alkylcarbonyl, $C_1$-$C_{12}$haloalkylcarbonyl, $C_1$-$C_{12}$alkylcarbonyloxy, $C_1$-$C_{12}$alkylcarbonylamino, $C_1$-$C_{12}$alkylsulfonyloxy, $C_1$-$C_{12}$alkoxycarbonyl, $C_1$-$C_{12}$alkoxy$C_1$-$C_{12}$alkoxy, $C_1$-$C_{12}$alkoxycarbonyl$C_1$-$C_{12}$alkyl, $C_1$-$C_{12}$alkoxycarbonylamino, $C_1$-$C_{12}$alkoxycarbonyl$C_1$-$C_{12}$alkoxy, CHO, $CO_2H$, $CO_2Na$, $CO_2NH_4$, $NR_9R_{10}$, C(=O)$NR_9R_{10}$, OC(=O)$NR_9R_{10}$, C(=S)$NR_9R_{10}$ or $SO_2NR_9R_{10}$;

$R_9$ and $R_{10}$ may be the same or different, mutually independently selected from H, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$haloalkylthio, $C_3$-$C_6$cycloalkyl or $R_8$;

(CHR$_3$)mCON(Q$_2$) links with phenyl ring at the 2, 3 or 4-position.

2. The compound according to claim 1, wherein:

R$_1$ is selected from H, C$_1$-C$_6$ alkyl, C$_1$-C$_6$haloalkyl, C$_1$-C$_6$cyanoalkyl, C$_1$-C$_6$alkoxyC$_1$-C$_6$alkyl, C$_1$-C$_6$alkylcarbonyl, C$_1$-C$_6$haloalkylcarbonyl, C$_1$-C$_6$alkoxycarbonyl, C$_1$-C$_6$haloalkoxycarbonyl, C$_1$-C$_6$alkylaminocarbonyl, C$_1$-C$_6$haloalkylaminocarbonyl, C$_3$-C$_6$cycloalkyl or R$_8$;

R$_2$ is selected from H, halogen, CN, C$_1$-C$_6$alkyl, C$_1$-C$_6$haloalkyl, C$_1$-C$_6$alkoxy, C$_1$-C$_6$haloalkoxy, C$_1$-C$_6$cyanoalkoxy, C$_1$-C$_6$alkylthio, C$_1$-C$_6$alkoxyC$_1$-C$_6$alkyl, C$_1$-C$_6$haloalkoxyC$_1$-C$_6$alkyl, C$_1$-C$_6$alkylsulfinyl, C$_1$-C$_6$alkylsulfonyl, C$_3$-C$_6$cycloalkyl or R$_8$;

R$_3$ is selected from H or C$_1$-C$_4$alkyl; m is selected from 1 to 3;

R$_4$ is selected from halogen, CN, CONH$_2$, CSNH$_2$, NO$_2$, C$_1$-C$_4$alkyl, C$_1$-C$_4$haloalkyl, C$_1$-C$_4$alkoxy, C$_1$-C$_4$haloalkoxy, C$_1$-C$_4$alkylthio, C$_1$-C$_4$haloalkylthio, C$_1$-C$_4$alkoxyC$_1$-C$_4$alkyl, C$_1$-C$_4$haloalkoxyC$_1$-C$_4$alkyl, C$_1$-C$_4$alkylthioC$_1$-C$_4$alkyl, C$_1$-C$_4$haloalkylthioC$_1$-C$_4$alkyl, C$_1$-C$_4$alkylamino, C$_1$-C$_4$haloalkylamino, C$_2$-C$_4$dialkylamino, piperidyl, Pyrrolidyl, N-methyl piperazinyl, morpholinyl, C$_2$-C$_4$alkenyl, C$_2$-C$_4$haloalkenyl, C$_2$-C$_4$alkenoxy, C$_2$-C$_4$haloalkenoxy, C$_2$-C$_4$alkynyl, C$_2$-C$_4$haloalkynyl, C$_2$-C$_4$alkynoxy, C$_2$-C$_4$haloalkynoxy, C$_1$-C$_4$alkylsulfinyl, C$_1$-C$_4$alkylsulfonyl or R$_8$; n is selected from 0 to 3;

R$_5$ is selected from H, C$_1$-C$_4$alkyl, C$_1$-C$_4$haloalkyl, C$_1$-C$_4$alkoxyC$_1$-C$_4$alkyl, C$_3$-C$_6$cycloalkyl, C$_1$-C$_4$cyanoalkyl, C$_1$-C$_4$alkylamino, C$_1$-C$_4$haloalkylamino, C$_2$-C$_6$dialkylamino, C$_2$-C$_4$alkenyl, C$_2$-C$_4$haloalkenyl, C$_2$-C$_4$alkynyl, C$_2$-C$_4$haloalkynyl, C$_1$-C$_4$alkylsulfonyl, C$_1$-C$_4$haloalkylsulfonyl, C$_1$-C$_4$alkylcarbonyl, C$_1$-C$_4$haloalkylcarbonyl, C$_1$-C$_4$alkyloxycarbonylC$_1$-C$_4$alkyl, C$_1$-C$_4$alkylcarbonylamino,

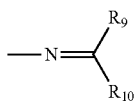

or R$_8$;

R$_6$ is selected from H, CN, SCN, H(C=O), C$_1$-C$_4$alkyl, C$_1$-C$_4$haloalkyl, C$_1$-C$_4$alkoxy, C$_1$-C$_4$haloalkoxy, C$_1$-C$_4$alkylthio, C$_1$-C$_4$haloalkylthio, C$_1$-C$_4$alkylcarbonyl, C$_1$-C$_4$alkyloxycarbonyl, C$_1$-C$_4$alkylsulfinyl, C$_1$-C$_4$alkylsulfonyl, C$_1$-C$_4$cyanoalkyl, C$_1$-C$_4$hydroxyalkyl, C$_3$-C$_6$cycloalkyl or R$_8$; p is selected from 0 to 4;

X$_1$ is selected from H, halogen, NO$_2$, CN, SCN, C$_1$-C$_4$alkyl, C$_1$-C$_4$haloalkyl, C$_1$-C$_4$alkoxy, C$_1$-C$_4$haloalkoxy, C$_1$-C$_4$alkylthio, C$_1$-C$_4$alkylsulfinyl, C$_1$-C$_4$alkylsulfonyl, C$_1$-C$_4$haloalkylsulfinyl, C$_1$-C$_4$haloalkylsulfonyl, C$_1$-C$_4$haloalkylthio, C$_1$-C$_4$alkoxyC$_1$-C$_4$alkyl, C$_1$-C$_4$haloalkoxyC$_1$-C$_4$alkyl, C$_1$-C$_4$alkylthioC$_1$-C$_4$alkyl or C$_1$-C$_4$haloalkylthioC$_1$-C$_4$alkyl;

X$_2$, X$_3$, X$_4$ and X$_5$ may be the same or different, mutually independently selected from H, halogen, CN, NO$_2$, OH, C$_1$-C$_4$alkyl, C$_1$-C$_4$haloalkyl, C$_1$-C$_4$alkoxy, C$_1$-C$_4$haloalkoxy, C$_1$-C$_4$alkylthio or C$_1$-C$_4$alkylsulfonyl;

Q$_1$ and Q$_2$ may be the same or different, mutually independently selected from H, NH$_2$, OH, CN, SCN, C$_1$-C$_4$cyanoalkyl, C$_1$-C$_4$alkyl, C$_1$-C$_4$haloalkyl, C$_1$-C$_4$alkylcarbonyl, C$_1$-C$_4$alkoxy, C$_1$-C$_4$haloalkoxy, C$_1$-C$_4$alkoxyC$_1$-C$_4$alkyl, C$_1$-C$_4$alkylsulfinyl, C$_1$-C$_4$alkylsulfonyl, C$_1$-C$_4$haloalkylsulfinyl, C$_1$-C$_4$haloalkylsulfonyl, C$_1$-C$_4$alkylamino, C$_2$-C$_6$dialkylamino, piperidyl, Pyrrolidyl, N-methylpiperazinyl, morpholinyl, H(C=O), C$_1$-C$_4$alkylaminocarbonyl, C$_1$-C$_4$alkoxycarbonyl, C$_1$-C$_4$alkylaminothio, C$_2$-C$_4$dialkylaminothio, C$_3$-C$_6$cycloalkyl or R$_8$;

Y is selected from O, S or NR$_7$;

Z is O;

R$_7$ is selected from H, CN, NH$_2$, OH, C$_1$-C$_4$alkyl, C$_1$-C$_4$haloalkyl, C$_1$-C$_4$alkoxy, C$_1$-C$_4$haloalkoxy, C$_3$-C$_6$cycloalkyl, C$_1$-C$_4$cyanoalkyl, C$_1$-C$_4$cyanoalkoxy, C$_1$-C$_4$alkylamino, C$_1$-C$_4$haloalkylamino, C$_2$-C$_4$dialkylamino, piperidyl, pyrrolidyl, N-methylpiperazinyl, morpholinyl, 2,6-dimethylmorpholinyl, C$_2$-C$_4$alkenyl, C$_2$-C$_4$haloalkenyl, C$_2$-C$_4$alkenoxy, C$_2$-C$_4$haloalkenoxy, C$_2$-C$_4$alkynyl, C$_2$-C$_4$haloalkynyl, C$_2$-C$_4$alkynoxy, C$_2$-C$_4$haloalkynoxy, C$_1$-C$_4$alkylthio, C$_1$-C$_4$haloalkylthio, C$_1$-C$_4$alkylsulfonyl, C$_1$-C$_4$haloalkylsulfonyl, C$_1$-C$_4$alkylcarbonyl, C$_1$-C$_4$haloalkylcarbonyl, C$_1$-C$_4$alkoxycarbonylC$_1$-C$_4$alkyl, C$_1$-C$_4$alkylcarbonylamino,

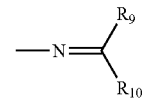

or R$_8$;

Or, when Y is selected from NR$_7$, NR$_7$ and R$_5$ form a unsubstituted or substituted five-membered or six-membered ring with 1-2 substitutents selected independently from C$_1$-C$_3$alkyl;

R$_8$ is selected from phenyl, benzoyl, phenoxycarbonyl, phenylaminocarbonyl, benzyl, phenethyl, naphthyl, pyridyl, picolyl, pyridylethyl, pyrimidyl, pyridazinyl, pyrazinyl, cyanuro, unsym-triazinyl, furanyl, thienyl, pyrrolyl, thiazolyl, pyrazolyl, imidazolyl, oxazolyl, isoxazolyl, thiadiazolyl, oxadizolyl, benzofuryl, benzothiophenyl, benzothiazolyl, benzoxazolyl, benzoxazolylmethyl, benzopyranyl, benzopyronyl, benzopyridazinyl, indolyl, quinolyl, quinoxalinyl, triazolopyrimidinyl, imidazopyridinyl, imidazothiazolyl, purinyl, pyridylformoxyl, pyrimidinylformoxyl, pyridyloxycarbonyl, pyrimidinyloxycarbonyl, pyridylaminocarbonyl, pyrimidinylaminocarbonyl or thiazolylmethyl, which can be unsubstituted or further substituted with 1-3 substitutents, the substitutent(s) mentioned was (were) selected independently from halogen, NO$_2$, CN, SH, C$_1$-C$_4$alkyl, C$_1$-C$_4$haloalkyl, C$_3$-C$_6$cycloalkyl, C$_1$-C$_4$alkoxy, C$_1$-C$_4$haloalkoxy, C$_1$-C$_4$alkylthio, C$_1$-C$_4$haloalkylthio, C$_2$-C$_4$alkenyl, C$_2$-C$_4$haloalkenyl, C$_2$-C$_4$alkynyl, C$_2$-C$_4$haloalkynyl, C$_3$-C$_6$alkenoxy, C$_3$-C$_6$haloalkenoxy, C$_3$-C$_6$alkynoxy, C$_3$-C$_6$haloalkynoxy, C$_1$-C$_4$alkylsulfinyl, C$_1$-C$_4$haloalkylsulfinyl, C$_1$-C$_4$alkylsulfonyl, C$_1$-C$_4$haloalkylsulfonyl, C$_1$-C$_4$alkylcarbonyl, C$_1$-C$_4$haloalkylcarbonyl, C$_1$-C$_4$alkylcarbonylamino, C$_1$-C$_4$alkylsulfonyloxy, C$_1$-C$_4$alkoxycarbonyl, C$_1$-C$_4$alkoxyC$_1$-C$_4$alkoxy, $C_1$-$C_4$alkoxycarbonyl$C_1$-$C_4$alkyl, $C_1$-$C_4$alkoxycarbonylamino, $C_1$-$C_4$alkoxycarbonyl$C_1$-$C_4$alkoxy, CHO, $CO_2H$, $CO_2Na$, $CO_2NH_4$, $NR_9R_{10}$, C(=O)$NR_9R_{10}$, OC(=O)$NR_9R_{10}$, C(=S)$NR_9R_{10}$ or $SO_2NR_9R_{10}$;

$R_9$ and $R_{10}$ may be the same or different, mutually independently selected from H, $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$haloalkylthio, $C_3$-$C_6$cycloalkyl or $R_8$;

(CH$R_3$)mCON($Q_2$) links with phenyl ring at the 2, 3 or 4-position.

3. The compound according to claim 2, wherein:

$R_1$ is selected from H, $C_1$-$C_4$alkyl, $C_1$-$C_4$haloalkyl, $C_1$-$C_4$alkoxy$C_1$-$C_4$alkyl, $C_3$-$C_6$cycloalkyl or $R_8$;

$R_2$ is selected from H, chloride, bromine, fluorine, iodine, CN, $C_1$-$C_4$alkyl, $C_1$-$C_4$haloalkyl, $C_1$-$C_4$alkoxy, $C_1$-$C_4$haloalkoxy, $C_1$-$C_4$cyanoalkoxy, $C_1$-$C_4$alkoxy$C_1$-$C_4$alkyl, $C_1$-$C_4$haloalkoxy$C_1$-$C_4$alkyl, $C_3$-$C_6$cycloalkyl or $R_8$;

$R_3$ is selected from H, methyl or ethyl; m is selected from 1, 2 or 3;

$R_4$ is selected from fluorine, chloride, bromine, iodine, CN, $NO_2$, $C_1$-$C_3$alkyl, $C_3$haloalkyl, $C_1$-$C_3$alkoxy, $C_1$-$C_3$haloalkoxy, $C_1$-$C_3$alkylamino, $C_2$-$C_4$dialkylamino or $C_1$-$C_3$alkylsulfonyl; n is selected from 0, 1, 2 or 3;

$R_5$ is selected from H, $C_1$-$C_4$alkyl, $C_1$-$C_4$haloalkyl, $C_1$-$C_4$alkoxy$C_1$-$C_3$alkyl, $C_3$-$C_6$cycloalkyl, $C_1$-$C_4$cyanoalkyl, $C_1$-$C_4$alkylamino, $C_2$-$C_6$dialkylamino, $C_3$-$C_4$alkenyl, $C_3$-$C_4$alkynyl or $R_8$;

$R_6$ is selected from H, CN, SCN, $C_1$-$C_3$alkyl, $C_1$-$C_3$haloalkyl, $C_1$-$C_3$alkoxy, $C_1$-$C_3$alkylthio or $C_1$-$C_3$hydroxyalkyl; p is selected from 0, 1, 2 or 3;

$X_1$ is selected from H, fluorine, chloride, bromine, iodine, $NO_2$, CN, SCN, $C_1$-$C_3$alkyl or $C_1$-$C_3$haloalkyl;

$X_2$, $X_3$, $X_4$ and $X_5$ may be the same or different, mutually independently selected from H, fluorine, chloride, bromine, iodine, CN, $NO_2$, OH, $C_1$-$C_3$alkyl, $C_1$-$C_3$haloalkyl, $C_1$-$C_3$alkoxy or $C_1$-$C_3$haloalkoxy;

$Q_1$ and $Q_2$ may be the same or different, mutually independently selected from H, CN, SCN, $C_1$-$C_3$alkyl, $C_1$-$C_3$alkylcarbonyl, $C_1$-$C_3$alkoxy$C_1$-$C_2$alkyl or H(C=O);

Y is selected from O or $NR_7$;

Z is O;

$R_7$ is selected from H, CN, $NH_2$, OH, $C_1$-$C_4$alkyl, $C_1$-$C_4$haloalkyl, $C_1$-$C_4$alkoxy, $C_1$-$C_4$haloalkoxy, $C_3$-$C_6$cycloalkyl, $C_1$-$C_3$cyanoalkyl, $C_1$-$C_3$cyanoalkoxy, $C_1$-$C_3$alkylamino, $C_1$-$C_3$haloalkylamino, $C_2$-$C_4$dialkylamino, piperidyl, pyrrolidyl, N-methylpiperazinyl, morpholinyl, 2,6-dimethylmorpholinyl, $C_3$-$C_4$alkenyl, $C_3$-$C_4$haloalkenyl, $C_3$-$C_4$alkenoxy, $C_3$-$C_4$haloalkenoxy, $C_3$-$C_4$alkynyl, $C_3$-$C_4$haloalkynyl, $C_3$-$C_4$alkynoxy, $C_3$-$C_4$haloalkynoxy, $C_1$-$C_3$alkylsulfonyl, $C_1$-$C_3$haloalkylsulfonyl or $R_8$;

Or, when Y is selected from $NR_7$, $NR_7$ and $R_5$ form piperidine, tetrahydropyrrole, N-methylpiperazine, morpholine or 2,6-dimethylmorpholine;

$R_8$ is selected from phenyl, 4-chlorophenyl, 2,4-dichlorophenyl, 4-methylphenyl, trifluoromethylphenyl, 4-methoxylphenyl, 2,6-dichloro-4-trifluoromethylphenyl, benzoyl, 4-chlorobenzoyl, 2,4-dichlorobenzoyl, 4-trifluoromethylbenzoyl, phenoxycarbonyl, chlorophenoxycarbonyl, 2,4-dichlorophenoxycarbonyl, 4-trifluoromethylphenoxycarbonyl, phenylaminocarbonyl, 4-chlorophenylaminocarbonyl, 2,4-dichlorophenylaminocarbonyl, 4-trifluoromethyphenylaminocarbonyl, benzyl, 4-chlorobenzyl, 4-tert-butylbenzyl, 4-trifluoromethylbenzyl, phenethyl, 2-pyridyl, 3-chloro-2-pyridyl, 3,5-dichloro-2-pyridyl, 3,5,6-trichloro-2-pyridyl, 5-trifluoromethyl-2-pyridyl, 5-methyl-2-pyridyl, 3-chloro-5-cyano-2-pyridyl, 3-chloro-5-trifluoromethyl-2-pyridyl, 2-picolyl, 2-chloro-5-picolyl, 3-chloro-5-trifluoro-2-picolyl, 2-pyridinylethyl, 3-chloro-5-trifluoromethyl-2-pyridinylethyl, 2-pyrimidinyl, 4-pyrimidinyl, 5-pyrimidinyl, thiazole-2-yl, 2-chloro-5-thiazolylmethyl, 3-pyridylformoxyl, 2-chloro-3-pyridylformoxyl, 2-chloro-5-pyridylformoxyl, 2-pyrimidinylformoxyl, 5-trifluoromethyl-2-pyrimidinylformoxyl, 2-pyridyloxycarbonyl, 3-chloro-2-pyridyloxycarbonyl, 3,5-dichloro-2-pyridyloxycarbonyl, 5-trifluoromethyl-2-pyridyloxycarbonyl, 5-methyl-2-pyridyloxycarbonyl, 3-chloro-5-cyano-2-pyridyloxycarbonyl, 3-chloro-5-trifluoromethyl-2-pyridyloxycarbonyl, 2-pyrimidinyloxycarbonyl, 5-trifluoromethyl-2-pyrimidinyloxycarbonyl, 2-pyridylaminocarbonyl, 3-chloro-2-pyridylaminocarbonyl or 2-pyrimidinylaminocarbonyl;

(CH$R_3$)mCON($Q_2$) links with phenyl ring at the 2, 3 or 4-position.

4. The compound according to claim 3, wherein:

$R_1$ is selected from H, methyl, ethyl, n-propyl, isopropyl, n-butyl, s-butyl, isobutyl, t-butyl, trifluoromethyl, trifluoroethyl, methoxymethyl, ethoxymethyl, cyclopropyl, cyclobutyl, cyclopentyl, cyclohexyl or $R_8$;

$R_2$ is selected from H, chloride, bromine, fluorine, CN, methyl, ethyl, n-propyl, i-propyl, n-butyl, s-butyl, i-butyl, t-butyl, trifluoromethyl, difluoromethyl, fluoromethyl, trifluoromethoxy, trifluoroethoxy, fluoromethoxy, cyanomethoxyl, methoxymethyl, trifluoromethoxymethyl, trifluoroethoxymethyl, cyclopropyl, cyclobutyl, cyclopentyl, cyclohexyl or $R_8$;

$R_3$ is selected from H or methyl; m is 1;

$R_4$ is selected from fluorine, chloride, bromine, iodine, CN, methyl, ethyl, trifluoromethyl, methoxyl, trifluoromethoxyl or methylsulfonyl; n is selected from 0, 1, 2 or 3;

$R_5$ is selected from H, methyl, ethyl, n-propyl, i-propyl, n-butyl, i-butyl, t-butyl, trifluoromethyl, trifluoroethyl, cyclopropyl, cyclohexyl, cyanomethyl, allyl, propargyl or $R_8$;

$R_6$ is selected from H, CN, SCN, methyl or ethyl; p is selected from 0, 1, 2 or 3;

$X_1$ is selected from H, fluorine, chloride, bromine, iodine, $NO_2$, methyl or chloromethyl;

$X_2$, $X_3$, $X_4$ and $X_5$ may be the same or different, mutually independently selected from H, chloride, bromine or methoxyl;

$Q_1$ and $Q_2$ are H;

Y is selected from O or $NR_7$;

Z is O;

$R_7$ is selected from H, CN, $NH_2$, OH, methyl, ethyl, cyclopropyl, cyclopentyl, cyclohexyl, cyanomethyl, methylamino, dimethylamino, methylsulfonyl or $R_8$;

Or, when Y is selected from $NR_7$, $NR_7$ and $R_5$ form piperidine, tetrahydropyrrole, N-methylpiperazine, morpholine or 2,6-dimethylmorpholine;

$R_8$ is selected from phenyl, 4-chlorophenyl, 2,4-dichlorophenyl, 4-methylphenyl, 4-trifluoromethylphenyl, 4-methoxylphenyl, 2,6-dichloro-4-trifluoromethylphenyl, benzyl, 4-chlorobenzyl, 4-tert-butylbenzyl, 4-trifluoromethylbenzyl, phenethyl, 2-pyridyl, 3-chloro-2-pyridyl, 3,5-dichloro-2-pyridyl, 3,5,6-trichloro-2-pyridyl, 5-trifluoromethyl-2-pyridyl, 5-methyl-2- pyridyl, 3-chloro-5-cyano-2-pyridyl, 3-chloro-5-trifluoromethyl-2-pyridyl, 2-picolyl, 2-chloro-5-picolyl, 3-chloro-5-trifluoromethyl-2-picolyl, 2-pyridinylethyl, 3-chloro-5-trifluoromethyl-2-pyridinylethyl, thiazole-2-yl, 2-chloro-5-thiazolylmethyl or 2-pyrimidinyl;

$(CHR_3)mCON(Q_2)$ links with phenyl ring at the 2, 3 or 4-position.

5. The compound according to claim 4, wherein:

$R_2$ is selected from bromine, methyl, ethyl, n-propyl, i-propyl, n-butyl, i-butyl, t-butyl, trifluoromethyl, cyclopropyl or 4-chlorophenyl;

$R_3$ is selected from H or methyl; m is 1;

$R_4$ is selected from fluorine, chloride, bromine, iodine, CN or methyl; n is selected from 0, 1 or 2;

$R_6$ is selected from H or methyl; p is selected from 0, 1, 2 or 3;

$X_1$ is selected from H, chloride or methyl;

$X_2, X_3, X_4, X_5, Q_1, Q_2$ are H;

Z is O;

$YR_5$ is selected from amino, methylamino, ethylamino, dimethylamino, methoxyl, ethoxyl or morpholinyl;

$(CHR_3)mCON(Q_2)$ links with phenyl ring at the 2, 3 or 4-position.

6. A method of preparation of a compound of general formula (I) (when $Q_1$=H) according to claim 1, according to the following reaction routes:

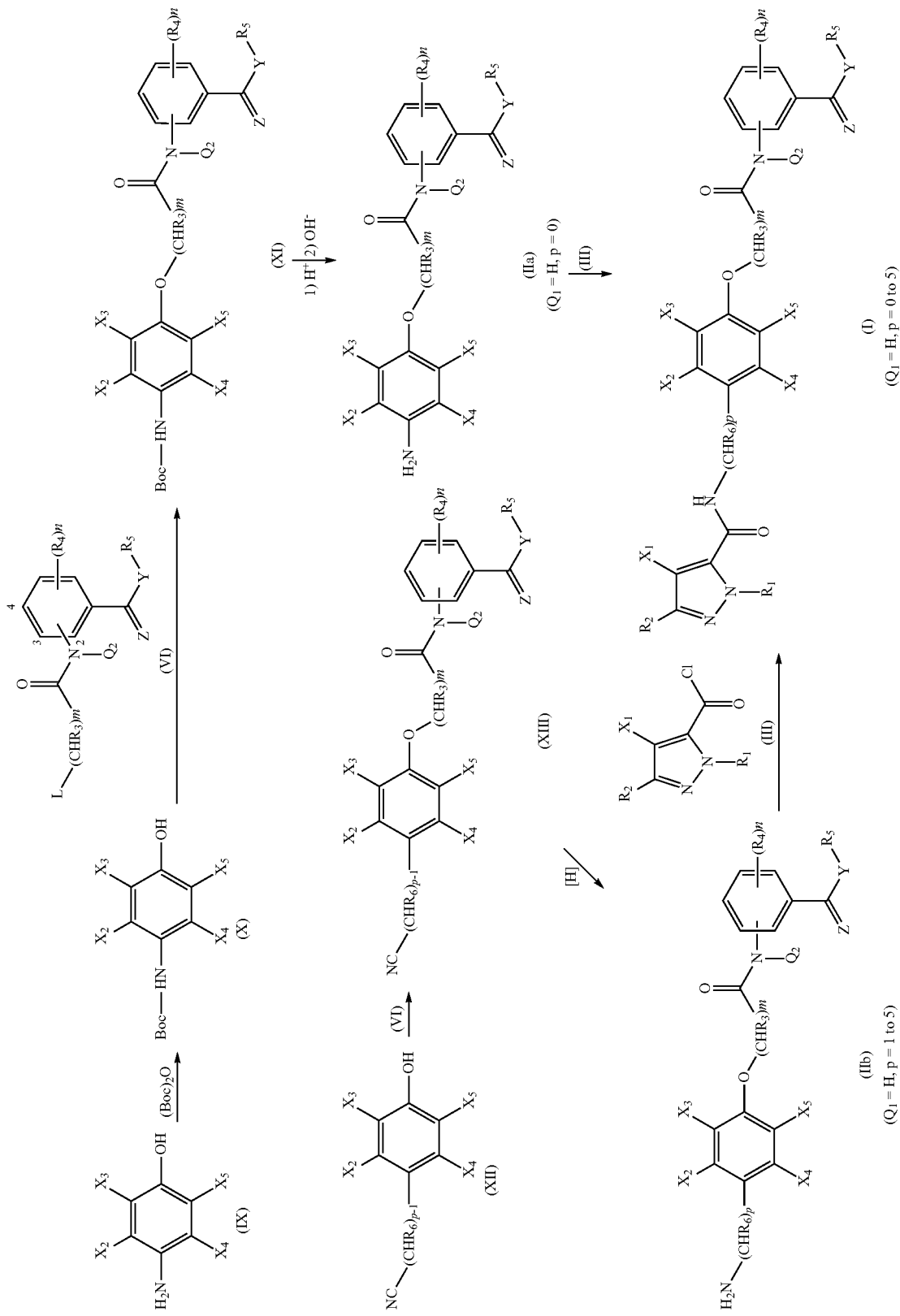

Wherein:

$R_1$ is selected from H, $C_1$-$C_{12}$alkyl, $C_1$-$C_{12}$haloalkyl, $C_1$-$C_{12}$cyanoalkyl, $C_1$-$C_{12}$alkoxy$C_1$-$C_{12}$alkyl, $C_1$-$C_{12}$alkylcarbonyl, $C_1$-$C_{12}$haloalkylcarbonyl, $C_1$-$C_{12}$alkoxycarbonyl, $C_1$-$C_{12}$haloalkoxycarbonyl, $C_1$-$C_{12}$alkylaminocarbonyl, $C_1$-$C_{12}$haloalkylaminocarbonyl, $C_3$-$C_6$cycloalkyl or $R_8$;

$R_2$ is selected from H, halogen, CN, $C_1$-$C_{12}$cyanoalkyl, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$cyanoalkoxy, $C_1$-$C_{12}$alkylthio, $C_1$-$C_{12}$haloalkylthio, $C_1$-$C_{12}$alkoxy$C_1$-$C_{12}$alkyl, $C_1$-$C_{12}$haloalkoxy$C_1$-$C_{12}$alkyl, $C_1$-$C_{12}$alkylthio$C_1$-$C_{12}$alkyl, $C_1$-$C_{12}$haloalkylthio$C_1$-$C_{12}$alkyl, $C_1$-$C_{12}$alkylsulfinyl, $C_1$-$C_{12}$alkylsulfonyl, $C_3$-$C_6$cycloalkyl or $R_8$;

$R_3$ is selected from H or $C_1$-$C_{12}$alkyl; m is selected from 0 to 5;

$R_4$ is selected from halogen, CN, $CONH_2$, $CSNH_2$, $NO_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$haloalkylthio, $C_1$-$C_{12}$alkoxy$C_1$-$C_{12}$alkyl, $C_1$-$C_{12}$haloalkoxy$C_1$-$C_{12}$alkyl, $C_1$-$C_{12}$alkylthio$C_1$-$C_{12}$alkyl, $C_1$-$C_{12}$haloalkylthio$C_1$-$C_{12}$alkyl, $C_1$-$C_{12}$alkylamino, $C_1$-$C_{12}$haloalkylamino, $C_2$-$C_{12}$dialkylamino, piperidyl, pyrrolidyl, N-methyl piperazinyl, morpholinyl, $C_2$-$C_{12}$alkenyl, $C_2$-$C_{12}$haloalkenyl, $C_2$-$C_{12}$alkenoxy, $C_2$-$C_{12}$haloalkenoxy, $C_2$-$C_{12}$alkynyl, $C_2$-$C_{12}$haloalkynyl, $C_2$-$C_{12}$alkynoxy, $C_2$-$C_{12}$haloalkynoxy, $C_1$-$C_{12}$alkylsulfinyl, $C_1$-$C_{12}$alkylsulfonyl or $R_8$; n is selected from 0 to 4;

$R_5$ is selected from H, $C_1$-$C_{12}$haloalkyl, $C_1$-$C_{12}$alkoxy$C_1$-$C_{12}$alkyl, $C_3$-$C_6$cycloalkyl, $C_1$-$C_{12}$cyanoalkyl, $C_1$-$C_{12}$alkylamino, $C_1$-$C_{12}$haloalkylamino, $C_2$-$C_{12}$dialkylamino, $C_2$-$C_{12}$alkenyl, $C_2$-$C_{12}$haloalkenyl, $C_2$-$C_{12}$alkynyl, $C_2$-$C_{12}$haloalkynyl, $C_1$-$C_{12}$alkylsulfonyl, $C_1$-$C_{12}$haloalkylsulfonyl, $C_1$-$C_{12}$alkylcarbonyl, $C_1$-$C_{12}$haloalkylcarbonyl, $C_1$-$C_{12}$alkoxycarbonyl$C_1$-$C_{12}$alkyl, $C_1$-$C_{12}$alkylcarbonylamino,

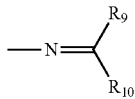

or $R_8$;

$R_6$ is selected from H, CN, SCN, H(C=O), $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$haloalkylthio, $C_1$-$C_{12}$alkylcarbonyl, $C_1$-$C_{12}$alkoxycarbonyl, $C_1$-$C_{12}$alkoxycarbonyl$C_1$-$C_{12}$alkyl, $C_1$-$C_{12}$alkylsulfinyl, $C_1$-$C_{12}$alkylsulfonyl, $C_1$-$C_{12}$cyanoalkyl, $C_1$-$C_{12}$hydroxyalkyl, $C_3$-$C_6$cycloalkyl or $R_8$; p is selected from 0 to 5;

$X_1$ is selected from H, halogen, $NO_2$, CN, SCN, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$alkylsulfinyl, $C_1$-$C_{12}$alkylsulfonyl, $C_1$-$C_{12}$haloalkylsulfinyl, $C_1$-$C_{12}$haloalkylsulfonyl, $C_1$-$C_{12}$haloalkylthio, $C_1$-$C_{12}$alkoxy$C_1$-$C_{12}$alkyl, $C_1$-$C_{12}$haloalkoxy$C_1$-$C_{12}$alkyl, $C_1$-$C_{12}$alkylthio$C_1$-$C_{12}$alkyl or $C_1$-$C_{12}$haloalkylthio$C_1$-$C_{12}$alkyl;

$X_2$, $X_3$, $X_4$ and $X_5$ may be the same or different, mutually independently selected from H, halogen, CN, $NO_2$, OH, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio or $C_1$-$C_{12}$alkylsulfonyl;

$Q_2$ is selected from H, $NH_2$, OH, CN, SCN, $C_1$-$C_{12}$cyanoalkyl, $C_1$-$C_{12}$alkyl, $C_1$-$C_{12}$haloalkyl, $C_1$-$C_{12}$alkylcarbonyl, $C_1$-$C_{12}$alkoxy, $C_1$-$C_{12}$haloalkoxy, $C_1$-$C_{12}$alkoxy$C_1$-$C_{12}$alkyl, $C_1$-$C_{12}$alkylsulfinyl, $C_1$-$C_{12}$alkylsulfonyl, $C_1$-$C_{12}$haloalkylsulfinyl, $C_1$-$C_{12}$haloalkylsulfonyl, $C_1$-$C_{12}$alkylamino, $C_2$-$C_{12}$dialkylamino, piperidyl, pyrrolidyl, N-methyl piperazinyl, morpholinyl, H(C=O), $C_1$-$C_{12}$alkylaminocarbonyl, $C_1$-$C_{12}$alkoxycarbonyl, $C_1$-$C_{12}$alkoxycarbonyl$C_1$-$C_{12}$alkyl, $C_1$-$C_{12}$alkylaminothio, $C_2$-$C_{12}$dialkylaminothio, $C_3$-$C_6$cycloalkyl or $R_8$;

Y is selected from O, S or $NR_7$;

Z is selected from O or S;

$R_7$ is selected from H, CN, $NH_2$, OH, $C_1$-$C_{12}$alkyl, $C_1$-$C_{12}$haloalkyl, $C_1$-$C_{12}$alkoxy, $C_1$-$C_{12}$haloalkoxy, $C_3$-$C_6$cycloalkyl, $C_1$-$C_{12}$cyanoalkyl, $C_1$-$C_{12}$cyanoalkoxy, $C_1$-$C_{12}$alkylamino, $C_1$-$C_{12}$haloalkylamino, $C_2$-$C_{12}$dialkylamino, piperidyl, Pyrrolidyl, N-methylpiperazinyl, morpholinyl, 2,6-dimethylmorpholinyl, $C_2$-$C_{12}$alkenyl, $C_2$-$C_{12}$haloalkenyl, $C_2$-$C_{12}$alkenoxy, $C_2$-$C_{12}$haloalkenoxy, $C_2$-$C_{12}$alkynyl, $C_2$-$C_{12}$haloalkynyl, $C_2$-$C_{12}$alkynoxy, $C_2$-$C_{12}$haloalkynoxy, $C_1$-$C_{12}$alkylthio, $C_1$-$C_{12}$haloalkylthio, $C_1$-$C_{12}$alkylsulfonyl, $C_1$-$C_{12}$haloalkylsulfonyl, $C_1$-$C_{12}$alkylcarbonyl, $C_1$-$C_{12}$haloalkylcarbonyl, $C_1$-$C_{12}$alkoxycarbonyl$C_1$-$C_{12}$alkyl, $C_1$-$C_{12}$alkylcarbonylamino,

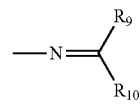

or $R_8$;

Or, when Y is selected from $NR_7$, $NR_7$ and $R_5$ form a unsubstituted or substituted five-membered or six-membered ring with 1-4 substitutents selected independently from $C_1$-$C_4$alkyl, $C_1$-$C_4$haloalkyl, $C_1$-$C_4$alkoxy, $C_1$-$C_4$haloalkoxy or $C_3$-$C_6$cycloalkyl;

$R_8$ is selected from phenyl, benzoyl, phenoxycarbonyl, phenylaminocarbonyl, phenyl$C_1$-$C_6$alkyl, naphthyl, naphthyl$C_1$-$C_6$alkyl, heteroaryl, heteroarylcarbonyl, heteroaryloxycarbonyl, heteroarylaminocarbonyl or heteroaryl$C_1$-$C_6$alkyl, which can be unsubstituted or further substituted with 1-5 substitutents, the substitutent(s) mentioned was (were) selected independently from halogen, $NO_2$, CN, SH, $C_1$-$C_{12}$alkyl, $C_1$-$C_{12}$haloalkyl, $C_3$-$C_{12}$cycloalkyl, $C_1$-$C_{12}$alkoxy, $C_1$-$C_{12}$haloalkoxy, $C_1$-$C_{12}$alkylthio, $C_1$-$C_{12}$haloalkylthio, $C_2$-$C_{12}$alkenyl, $C_2$-$C_{12}$haloalkenyl, $C_2$-$C_{12}$alkynyl, $C_2$-$C_{12}$haloalkynyl, $C_3$-$C_{12}$alkenoxy, $C_3$-$C_{12}$haloalkenoxy, $C_3$-$C_{12}$alkynoxy, $C_3$-$C_{12}$haloalkynoxy, $C_1$-$C_{12}$haloalkylsulfinyl, $C_1$-$C_{12}$alkylsulfonyl, $C_1$-$C_{12}$haloalkylsulfonyl, $C_1$-$C_{12}$alkylcarbonyl, $C_1$-$C_{12}$haloalkylcarbonyl, $C_1$-$C_{12}$alkylcarbonyloxy, $C_1$-$C_{12}$alkylcarbonylamino, $C_1$-$C_{12}$alkylsulfonyloxy, $C_1$-$C_{12}$alkoxycarbonyl, $C_1$-$C_{12}$alkoxy$C_1$-$C_{12}$alkoxy, $C_1$-$C_{12}$alkoxycarbonyl$C_1$-$C_{12}$alkyl, $C_1$-$C_{12}$alkoxycarbonylamino, $C_1$-$C_{12}$alkoxycarbonyl$C_1$-$C_{12}$alkoxy, CHO, $CO_2H$, $CO_2Na$, $CO_2NH_4$, $NR_9R_{10}$, $C(=O)NR_9R_{10}$, $OC(=O)NR_9R_{10}$, $C(=S)NR_9R_{10}$ or $SO_2NR_9R_{10}$;

$R_9$ and $R_{10}$ may be the same or different, mutually independently selected from H, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$haloalkylthio, $C_3$-$C_6$ cycloalkyl or $R_8$;

$(CHR_3)mCON(Q_2)$ links with phenyl ring at the 2, 3 or 4-position.

7. A method of controlling fungi which comprises applying the compound having general formula (I) according to claim 1 to agricultural fields.

8. A fungicidal composition comprising the compound having general formula (I) of claim 1 as an active ingredient, wherein the weight percentage of the active ingredient in the composition is from 0.1-99%.

9. A method of controlling fungi which comprises applying the composition according to claim 8 to agricultural fields.

10. A method of controlling fungi which comprises applying the compound having general formula (I) according to claim 2 to agricultural fields.

11. A fungicidal composition comprising the compound having general formula (I) of claim 2 as an active ingredient, wherein the weight percentage of the active ingredient in the composition is from 0.1-99%.

12. A method of controlling fungi which comprises applying the composition according to claim 11 to agricultural fields.

13. A method of controlling fungi which comprises applying the compound having general formula (I) according to claim 3 to agricultural fields.

14. A fungicidal composition comprising the compound having general formula (I) of claim 3 as an active ingredient, wherein the weight percentage of the active ingredient in the composition is from 0.1-99%.

15. A method of controlling fungi which comprises applying the composition according to claim 14 to agricultural fields.

16. A method of controlling fungi which comprises applying the compound having general formula (I) according to claim 4 to agricultural fields.

17. A fungicidal composition comprising the compound having general formula (I) of claim 4 as an active ingredient, wherein the weight percentage of the active ingredient in the composition is from 0.1-99%.

18. A method of controlling fungi which comprises applying the composition according to claim 17 to agricultural fields.

19. A method of controlling fungi which comprises applying the compound having general formula (I) according to claim 5 to agricultural fields.

20. A fungicidal composition comprising the compound having general formula (I) of claim 5 as an active ingredient, wherein the weight percentage of the active ingredient in the composition is from 0.1-99%.

21. A method of controlling fungi which comprises applying the composition according to claim 20 to agricultural fields.

\* \* \* \* \*

UNITED STATES PATENT AND TRADEMARK OFFICE
CERTIFICATE OF CORRECTION

Page 1 of 1

| | |
|---|---|
| PATENT NO. | : 8,614,214 B2 |
| APPLICATION NO. | : 13/883146 |
| DATED | : December 24, 2013 |
| INVENTOR(S) | : Changling Liu et al. |

It is certified that error appears in the above-identified patent and that said Letters Patent is hereby corrected as shown below:

At Item (73), of the Title page of the Letters Patent, please insert the following as the Second Assignee of Record

-- SHENYANG RESEARCH INSTITUTE OF CHEMICAL INDUSTRY CO., LTD.

Shenyang, Liaoning, China --

Signed and Sealed this
Fourteenth Day of April, 2015

Michelle K. Lee
*Director of the United States Patent and Trademark Office*